US008207186B2

(12) United States Patent
Jewell et al.

(10) Patent No.: US 8,207,186 B2
(45) Date of Patent: Jun. 26, 2012

(54) BENZOCYCLOHEPTAPYRIDINES AS INHIBITORS OF THE RECEPTOR TYROSINE KINASE MET

(75) Inventors: James P. Jewell, Sandwich, MA (US); Jason D. Katz, Newton Highlands, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 1219 days.

(21) Appl. No.: 11/921,350

(22) PCT Filed: Jun. 22, 2006

(86) PCT No.: PCT/US2006/024247
§ 371 (c)(1),
(2), (4) Date: Nov. 30, 2007

(87) PCT Pub. No.: WO2007/002254
PCT Pub. Date: Jan. 4, 2007

(65) Prior Publication Data
US 2009/0197908 A1   Aug. 6, 2009

Related U.S. Application Data

(60) Provisional application No. 60/693,229, filed on Jun. 23, 2005, provisional application No. 60/729,061, filed on Oct. 21, 2005.

(51) Int. Cl.
*A01N 43/42* (2006.01)
*A61K 31/44* (2006.01)
*C07D 221/00* (2006.01)

(52) U.S. Cl. .......................................... 514/290; 546/93

(58) Field of Classification Search .................. 514/290; 546/93
See application file for complete search history.

(56) References Cited

U.S. PATENT DOCUMENTS

| | | | |
|---|---|---|---|
| 3,366,635 | A | 1/1968 | Villani et al. |
| 4,948,796 | A | 8/1990 | Hiraiwa et al. |
| 5,726,325 | A | 3/1998 | Yoshida et al. |
| 6,365,588 | B1 | 4/2002 | Bishop et al. |
| 7,018,979 | B1 | 3/2006 | Black et al. |
| 2003/0114432 | A1 | 6/2003 | Clare et al. |

FOREIGN PATENT DOCUMENTS

| | | |
|---|---|---|
| WO | WO 88/03138 | 5/1988 |
| WO | WO 92/00293 | 1/1992 |
| WO | WO 98/11096 | 3/1998 |
| WO | WO 98/11097 | 3/1998 |
| WO | WO0154771 A2 * | 8/2001 |
| WO | WO 03/084931 | 10/2003 |
| WO | WO 2004/043966 | 5/2004 |
| WO | WO 2004/058742 | 7/2004 |
| WO | WO 2007/002254 | 1/2007 |
| WO | WO 2007/050380 | 5/2007 |
| WO | WO 2007/050383 | 5/2007 |
| WO | WO 2007/050401 | 5/2007 |
| WO | WO 2008/008310 | 1/2008 |

OTHER PUBLICATIONS

Beger et. al., World J. Surg., 2003, Internationale de Chirurgie, vol. 27, pp. 1075-1084.*
Stadler et. al., Clinical Cancer Research, 2004, American Association for Cancer Research, vol. 10, pp. 3365-3370.*
Correa, Gut, 2004, British Medical Association, vol. 53, pp. 1217-1219.*
Young et. al., Clinical Cancer Research, 2002, American Association for Cancer Research, vol. 8, pp. 11-16.*
Chabner et. al., Nature Reviews Cancer, 2005, Nature Publishing Group, vol. 5, pp. 65-72.*
Rich et. al., Nature Reviews, 2004, Nature Publishing Group, vol. 3, pp. 430-446.*
Ma, PC et al. Cancer Research, vol. 65, No. 4, pp. 1479-1488 (2005), Functional expression and mutations of c-Met and its therapeutic inhibition with SU11274 and small interfering RNA in non-small cell lung cancer.
Ma, PC et al. Cancer Research, vol. 63, pp. 6272-6281 (2003), "c-MET mutational analysis in small cell lung cancer: novel juxtamembrane domain mutations regulating cytoskeletal functions".
Christensen, JG et al., Cancer Research., vol. 63, pp. 7345-7355 (2003), "A selective small molecule inhibitor of c-Met kinase inhibits c-Met-dependent phenotypes in vitro and exhibits cytoreductive antitumor activity in vivo".
Sattler, M et al., Cancer Research, vol. 63, pp. 5462-5469 (2003), "A novel small molecule Met inhibitor induces apoptosis in cells transformed by the oncogenic TPR-MET tyrosine kinase".
Christensen, JG et al., Cancer Letters, vol. 225, pp. 1-26 (2005), "c-Met as a target for human cancer and characterization of inhibitors for therapeutic intervention".
Office Communication from the USPTO mailed Apr. 28, 2008 with a three-month reply due of Jul. 28, 2008.
Amendment and Response dated Jun. 4, 2008 in reply to the Office Action mailed Apr. 28, 2008 from the USPTO.
Puri, N. et al., Cancer Research, vol. 67, No. 8, pp. 3529-3534 (2007), "A selective small molecule inhibitor of c-Met, PHA665752, inhibits tumorigenicity and angiogenesis in mouse lung cancer xenografts".
Zou, HY et al., Cancer Research, vol. 67, No. 9, pp. 4408-4417 (2007), "An orally available small-molecule inhibitor of c-Met, PF-2341066, exhibits cytoreductive antitumor efficacy through antiproliferative and antiangiogenic mechanisms".
Cassinelli, G et al., Molecular Cancer Therapeutics, vol. 5, No. 9, pp. 2388-2397 (2006), "Inhibition of c-Met and prevention of spontaneous metastatic spreading by the 2-indolinone RPI-1".
Martens, T et al., Clinical Cancer Research, vol. 12, No. 20, pp. 6144-6152 (2006), "A novel one-armed anti-c-Met antibody inhibits glioblastoma growth in vivo".
Ross, R et al., Poster B249, 2007 AARC-NCI-EORTC International Conference on Molecular Targets and Cancer Therapeutics, Oct. 2007, "A Phase 2 Study of the Dual MET/VEGFR2 Inhibitor XL880 in Patients (pts) with Papillary Renal Carcinoma (PRC)".
Office Communication from the USPTO mailed Jul. 29, 2008 with a three-month reply due of Oct. 29, 2008.
Amendment and Response dated Sep. 5, 2008 in reply to the Office Action mailed Jul. 29, 2008 from the USPTO.
Dermer, GB, Bio/technology, vol. 12, pp. 320 (1994), "Another anniversary for the war on cancer".
Freshney, R, Culture of Animal Cells, pp. 1-6 (1983).

* cited by examiner

*Primary Examiner* — Sreeni Padmanabhan
*Assistant Examiner* — Sarah Pihonak
(74) *Attorney, Agent, or Firm* — David A. Muthard

(57) ABSTRACT

The present invention relates to 5H-benzo[4,5]cyclohepta[1,2-*b*]pyridine compounds, that are useful for treating cellular proliferative diseases, for treating disorders associated with MET activity, and for inhibiting the receptor tyrosine kinase MET. The invention also related to compositions which comprise these compounds, and methods of using them to treat cancer in mammals.

1 Claim, No Drawings

BENZOCYCLOHEPTAPYRIDINES AS INHIBITORS OF THE RECEPTOR TYROSINE KINASE MET

CROSS REFERENCE TO RELATED APPLICATIONS

This application is the National Stage of International Application No. PCT/US2006/024247, filed 22 Jun. 2006, which claims the benefit under 35 U.S.C. 119(e) of U.S. Provisional Application No. 60/693,229, filed on 23 Jun. 2005 and U.S. Provisional Application No. 60/729,061, filed 21 Oct. 2005.

BACKGROUND OF THE INVENTION

This invention relates to 5H-benzo[4,5]cyclohepta[1,2-b]pyridine compounds that are inhibitors of tyrosine kinases, in particular the receptor tyrosine kinase MET, and are useful in the treatment of cellular proliferative diseases, for example cancer, hyperplasias, restenosis, cardiac hypertrophy, immune disorders and inflammation.

Studies on signal transduction pathways have generated various promising molecular targets for therapeutic inhibition in cancer therapy. Receptor tyrosine kinases (RTK) represent an important class of such therapeutic targets. Recently, members of the MET proto-oncogene family, a subfamily of receptortyrosine kinases, have drawn special attention to the association between invasion and metastasis. The MET family, including MET (also referred to as c-Met) and RON receptors, can function as oncogenes like most tyrosine kinases. MET has been shown to be overexpressed and/or mutated in a variety of malignancies. A number of MET activating mutations, many of which are located in the tyrosine kinase domain, have been detected in various solid tumors and have been implicated in invasion and metastasis of tumor cells.

The c-Met proto-oncogene encodes the MET receptor tyrosine kinase. The MET receptor is a 190 kDa glycosylated dimeric complex composed of a 50 kDa alpha chain disulfide-linked to a 145 kDa beta chain. The alpha chain is found extracellularly while the beta chain contains extracellular, transmembrane and cytosolic domains. MET is synthesized as a precursor and is proteolytically cleaved to yield mature alpha and beta subunits. It displays structural similarities to semaphoring and plexins, a ligand-receptor family that is involved in cell-cell interaction.

The natural ligand for MET is hepatocyte growth factor (HGF), a disulfide linked heterodimeric member of the scatter factor family that is produced predominantly by mesenchymal cells and acts primarily on MET-expressing epithelial and endothelial cells in an endocrine and/or paraendocrine fashion. HGF has some homology to plasminogen.

It is known that stimulation of MET via hepatocyte growth factor (also known as scatter factor, HGF/SF) results in a plethora of biological and biochemical effects in the cell. Activation of c-Met signaling can lead to a wide array of cellular responses including proliferation, survival, angiogenesis, wound healing, tissue regeneration, scattering, motility, invasion and branching morphogenesis. HGF/MET signaling also plays a major role in the invasive growth that is found in most tissues, including cartilage, bone, blood vessels, and neurons.

Various c-Met mutations have been well described in multiple solid tumors and some hematologic malignancies. The prototypic c-Met mutation examples are seen in hereditary and sporadic human papillary renal carcinoma (Schmidt, L. et al., *Nat. Tenet.* 1997, 16, 68-73; Jeffers, M. et al., *Proc. Nat. Acad. Sci.* 1997, 94, 11445-11500). Other reported examples of c-Met mutations include ovarian cancer, childhood hepatocellular carcinoma, metastatic head and neck squamous cell carcinomas and gastric cancers. HGF/MET has been shown to inhibit anoikis, suspension-induced programmed cell death (apoptosis), in head and neck squamous cell carcinoma cells.

MET signaling is implicated in various cancers, especially renal. The nexus between MET and colorectal cancer has also been established. Analysis of c-Met expression during colorectal cancer progression showed that 50% of the carcinoma specimens analyzed expressed 5-50-fold higher levels of MET mRNA transcripts and protein versus the adjacent normal colonic mucosa. In addition, when compared to the primary tumor, 70% of colorectal cancer liver metastasis showed MET overexpression.

MET is also implicated in glioblastoma. High-grade malignant gliomas are the most common cancers of the central nervous system. Despite treatment with surgical resection, radiation therapy, and chemotherapy, the mean overall survival is <1.5 years, and few patients survive for >3 years. Human malignant gliomas frequently express both HGF and MET, which can establish an autocrine loop of biological significance. Glioma MET expression correlates with glioma grade, and an analysis of human tumor specimens showed that malignant gliomas have a 7-fold higher HGF content than low-grade gliomas. Multiple studies have demonstrated that human gliomas frequently co-express HGF and MET and that high levels of expression are associated with malignant progression. It was further shown that HGF-MET is able to activate Akt and protect glioma cell lines from apoptotic death, both in vitro and in vivo.

RON shares a similar structure, biochemical features, and biological properties with MET. Studies have shown RON overexpression in a significant fraction of breast carcinomas and colorectal adenocarcinomas, but not in normal breast epithelia or benign lesions. Cross-linking experiments have shown that RON and MET form a non-covalent complex on the cell surface and cooperate in intracellular signaling. RON and MET genes are significantly co-expressed in ovarian cancer cell motility and invasiveness. This suggests that co-expression of these two related receptors might confer a selective advantage to ovarian carcinoma cells during either tumor onset or progression.

A number of reviews on MET and its function as an oncogene have recently been published: *Cancer and Metastasis Review* 22:309-325 (2003); *Nature Reviews/Molecular Cell Biology* 4:915-925 (2003); *Nature Reviews/Cancer* 2:289-300 (2002).

Since dysregulation of the HGF/MET signaling has been implicated as a factor in tumorgenesis and disease progression in many tumors, different strategies for therapeutic inhibition of this important RTK molecule should be investigated. Specific small molecule inhibitors against HGF/MET signaling and against RON/MET signaling have important therapeutic value for the treatment of cancers in which Met activity contributes to the invasive/metastatic phenotype.

SUMMARY OF THE INVENTION

The present invention relates to 5H-benzo[4,5]cyclohepta[1,2-b]pyridine derivatives, that are useful for treating cellular proliferative diseases, for treating disorders associated with MET activity, and for inhibiting the receptor tyrosine kinase MET. The compounds of the invention may be illustrated by the Formula I:

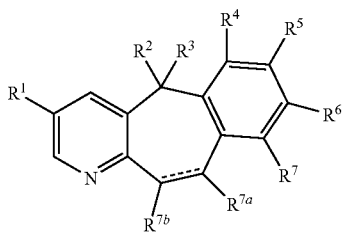

DETAILED DESCRIPTION OF THE INVENTION

The compounds of this invention are useful in the inhibition of tyrosine kinases, in particular the receptor tyrosine kinase MET, and are illustrated by a compound of Formula I:

I or pharmaceutically acceptable salts thereof, wherein:
a dashed line represents an optional double bond;
a is independently 0 or 1;
b is independently 0 or 1;
m is independently 0, 1, or 2;
$R^1$ is selected from halogen, aryl, heterocyclyl, —C(=O)NR$^{10}$R$^{11}$, (C=O)OC$_1$-C$_6$ alkyl and NR$^{10}$R$^{11}$; said alkyl, aryl and heterocyclyl group optionally substituted with one to five substituents, each substituent independently selected from $R^8$;
$R^2$ and $R^3$ are independently selected from hydrogen, OH, —O—C$_{1-6}$ alkyl, —O—C(=O)C$_{1-6}$ alkyl, —O-aryl and NR$^{10}$R$^{11}$, each alkyl and aryl optionally substituted with one to five substituents, each substituent independently selected from $R^8$; or
$R^2$ and $R^3$ are combined to form =O or =N—OR$^c$;
$R^4$, $R^6$ and $R^7$ are each independently hydrogen, halogen, C$_{1-6}$alkyl, C$_{2-6}$ alkenyl, C$_{2-6}$ alkynyl, OH, —O—C$_{1-6}$alkyl, —O—C(=O)C$_{1-16}$ alkyl, —O-aryl, S(O)$_m$R$^a$ and NR$^{10}$R$^{11}$, each alkyl and aryl optionally substituted with one to five substituents, each substituent independently selected from $R^8$;
$R^{7a}$ and $R^{7b}$ are each independently hydrogen, halogen, C$_{1-6}$alkyl, OH, —O—C$_{1-6}$alkyl, —O—C(=O)C$_{1-6}$ alkyl, —O-aryl, NO$_2$ and NR$^{10}$R$^{11}$, each alkyl and aryl optionally substituted with one to five substituents, each substituent independently selected from $R^8$;
$R^5$ is selected from hydrogen, C$_{1-6}$alkyl, C$_{2-6}$ alkenyl, C$_{2-6}$ alkynyl, OH, —O—C$_{1-6}$alkyl, —O—C(=O)C$_{1-6}$ alkyl, —O-aryl, S(O)$_m$R$^a$, —C(=O)NR$^{10}$R$^{11}$, —NHS(O)$_2$NR$^{10}$R$^{11}$ and NR$^{10}$R$^{11}$, each alkyl, alkenyl, alkynyl and aryl optionally substituted with one to five substituents, each substituent independently selected from $R^8$;
provided that at least one of $R^4$, $R^5$ and $R^6$ is not hydrogen;
$R^8$ independently is:
  1) (C=O)$_a$O$_b$C$_1$-C$_{10}$ alkyl,
  2) (C=O)$_a$O$_b$aryl,
  3) C$_2$-C$_{10}$ alkenyl,
  4) C$_2$-C$_{10}$ alkynyl,
  5) (C=O)$_a$O$_b$ heterocyclyl,
  6) CO$_2$H,
  7) halo,
  8) CN,
  9) OH,
  10) O$_b$C$_1$-C$_6$ perfluoroalkyl,
  11) O$_a$(C=O)$_b$NR$^{10}$R$^{11}$,
  12) S(O)$_m$R$^a$,
  13) S(O)$_2$NR$^{10}$R$^{11}$,
  14) OS(=O)R$^a$,
  15) oxo,
  16) CHO,
  17) (N=O)R$^{10}$R$^{11}$,
  18) (C=O)$_a$O$_b$C$_3$-C$_8$ cycloalkyl,
  19) O$_b$SiR$^a_3$, or
  20) NO$_2$;
said alkyl, aryl, alkenyl, alkynyl, heterocyclyl, and cycloalkyl optionally substituted with one, two or three substituents selected from $R^9$;
two of the carbon atoms is optionally replaced by a moiety selected from O, S(O)$_m$, —N(R$^a$)C(O)—, —N(R$^b$)— and —N(COR$^a$)—;
$R^9$ is independently selected from:
  1) (C=O)$_a$O$_b$(C$_1$-C$_{10}$)alkyl,
  2) O$_b$(C$_1$-C$_3$)perfluoroalkyl,
  3) oxo,
  4) OH,
  5) halo,
  6) CN,
  7) (C$_2$-C$_{10}$)alkenyl,
  8) (C$_2$-C$_{10}$)alkynyl,
  9) (C=O)$_a$O$_b$(C$_3$-C$_6$)cycloalkyl,
  10) (C=O)$_a$O$_b$(C$_0$-C$_6$)alkylene-aryl,
  11) (C=O)$_a$O$_b$(C$_0$-C$_6$)alkylene-heterocyclyl,
  12) (C=O)$_a$O$_b$(C$_0$-C$_6$)alkylene-N(R$^b$)$_2$,
  13) C(O)R$^a$,
  14) (C$_0$-C$_6$)alkylene-CO$_2$R$^a$,
  15) C(O)H,
  16) (C$_0$-C$_6$)alkylene-CO$_2$H,
  17) C(O)N(R$^b$)$_2$,
  18) S(O)$_m$R$^a$, and
  19) S(O)$_2$NR$^{10}$R$^{11}$;
said alkyl, alkenyl, alkynyl, cycloalkyl, aryl, and heterocyclyl is optionally substituted with one, two or three substituents selected from R$^b$, OH, (C$_1$-C$_6$)alkoxy, halogen, CO$_2$H, CN, O(C=O)C$_1$-C$_6$ alkyl, oxo, and N(R$^b$)$_2$; or
two R$^9$s, attached to the same carbon atom are combined to form —(CH$_2$)$_u$— wherein u is 3 to 6 and one or two of the carbon atoms is optionally replaced by a moiety selected from O, S(O)$_m$, —N(R$^a$)C(O)—, —N(R$^b$)— and —N(COR$^a$)—;
$R^{10}$ and $R^{11}$ are independently selected from:
  1) H,
  2) (C=O)O$_b$C$_1$-C$_{10}$ alkyl,
  3) (C=O)O$_b$C$_3$-C$_8$ cycloalkyl,
  4) (C=O)O$_b$aryl,
  5) (C=O)O$_b$heterocyclyl,
  6) C$_1$-C$_{10}$ alkyl,
  7) aryl,
  8) C$_2$-C$_{10}$ alkenyl,
  9) C$_2$-C$_{10}$ alkynyl,
  10) heterocyclyl,
  11) C$_3$-C$_8$ cycloalkyl,
  12) SO$_2$R$^a$, and
  13) (C=O)NR$^b_2$, said alkyl, cycloalkyl, aryl, heterocyclyl, alkenyl, and alkynyl is optionally substituted with one, two or three substituents selected from $R^8$, or $R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;

$R^a$ is independently selected from: $(C_1-C_6)$alkyl, $(C_2-C_6)$alkenyl, $(C_3-C_6)$cycloalkyl, aryl, —$(C_1-C_6)$alkylenearyl, heterocyclyl and —$(C_1-C_6)$alkyleneheterocyclyl;

$R^b$ is independently selected from: H, $(C_1-C_6)$alkyl, aryl, —$(C_1-C_6)$alkylenearyl, heterocyclyl, —$(C_1-C_6)$alkyleneheterocyclyl, $(C_3-C_6)$cycloalkyl, $(C=O)OC_1-C_6$ alkyl, $(C=O)C_1-C_6$ alkyl or $S(O)_2R^a$; and $R^c$ is independently selected from: H, $(C_1-C_6)$alkyl, $(C_2-C_6)$alkenyl, $(C_3-C_6)$cycloalkyl, aryl, —$(C_1-C_6)$alkylenearyl, heterocyclyl and —$(C_1-C_6)$alkyleneheterocyclyl;

but excluding compounds represented by the following exclusion table ($R^{7a}$ and $R^{7b}$ are H):

| $R^1$ | $R^2$ | $R^3$ | $R^4$ | $R^5$ | $R^6$ | $R^7$ | Dashed line |
|---|---|---|---|---|---|---|---|
| Ph | Form | =O | H | H | H | Br | double bond |
| Ph | Form | =O | H | H | H | H | double bond |
| Ph | Form | =O | H | Br | H | H | double bond |
| Ph | Form | =O | H | H | H | Cl | double bond |
| Cl | Form | =O | H | H | H | Br | double bond |
| Ph | H | OH | H | H | H | 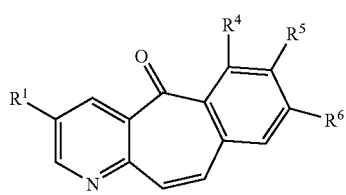 | double bond |
| Ph | Form | =O | H | H | H | 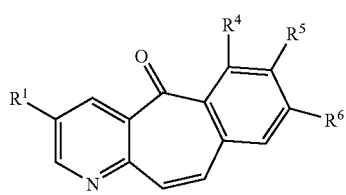 | double bond |
| Ph | H | H | H | H | H | oxazolyl | absent |

Another embodiment of the present invention is illustrated by a compound of Formula II:

II or pharmaceutically acceptable salts thereof, wherein a is independently 0 or 1;
b is independently 0 or 1;
m is independently 0, 1, or 2;
$R^1$ is selected from aryl, heterocyclyl and $NR^{10}R^{11}$; said aryl and heterocyclyl group optionally substituted with one to five substituents, each substituent independently selected from $R^8$;

$R^4$ and $R^6$ are each independently hydrogen, halogen, $C_{1-6}$alkyl, OH, —O—$C_{1-6}$alkyl, —O—C(=O)$C_{1-6}$ alkyl, —O-aryl and $NR^{10}R^{11}$, each alkyl and aryl optionally substituted with one to five substituents, each substituent independently selected from $R^8$;

$R^5$ is selected from hydrogen, $C_{1-6}$alkyl, $C_{2-6}$ alkenyl, OH, —O—$C_{1-6}$alkyl, —O—C(=O)$C_{1-6}$ alkyl, —O-aryl, $S(O)_m R^a$, —C(=O)$NR^{10}R^{11}$, —NHS(O)$_2NR^{10}R^{11}$ and $NR^{10}R^{11}$, each alkyl, alkenyl and aryl optionally substituted with one to five substituents, each substituent independently selected from $R^8$;

provided that one of $R^4$, $R^5$ and $R^6$ are not hydrogen;
$R^8$ independently is:
1) $(C=O)_a O_b C_1-C_{10}$ alkyl,
2) $(C=O)_a O_b$aryl,
3) $C_2-C_{10}$ alkenyl,
4) $C_2-C_{10}$ alkynyl,
5) $(C=O)_a O_b$ heterocyclyl,
6) $CO_2H$,
7) halo,
8) CN,
9) OH,
10) $O_b C_1-C_6$ perfluoroalkyl,
11) $O_a(C=O)_b NR^{10}R^{11}$,
12) $S(O)_m R^a$,
13) $S(O)_2 NR^{10}R^{11}$,
14) $OS(=O)R^a$,
15) oxo,
16) CHO,
17) $(N=O)R^{10}R^{11}$, or
18) $(C=O)_a O_b C_3-C_8$ cycloalkyl, said alkyl, aryl, alkenyl, alkynyl, heterocyclyl, and cycloalkyl optionally substituted with one, two or three substituents selected from $R^9$; or two $R^8$s, attached to the same carbon atom are combined to form —$(CH_2)_u$— wherein u is 3 to 6 and one or two of the carbon atoms is optionally replaced by a moiety selected from O, $S(O)_m$, —$N(R^a)C(O)$—, —$N(R^b)$— and —$N(COR^a)$—;

$R^9$ is independently selected from:
1) $(C=O)_a O_b (C_1-C_{10})$alkyl,
2) $O_b (C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_a O_b (C_3-C_6)$cycloalkyl,
10) $(C=O)_a O_b (C_0-C_6)$alkylene-aryl,
11) $(C=O)_a O_b (C_0-C_6)$alkylene-heterocyclyl,
12) $(C=O)_a O_b (C_0-C_6)$alkylene-$N(R^b)_2$,
13) $C(O)R^a$,
14) $(C_0-C_6)$alkylene-$CO_2R^a$,
15) $C(O)H$,
16) $(C_0-C_6)$alkylene-$CO_2H$,
17) $C(O)N(R^b)_2$,
18) $S(O)_m R^a$, and
19) $S(O)_2 NR^{10}R^{11}$;

said alkyl, alkenyl, alkynyl, cycloalkyl, aryl, and heterocyclyl is optionally substituted with one, two or three substituents selected from $R^b$, OH, ($C_1$-$C_6$)alkoxy, halogen, $CO_2H$, CN, O(C=O)$C_1$-$C_6$ alkyl, oxo, and N($R^b$)$_2$; or
$R^{10}$ and $R^{11}$ are independently selected from:
1) H,
2) (C=O)$O_b$$C_1$-$C_{10}$ alkyl,
3) (C=O)$O_b$$C_3$-$C_8$ cycloalkyl,
4) (C=O)$O_b$aryl,
5) (C=O)$O_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) (C=O)$NR^b{}_2$,
said alkyl, cycloalkyl, aryl, heterocyclyl, alkenyl, and alkynyl is optionally substituted with one, two or three substituents selected from $R^8$, or
$R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;
$R^a$ is independently selected from: ($C_1$-$C_6$)alkyl, ($C_2$-$C_6$)alkenyl, ($C_3$-$C_6$)cycloalkyl, aryl, —($C_1$-$C_6$)alkylenearyl, heterocyclyl and —($C_1$-$C_6$)alkyleneheterocyclyl; and
$R^b$ is independently selected from: H, ($C_1$-$C_6$)alkyl, aryl, —($C_1$-$C_6$)alkylenearyl, heterocyclyl, —($C_1$-$C_6$)alkyleneheterocyclyl, ($C_3$-$C_6$)cycloalkyl, (C=O)O$C_1$-$C_6$ alkyl, (C=O) $C_1$-$C_6$ alkyl or $S(O)_2R^a$.

A further embodiment of the present invention is illustrated by a compound of Formula III:

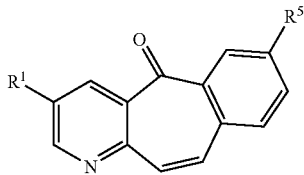

III or a pharmaceutically acceptable salt or stereoisomer thereof, wherein
a is independently 0 or 1;
b is independently 0 or 1;
m is independently 0, 1, or 2;
$R^1$ is selected from aryl, heterocyclyl and $NR^{10}R^{11}$; said aryl and heterocyclyl group optionally substituted with one to five substituents, each substituent independently selected from $R^8$;
$R^5$ is selected from hydrogen, $C_{1-6}$alkyl, $C_{2-6}$ alkenyl, OH, —O—$C_{1-6}$alkyl, —O—C(=O)$C_{1-6}$ alkyl, —O-aryl, $S(O)_m$ $R^a$, —C(=O)$NR^{10}R^{11}$, —NHS(O)$_2NR^{10}R^{11}$ and $NR^{10}R^{11}$, each alkyl, alkenyl and aryl optionally substituted with one to five substituents, each substituent independently selected from $R^8$;
$R^8$ independently is:
1) (C=O)$_aO_bC_1$-$C_{10}$ alkyl,
2) (C=O)$_aO_b$aryl,
3) $C_2$-$C_{10}$ alkenyl,
4) $C_2$-$C_{10}$ alkynyl,
5) (C=O)$_aO_b$ heterocyclyl,
6) $CO_2H$,
7) halo,
8) CN,
9) OH,
10) $O_bC_1$-$C_6$ perfluoroalkyl,
11) $O_a$(C=O)$_bNR^{10}R^{11}$,
12) $S(O)_mR^a$,
13) $S(O)_2NR^{10}R^{11}$,
14) OS(=O)$R^a$,
15) oxo,
16) CHO,
17) (N=O)$R^{10}R^{11}$, or
18) (C=O)$_aO_bC_3$-$C_8$ cycloalkyl,
said alkyl, aryl, alkenyl, alkynyl, heterocyclyl, and cycloalkyl optionally substituted with one, two or three substituents selected from $R^9$;
$R^9$ is independently selected from:
1) (C=O)$_aO_b$($C_1$-$C_{10}$)alkyl,
2) $O_b$($C_1$-$C_3$)perfluoroalkyl,
3) oxo,
4) OH,
5) halo,
6) CN,
7) ($C_2$-$C_{10}$)alkenyl,
8) ($C_2$-$C_{10}$)alkynyl,
9) (C=O)$_aO_b$($C_3$-$C_6$)cycloalkyl,
10) (C=O)$_aO_b$($C_0$-$C_6$)alkylene-aryl,
11) (C=O)$_aO_b$($C_0$-$C_6$)alkylene-heterocyclyl,
12) (C=O)$_aO_b$($C_0$-$C_6$)alkylene-N($R^b$)$_2$,
13) C(O)$R^a$,
14) ($C_0$-$C_6$)alkylene-$CO_2R^a$,
15) C(O)H,
16) ($C_0$-$C_6$)alkylene-$CO_2H$, and
17) C(O)N($R^b$)$_2$,
18) $S(O)_mR^a$, and
19) $S(O)_2NR^{10}R^{11}$;
said alkyl, alkenyl, alkynyl, cycloalkyl, aryl, and heterocyclyl is optionally substituted with one, two or three substituents selected from $R^b$, OH, ($C_1$-$C_6$)alkoxy, halogen, $CO_2H$, CN, O(C=O)$C_1$-$C_6$ alkyl, oxo, and N($R^b$)$_2$;
$R^{10}$ and $R^{11}$ are independently selected from:
1) H,
2) (C=O)$O_bC_1$-$C_{10}$ alkyl,
3) (C=O)$O_bC_3$-$C_8$ cycloalkyl,
4) (C=O)$O_b$aryl,
5) (C=O)$O_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) (C=O)$NR^b{}_2$,
said alkyl, cycloalkyl, aryl, heterocyclyl, alkenyl, and alkynyl is optionally substituted with one, two or three substituents selected from $R^8$, or
$R^{10}$ and $R^{11}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^9$;
$R^a$ is independently selected from: ($C_1$-$C_6$)alkyl, ($C_2$-$C_6$)alkenyl, ($C_3$-$C_6$)cycloalkyl, aryl, —($C_1$-$C_6$)alkylenearyl, heterocyclyl and —($C_1$-$C_6$)alkyleneheterocyclyl; and R$^b$ is independently selected from: H, (C$_1$-C$_6$)alkyl, aryl, —(C$_1$-C$_6$)alkylenearyl, heterocyclyl, —(C$_1$-C$_6$)alkyleneheterocyclyl, (C$_3$-C$_6$)cycloalkyl, (C=O)OC$_1$-C$_6$ alkyl, (C=O) C$_1$-C$_6$ alkyl or S(O)$_2$R$^a$.

Specific examples of the compounds of the instant invention include:

7-bromo-3-chloro-5H-benzo[4,5]cyclohepta[1,2-b]pyridin-5-one;
6-bromo-3-phenyl-5H-benzo[4,5]cyclohepta[1,2-b]pyridin-5-one;
8-bromo-3-phenyl-5H-benzo[4,5]cyclohepta[1,2-b]pyridin-5-one;
3-chloro-7-[(2,4-dimethoxybenzyl)amino]-5H-benzo[4,5]cyclohepta[1,2-b]pyridin-5-one;
7-amino-3-chloro-5H-benzo[4,5]cyclohepta[1,2-b]pyridin-5-one;
N-(3-chloro-5-oxo-5H-benzo[4,5]cyclohepta[1,2-b]pyridin-7-yl)methanesulfonamide;
6-(methylthio)-3-phenyl-5H-benzo[4,5]cyclohepta[1,2-b]pyridin-5-one;
6-(methylsulfonyl)-3-phenyl-5H-benzo[4,5]cyclohepta[1,2-b]pyridin-5-one;
Methyl 5-oxo-3-phenyl-5H-benzo[4,5]cyclohepta[1,2-b]pyridine-7-carboxylate;
6-methyl-3-phenyl-5H-benzo[4,5]cyclohepta[1,2-b]pyridin-5-one;
3-phenyl-7-[(trimethylsilyl)ethynyl]-5H-benzo[4,5]cyclohepta[1,2-b]pyridin-5-one;
3-phenyl-7-vinyl-5H-benzo[4,5]cyclohepta[1,2-b]pyridin-5-one;
7-ethyl-3-phenyl-5H-benzo[4,5]cyclohepta[1,2-b]pyridin-5-one;
N-(5-oxo-3-phenyl-5H-benzo[4,5]cyclohepta[1,2-b]pyridin-7-yl)acetamide;
3-chloro-7-hydroxy-5H-benzo[4,5]cyclohepta[1,2-b]pyridin-5-one;
7-[(2,4-dimethoxybenzyl)amino]-3-phenyl-5H-benzo[4,5]cyclohepta[1,2-b]pyridin-5-one;
6-amino-3-phenyl-5H-benzo[4,5]cyclohepta[1,2-b]pyridin-5-one;
7-amino-3-phenyl-5H-benzo[4,5]cyclohepta[1,2-b]pyridin-5-one;
8-amino-3-phenyl-5H-benzo[4,5]cyclohepta[1,2-b]pyridin-5-one;
9-amino-3-phenyl-5H-benzo[4,5]cyclohepta[1,2-b]pyridin-5-one;
2-hydroxy-N-(5-oxo-3-phenyl-5H-benzo[4,5]cyclohepta[1,2-b]pyridin-7-yl)propanamide;
3-phenyl-7-(pyridin-2-ylamino)-5H-benzo[4,5]cyclohepta[1,2-b]pyridin-5-one;
7-[(3-methoxypropyl)amino]-3-phenyl-5H-benzo[4,5]cyclohepta[1,2-b]pyridin-5-one;
7-[(2-methoxyethyl)amino]-3-phenyl-5H-benzo[4,5]cyclohepta[1,2-b]pyridin-5-one;
7-[(3-methoxypropyl)amino]-3-phenyl-5H-benzo[4,5]cyclohepta[1,2-b]pyridin-5-ol;
7-[(2-methoxyethyl)amino]-3-phenyl-5H-benzo[4,5]cyclohepta[1,2-b]pyridin-5-one;
3-phenyl-7-[(2,2,2-trifluoroethyl)amino]-5H-benzo[4,5]cyclohepta[1,2-b]pyridin-5-one;
5-oxo-3-phenyl-5H-benzo[4,5]cyclohepta[1,2-b]pyridine-7-carboxylic acid;
N-methyl-5-oxo-3-phenyl-5H-benzo[4,5]cyclohepta[1,2-b]pyridine-7-carboxamide;
7-methyl-3-phenyl-5H-benzo[4,5]cyclohepta[1,2-b]pyridin-5-one;
8-methyl-3-phenyl-5H-benzo[4,5]cyclohepta[1,2-b]pyridin-5-one;
9-methyl-3-phenyl-5H-benzo[4,5]cyclohepta[1,2-b]pyridin-5-one;
7-ethynyl-3-phenyl-5H-benzo[4,5]cyclohepta[1,2-b]pyridin-5-one;
3-phenyl-7-[(1E/Z)-prop-1-en-1-yl]-5H-benzo[4,5]cyclohepta[1,2-b]pyridin-5-one;
3-phenyl-7-propyl-5H-benzo[4,5]cyclohepta[1,2-b]pyridin-5-one;
7-isobutyl-3-phenyl-5H-benzo[4,5]cyclohepta[1,2-b]pyridin-5-one;
9-(methylthio)-3-phenyl-5H-benzo[4,5]cyclohepta[1,2-b]pyridin-5-one;
7-(methylthio)-3-phenyl-10,11-dihydro-5H-benzo[4,5]cyclohepta[1,2-b]pyridin-5-one;
9-(methylsulfonyl)-3-phenyl-5H-benzo[4,5]cyclohepta[1,2-b]pyridin-5-one;
6-methoxy-3-phenyl-5H-benzo[4,5]cyclohepta[1,2-b]pyridin-5-one;
N-(5-oxo-3-phenyl-5H-benzo[4,5]cyclohepta[1,2-b]pyridin-7-yl)methanesulfonamide;
N'-(3-chloro-5-oxo-5H-benzo[4,5]cyclohepta[1,2-b]pyridin-7-yl)-N,N-dimethylsulfamide;
N-benzyl-N'-(3-chloro-5-oxo-5H-benzo[4,5]cyclohepta[1,2-b]pyridin-7-yl)-N-methylsulfamide;
N-(3-chloro-5-oxo-5H-benzo[4,5]cyclohepta[1,2-b]pyridin-7-yl)-1,1,1-trifluoromethanesulfonamide;
3-chloro-7-{[(3-methylpyridin-4-yl)methyl]amino}-5H-benzo[4,5]cyclohepta[1,2-b]pyridin-5-one;
N'-(3-chloro-5-oxo-5H-benzo[4,5]cyclohepta[1,2-b]pyridin-7-yl)-N-(isoxazol-3-ylmethyl)-N-methylsulfamide;
N-(3-chloro-5-oxo-5H-benzo[4,5]cyclohepta[1,2-b]pyridin-7-yl)-N'-[(1-morpholin-4-ylcyclopentyl)methyl]sulfamide;
3,7-bis[(pyridin-3-ylmethyl)amino]-5H-benzo[4,5]cyclohepta[1,2-b]pyridin-5-one;
3-chloro-7-[(pyridin-2-ylmethyl)amino]-5H-benzo[4,5]cyclohepta[1,2-b]pyridin-5-one;
N-[5-oxo-3-(3-thienyl)-5H-benzo[4,5]cyclohepta[1,2-b]pyridin-7-yl]methanesulfonamide;
7-[(2,4-dimethoxybenzyl)amino]-3-(1-methyl-1H-pyrazol-4-yl)-5H-benzo[4,5]cyclohepta[1,2-b]pyridin-5-one;
7-(isopropylamino)-3-(1-methyl-1H-pyrazol-4-yl)-5H-benzo[4,5]cyclohepta[1,2-b]pyridin-5-one;
3-chloro-7-{[(3-methylpyridin-2-yl)methyl]amino}-5H-benzo[4,5]cyclohepta[1,2-b]pyridin-5-one;
3-(1-methyl-1H-pyrazol-4-yl)-7-{[(3-methylpyridin-2-yl)methyl]amino}-5H-benzo[4,5]cyclohepta[1,2-b]pyridin-5-one;
N'-(3-chloro-5-oxo-5H-benzo[4,5]cyclohepta[1,2-b]pyridin-7-yl)-N-((2R)-1,4-dioxan-2-ylmethyl)-N-methylsulfamide;
N'-(3-chloro-5-oxo-5H-benzo[4,5]cyclohepta[1,2-b]pyridin-7-yl)-N-((2S)-1,4-dioxan-2-ylmethyl)-N-methylsulfamide;
N'-(3-chloro-5-oxo-5H-benzo[4,5]cyclohepta[1,2-b]pyridin-7-yl)-N-(1,4-dioxan-2-ylmethyl)-N-methylsulfamide;
N-((2R)-1,4-dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide;
N-((2S)-1,4-dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide;
N-(1,4-dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide;

N-methyl-N'-[3-(1-methyl-1H-pyrazol-4-yl)-5-oxo-5H-benzo[4,5]cyclohepta[1,2-b]pyridin-7-yl]-N-({3R}-tetrahydrofuran-3-yl)sulfamide;
N-methyl-N'-[3-(1-methyl-1H-pyrazol-4-yl)-5-oxo-5H-benzo[4,5]cyclohepta[1,2-b]pyridin-7-yl]-N-({3S}-tetrahydrofuran-3-yl)sulfamide;
N-methyl-N'-[3-(1-methyl-1H-pyrazol-4-yl)-5-oxo-5H-benzo[4,5]cyclohepta[1,2-b]pyridin-7-yl]-N-(tetrahydrofuran-3-yl)sulfamide;
N-[3-(4-chlorophenyl)-5-oxo-5H-benzo[4,5]cyclohepta[1,2-b]pyridin-7-yl]methanesulfonamide;
N-[3-(2-chlorophenyl)-5-oxo-5H-benzo[4,5]cyclohepta[1,2-b]pyridin-7-yl]methanesulfonamide;
N-(5-oxo-3-pyridin-4-yl-5H-benzo[4,5]cyclohepta[1,2-b]pyridin-7-yl)methanesulfonamide;
N-(5-oxo-3-pyridin-3-yl-5H-benzo[4,5]cyclohepta[1,2-b]pyridin-7-yl)methanesulfonamide;
N-[5-oxo-3-(1H-pyrazol-3-yl)-5H-benzo[4,5]cyclohepta[1,2-b]pyridin-7-yl]methanesulfonamide;
N-[3-(3-chlorophenyl)-5-oxo-5H-benzo[4,5]cyclohepta[1,2-b]pyridin-7-yl]methanesulfonamide;
N-(5-oxo-3-pyrimidin-5-yl-5H-benzo[4,5]cyclohepta[1,2-b]pyridin-7-yl)methanesulfonamide;
N-(5-oxo-3-quinolin-6-yl-5H-benzo[4,5]cyclohepta[1,2-b]pyridin-7-yl)methanesulfonamide;
N-[3-(3-furyl)-5-oxo-5H-benzo[4,5]cyclohepta[1,2-b]pyridin-7-yl]methanesulfonamide;
N-[3-(2-furyl)-5-oxo-5H-benzo[4,5]cyclohepta[1,2-b]pyridin-7-yl]methanesulfonamide;
N-[3-(4-fluorophenyl)-5-oxo-5H-benzo[4,5]cyclohepta[1,2-b]pyridin-7-yl]methanesulfonamide;
N-[3-(3-fluorophenyl)-5-oxo-5H-benzo[4,5]cyclohepta[1,2-b]pyridin-7-yl]methanesulfonamide;
N-[3-(2-fluorophenyl)-5-oxo-5H-benzo[4,5]cyclohepta[1,2-b]pyridin-7-yl]methanesulfonamide;
N-(5-oxo-3-quinolin-8-yl-5H-benzo[4,5]cyclohepta[1,2-b]pyridin-7-yl)methanesulfonamide;
N-(5-oxo-3-quinolin-3-yl-5H-benzo[4,5]cyclohepta[1,2-b]pyridin-7-yl)methanesulfonamide;
N-(5-oxo-3-quinolin-5-yl-5H-benzo[4,5]cyclohepta[1,2-b]pyridin-7-yl)methanesulfonamide;
N-[3-(2,4-dichlorophenyl)-5-oxo-5H-benzo[4,5]cyclohepta[1,2-b]pyridin-7-yl]methanesulfonamide;
N-(3-imidazo[1,2-a]pyrazin-3-yl-5-oxo-5H-benzo[4,5]cyclohepta[1,2-b]pyridin-7-yl)methanesulfonamide;
N-[5-oxo-3-(1,3-thiazol-4-yl)-5H-benzo[4,5]cyclohepta[1,2-b]pyridin-7-yl]methanesulfonamide;
N-(3-isothiazol-4-yl-5-oxo-5H-benzo[4,5]cyclohepta[1,2-b]pyridin-7-yl)methanesulfonamide;
N-[3-(1-methyl-1H-pyrazol-4-yl)-5-oxo-5H-benzo[4,5]cyclohepta[1,2-b]pyridin-7-yl]methanesulfonamide;
N-(3-isothiazol-5-yl-5-oxo-5H-benzo[4,5]cyclohepta[1,2-b]pyridin-7-yl)methanesulfonamide;
N-[3-(3,5-dimethylisoxazol-4-yl)-5-oxo-5H-benzo[4,5]cyclohepta[1,2-b]pyridin-7-yl]methanesulfonamide;
N-[5-oxo-3-(1H-pyrazol-4-yl)-5H-benzo[4,5]cyclohepta[1,2-b]pyridin-7-yl]methanesulfonamide;
methyl (4-{7-[(methylsulfonyl)amino]-5-oxo-5H-benzo[4,5]cyclohepta[1,2-b]pyridin-3-yl}-1H-pyrazol-1-yl)acetate;
ethyl 3-(4-{7-[(methylsulfonyl)amino]-5-oxo-5H-benzo[4,5]cyclohepta[1,2-b]pyridin-3-yl}-1H-pyrazol-1-yl)propanoate;
N-(3-{1-[2-(dimethylamino)ethyl]-1H-pyrazol-4-yl}-5-oxo-5H-benzo[4,5]cyclohepta[1,2-b]pyridin-7-yl)methanesulfonamide;
N-[3-(1-isobutyl-1H-pyrazol-4-yl)-5-oxo-5H-benzo[4,5]cyclohepta[1,2-b]pyridin-7-yl]methanesulfonamide;
N-[5-oxo-3-(1-propyl-1H-pyrazol-4-yl)-5H-benzo[4,5]cyclohepta[1,2-b]pyridin-7-yl]methanesulfonamide;
N-(3-{1-[3-(dimethylamino)propyl]-1H-pyrazol-4-yl}-5-oxo-5H-benzo[4,5]cyclohepta[1,2-b]pyridin-7-yl)methanesulfonamide;
N-{3-[1-(2-morpholin-4-yl-2-oxoethyl)-1H-pyrazol-4-yl]-5-oxo-5H-benzo[4,5]cyclohepta[1,2-b]pyridin-7-yl}methanesulfonamide;
N-{5-oxo-3-[1-(2-pyrrolidin-1-ylethyl)-1H-pyrazol-4-yl]-5H-benzo[4,5]cyclohepta[1,2-b]pyridin-7-yl}methanesulfonamide;
N-[3-(1-benzyl-1H-pyrazol-4-yl)-5-oxo-5H-benzo[4,5]cyclohepta[1,2-b]pyridin-7-yl]methanesulfonamide;
(4-{7-[(methylsulfonyl)amino]-5-oxo-5H-benzo[4,5]cyclohepta[1,2-b]pyridin-3-yl}-1H-pyrazol-1-yl)acetic acid;
3-(4-{7-[(methylsulfonyl)amino]-5-oxo-5H-benzo[4,5]cyclohepta[1,2-b]pyridin-3-yl}-1H-pyrazol-1-yl)propanoic acid;
N-(3-{7-[(methylsulfonyl)amino]-5-oxo-5H-benzo[4,5]cyclohepta[1,2-b]pyridin-3-yl}phenyl)-3-piperidin-1-ylpropanamide;
N-(4-{7-[(methylsulfonyl)amino]-5-oxo-5H-benzo[4,5]cyclohepta[1,2-b]pyridin-3-yl}phenyl)methanesulfonamide;
N-(3-{1-[3-(benzyloxy)propyl]-1H-pyrazol-4-yl}-5-oxo-5H-benzo[4,5]cyclohepta[1,2-b]pyridin-7-yl)methanesulfonamide;
N-[3-(1-isopropyl-1H-pyrazol-4-yl)-5-oxo-5H-benzo[4,5]cyclohepta[1,2-b]pyridin-7-yl]methanesulfonamide;
N-{3-[1-(3-methylbutyl)-1H-pyrazol-4-yl]-5-oxo-5H-benzo[4,5]cyclohepta[1,2-b]pyridin-7-yl}methanesulfonamide;
N-[3-(1-cyclopentyl-1H-pyrazol-4-yl)-5-oxo-5H-benzo[4,5]cyclohepta[1,2-b]pyridin-7-yl]methanesulfonamide;
N-{3-[1-(3-hydroxypropyl)-1H-pyrazol-4-yl]-5-oxo-5H-benzo[4,5]cyclohepta[1,2-b]pyridin-7-yl}methanesulfonamide;
3-{7-[(methylsulfonyl)amino]-5-oxo-5H-benzo[4,5]cyclohepta[1,2-b]pyridin-3-yl}benzoic acid;
3-(2,3-dihydro-1H-pyrazolo[1,2-a]pyrazol-4-ium-6-yl)-7-[(methylsulfonyl)amino]-5-oxo-5H-benzo[4,5]cyclohepta[1,2-b]pyridinium bis(trifluoroacetate);
methyl 2-(4-{7-[(methylsulfonyl)amino]-5-oxo-5H-benzo[4,5]cyclohepta[1,2-b]pyridin-3-yl}-1H-pyrazol-1-yl)propanoate;
N-{3-[1-(3,3-dimethyl-2-oxobutyl)-1H-pyrazol-4-yl]-oxo-5H-benzo[4,5]cyclohepta[1,2-b]pyridin-7-yl}methanesulfonamide;
4-{7-[(methylsulfonyl)amino]-5-oxo-5H-benzo[4,5]cyclohepta[1,2-b]pyridin-3-yl}benzoic acid;
N-[3-(3-nitrophenyl)-5-oxo-5H-benzo[4,5]cyclohepta[1,2-b]pyridin-7-yl]methanesulfonamide;
N-[3-(4-nitrophenyl)-5-oxo-5H-benzo[4,5]cyclohepta[1,2-b]pyridin-7-yl]methanesulfonamide;
N-isobutyl-3-{7-[(methylsulfonyl)amino]-5-oxo-5H-benzo[4,5]cyclohepta[1,2-b]pyridin-3-yl}benzamide;
3-{7-[(methylsulfonyl)amino]-5-oxo-5H-benzo[4,5]cyclohepta[1,2-b]pyridin-3-yl}-N-(2-morpholin-4-ylethyl)benzamide;
N-[2-(1-methylpyrrolidin-2-yl)ethyl]-3-{7-[(methylsulfonyl)amino]-5-oxo-5H-benzo[4,5]cyclohepta[1,2-b]pyridin-3-yl}benzamide;
N-[(1-methyl-1H-pyrazol-4-yl)methyl]-3-{7-[(methylsulfonyl)amino]-5-oxo-5H-benzo[4,5]cyclohepta[1,2-b]pyridin-3-yl}benzamide;

N-{3-[1-(3-hydroxypropyl)-1H-pyrazol-4-yl]-5-oxo-5H-benzo[4,5]cyclohepta[1,2-b]pyridin-7-yl}methanesulfonamide;
N-[(5-methylpyrazin-2-yl)methyl]-3-{7-[(methylsulfonyl)amino]-5-oxo-5H-benzo[4,5]cyclohepta[1,2-b]pyridin-3-yl}benzamide;
N-isobutyl-4-{7-[(methylsulfonyl)amino]-5-oxo-5H-benzo[4,5]cyclohepta[1,2-b]pyridin-3-yl}benzamide;
N-[(1-methyl-1H-pyrazol-4-yl)methyl]-4-{7-[(methylsulfonyl)amino]-5-oxo-5H-benzo[4,5]cyclohepta[1,2-b]pyridin-3-yl}benzamide;
2-methyl-N-[3-(1-methyl-1H-pyrazol-4-yl)-5-oxo-5H-benzo[4,5]cyclohepta[1,2-b]pyridin-7-yl]propane-2-sulfonamide;
N,N-dimethyl-N-[3-(1-methyl-1H-pyrazol-4-yl)-5-oxo-5H-benzo[4,5]cyclohepta[1,2-b]pyridin-7-yl]sulfamide;
N-benzyl-N-methyl-N'-[3-(1-methyl-1H-pyrazol-4-yl)-5-oxo-5H-benzo[4,5]cyclohepta[1,2-b]pyridin-7-yl]sulfamide;
N,N-diethyl-N'-[3-(1-methyl-1H-pyrazol-4-yl)-5-oxo-5H-benzo[4,5]cyclohepta[1,2-b]pyridin-7-yl]sulfamide;
N-[3-(1-methyl-1H-pyrazol-4-yl)-5-oxo-5H-benzo[4,5]cyclohepta[1,2-b]pyridin-7-yl]pyrrolidine-1-sulfonamide;
N-ethyl-N-methyl-N'-[3-(1-methyl-1H-pyrazol-4-yl)-5-oxo-5H-benzo[4,5]cyclohepta[1,2-b]pyridin-7-yl]sulfamide;
N,N-dimethyl-N-[5-oxo-3-(1-propyl-1H-pyrazol-4-yl)-5H-benzo[4,5]cyclohepta[1,2-b]pyridin-7-yl]sulfamide;
N,N-dimethyl-N-{3-[1-(2-morpholin-4-yl-2-oxoethyl)-1H-pyrazol-4-yl]-5-oxo-5H-benzo[4,5]cyclohepta[1,2-b]pyridin-7-yl}sulfamide;
N'-(3-{1-[3-(dimethylamino)propyl]-1H-pyrazol-4-yl}-5-oxo-5H-benzo[4,5]cyclohepta[1,2-b]pyridin-7-yl)-N,N-dimethylsulfamide;
N-isopropyl-N-methyl-N'-[3-(1-methyl-1H-pyrazol-4-yl)-5-oxo-5H-benzo[4,5]cyclohepta[1,2-b]pyridin-7-yl]sulfamide;
7-(5-methyl-1,1-dioxido-1,2,5-thiadiazolidin-2-yl)-3-(1-methyl-1H-pyrazol-4-yl)-5H-benzo[4,5]cyclohepta[1,2-b]pyridin-5-one;
N-methyl-N'-[3-(1-methyl-1H-pyrazol-4-yl)-5-oxo-5H-benzo[4,5]cyclohepta[1,2-b]pyridin-7-yl]sulfamide;
1,1,1-trifluoro-N-[3-(1-methyl-1H-pyrazol-4-yl)-5-oxo-5H-benzo[4,5]cyclohepta[1,2-b]pyridin-7-yl]methanesulfonamide;
7-[(2,4-dimethoxybenzyl)amino]-3-(3-thienyl)-5H-benzo[4,5]cyclohepta[1,2-b]pyridin-5-one;
7-[(2,4-dimethoxybenzyl)amino]-3-(1H-pyrazol-3-yl)-5H-benzo[4,5]cyclohepta[1,2-b]pyridin-5-one;
7-[(2,4-dimethoxybenzyl)amino]-3-(5-methyl-2-thienyl)-5H-benzo[4,5]cyclohepta[1,2-b]pyridin-5-one;
3-(1-benzothien-3-yl)-7-[(2,4-dimethoxybenzyl)amino]-5H-benzo[4,5]cyclohepta[1,2-b]pyridin-5-one;
N-(4-{7-[(2,4-dimethoxybenzyl)amino]-5-oxo-5H-benzo[4,5]cyclohepta[1,2-b]pyridin-3-yl}phenyl)acetamide;
4-{7-[(2,4-dimethoxybenzyl)amino]-5-oxo-5H-benzo[4,5]cyclohepta[1,2-b]pyridin-3-yl}benzoic acid;
7-amino-3-(3-thienyl)-5H-benzo[4,5]cyclohepta[1,2-b]pyridin-5-one;
7-amino-3-(2-thienyl)-5H-benzo[4,5]cyclohepta[1,2-b]pyridin-5-one;
7-amino-3-(1H-pyrazol-4-yl)-5H-benzo[4,5]cyclohepta[1,2-b]pyridin-5-one;
7-amino-3-(1-methyl-1H-pyrazol-4-yl)-5H-benzo[4,5]cyclohepta[1,2-b]pyridin-5-one;
7-amino-3-(1H-pyrazol-3-yl)-5H-benzo[4,5]cyclohepta[1,2-b]pyridin-5-one;
7-amino-3-(5-methyl-2-thienyl)-5H-benzo[4,5]cyclohepta[1,2-b]pyridin-5-one;
7-amino-3-(1-benzothien-3-yl)-5H-benzo[4,5]cyclohepta[1,2-b]pyridin-5-one;
N-[4-(7-amino-5-oxo-5H-benzo[4,5]cyclohepta[1,2-b]pyridin-3-yl)phenyl]acetamide;
4-(7-amino-5-oxo-5H-benzo[4,5]cyclohepta[1,2-b]pyridin-3-yl)benzoic acid;
7-hydroxy-3-(3-thienyl)-5H-benzo[4,5]cyclohepta[1,2-b]pyridin-5-one;
7-[(cyclohexylmethyl)amino]-3-(1-methyl-1H-pyrazol-4-yl)-5H-benzo[4,5]cyclohepta[1,2-b]pyridin-5-one;
7-[(4-fluorobenzyl)amino]-3-(1-methyl-1H-pyrazol-4-yl)-5H-benzo[4,5]cyclohepta[1,2-b]pyridin-5-one;
3-(1-methyl-1H-pyrazol-4-yl)-7-vinyl-5H-benzo[4,5]cyclohepta[1,2-b]pyridin-5-one;
7-[(2,4-difluorobenzyl)amino]-3-(1-methyl-1H-pyrazol-4-yl)-5H-benzo[4,5]cyclohepta[1,2-b]pyridin-5-one;
3-(1-methyl-1H-pyrazol-4-yl)-7-[(2-phenylethyl)amino]-5H-benzo[4,5]cyclohepta[1,2-b]pyridin-5-one;
7-[(3,4-difluorobenzyl)amino]-3-(1-methyl-1H-pyrazol-4-yl)-5H-benzo[4,5]cyclohepta[1,2-b]pyridin-5-one;
7-[(4-methylbenzyl)amino]-3-(1-methyl-1H-pyrazol-4-yl)-5H-benzo[4,5]cyclohepta[1,2-b]pyridin-5-one;
7-[(2,4-dimethylbenzyl)amino]-3-(1-methyl-1H-pyrazol-4-yl)-5H-benzo[4,5]cyclohepta[1,2-b]pyridin-5-one;
7-{[2-(4-fluorophenyl)ethyl]amino}-3-(1-methyl-1H-pyrazol-4-yl)-5H-benzo[4,5]cyclohepta[1,2-b]pyridin-5-one;
7-(butylamino)-3-(1-methyl-1H-pyrazol-4-yl)-5H-benzo[4,5]cyclohepta[1,2-b]pyridin-5-one;
3-(1-methyl-1H-pyrazol-4-yl)-7-(propylamino)-5H-benzo[4,5]cyclohepta[1,2-b]pyridin-5-one;
7-[(3-methylbutyl)amino]-3-(1-methyl-1H-pyrazol-4-yl)-5H-benzo[4,5]cyclohepta[1,2-b]pyridin-5-one;
7-(isopropylamino)-3-(1-methyl-1H-pyrazol-4-yl)-5H-benzo[4,5]cyclohepta[1,2-b]pyridin-5-one;
7-[(1,3-benzodioxol-5-ylmethyl)amino]-3-(1-methyl-1H-pyrazol-4-yl)-5H-benzo[4,5]cyclohepta[1,2-b]pyridin-5-one;
7-(isobutylamino)-3-(1-methyl-1H-pyrazol-4-yl)-5H-benzo[4,5]cyclohepta[1,2-b]pyridin-5-one;
7-[(2-methylbenzyl)amino]-3-(1-methyl-1H-pyrazol-4-yl)-5H-benzo[4,5]cyclohepta[1,2-b]pyridin-5-one;
3-(1-methyl-1H-pyrazol-4-yl)-7-{[2-(trifluoromethyl)benzyl]amino}-5H-benzo[4,5]cyclohepta[1,2-b]pyridin-5-one;
7-[(biphenyl-2-ylmethyl)amino]-3-(1-methyl-1H-pyrazol-4-yl)-5H-benzo[4,5]cyclohepta[1,2-b]pyridin-5-one;
7-[(2-chlorobenzyl)amino]-3-(1-methyl-1H-pyrazol-4-yl)-5H-benzo[4,5]cyclohepta[1,2-b]pyridin-5-one;
7-[(2,3-dimethylbenzyl)amino]-3-(1-methyl-1H-pyrazol-4-yl)-5H-benzo[4,5]cyclohepta[1,2-b]pyridin-5-one;
N-methyl-N'-[3-(1-methyl-1H-pyrazol-4-yl)-5-oxo-5H-benzo[4,5]cyclohepta[1,2-b]pyridin-7-yl]-N-(tetrahydrofuran-3-yl)sulfamide;
N'-(3-{1-[3-(benzyloxy)propyl]-1H-pyrazol-4-yl}-5-oxo-5H-benzo[4,5]cyclohepta[1,2-b]pyridin-7-yl)-N,N-dimethylsulfamide;
N'-{3-[1-(3-hydroxypropyl)-1H-pyrazol-4-yl]-5-oxo-5H-benzo[4,5]cyclohepta[1,2-b]pyridin-7-yl}-N,N-dimethylsulfamide;
7-[(imidazo[1,2-a]pyridin-3-ylmethyl)amino]-3-(1-methyl-1H-pyrazol-4-yl)-5H-benzo[4,5]cyclohepta[1,2-b]pyridin-5-one;
N,N-dimethyl-N'-(3-{1-[(3-methyloxetan-3-yl)methyl]-1H-pyrazol-4-yl}-5-oxo-5H-benzo[4,5]cyclohepta[1,2-b]pyridin-7-yl)sulfamide;

7-{[(1-methyl-5-oxopyrrolidin-2-yl)methyl]amino}-3-(1-methyl-1H-pyrazol-4-yl)-5H-benzo[4,5]cyclohepta[1,2-b]pyridin-5-one;
3,7-bis(1-methyl-1H-pyrazol-4-yl)-5H-benzo[4,5]cyclohepta[1,2-b]pyridin-5-one;
3-(1-methyl-1H-pyrazol-4-yl)-7-(1H-pyrrol-2-yl)-5H-benzo[4,5]cyclohepta[1,2-b]pyridin-5-one;
3-(1-methyl-1H-pyrazol-4-yl)-7-{[(3-methylpyridin-4-yl)methyl]amino}-5H-benzo[4,5]cyclohepta[1,2-b]pyridin-5-one;
3-(1-methyl-1H-pyrazol-4-yl)-7-(1H-pyrazol-3-yl)-5H-benzo[4,5]cyclohepta[1,2-b]pyridin-5-one;
N-[3-(1-methyl-1H-pyrazol-4-yl)-5-oxo-5H-benzo[4,5]cyclohepta[1,2-b]pyridin-7-yl]-2-(trifluoromethyl)benzamide;
7-{[(1-ethylpyrrolidin-2-yl)methyl]amino}-3-(1-methyl-1H-pyrazol-4-yl)-5H-benzo[4,5]cyclohepta[1,2-b]pyridin-5-one;
7-[(2,6-dimethylbenzyl)amino]-3-(1-methyl-1H-pyrazol-4-yl)-5H-benzo[4,5]cyclohepta[1,2-b]pyridin-5-one;
N-methyl-N-[(1-methyl-5-oxopyrrolidin-2-yl)methyl]-N'-[3-(1-methyl-1H-pyrazol-4-yl)-5-oxo-5H-benzo[4,5]cyclohepta[1,2-b]pyridin-7-yl]sulfamide;
N-methyl-N-[(1-methyl-1H-imidazol-2-yl)methyl]-N'-[3-(1-methyl-1H-pyrazol-4-yl)-5-oxo-5H-benzo[4,5]cyclohepta[1,2-b]pyridin-7-yl]sulfamide;
N-methyl-N'-[3-(1-methyl-1H-pyrazol-4-yl)-5-oxo-5H-benzo[4,5]cyclohepta[1,2-b]pyridin-7-yl]-N-(tetrahydro-2H-pyran-2-ylmethyl)sulfamide;
N-[3-(1-methyl-1H-pyrazol-4-yl)-5-oxo-5H-benzo[4,5]cyclohepta[1,2-b]pyridin-7-yl]-2-(trifluoromethyl)benzenesulfonamide;
N-[3-(1-methyl-1H-pyrazol-4-yl)-5-oxo-5H-benzo[4,5]cyclohepta[1,2-b]pyridin-7-yl]-N'-[2-(trifluoromethyl)benzyl]sulfamide;
methyl 4-(7-{[(3-methylpyridin-2-yl)methyl]amino}-5-oxo-5H-benzo[4,5]cyclohepta[1,2-b]pyridin-3-yl)benzoate;
N-[3-(1-methyl-1H-pyrazol-4-yl)-5-oxo-5H-benzo[4,5]cyclohepta[1,2-b]pyridin-7-yl]-N'-(tetrahydrofuran-3-yl)sulfamide;
tert-butyl 4-[4-(7-{[(3-methylpyridin-2-yl)methyl]amino}-5-oxo-5H-benzo[4,5]cyclohepta[1,2-b]pyridin-3-yl)phenyl]piperazine-1-carboxylate;
7-{[(3-methylpyridin-2-yl)methyl]amino}-3-(4-piperazin-1-ylphenyl)-5H-benzo[4,5]cyclohepta[1,2-b]pyridin-5-one;
3-[3-(dimethylamino)phenyl]-7-{[(3-methylpyridin-2-yl)methyl]amino}-5H-benzo[4,5]cyclohepta[1,2-b]pyridin-5-one;
7-{[(3-methylpyridin-2-yl)methyl]amino}-3-pyridin-4-yl-5H-benzo[4,5]cyclohepta[1,2-b]pyridin-5-one;
N-[3-(1-methyl-1H-pyrazol-4-yl)-5-oxo-5H-benzo[4,5]cyclohepta[1,2-b]pyridin-7-yl]-N'-(tetrahydrofuran-3-ylmethyl)sulfamide;
N-[(1-methyl-1H-pyrazol-4-yl)methyl]-N'-[3-(1-methyl-1H-pyrazol-4-yl)-5-oxo-5H-benzo[4,5]cyclohepta[1,2-b]pyridin-7-yl]sulfamide;
N-[3-(1-methyl-1H-pyrazol-4-yl)-5-oxo-5H-benzo[4,5]cyclohepta[1,2-b]pyridin-7-yl]morpholine-4-sulfonamide;
N-[3-(1-methyl-1H-pyrazol-4-yl)-5-oxo-5H-benzo[4,5]cyclohepta[1,2-b]pyridin-7-yl]-2-(trifluoromethyl)-5,6-dihydroimidazo[1,2-a]pyrazine-7(8H)-sulfonamide;
N-isobutyl-4-(7-{[(3-methylpyridin-2-yl)methyl]amino}-5-oxo-5H-benzo[4,5]cyclohepta[1,2-b]pyridin-3-yl)benzamide;
7-{[(3-methylpyridin-2-yl)methyl]amino}-3-pyrimidin-5-yl-5H-benzo[4,5]cyclohepta[1,2-b]pyridin-5-one;
4-(7-{[(3-methylpyridin-2-yl)methyl]amino}-5-oxo-5H-benzo[4,5]cyclohepta[1,2-b]pyridin-3-yl)-N-phenylbenzamide;
3-(6-fluoropyridin-3-yl)-7-{[(3-methylpyridin-2-yl)methyl]amino}-5H-benzo[4,5]cyclohepta[1,2-b]pyridin-5-one;
N-[3-(dimethylamino)propyl]-4-(7-{[(3-methylpyridin-2-yl)methyl]amino}-5-oxo-5H-benzo[4,5]cyclohepta[1,2-b]pyridin-3-yl)benzamide;
3-(1-methyl-1H-pyrazol-4-yl)-7-[(tetrahydro-2H-pyran-4-ylmethyl)amino]-5H-benzo[4,5]cyclohepta[1,2-b]pyridin-5-one;
3-pyridin-4-yl-7-[(tetrahydro-2H-pyran-4-ylmethyl)amino]-5H-benzo[4,5]cyclohepta[1,2-b]pyridin-5-one;
7-[(1,4-dioxan-2-ylmethyl)amino]-3-(1-methyl-1H-pyrazol-4-yl)-5H-benzo[4,5]cyclohepta[1,2-b]pyridin-5-one;
N-[3-(4-isopropylpiperazin-1-yl)-5-oxo-5H-benzo[4,5]cyclohepta[1,2-b]pyridin-7-yl]methanesulfonamide;
3-(4-isopropylpiperazin-1-yl)-7-phenyl-5H-benzo[4,5]cyclohepta[1,2-b]pyridin-5-one;
N-(5-oxo-3-piperidin-1-yl-5H-benzo[4,5]cyclohepta[1,2-b]pyridin-7-yl)methanesulfonamide;
N-(3-morpholin-4-yl-5-oxo-5H-benzo[4,5]cyclohepta[1,2-b]pyridin-7-yl)methanesulfonamide;
N-(5-oxo-3-pyrrolidin-1-yl-5H-benzo[4,5]cyclohepta[1,2-b]pyridin-7-yl)methanesulfonamide;
N-[3-(benzylamino)-5-oxo-5H-benzo[4,5]cyclohepta[1,2-b]pyridin-7-yl]methanesulfonamide;
N-{3-[(2,4-dimethoxybenzyl)amino]-5-oxo-5H-benzo[4,5]cyclohepta[1,2-b]pyridin-7-yl}methanesulfonamide;
N-{3-[butyl(methyl)amino]-5-oxo-5H-benzo[4,5]cyclohepta[1,2-b]pyridin-7-yl}methanesulfonamide;
N-{3-[(cyclopropylmethyl)amino]-5-oxo-5H-benzo[4,5]cyclohepta[1,2-b]pyridin-7-yl}methanesulfonamide;
N-(3-amino-5-oxo-5H-benzo[4,5]cyclohepta[1,2-b]pyridin-7-yl)methanesulfonamide;
N,N'-(5-oxo-5H-benzo[4,5]cyclohepta[1,2-b]pyridine-3,7-diyl)dimethanesulfonamide;
N-(3-anilino-5-oxo-5H-benzo[4,5]cyclohepta[1,2-b]pyridin-7-yl)methanesulfonamide;
N-[3-(cyclohexylamino)-5-oxo-5H-benzo[4,5]cyclohepta[1,2-b]pyridin-7-yl]methanesulfonamide;
N-[5-oxo-3-(pyridin-4-ylamino)-5H-benzo[4,5]cyclohepta[1,2-b]pyridin-7-yl]methanesulfonamide;
N-[5-oxo-3-(pyridin-3-ylamino)-5H-benzo[4,5]cyclohepta[1,2-b]pyridin-7-yl]methanesulfonamide;
N-[5-oxo-3-(pyridin-2-ylamino)-5H-benzo[4,5]cyclohepta[1,2-b]pyridin-7-yl]methanesulfonamide;
tert-butyl 4-{7-[(methylsulfonyl)amino]-5-oxo-5H-benzo[4,5]cyclohepta[1,2-b]pyridin-3-yl}piperazine-1-carboxylate;
N-[3-(4-methylpiperazin-1-yl)-5-oxo-5H-benzo[4,5]cyclohepta[1,2-b]pyridin-7-yl]methanesulfonamide;
N-[3-(1,4-dioxa-8-azaspiro[4.5]dec-8-yl)-5-oxo-5H-benzo[4,5]cyclohepta[1,2-b]pyridin-7-yl]methanesulfonamide;
N-[5-oxo-3-(4-quinolin-2-ylpiperazin-1-yl)-5H-benzo[4,5]cyclohepta[1,2-b]pyridin-7-yl]methanesulfonamide;
N-{3-[(4-chlorobenzyl)amino]-5-oxo-5H-benzo[4,5]cyclohepta[1,2-b]pyridin-7-yl}methanesulfonamide;
N-{5-oxo-3-[(1-phenylethyl)amino]-5H-benzo[4,5]cyclohepta[1,2-b]pyridin-7-yl}methanesulfonamide;
N-{3-[(2-morpholin-4-ylethyl)amino]-5-oxo-5H-benzo[4,5]cyclohepta[1,2-b]pyridin-7-yl}methanesulfonamide;
N-{5-hydroxy-3-[3-(trifluoromethyl)-5,6-dihydro[1,2,4]triazolo[4,3-a]pyrazin-7(8H)-yl]-5H-benzo[4,5]cyclohepta[1,2-b]pyridin-7-yl}methane sulfonamide;
N-(3-chloro-5-hydroxy-5H-benzo[4,5]cyclohepta[1,2-b]pyridin-7-yl)methanesulfonamide;

N-(3-{4-[(2-methyl-1,3-thiazol-4-yl)methyl]piperazin-1-yl}-5-oxo-5H-benzo[4,5]cyclohepta[1,2-b]pyridin-7-yl)methanesulfonamide;
N-{3-[4-(4-chloropyridin-2-yl)piperazin-1-yl]-5-oxo-5H-benzo[4,5]cyclohepta[1,2-b]pyridin-7-yl}methanesulfonamide;
N-{5-oxo-3-[4-(pyridin-3-ylmethyl)piperazin-1-yl]-5H-benzo[4,5]cyclohepta[1,2-b]pyridin-7-yl}methanesulfonamide;
N-(5-oxo-3-piperazin-1-yl-5H-benzo[4,5]cyclohepta[1,2-b]pyridin-7-yl)methanesulfonamide;
N-{5-oxo-3-[4-(pyridin-2-ylmethyl)piperazin-1-yl]-5H-benzo[4,5]cyclohepta[1,2-b]pyridin-7-yl}methanesulfonamide;
N-[5-oxo-3-(4-pyridin-3-ylpiperazin-1-yl)-5H-benzo[4,5]cyclohepta[1,2-b]pyridin-7-yl]methanesulfonamide;
N-{5-oxo-3-[2-(trifluoromethyl)-5,6-dihydroimidazo[1,2-a]pyrazin-7(8H)-yl]-5H-benzo[4,5]cyclohepta[1,2-b]pyridin-7-yl}methanesulfonamide;
N-(3-{4-[3,5-bis(trifluoromethyl)phenyl]piper-azin-1-yl}-5-oxo-5H-benzo[4,5]cyclohepta[1,2-b]pyridin-7-yl)methanesulfonamide;
N-{3-[(1-methyl-1H-pyrazol-3-yl)amino]-5-oxo-5H-benzo[4,5]cyclohepta[1,2-b]pyridin-7-yl}methanesulfonamide;
7-[(2,4-dimethoxybenzyl)amino]-3-(1,4-dioxa-8-azaspiro[4.5]dec-8-yl)-5H-benzo[4,5]cyclohepta[1,2-b]pyridin-5-one;
7-[(2,4-dimethoxybenzyl)amino]-3-(4-isopropylpiperazin-1-yl)-5H-benzo[4,5]cyclohepta[1,2-b]pyridin-5-one;
3-(4-isopropylpiperazin-1-yl)-7-morpholin-4-yl-5H-benzo[4,5]cyclohepta[1,2-b]pyridin-5-one;
3-(4-acetylpiperazin-1-yl)-7-morpholin-4-yl-5H-benzo[4,5]cyclohepta[1,2-b]pyridin-5-one;
3-(4-isopropylpiperazin-1-yl)-7-[(1-phenylethyl)amino]-5H-benzo[4,5]cyclohepta[1,2-b]pyridin-5-one;
7-anilino-3-(4-isopropylpiperazin-1-yl)-5H-benzo[4,5]cyclohepta[1,2-b]pyridin-5-one;
7-(benzylamino)-3-(4-isopropylpiperazin-1-yl)-5H-benzo[4,5]cyclohepta[1,2-b]pyridin-5-one;
4-[7-(benzylamino)-5-oxo-5H-benzo[4,5]cyclohepta[1,2-b]pyridin-3-yl]-N,N-dimethylpiperazine-1-carboxamide;
7-(tert-butylamino)-3-(4-isopropylpiperazin-1-yl)-5H-benzo[4,5]cyclohepta[1,2-b]pyridin-5-one;
3-(4-isopropylpiperazin-1-yl)-7-[(2-methoxyethyl)amino]-5H-benzo[4,5]cyclohepta[1,2-b]pyridin-5-one;
3-(4-isopropylpiperazin-1-yl)-7-[(3-methoxypropyl)amino]-5H-benzo[4,5]cyclohepta[1,2-b]pyridin-5-one;
7-[(1-ethylpropyl)amino]-3-(4-isopropylpiperazin-1-yl)-5H-benzo[4,5]cyclohepta[1,2-b]pyridin-5-one;
7-[(1-ethylpropyl)amino]-3-(4-methyl-1,4-diazepan-1-yl)-5H-benzo[4,5]cyclohepta[1,2-b]pyridin-5-one;
7-[(3-methoxypropyl)amino]-3-(4-methyl-1,4-diazepan-1-yl)-5H-benzo[4,5]cyclohepta[1,2-b]pyridin-5-one;
7-amino-3-(4-isopropylpiperazin-1-yl)-5H-benzo[4,5]cyclohepta[1,2-b]pyridin-5-one;
7-amino-3-(4-oxopiperidin-1-yl)-5H-benzo[4,5]cyclohepta[1,2-b]pyridin-5-one;
7-hydroxy-3-(4-isopropylpiperazin-1-yl)-5H-benzo[4,5]cyclohepta[1,2-b]pyridin-5-one;
3-(4-isopropylpiperazin-1-yl)-7-piperidin-1-yl-5H-benzo[4,5]cyclohepta[1,2-b]pyridin-5-one;
3,7-bis{[(3-methylpyridin-4-yl)methyl]amino}-5H-benzo[4,5]cyclohepta[1,2-b]pyridin-5-one;
N-(3-chloro-5-oxo-5H-benzo[4,5]cyclohepta[1,2-b]pyridin-7-yl)-2-methoxyacetamide;
ethyl (5-oxo-3-phenyl-5H-benzo[4,5]cyclohepta[1,2-b]pyridin-8-yl)carbamate;
N-ethyl-N'-(5-oxo-3-phenyl-5H-benzo[4,5]cyclohepta[1,2-b]pyridin-8-yl)urea;
N-(2,4-dimethoxybenzyl)-N-(5-oxo-3-phenyl-5H-benzo[4,5]cyclohepta[1,2-b]pyridin-7-yl)ethylenesulfonamide;
N-(5-oxo-3-phenyl-5H-benzo[4,5]cyclohepta[1,2-b]pyridin-7-yl)ethylenesulfonamide;
N-(5-oxo-3-phenyl-5H-benzo[4,5]cyclohepta[1,2-b]pyridin-7-yl)-2-pyrrolidin-1-ylethanesulfonamide;
N-methyl-N-(5-oxo-3-phenyl-5H-benzo[4,5]cyclohepta[1,2-b]pyridin-7-yl)methanesulfonamide;
3-chloro-7-[(2,4-dimethoxybenzyl)(methyl)amino]-5H-benzo[4,5]cyclohepta[1,2-b]pyridin-5-one;
dimethyl [3-(1-methyl-1H-pyrazol-4-yl)-5-oxo-5H-benzo[4,5]cyclohepta[1,2-b]pyridin-7-yl]amidophosphate;
N,N-(5-oxo-3-phenyl-5H-benzo[4,5]cyclohepta[1,2-b]pyridin-7-yl)bis-methanesulfonamide;
N,N-(5-oxo-3-phenyl-5H-benzo[4,5]cyclohepta[1,2-b]pyridin-7-yl)bis-benzenesulfonamide;
N-(5-oxo-3-phenyl-5H-benzo[4,5]cyclohepta[1,2-b]pyridin-7-yl)benzenesulfonamide;
N-(5-oxo-3-phenyl-5H-benzo[4,5]cyclohepta[1,2-b]pyridin-7-yl)ethanesulfonamide;
N-[3-(1-methyl-1H-pyrazol-4-yl)-5-oxo-5H-benzo[4,5]cyclohepta[1,2-b]pyridin-7-yl]propane-2-sulfonamide;
2-chloro-N-[3-(1-methyl-1H-pyrazol-4-yl)-5-oxo-5H-benzo[4,5]cyclohepta[1,2-b]pyridin-7-yl]propane-2-sulfinamide;
N-(5-oxo-3-phenyl-5H-benzo[4,5]cyclohepta[1,2-b]pyridin-7-yl)-2-phenylacetamide;
2-methoxy-N-(5-oxo-3-phenyl-5H-benzo[4,5]cyclohepta[1,2-b]pyridin-7-yl)acetamide;
N-acetyl-N'-(5-oxo-3-phenyl-5H-benzo[4,5]cyclohepta[1,2-b]pyridin-9-yl)acetamide;
N-[3-(4-isopropylpiperazin-1-yl)-5-oxo-5H-benzo[4,5]cyclohepta[1,2-b]pyridin-7-yl]-2-methoxyacetamide;
N-[3-(1,4-dioxa-8-azaspiro[4.5]dec-8-yl)-5-oxo-5H-benzo[4,5]cyclohepta[1,2-b]pyridin-7-yl]-2-methoxyacetamide;
2-methoxy-N-[5-oxo-3-(3-thienyl)-5H-benzo[4,5]cyclohepta[1,2-b]pyridin-7-yl]acetamide;
2-{[(3-chloro-5-oxo-5H-benzo[4,5]cyclohepta[1,2-b]pyridin-7-yl)amino]carbonyl}benzoic acid;
ethyl [3-(1-methyl-1H-pyrazol-4-yl)-5-oxo-5H-benzo[4,5]cyclohepta[1,2-b]pyridin-7-yl]carbamate;
N-ethyl-N'-[3-(1-methyl-1H-pyrazol-4-yl)-5-oxo-5H-benzo[4,5]cyclohepta[1,2-b]pyridin-7-yl]urea;
7-amino-3-(1,4-dioxa-8-azaspiro[4.5]dec-8-yl)-5H-benzo[4,5]cyclohepta[1,2-b]pyridin-5-one;
2-(diethylamino)-N-(5-oxo-3-phenyl-5H-benzo[4,5]cyclohepta[1,2-b]pyridin-7-yl)ethanesulfonamide;
2-morpholin-4-yl-N-(5-oxo-3-phenyl-5H-benzo[4,5]cyclohepta[1,2-b]pyridin-7-yl)ethanesulfonamide;
2-(1H-imidazol-1-yl)-N-(5-oxo-3-phenyl-5H-benzo[4,5]cyclohepta[1,2-b]pyridin-7-yl)ethanesulfonamide;
2-[(2,4-dimethoxybenzyl)amino]-N-(5-oxo-3-phenyl-5H-benzo[4,5]cyclohepta[1,2-b]pyridin-7-yl)ethanesulfonamide;
2-[(2-morpholin-4-ylethyl)amino]-N-(5-oxo-3-phenyl-5H-benzo[4,5]cyclohepta[1,2-b]pyridin-7-yl)ethanesulfonamide;
2-(benzylamino)-N-(5-oxo-3-phenyl-5H-benzo[4,5]cyclohepta[1,2-b]pyridin-7-yl)ethanesulfonamide;
2-(dimethylamino)-N-(5-oxo-3-phenyl-5H-benzo[4,5]cyclohepta[1,2-b]pyridin-7-yl)ethanesulfonamide;
N-(5-oxo-3-phenyl-5H-benzo[4,5]cyclohepta[1,2-b]pyridin-7-yl)-2-(1H-pyrazol-1-yl)ethanesulfonamide;

N-(3-chloro-5-oxo-5H-benzo[4,5]cyclohepta[1,2-b]pyridin-7-yl)-2-(1H-imidazol-1-yl)ethanesulfonamide;
N-[3-(1,4-dioxa-8-azaspiro[4.5]dec-8-yl)-5-oxo-5H-benzo[4,5]cyclohepta[1,2-b]pyridin-7-yl]-2-(1H-imidazol-1-yl)ethanesulfonamide;
7-(methylamino)-3-(1-methyl-1H-pyrazol-4-yl)-5H-benzo[4,5]cyclohepta[1,2-b]pyridin-5-one;
N-[3-(1-methyl-1H-pyrazol-4-yl)-5-oxo-5H-benzo[4,5]cyclohepta[1,2-b]pyridin-7-yl]sulfamide;
tert-butyl({[3-(1-methyl-1H-pyrazol-4-yl)-5-oxo-5H-benzo[4,5]cyclohepta[1,2-b]pyridin-7-yl]amino}sulfonyl)carbamate;
N-(5-hydroxy-3-phenyl-5H-benzo[4,5]cyclohepta[1,2-b]pyridin-7-yl)methanesulfonamide;
7-[(methylsulfonyl)amino]-3-phenyl-5H-benzo[4,5]cyclohepta[1,2-b]pyridin-5-yl acetate;
N-(5-methoxy-3-phenyl-5H-benzo[4,5]cyclohepta[1,2-b]pyridin-7-yl)-N-methylmethanesulfonamide;
N-(3-phenyl-5H-benzo[4,5]cyclohepta[1,2-b]pyridin-7-yl)methanesulfonamide;
N-[(5E/Z)-5-(hydroxyimino)-3-phenyl-5H-benzo[4,5]cyclohepta[1,2-b]pyridin-7-yl]methanesulfonamide;
N-(3-phenyl-5-pyrrolidin-1-yl-5H-benzo[4,5]cyclohepta[1,2-b]pyridin-7-yl)methanesulfonamide;
N-[(5E/Z)-5-(methoxyimino)-3-phenyl-5H-benzo[4,5]cyclohepta[1,2-b]pyridin-7-yl]methanesulfonamide;
N-[(5E/Z)-5-(tert-butoxyimino)-3-phenyl-5H-benzo[4,5]cyclohepta[1,2-b]pyridin-7-yl]methanesulfonamide;
(5E/Z)-7-amino-3-phenyl-5H-benzo[4,5]cyclohepta[1,2-b]pyridin-5-one oxime;
N-[5-(dimethylamino)-3-phenyl-5H-benzo[4,5]cyclohepta[1,2-b]pyridin-7-yl]methanesulfonamide;
N-[5-(isopropylamino)-3-phenyl-5H-benzo[4,5]cyclohepta[1,2-b]pyridin-7-yl]methanesulfonamide;
N-[5-(cyclopropylamino)-3-phenyl-5H-benzo[4,5]cyclohepta[1,2-b]pyridin-7-yl]methanesulfonamide;
N-[5-(benzylamino)-3-phenyl-5H-benzo[4,5]cyclohepta[1,2-b]pyridin-7-yl]methanesulfonamide;
N-(5-azetidin-1-yl-3-phenyl-5H-benzo[4,5]cyclohepta[1,2-b]pyridin-7-yl)methanesulfonamide;
N-(3-phenyl-5-piperidin-1-yl-5H-benzo[4,5]cyclohepta[1,2-b]pyridin-7-yl)methanesulfonamide;
N-(5-morpholin-4-yl-3-phenyl-5H-benzo[4,5]cyclohepta[1,2-b]pyridin-7-yl)methanesulfonamide;
7-[(methylsulfonyl)amino]-3-phenyl-5-piperazinediium-1-yl-5H-benzo[4,5]cyclohepta[1,2-b]pyridine;
7-(hydroxymethyl)-3-phenyl-5H-benzo[4,5]cyclohepta[1,2-b]pyridin-5-ol;
7-({[tert-butyl(dimethyl)silyl]oxy}methyl)-3-phenyl-5H-benzo[4,5]cyclohepta[1,2-b]pyridin-5-ol;
7-({[tert-butyl(dimethyl)silyl]oxy}methyl)-3-phenyl-5H-benzo[4,5]cyclohepta[1,2-b]pyridin-5-one;
7-(hydroxymethyl)-3-phenyl-5H-benzo[4,5]cyclohepta[1,2-b]pyridin-5-one;
7-({[tert-butyl(dimethyl)silyl]oxy}methyl)-3-chloro-5H-benzo[4,5]cyclohepta[1,2-b]pyridin-5-one;
7-({[tert-butyl(dimethyl)silyl]oxy}methyl)-3-(1-methyl-1H-pyrazol-4-yl)-5H-benzo[4,5]cyclohepta[1,2-b]pyridin-5-one;
7-(hydroxymethyl)-3-(1-methyl-1H-pyrazol-4-yl)-5H-benzo[4,5]cyclohepta[1,2-b]pyridin-5-one;
[3-(1-methyl-1H-pyrazol-4-yl)-5-oxo-5H-benzo[4,5]cyclohepta[1,2-b]pyridin-7-yl]methyl acetate;
[3-(1-methyl-1H-pyrazol-4-yl)-5-oxo-5H-benzo[4,5]cyclohepta[1,2-b]pyridin-7-yl]methyl benzoate;
7-[(methylsulfonyl)methyl]-3-phenyl-5H-benzo[4,5]cyclohepta[1,2-b]pyridin-5-one;
(5-oxo-3-phenyl-5H-benzo[4,5]cyclohepta[1,2-b]pyridin-7-yl)methyl methanesulfinate;
7-(aminomethyl)-3-(1-methyl-1H-pyrazol-4-yl)-5H-benzo[4,5]cyclohepta[1,2-b]pyridin-5-one;
N-{[3-(1-methyl-1H-pyrazol-4-yl)-5-oxo-5H-benzo[4,5]cyclohepta[1,2-b]pyridin-7-yl]methyl}methanesulfonamide;
N-(5-oxo-3-phenyl-10,11-dihydro-5H-benzo[4,5]cyclohepta[1,2-b]pyridin-7-yl)methanesulfonamide;
7-amino-6-chloro-3-(1-methyl-1H-pyrazol-4-yl)-5H-benzo[4,5]cyclohepta[1,2-b]pyridin-5-one;
methyl 7-{[(dimethylamino)sulfonyl]amino}-5-oxo-5H-benzo[4,5]cyclohepta[1,2-b]pyridine-3-carboxylate;
7-{[(dimethylamino)sulfonyl]amino}-5-oxo-N-1,3-thiazol-2-yl-5H-benzo[4,5]cyclohepta[1,2-b]pyridine-3-carboxamide;
3-chloro-7-vinyl-5H-benzo[4,5]cyclohepta[1,2-b]pyridin-5-one;
3-chloro-7-oxiran-2-yl-5H-benzo[4,5]cyclohepta[1,2-b]pyridin-5-one;
3-chloro-7-(1-hydroxyethyl)-5H-benzo[4,5]cyclohepta[1,2-b]pyridin-5-ol;
3-chloro-7-(2-hydroxyethyl)-5H-benzo[4,5]cyclohepta[1,2-b]pyridin-5-ol;
7-(1-{[tert-butyl(dimethyl)silyl]oxy}ethyl)-3-chloro-5H-benzo[4,5]cyclohepta[1,2-b]pyridin-5-one;
7-(2-{[tert-butyl(dimethyl)silyl]oxy}ethyl)-3-chloro-5H-benzo[4,5]cyclohepta[1,2-b]pyridin-5-one;
7-(1-{[tert-butyl(dimethyl)silyl]oxy}ethyl)-3-(1-methyl-1H-pyrazol-4-yl)-5H-benzo[4,5]cyclohepta[1,2-b]pyridin-5-one;
7-[(1R)-1-hydroxyethyl]-3-(1-methyl-1H-pyrazol-4-yl)-5H-benzo[4,5]cyclohepta[1,2-b]pyridin-5-one;
7-[(1S)-1-hydroxyethyl]-3-(1-methyl-1H-pyrazol-4-yl)-5H-benzo[4,5]cyclohepta[1,2-b]pyridin-5-one;
7-(2-hydroxyethyl)-3-(1-methyl-1H-pyrazol-4-yl)-5H-benzo[4,5]cyclohepta[1,2-b]pyridin-5-one;
3-chloro-7-(1-hydroxyethyl)-5H-benzo[4,5]cyclohepta[1,2-b]pyridin-5-one;
3-chloro-7-ethyl-5H-benzo[4,5]cyclohepta[1,2-b]pyridin-5-ol;
3-chloro-7-(1,2-dihydroxyethyl)-5H-benzo[4,5]cyclohepta[1,2-b]pyridin-5-one;
7-(1,2-dihydroxyethyl)-3-(1-methyl-1H-pyrazol-4-yl)-5H-benzo[4,5]cyclohepta[1,2-b]pyridin-5-one;
3-chloro-5-oxo-5H-benzo[4,5]cyclohepta[1,2-b]pyridine-7-carbaldehyde;
3-chloro-7-(1-hydroxypropyl)-5H-benzo[4,5]cyclohepta[1,2-b]pyridin-5-one;
7-[(1R)-1-methoxyethyl]-3-(1-methyl-1H-pyrazol-4-yl)-5H-benzo[4,5]cyclohepta[1,2-b]pyridin-5-one;
7-[(1S)-1-methoxyethyl]-3-(1-methyl-1H-pyrazol-4-yl)-5H-benzo[4,5]cyclohepta[1,2-b]pyridin-5-one;
tert-butyl 4-[2-(3-chloro-5-oxo-5H-benzo[4,5]cyclohepta[1,2-b]pyridin-7-yl)-2-hydroxyethyl]piperazine-1-carboxylate;
tert-butyl 4-{2-hydroxy-2-[3-(1-methyl-1H-pyrazol-4-yl)-5-oxo-5H-benzo[4,5]cyclohepta[1,2-b]pyridin-7-yl]ethyl}piperazine-1-carboxylate;
7-(1-hydroxy-2-piperazin-1-ylethyl)-3-(1-methyl-1H-pyrazol-4-yl)-5H-benzo[4,5]cyclohepta[1,2-b]pyridin-5-one;
N'-[11-Chloro-3-(1-methyl-1H-pyrazol-4-yl)-5-oxo-5H-benzo[4,5]cyclohepta[1,2-b]pyridin-7-yl]-N,N-dimethylsulfamide;
7-[(2-morpholin-4-yl-2-oxoethyl)amino]-3-[1-(2,2,2-trifluoroethyl)-1H-pyrazol-4-yl]-5H-benzo[4,5]cyclohepta[1,2-b]pyridin-5-one;

3-(1-methyl-1H-pyrazol-4-yl)-7-{[2-(3-oxomorpholin-4-yl)
ethyl]amino}-5H-benzo[4,5]cyclohepta[1,2-b]pyridin-5-
one;
3-fluoro-N-[3-(1-methyl-1H-pyrazol-4-yl)-5-oxo-5H-benzo
[4,5]cyclohepta[1,2-b]pyridin-7-yl]azetidine-1-sulfona-
mide;
N-[3-(1-methyl-1H-pyrazol-4-yl)-5-oxo-5H-benzo[4,5]cy-
clohepta[1,2-b]pyridin-7-yl]azetidine-1-sulfonamide;
3-(1-methyl-1H-pyrazol-4-yl)-7-[(2-morpholin-4-yl-2-oxo-
ethyl)amino]-5H-benzo[4,5]cyclohepta[1,2-b]pyridin-5-
one;
N-(2-fluoro-3-methoxypropyl)-N-methyl-N'-[3-(1-methyl-
1H-pyrazol-4-yl)-5-oxo-5H-benzo[4,5]cyclohepta[1,2-b]
pyridin-7-yl]sulfamide
7-(2,2-difluoro-1-hydroxyethyl)-3-(1-methyl-1H-pyrazol-4-
yl)-5H-benzo[4,5]cyclohepta[1,2-b]pyridin-5-one
7-(2,2-difluoro-1(R)-hydroxyethyl)-3-(1-methyl-1H-pyra-
zol-4-yl)-5H-benzo[4,5]cyclohepta[1,2-b]pyridin-5-one
7-(2,2-difluoro-1-hydroxyethyl)-3-(1-methyl-1H-pyrazol-4-
yl)-5H-benzo[4,5]cyclohepta[1,2-b]pyridin-5-one
7-(2,2-difluoro-1(S)-hydroxyethyl)-3-(1-methyl-1H-pyra-
zol-4-yl)-5H-benzo[4,5]cyclohepta[1,2-b]pyridin-5-one
N-(1,4-dioxan-2-ylmethyl)-N'-[6-fluoro-3-(1-methyl-1H-
pyrazol-4-yl)-5-oxo-5H-benzo[4,5]cyclohepta[1,2-b]py-
ridin-7-yl]-N-methylsulfamide;
N-(1,4-dioxan-2-ylmethyl)-N'-[8-fluoro-3-(1-methyl-1H-
pyrazol-4-yl)-5-oxo-5H-benzo[4,5]cyclohepta[1,2-b]py-
ridin-7-yl]-N-methylsulfamide;
6-fluoro-7-(2-fluoro-1-hydroxyethyl)-3-(1-methyl-1H-pyra-
zol-4-yl)-5H-benzo[4,5]cyclohepta[1,2-b]pyridin-5-one;
or a pharmaceutically acceptable salt or stereoisomer thereof.

In a further embodiment, specific examples of the compounds of the instant invention include those compounds listed above except for the following compounds:
7-bromo-3-chloro-5H-benzo[4,5]cyclohepta[1,2-b]pyridin-
5-one;
6-bromo-3-phenyl-5H-benzo[4,5]cyclohepta[1,2-b]pyridin-
5-one;
8-bromo-3-phenyl-5H-benzo[4,5]cyclohepta[1,2-b]pyridin-
5-one;
or a stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

When any variable (e.g. $R^7$, $R^8$, $R^b$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases another embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —CH$_2$—, —CH$_2$CH$_2$— and the like.

When used in the phrases "$C_1$-$C_6$ aralkyl" and "$C_1$-$C_6$ heteroaralkyl" the term "$C_1$-$C_6$" refers to the alkyl portion of the moiety and does not describe the number of atoms in the aryl and heteroaryl portion of the moiety.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —CH$_2$Ph, —CH$_2$CH$_2$Ph, CH(CH$_3$) CH$_2$CH(CH$_3$)Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, the term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" in this embodiment therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In another embodiment, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a $(C_1-C_6)$ alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C(=O)CH$_2$CH(OH)CH$_3$, —(C=O)OH, —CH$_2$(OH)CH$_2$CH(O), and so on.

The moiety formed when, in the definition of two $R^8$s or two $R^9$s on the same carbon atom are combined to form —(CH$_2$)$_u$— is illustrated by the following:

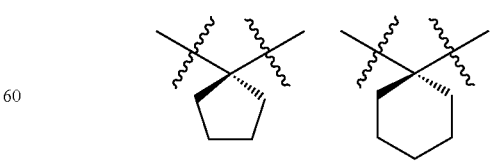

In addition, such cyclic moieties may optionally include one or two heteroatom(s). Examples of such heteroatom-containing cyclic moieties include, but are not limited to:

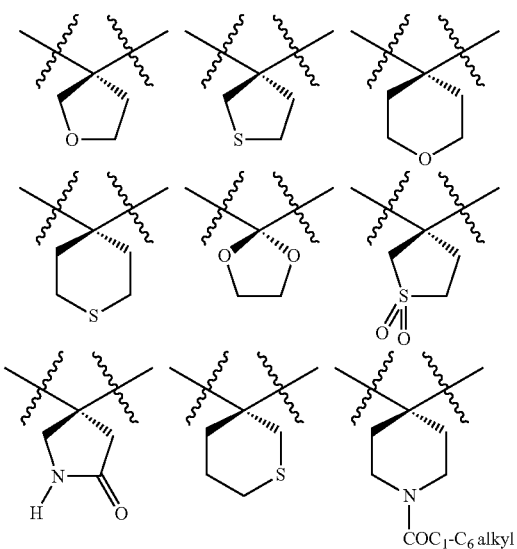

In certain instances, $R^{10}$ and $R^{11}$ are defined such that they can be taken together with the nitrogen to which they are attached to form a monocyclic or bicyclic heterocycle with 5-7 members in each ring and optionally containing, in addition to the nitrogen, one or two additional heteroatoms selected from N, O and S, said heterocycle optionally substituted with one or more substituents selected from $R^8$. Examples of the heterocycles that can thus be formed include, but are not limited to the following, keeping in mind that the heterocycle is optionally substituted with one or more (and in another embodiment, one, two or three) substituents chosen from $R^8$:

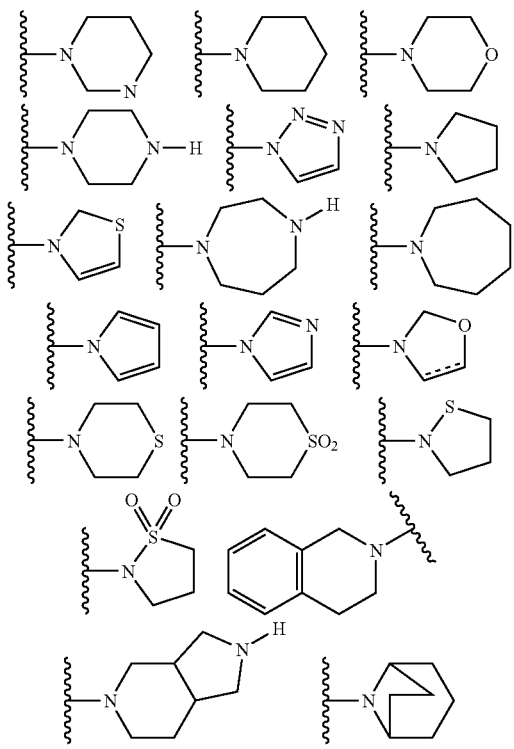

In an embodiment of the compound of the Formula I, the dashed line represents a double bond.

In an embodiment of the compounds of Formula I, $R^1$ is selected from halogen, aryl, heterocyclyl and $NR^{10}R^{11}$; said aryl and heterocyclyl group optionally substituted with one to five substituents, each substituent independently selected from $R^8$;

$R^8$ independently is:
1) $(C=O)_aO_bC_1-C_{10}$ alkyl, 2) $(C=O)_aO_b$aryl, 3)$C_2-C_{10}$ alkenyl, 4) $C_2-C_{10}$ alkynyl, 5) $(C=O)_aO_b$ heterocyclyl, 6) $CO_2H$, 7) halo, 8) CN, 9) OH, 10) $O_bC_1-C_6$ perfluoroalkyl, 11) $O_a(C=O)_bNR^{10}R^{11}$, 12) $S(O)_mR^a$, 13) $S(O)_2NR^{10}R^{11}$, 14) $OS(=O)R^a$, 15) oxo, 16) CHO, 17) $(N=O)R^{10}R^{11}$, 18) $(C=O)_aO_bC_3-C_8$ cycloalkyl, or 19) $O_bSiR^a_3$,
said alkyl, aryl, alkenyl, alkynyl, heterocyclyl, and cycloalkyl optionally substituted with one, two or three substituents selected from $R^9$; and
$R^{7a}$ and $R^{7b}$ are each hydrogen.

In an embodiment of the compounds of Formula I, $R^1$ is selected from Cl, aryl, heterocyclyl, and $NR^{10}R^{11}$; said aryl and heterocyclyl group optionally substituted with one to five substituents, each substituent independently selected from $R^8$. In a further embodiment of the compounds of Formula I, $R^1$ is selected from aryl, heterocyclyl, and $NR^{10}R^{11}$; said aryl and heterocyclyl group optionally substituted with one to five substituents, each substituent independently selected from $R^8$. In another embodiment of the Formulae I and II, $R^1$ is selected from aryl and heterocyclyl; said aryl and heterocyclyl group optionally substituted with one to five substituents, each substituent independently selected from $R^8$.

In an embodiment of the compound of the Formula I, $R^2$ and $R^3$ are combined to form $=O$.

In an embodiment of the compound of the Formula I, $R^4$ and $R^6$ are each independently hydrogen, halogen, $C_{1-6}$alkyl, OH, $-O-C_{1-6}$alkyl, $-O-C(=O)C_{1-6}$ alkyl, $-O$-aryl, $S(O)_mR^a$ and $NR^{10}R^{11}$, each alkyl and aryl optionally substituted with one to five substituents, each substituent independently selected from $R^8$.

In an embodiment of the compound of the Formula I, $R^5$ is selected from $C_{1-6}$alkyl, $C_{2-6}$ alkenyl, $C_{2-6}$ alkynyl, OH, $-O-C_{1-6}$alkyl, $-O-C(=O)C_{1-6}$ alkyl, $-O$-aryl, $S(O)_mR^a$, $-C(=O)NR^{10}R^{11}$, $-NHS(O)_2NR^{10}R^{11}$ and $NR^{10}R^{11}$, each alkyl, alkenyl, alkynyl and aryl optionally substituted with one to five substituents, each substituent independently selected from $R^8$.

In an embodiment of the compound of the Formula II, $R^5$ is selected from $C_{1-6}$alkyl, $C_{2-6}$ alkenyl, $C_{2-6}$ alkynyl, OH, $-O-C_{1-6}$alkyl, $-O-C(=O)C_{1-6}$ alkyl, $-O$-aryl, $S(O)_mR^a$, $-C(=O)NR^{10}R^{11}$, $-NHS(O)_2NR^{10}R^{11}$ and $NR^{10}R^{11}$, each alkyl, alkenyl, alkynyl and aryl optionally substituted with one to five substituents, each substituent independently selected from $R^8$.

In an embodiment of the compounds of the Formula I, if $R^5$ is hydrogen, then $R^4$, $R^6$ and $R^7$ are not independently selected from hydrogen and halogen.

In an embodiment of the Formula I, $R^7$ is hydrogen.

In an embodiment, $R^6$ is selected from: $(C=O)_aO_b(C_1-C_{10})$alkyl, $O_b(C_1-C_3)$perfluoroalkyl, oxo, OH, halo, $(C=O)_aO_b(C_0-C_6)$alkylene-aryl, $(C=O)_aO_b(C_0-C_6)$alkylene-heterocyclyl, and $S(O)_mR^a$; said alkyl, aryl, and heterocyclyl is optionally substituted with one or two substituents selected from $R^7$.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. When the compound of the present invention is acidic, the term "free form" refers to the compound in its non-salt form, such that the acidic functionality is still protonated.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom. An isolated compound having internally balance charges, and thus not associated with a intermolecular counterion, may also be considered the "free form" of a compound.

Certain abbreviations, used in the Schemes and Examples, are defined below:

| | |
|---|---|
| APCI | Atmospheric pressure chemical ionization |
| DCM | dichloromethane |
| DMF | Dimethylformamide |
| DMSO | Dimethyl sulfoxide |
| EtOAc | Ethyl acetate |
| LCMS | Liquid chromatographic mass spectrometry |
| MPLC | Medium pressure liquid chromatography |
| NBS | N-bromosuccinamide |
| TFA | Trifluoroacetic acid |
| TFAA | Trifluoroacetic anhydride |

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

Schemes

As shown in Scheme A, reaction of a suitably substituted 2-methylnicotinate A-1 with strong base followed by reaction with a suitably substituted bromobenzaldehyde provides the olefin intermediate A-2. Subsequent poplyphiosphonic acid mediated cyclization provides the intermediate/compound of the invention A-3.

Scheme B illustrates the use of intermediate A-3 in the preparation of instant compounds having a variety of amine and sulfide substituents.

Scheme C illustrates the incorporation of $R^1$ by a Suzuki coupling of an appropriately substituted boronic acid or boronic ester with the chloride of the fused pyridyl ring of the instant compounds.

Scheme D illustrates an alternative series of reactions to the instant compounds having substituted amine substituents on the phenyl ring.

The carbonyl moiety on the cycloheptenone ring of the instant compound may also be converted to a variety of substituents as shown in Scheme E. Thus hydride reduction provides the alcohol E-2, which can itself undergo alkylation or acylation to provide E-4 and E-3 respectively. Compound E-1 can also undergo a Clemmensen reduction to provide the hydrocarbon analog E-5. The carbonyl of E-1 may also be converted to the hydroximine of E-6 and the amine of E-7 as shown.

Preparation of the instant compounds wherein $R^5$ is a functionalized methyl is illustrated in Scheme F. Thus the ester F-1 is reduced to provide the diol F-2, which is selectively protected and then oxidized to provide the instant compound F-4. Deprotection provides the alcohol F-5 which may then be converted to a variety of other functional groups by techniques well known in the art.

Scheme G illustrates an alternative procedure for forming the tricyclic ring system of the instant compounds. Thus a suitably substituted nicotinoyl chloride G-1 is converted to intermediate G-2, which reacts with a suitably substituted boronic acid to provide the benzaldehyde G-3. Intermediate G-3 can then undergo base mediated cyclization to provide the instant compound G-4.

Preparation of a hydroxyl bearing alkyl sidechain for substituent $R^5$ is illustrated in Scheme H starting with the vinyl substituent.

Scheme I illustrates the preparation of suitably substituted amide moieties for substituent $R^1$.

SCHEME A

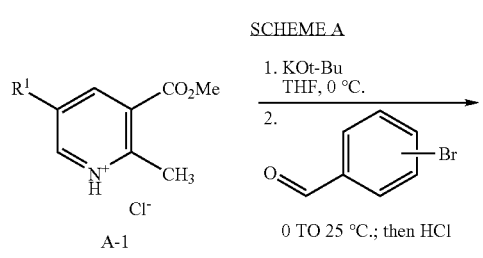

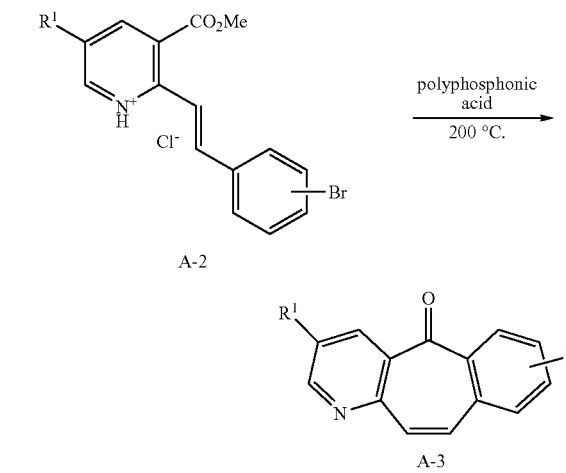

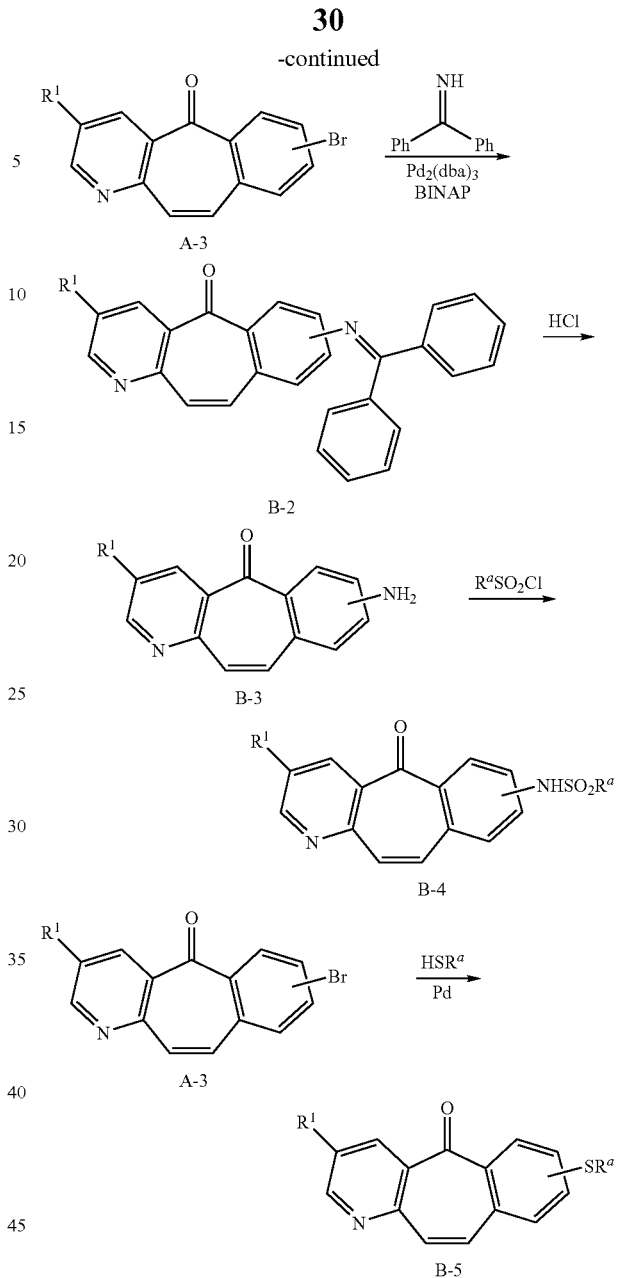

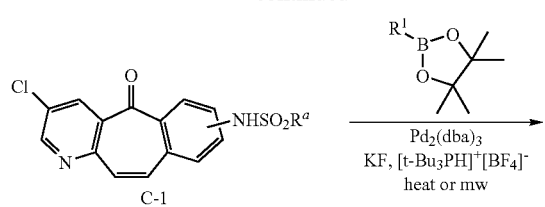
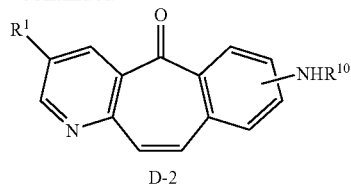
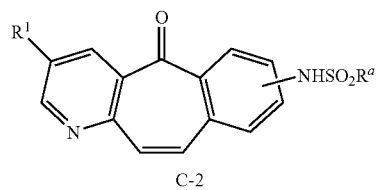
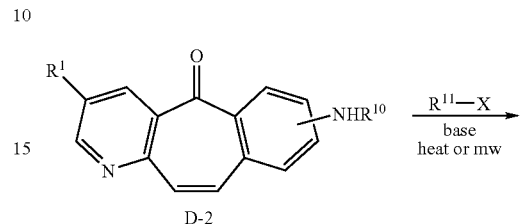
SCHEME D
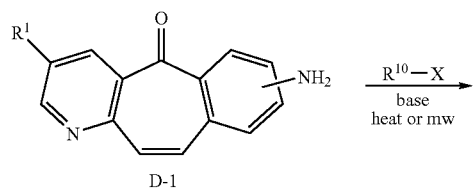
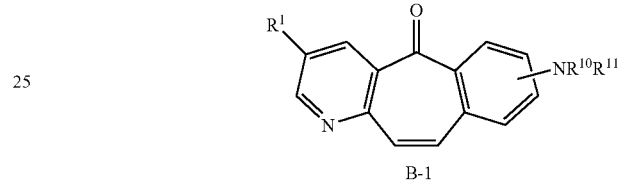
SCHEME E
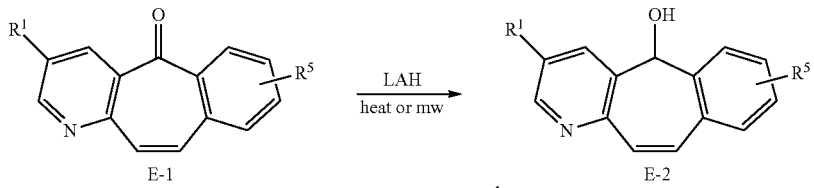
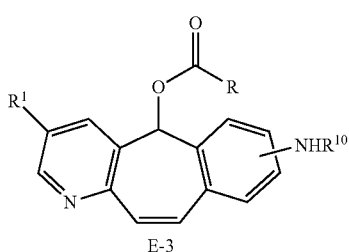
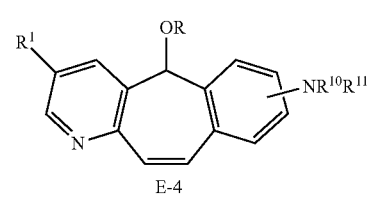
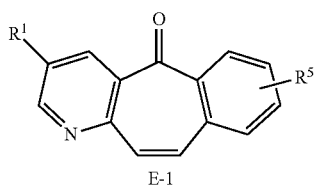
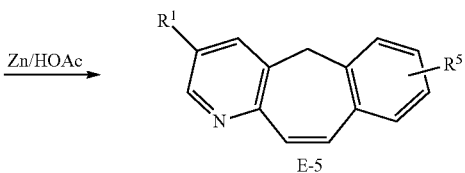

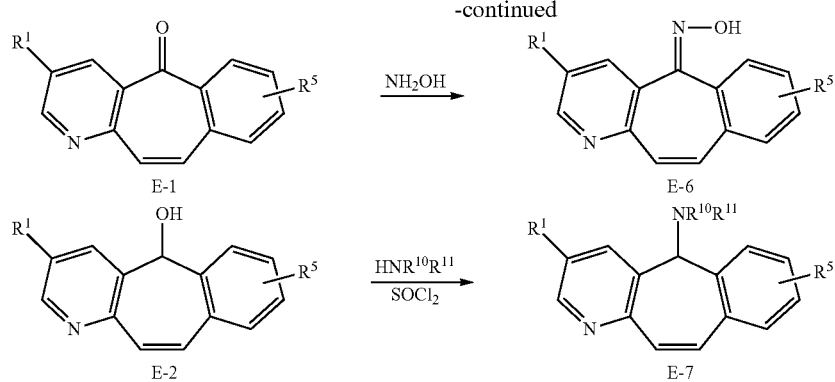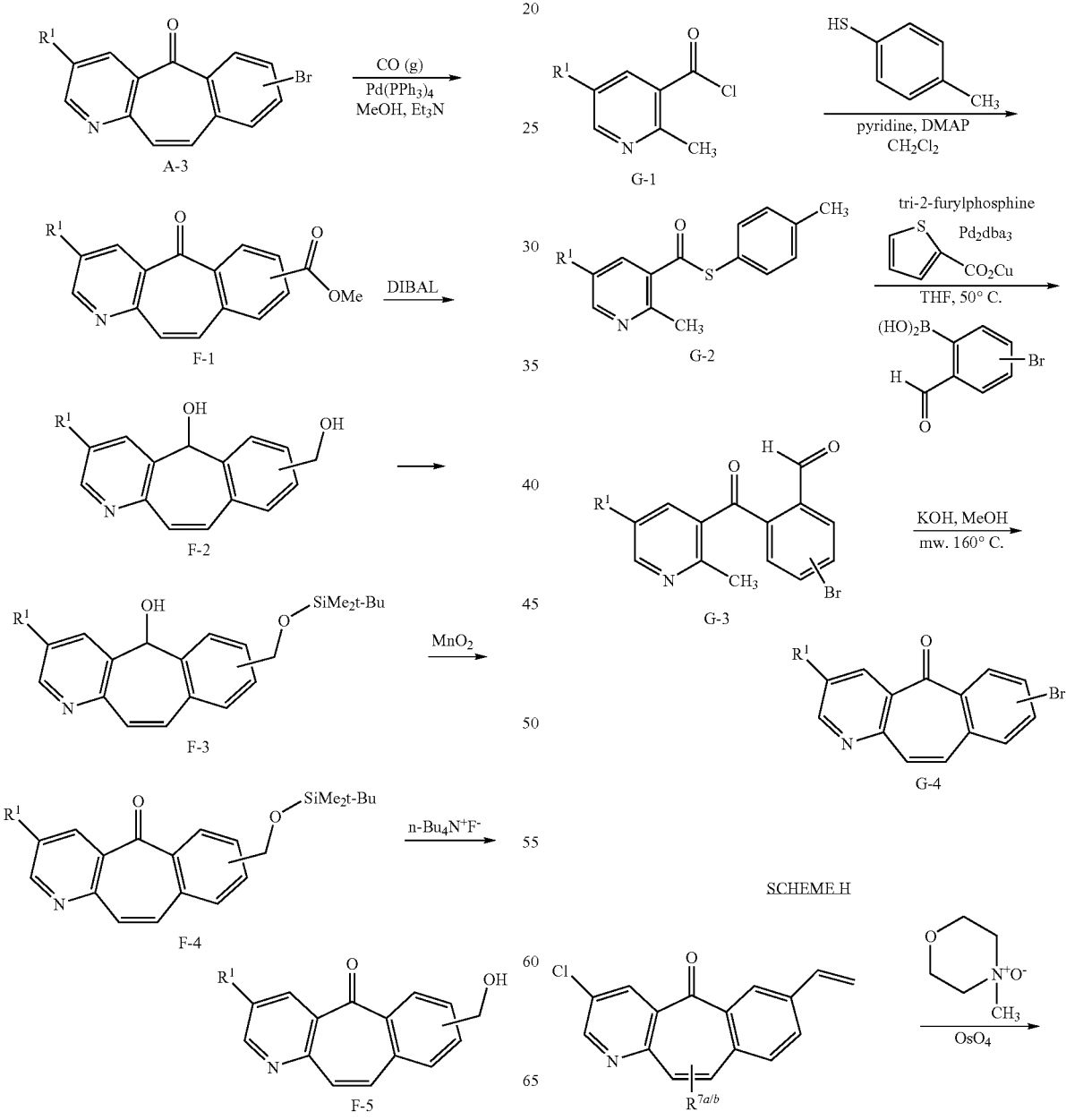

-continued

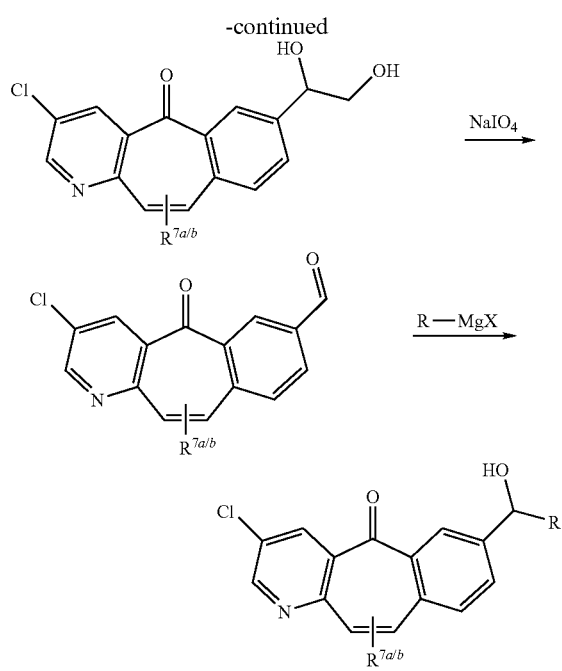

SCHEME I

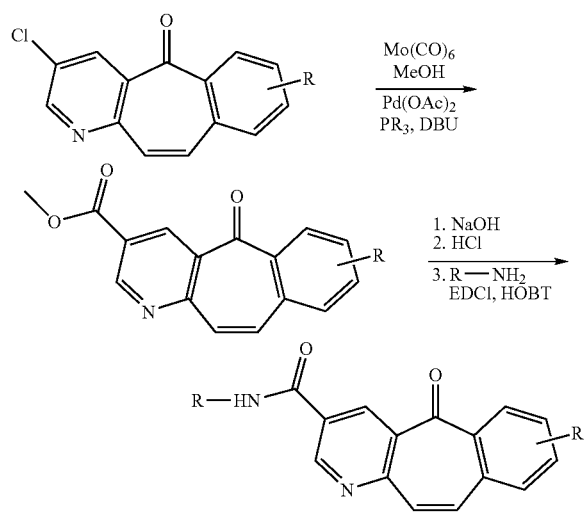

Utilities

The compounds of the invention are useful to bind to and/or modulate the activity of a tyrosine kinase, in particular, a receptor tyrosine kinase. In an embodiment, the receptor tyrosine kinase is a member of the MET subfamily. In a further embodiment, the MET is human MET, although the activity of receptor tyrosine kinases from other organisms may also be modulated by the compounds of the present invention. In this context, modulate means either increasing or decreasing kinase activity of MET. In an embodiment, the compounds of the instant invention inhibit the kinase activity of MET.

The compounds of the invention find use in a variety of applications. As will be appreciated by those skilled in the art, the kinase activity of MET may be modulated in a variety of ways; that is, one can affect the phosphorylation/activation of MET either by modulating the initial phosphorylation of the protein or by modulating the autophosphorylation of the other active sites of the protein. Alternatively, the kinase activity of MET may be modulated by affecting the binding of a substrate of MET phosphorylation.

The compounds of the invention are used to treat or prevent cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds, compositions and methods provided herein are particularly deemed useful for the treatment and prevention of cancer including solid tumors such as skin, breast, brain, cervical carcinomas, testicular carcinomas, etc. In an embodiment, the instant compounds are useful for treating cancer. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia,), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In an embodiment of the invention, cancers that may be treated by the compounds, compositions and methods of the invention include, in addition to the cancers listed above: Lung: bronchogenic carcinoma (non-small cell lung); Gastrointestinal: rectal, colorectal and colon; Genitourinary tract: kidney (papillary renal cell carcinoma); and Skin: head and neck squamous cell carcinoma.

In another embodiment, the compounds of the instant invention are useful for treating or preventing cancer selected from: head and neck squamous cell carcinomas, histiocytic lymphoma, lung adenocarcinoma, small cell lung cancer, non-small cell lung cancer, pancreatic cancer, papillary renal cell carcinoma, liver cancer, gastric cancer, colon cancer, multiple myeloma, glioblastomas and breast carcinoma. In yet another embodiment, the compounds of the instant invention are useful for treating or preventing cancer selected from: histiocytic lymphoma, lung adenocarcinoma, small cell lung cancer, pancreatic cancer, liver cancer, gastric cancer, colon cancer, multiple myeloma, glioblastomas and breast carcinoma. In still another embodiment, the compounds of the instant invention are useful for treating cancer selected from: histiocytic lymphoma, lung adenocarcinoma, small cell lung cancers, pancreatic cancer, liver cancer, gastric cancer, colon cancer, multiple myeloma, glioblastomas and breast carcinoma.

In another embodiment, the compounds of the instant invention are useful for the prevention or modulation of the metastases of cancer cells and cancer. In particular, the compounds of the instant invention are useful to prevent or modulate the metastases of ovarian cancer, childhood hepatocellular carcinoma, metastatic head and neck squamous cell carcinomas, gastric cancers, breast cancer, colorectal cancer, cervical cancer, lung cancer, nasopharyngeal cancer, pancreatic cancer, glioblastoma and sarcomas.

The compounds of this invention may be administered to mammals, preferably humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

In a further example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H, 15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of IMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol., Vol.* 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)-phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, Aug. 1998; 5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/

031137, WO 2004/031139, WO 2004/031138, WO 2004/101538, WO 2004/101539 and WO 02/47671 (including LY450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic γ-secretase inhibitors, agents that interfere with receptor tyrosine kinases (RTKs), an agent that interferes with a cell cycle checkpoint and any of the therapeutic agents listed above.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-$\alpha$, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-$\gamma$ agonist, a PPAR-$\delta$ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic and an agent that interferes with a cell cycle checkpoint.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-$\gamma$ agonist, a PPAR-$\delta$ agonist; an inhibitor of cell proliferation and survival signaling, a bisphosphonate, an aromatase inhibitor, an siRNA therapeutic and an agent that interferes with a cell cycle checkpoint.

Further included within the scope of the invention is a method of treating or preventing a disease in which angiogenesis is implicated, which is comprised of administering to a mammal in need of such treatment a therapeutically effective amount of a compound of the present invention. Other inhibitors of MET may also be administered for this method of treatment. Ocular neovascular diseases, which may result in certain forms of blindness, are examples of conditions where much of the resulting tissue damage can be attributed to aberrant infiltration of blood vessels in the eye. The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Routes of systemic administration of the compounds of the present invention described above may be utilized in the treatment of such ocular neovascular diseases. Other routes of ocular administration may also be employed, such as topical, periocular, intravitreal and the like. Intravitreal implants coated with a drug:polymer matrix may also be employed.

Ophthalmic pharmaceutical compositions that are adapted for topical administration to the eye may be in the form of solutions, suspensions, ointments, creams or as a solid insert. Ophthalmic formulations of this compound may contain from 0.01 ppm to 1% and especially 0.1 ppm to 1% of medicament. For a single dose, from between 0.01 to 5000 ng, preferably 0.1 to 500 ng, and especially 1 to 100 ng of the compound can be applied to the human eye. Formulations useful for intravitreal administration are similar to saline solutions described previously for intravenous administration.

These and other aspects of the invention will be apparent from the teachings contained herein.

Assays

The compounds of the instant invention described in the Examples were tested by the assays described below and were found to have MET inhibitory activity. Other assays are known in the literature and could be readily performed by those of skill in the art (see, for example, U.S. Patent Application Publications US 2005/0075340 A1, Apr. 7, 2005, pages 18-19; and PCT Publication WO 2005/028475, Mar. 31, 2005, pages 236-248).

I. In Vitro Kinase Assays

Recombinant GST-tagged cytosolic domains of human c-Met and other receptor tyrosine kinases including mouse c-Met, human Ron, KDR, IGFR, EGFR, FGFR, Mer, TrkA and Tie2 are used to determine whether the compounds of the instant invention modulate the enzymatic activities of these kinases.

Soluble recombinant GST-tagged cytosolic domains of c-Met and other receptor tyrosine kinases are expressed in a baculovirus system (Pharmingen) according to a protocol recommended by the manufacturer. The c-DNA encoding each cytosolic domain is subcloned into a baculovirus expression vector (pGcGHLT-A, B or C, Pharmingen) containing an in frame 6× histidine tag and a GST tag. The resulting plasmid construct and BaculoGold baculovirus DNA (Pharmingen) are used to co-transfect Sf9 or Sf21 insect cells. After confirming expression of GST-tagged kinase fusion, a high titer recombinant baculovirus stock is produced, expression conditions are optimized, and a scaled up expression of rat KDR-GST fusion is performed. The fusion kinase is then purified from the insect cell lysate by affinity chromatography using glutathione agarose (Pharmingen). The purified protein is dialyzed against 50% glycerol, 2 mM DTT, 50 mM Tris-HCl (pH 7.4) and stored at −20° C. The protein concentrations of the fusion proteins are determined using Coomassie Plus Protein Assay (Pierce) with BSA as standard.

The kinase activities of c-Met and other kinases are measured using a modified version of the homogeneous time-resolved tyrosine kinase assay described by Park et al. (1999, *Anal. Biochem.* 269:94-104).

The procedure for determining the potency of a compound to inhibit c-Met kinase comprises the following steps:
1. Prepare 3-fold serial diluted compound solutions in 100% dimethyl sulfoxide (DMSO) at 20× of the desired final concentrations in a 96 well plate.
2. Prepare a master reaction mix containing 6.67 MnM MgCl$_2$, 133.3 mM NaCl, 66.7 mM Tris-HCl (pH 7.4), 0.13 mg/ml BSA, 2.67 mM dithiothreitol, 0.27 nM recombinant c-Met and 666.7 nM biotinylated synthetic peptide substrate (biotin-ahx-EQEDEPEGDYFEWLE-CONH$_2$) (SEQ.ID.NO.:1).
3. In a black assay plate, add 2.5 µl of compound solution (or DMSO) and 37.5 µl of master reaction mix per well. Initiate the kinase reaction by adding 10 µl of 0.25 mM MgATP per well. Allow the reactions to proceed for 80 min at room temperature. The final conditions for the reaction are 0.2 nM c-Met, 0.5 µM substrate, 50 µM MgATP, 5 mM MgCl$_2$, 100 mM NaCl, 2 mM DTT, 0.1 mg/ml BSA, 50 mM Tris (pH 7.4) and 5% DMSO.
4. Stop the kinase reaction with 50 µl of Stop/Detection buffer containing 10 mM EDTA, 25 mM HEPES, 0.1% TRITON X-100, 0.126 µg/ml Eu-chelate labeled anti-phosphotyrosine antibody PY20 (cat. #AD0067, PerkinElmer) and 45 µg/ml Streptavidin-allophycocyanin conjugate (cat. #PJ25S, Prozyme).
5. Read HTRF signals on a Victor reader (PerkinElmer) in HTRF mode after 60 min.
6. IC$_{50}$ is determined by fitting the observed relationship between compound concentration and HTRF signal with a 4-parameter logistic equation.

Essentially the same procedure was used to determine the potency of compounds to inhibit mouse c-Met, human Ron, KDR, IGFR, EGFR, FGFR, Mer, TrkA and Tie2 except that the concentration of enzyme varied in individual assays (0.2 nM mouse c-Met; 2.5 nM Ron, 8 nM KDR; 0.24 nM IGFR; 0.24 nM EGFR; 0.14 nM FGFR; 16 nM Mer; 8 nM TrkA; 8 nM Tie2).

The compounds 3 and 5 to 235 in the Examples were tested in the above assay and found to have an IC$_{50}$≦50 µM.

II. Cell Based-c-Met Autophosphorylation Assay

A sandwich ELISA assay is used to assess MET autophosphorylation in MKN45 gastric cancer cells, in which MET is constitutively activated. Briefly a monolayer of cells was pre-treated with compounds or the vehicle and then lysed. The MET in a cell lysate was captured by an anti-MET antibody immobilized on a plastic surface. A generic anti-phosphotyrosine antibody or one of several specific anti-phospho-MET antibodies is then allowed to bind captured MET and is detected using HRP-conjugated secondary antibody.

The procedure for determining the potency of a compound to inhibit MET autophosphorylation in MKN45 cells comprises the following steps:

Day 1
1. Coat a 96-well ELISA plate overnight at 4° C. with 100 µl/well of 1 µg/ml capture antibody solution (Af276, R&D).
2. Seed a separate 96-well culture plate with MKN45 cells at 90,000 cells/well in 0.1 ml of growth media (RPMI 1640, 10% FBS, 100 ug/mL Pen-Strep, 100 ug/mL L-glutamine, and 10 mM HEPES) and culture overnight at 37° C./5% CO$_2$ to 80-90% confluence.

Day 2
1. Wash the ELISA plate 4× with 200 µl/well of wash buffer (TBST+0.25% BSA). Incubate the ELISA plate with 200 µl/well of blocking buffer (TBST+1.5% BSA) for 3-5 hrs at RT.
2. Prepare a half-long dilution series of 200× compound in DMSO. Dilute the series to 10× with assay media (RPMI 1640, 10% FBS, and 10 mM HEPES).
3. Add 10× compound solutions (11 µl/well) to the culture plate containing MKN45 cells. Incubate the plate at 37° C./5% CO$_2$ for 60 min.
4. Lyse the cells with 100 µl/well of lysis buffer (30 mM Tris, pH 7.5, 5 mM EDTA, 50 mM NaCl, 30 mM sodium pyrophosphate, 50 mM NaF, 0.5 mM Na$_3$VO$_4$, 0.25 mM potassium bisperoxo(1,10-phenanthroline)-oxovanadate, 0.5% NP40, 1% Triton X-100, 10% glycerol, and a protease inhibitor cocktail) at 4° C. for 90 min.
5. Remove blocking buffer from the ELISA plate, wash the plate 4× with 200 µl/well of wash buffer. Transfer 90 µl/well of MKN45 cell lysate from the culture plate to the ELISA plate. Incubate sealed assay plate at 4° C. with gentle shaking overnight.

Day 3
1. Wash the ELISA plates 4 times with 200 µl/well wash buffer.
2. Incubate with 100 µl/well primary detection antibody (1 µg/ml in TBST+1% BSA) for 1.5 hours at ambient temperature. The following primary antibodies have been used: 4G10 from UpState, anti-pMet(1349) and anti-pMet(1369), both from Biosource.
3. Wash the ELISA plates 4 times with wash buffer. Add 100 µl/well of secondary antibody (1:1000 anti-mouse IgG-HRP diluted in TBST+1% BSA for 4G10, or 1:1000 anti-rabbit IgG-HRP for anti-pMet(1349) and anti-pMet(1365)). Incubate at room temperature with gentle mixing for 1.5 hours. Wash 4× with 200 ul/well wash buffer.
4. Add 100 μl/well of Quanta Blu reagent (Pierce) and incubate at room temperature for 8 minutes. Read fluorescence (Excitation wavelength: 314 nm, emission wavelength: 425 nm) on a Spectramax Gemini EM plate reader (Molecular Devices).
5. $IC_{50}$ is calculated by fitting the relationship between compound concentration and fluorescence signal with a 4-parameter logistic equation.

III. MKN45 Cell Proliferation/Viability Assay

MKN45 human gastric cancer cells are known to overexpress constitutively activated c-met. siRNA-mediated partial knock down of c-Met was found to induce pronounced growth inhibition and apoptosis in MKN45 cells, suggesting a vital role of c-Met in this cell line. The assay described here measures the effect of c-Met inhibitors on proliferation/viability of MKN45 cells. The procedure for determining the potency of a compound to inhibit MKN45 proliferation/viability comprises the following steps.

On day 1, plate MKN45 cells at 3000 cells/95 t medium (RPMI/10% FCS, 100 mM HEPES, penicillin and streptomycin) per well in a 96 well plate. Maintain the plate in an incubator at 37° C./5% $CO_2$. Prepare 3-fold serial diluted compound solutions at 1000× of desired final concentrations in DMSO.

On day 2, prepare SOX compound solutions by diluting the 1000× compound solutions with the medium. Add 5 μl 20× compound solution per well to the MKN45 cell culture described above. Return the plate to the incubator.

On day 5, add 50 μl lysis buffer (ViaLight Reagents Kit, Catalog No. LT07-221, Cambrex): per well. Lyse the cells at room temperature for 15 minutes. Then add 50 μl detection reagent (ViaLight Reagents Kit) and incubate for 3 minutes. The plate is read on a TOPCOUNT (PerkinElmer) in luminescence mode. $IC_{50}$ is calculated by fitting the relationship between compound concentration and luminescence signal with a 4-parameter logistic equation.

IV. HGF-Induced Cell Migration Assay

The HGF-induced migration of HPAF pancreatic cancer cells was assessed using BD Falcon Fluoroblock 96-Multiwell Insert plates (Cat #351164, BD Discovery Labware). The plate consists of wells each of which is partitioned by a micro-porous membrane into the top and bottom chambers. Pancreatic cancer cells are plated on the top side of the membrane and migrate to the underside of the membrane in response to chemo-attractant added to the lower chamber. The cells on the under side of the membrane are labeled with a fluorescent dye and detected by a fluorescence plate reader. The procedure for determining the potency of a compound to inhibit cell migration comprises the following steps.
1. Prepare test compound solutions of 1000× final concentrations in 100% DMSO
2. Dilute the above solutions SOX with DMEM/10% FCS to obtain compound solutions 20× of the final concentrations.
3. Fill each lower chamber of a Fluoroblock 96-Muntiwell Insert plate with 180 μl DMEMI10% FCS, and plate 8,000 HPAF pancreatic cancer cells in 50 ul DMEM/10% FCS in each upper chamber.
4. 1-2 hours after plating, add 2.5 μl and 10 μl of a 20× compound solution to the upper and the lower chamber respectively. Incubate the plate at 37° C. for 60 min, and then add concentrated HGF to lower chamber to a final HGF concentration of 15 ng/ml. The insert plates are incubated overnight for 20 hours.
5. An aliquot of a concentrated Calcein dye (Molecular Probes) is added to each lower chamber to give 5 μg/ml final dye concentration and the cells are labeled for 1 hour. Wash each lower chamber with 200 μl DMEM/10% FCS
6. Read fluorescence on a Victor reader (PerkinElmer) in bottom read mode (Excitation wave length: 485 nm, emission wavelength: 535 nm).
7. $IC_{50}$ is calculated by fitting the relationship between compound concentration and fluorescence signal with a 4-parameter logistic equation.

EXAMPLES

Examples provided are intended to assist in a further understanding of the invention. Particular materials employed, species and conditions are intended to be illustrative of the invention and not limiting of the reasonable scope thereof.

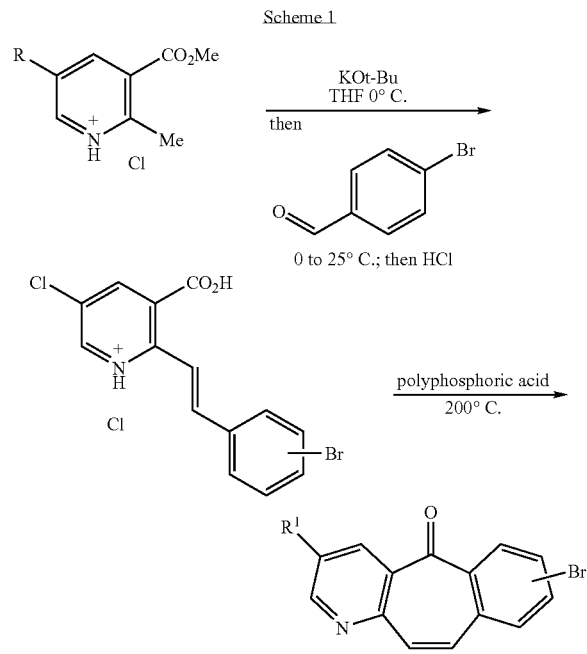

Example 1

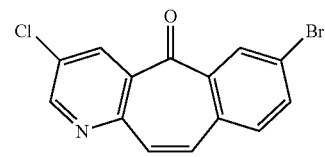

Step 1: 2-[(E/Z)-2-(4-bromophenyl)vinyl]-3-carboxy-5-chloropyridinium chloride

Potassium tert-butoxide (1M solution in THF, 60 mL, 60 mmol) was added to a solution of 4-bromobenzaldehyde (5.6 g, 30 mmol) and methyl 5-chloro-2-methylnicotinate (Marcoux, J.-F.; Marcotte, F.-A.; Wu, J.; Dormer, P. G.; Davies, I. W.; Hughes, D.; Reider, P. J. *J. Org. Chem.* 2001, 66, 4194-4199) (5.6 g, 30 mmol) in 200 mL THF at 0° C. The mixture was allowed to warm to ambient temperature and stirred for 12 hours. The reaction slurry was concentrated to give yellow/orange solids, then 50 mL of water and 50 mL of 6N HCl were added. After stirring the resulting slurry for 30 minutes, 200 mL of EtOH was added and the slurry was stirred for 4 hours. The slurry was filtered and dried to afford the title compound. $^1$H NMR (600 MHz, DMSO-$D_6$) δ 8.76 (d, 1H); 8.22 (d, 1H); 8.02 (d, 1H); 7.79 (d, 1H); 7.60-7.54 (m, 4H). LRMS (APCI) calculated for $C_{14}H_{10}BrClNO_2$ [M+H]+, 338.0; found 337.9.

Step 2: 7-bromo-3-chloro-5H-benzo[4,5]cyclohepta [1,2-b]pyridin-5-one (Compound 1)

2-[(E/Z)-2-(4-bromophenyl)vinyl]-3-carboxy-5-chloropyridinium chloride (11.2 g, 29.9 mmol) was added to 50 mL of polyphosphoric acid and heated to 200° C. After 12 hours, the solution was poured into ice and 250 mL of 5N sodium hydroxide solution, then 5N sodium hydroxide solution was added to adjust to pH 10. The mixture was diluted in 2 L of dichloromethane, 100 g of Celite were added and the suspension was stirred for 15 minutes. The solids were filtered through a sintered glass funnel and discarded. The liquid phase was poured into a separatory funnel and the organic layer was isolated. The organic layer was dried with magnesium sulfate, filtered, and concentrated to afford Compound 1. $^1$H NMR (600 MHz, CDCl$_3$) δ 8.82 (d, 1H); 8.50 (d, 1H); 8.41 (d, 1H); 7.80 (dd, 1H); 7.48 (d, 1H); 7.35 (d, 1H); 7.20 (d, 1H). LRMS (APCI) calculated for $C_{14}H_8BrClNO$ [M+H]+, 320.0; found 320.0.

Scheme 2

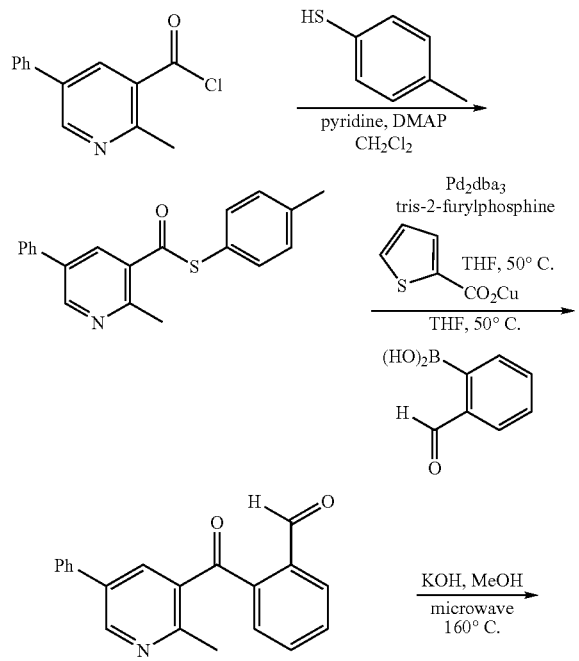

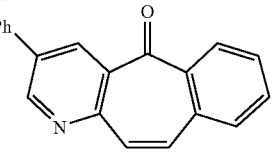

Example 2

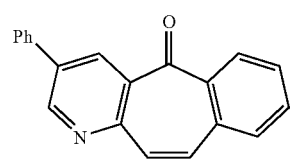

Step 1: S-(4-methylphenyl) 2-methyl-5-phenylpyridine-3-carbothioate

To a 0° C. solution of 2-methyl-5-phenylnicotinic acid (100 mg, 0.40 mmol) in CH$_2$Cl$_2$ (4 mL) was added oxalyl chloride (344 μL, 4.0 mmol). The mixture was stirred at 40° C. After 3 hours, the mixture was concentrated to dryness, dissolved in benzene (2×5 mL) and concentrated again. After dissolving the crude residue in CH$_2$Cl$_2$ (2 mL) at 0° C., pyridine (1 mL, 0.92 M in CH$_2$Cl$_2$), 4-dimethylaminopyridine (10 mg, 0.08 mmol) and 4-methylthiophenol (60 mg, 0.48 mmol) were added. The mixture was then allowed to warm to room temperature. After stirring for 2 hours, the mixture was diluted with EtOAc, washed with 1N HCl, brine, dried over sodium sulfate, filtered, and concentrated. The crude residue was purified by flash chromatography (100-80% hexanes/EtOAc gradient) to afford the title compound. LRMS (APCI) calculated for $C_{20}H_{18}NOS$ [M+H]+, 320.1; found 320.1.

Step 2: 2-[(2-methyl-5-phenylpyridin-3-yl)carbonyl] benzaldehyde

S-(4-methylphenyl) 2-methyl-5-phenylpyridine-3-carbothioate (100 mg, 0.31 mmol), copper (I) thiophene-2-carboxylate (89.6 mg, 0.47 mmol), Pd$_2$ dba$_3$CHCl$_3$ (26 mg, 0.025 mmol), tri-2-furylphosphine (17.3 mg, 0.074 mmol) and 2-formylphenylboronic acid (51.7 mg, 0.34 mmol) were combined in a dry flask. The flask was purged with argon and 3.0 mL of THF were added. Argon was bubbled through the solution for 5 minutes and the solution was stirred and heated to 50° C. After 18 hours, the reaction mixture was diluted with EtOAc, washed with 1N HCl, brine, dried over sodium sulfate, filtered, concentrated and purified by flash chromatography (100-70% hexanes/EtOAc gradient) to afford the title compound. LRMS (APCI) calculated for $C_{20}H_{16}NO_2$ [M+H]$^+$, 302.1; found 302.1.

Step 3: 3-phenyl-5H-benzo[4,5]cyclohepta[1,2-b] pyridin-5-one

A flask was charged with 2-[(2-methyl-5-phenylpyridin-3-yl)carbonyl]benzaldehyde (6.2 mg, 0.02 mmol) and MeOH (1 mL). LiHMDS (25 μl, 1.0 M in THF) was added and the vessel was heated in the Biotage Initiator series microwave for 30 min. at 100° C. The mixture was then diluted with EtOAc, washed with water and brine, then dried over Na$_2$SO$_4$. The solution was concentrated in vacuo and purified by reverse phase HPLC (0-100% CH$_3$CN/water with a 0.1% TFA modifier) to afford the title compound. $^1$H NMR (600 MHz, CD$_3$OD) δ 9.15 (d, 1H), 8.76 (d, 1H), 8.25 (d, 1H), 7.77 (m, 4H), 7.66 (t, 1H), 7.54 (t, 2l), 7.45 (m, 2H0, 7.36 (d, 1H). LRMS (APCI) calculated for C$_{20}$H$_{14}$NO [M+H]+, 284.1; found 283.8.

The following compounds were made according to Scheme 1, using the appropriately substituted 2-formylphenylboronic acids, which were prepared according to literature methods.

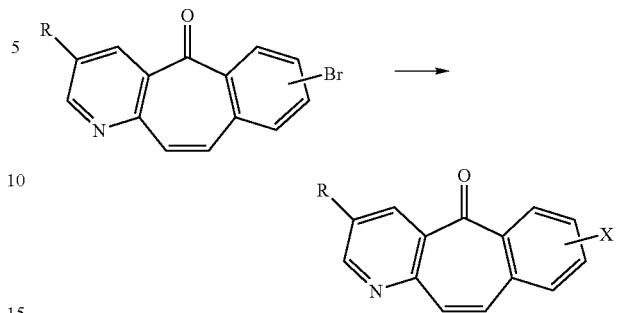

Scheme 3

TABLE 1

| Compound | Structure | Name | MS (M + 1) |
|---|---|---|---|
| 3 | 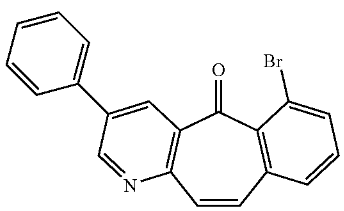 | 6-bromo-3-phenyl-5H-benzo[4,5]cyclohepta[1,2-b]pyridin-5-one | calc'd 362.0 (M + H)+; found (M + H)+ |
| 4 | 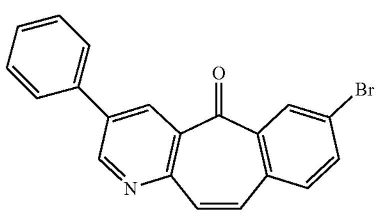 | 7-bromo-3-phenyl-5H-benzo[4,5]cyclohepta[1,2-b]pyridin-5-one | calc'd 362.0 (M + H)+; found 362.0 (M + H)+ |
| 5 | 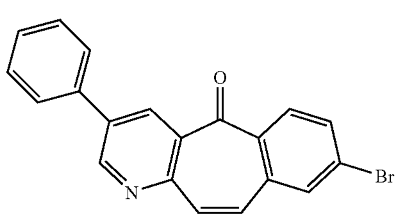 | 8-bromo-3-phenyl-5H-benzo[4,5]cyclohepta[1,2-b]pyridin-5-one | calc'd 362.0 (M + H)+; found (M + H)+ |
| 6 | 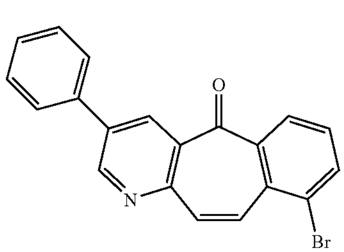 | 9-bromo-3-phenyl-5H-benzo[4,5]cyclohepta[1,2-b]pyridin-5-one | calc'd 362.0 (M + H)+; found (M + H)+ |

Example 3

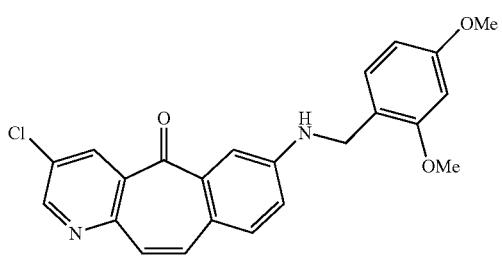

3-chloro-7-[(2,4-dimethoxybenzyl)amino]-5H-benzo[4,5]cyclohepta[1,2-b]pyridin-5-one 7-bromo-3-chloro-5H-benzo[4,5]cyclohepta[1,2-b]pyridin-5-one (3.0 g, 9.40 mmol), tris(dibenzylideneacetone)dipalladium (0) (Pd$_2$(dba)$_3$)) (43 mg, 0.047 mmol), rac-2,2'-bis(diphenylphosphino)-1,1'-binapthyl (BINAP) (88 mg, 0.141 mmol), and sodium tert-butoxide (1.08 g, 11.3 mmol) were combined in a dry flask through which argon was purged. The flask was charged with 100 mL of dry dioxane, 2,4-dimethoxybenzylamine (1.41 mL, 9.40 mmol) was added, and the mixture was sparged with argon for 5 minutes. The reaction was heated to 100° C. and stirred under argon. After 2 h the reaction was concentrated and dissolved in 400 ml of ethyl acetate and washed with 100 mL of saturated aqueous ammonium chloride solution. The organic layer was separated, dried with magnesium sulfate, filtered, and concentrated. The resultant solids were slurried in 50 mL hot methanol, then allowed to cool to ambient temperature. The solids were filtered and dried to afford the title compound. LRMS (APCI) calculated for C$_{23}$H$_{20}$ClN$_2$O$_3$ [M+H]+, 407.1; found 407.1.

Example 4

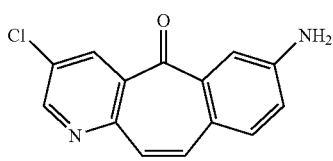

7-amino-3-chloro-5H-benzo[4,5]cyclohepta[1,2-b]pyridin-5-one

Method A:
7-bromo-3-chloro-5H-benzo[4,5]cyclohepta[1,2-b]pyridin-5-one (1.05 g, 3.30 mmol), Pd$_2$(dba)$_3$ (8 mg, 0.00825 mmol), BINAP (15 mg, 0.0248 mmol) and benzophenone imine (0.662 mL, 3.95 mmol) were combined in a dry flask. The flask was charged with 40 mL of dry toluene, followed by sodium tert-butoxide (0.444 g, 4.62 mmol). Argon was bubbled through the solution for 5 minutes. The reaction solution was heated to 110° C. and stirred under argon. After 2.5 hours, the reaction was concentrated, 20 mL of THF and 1 mL of 6N hydrochloric acid were added and the resulting solution was stirred. After 2 hours, the solution was poured into 300 mL of ethyl acetate, 100 mL of saturated sodium bicarbonate and 200 mL of water. The organic layers were separated, dried with magnesium sulfate, filtered, concentrated, and purified by flash column chromatography (0-30% ethyl acetate/hexanes gradient) to afford the title compound. $^1$H NMR (600 MHz, CDCl$_3$) δ 8.77 (d, 1H); 8.55 (d, 1H); 7.58 (d, 1H); 7.44 (d, 1H); 7.18 (d, 1H); 7.14 (d, 1H); 7.01 (dd, 1H); 4.15 (s, 2H). LRMS (APCI) calculated for C$_{14}$H$_{10}$ClN$_2$O [M+H]+, 257.0; found 257.1.

Method B:
3-chloro-7-[(2,4-dimethoxybenzyl)amino]-5H-benzo[4,5]cyclohepta[1,2-b]pyridin-5-one (1.1 g, 2.7 mmol) was dissolved in 8 mL methanol and 30 mL dichloromethane. Then 10 mL of trifluoroacetic acid was added and the solution was stirred at ambient temperature. After 1 hour, reaction was concentrated, dissolved in 500 mL of ethyl acetate and washed with 200 mL saturated sodium bicarbonate. The organic layer was separated, dried with magnesium sulfate, filtered, and purified by flash column chromatography (0-10% methanol/dichloromethane gradient) and reverse phase HPLC (20-100% acetonitrile/water gradient, 0.1% trifluoroacetic acid modifier) to afford title compound. LRMS (APCI) calculated for C$_{14}$H$_{10}$ClN$_2$O [M+H]+, 257.0; found 257.1.

Example 5

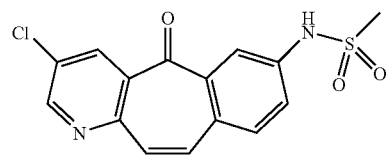

N-(3-chloro-5-oxo-5H-benzo[4,5]cyclohepta[1,2-b]pyridin-7-yl)methanesulfonamide

Method A:
7-bromo-3-chloro-5H-benzo[4,5]cyclohepta[1,2-b]pyridin-5-one (5.00 g, 15.7 mmol), methyl sulfonamide (1.49 g, 15.7 mmol), Pd$_2$(dba)$_3$ (0.714 g, 0.78 mmol), 9,9-dimethyl-4,5-bis(diphenylphosphino) xanthene (XANTPHOS) (1.36 g, 2.35 mmol) and cesium carbonate (15.3 g, 47.0 mmol) were added to a dry flask through which argon was purged. The flask was charged with 100 mL of dry dioxane and argon was bubbled through the solution for 10 minutes. The reaction mixture was heated to 95° C. and stirred under argon. After 12 hours, the reaction mixture was concentrated and dissolved in 2000 mL ethyl acetate and 1000 mL water. The organic layer was separated and washed with 500 mL of brine, dried with magnesium sulfate, filtered, and concentrated. The resultant solids were dissolved in 150 mL of a 3:1 mixture of hot dichloromethane/methanol and allowed to cool to ambient temperature with stirring. After 3 h, 150 mL of hexanes were added and the resulting slurry was allowed to stir. After 12 hours, an additional 50 mL hexanes were added. After 4 hours, the solids were filtered and dried to afford the title compound.

Method B:

7-amino-3-chloro-5H-benzo[4,5]cyclohepta[1,2-b]pyridin-5-one (0.70 g, 2.7 mmol), triethylamine (0.83 mL, 5.94 mmol) and methanesulfonylchloride (0.42 mL, 5.4 mmol) were added to 40 mL dichloromethane and cooled to 0° C. The solution was stirred and allowed to warm to ambient temperature. After 1 hour, the reaction was quenched with saturated sodium bicarbonate solution and stirred. After 30 minutes, the reaction mixture was poured into 300 mL ethyl acetate and 250 mL water. The organic layer was separated, dried with magnesium sulfate, filtered, and concentrated to afford crude N,N-(3-chloro-5-oxo-5H-benzo[4,5]cyclohepta[1,2-b]pyridin-7-yl)bis-methanesulfonamide.

The crude N,N-(3-chloro-5-oxo-5H-benzo[4,5]cyclohepta[1,2-b]pyridin-7-yl)bis-methanesulfonamide (1.1 g, 2.7 mmol) was dissolved in 150 mL methanol, then 5 mL of 5N sodium hydroxide solution was added and the solution was stirred at ambient temperature. After 1 hour, the reaction solution was partially concentrated and dissolved in 250 mL of ethyl acetate, 150 mL water, and 50 mL saturated aqueous ammonium chloride solution. The organic layer was separated, dried with magnesium sulfate, filtered, and concentrated to afford the title compound.

$^1$H NMR (600 MHz, CDCl$_3$) δ 8.82 (d, 1H); 8.54 (d, 1H); 7.98 (d, 1H); 7.70 (dd, 1H); 7.65 (d, 1H); 7.33 (d, 1H); 7.25 (d, 1H); 6.78 (s, 1H); 3.12 (s, 3H). LRMS (APCI) calculated for C$_{15}$H$_{12}$ClN$_2$O$_3$S [M+H]+, 335.0; found 335.1.

Example 6

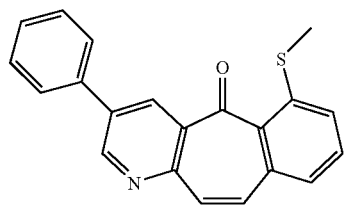

10

6-(methylthio)-3-phenyl-5H-benzo[4,5]cyclohepta[1,2-b]pyridin-5-one 6-bromo-3-phenyl-5H-benzo[4,5]cyclohepta[1,2-b]pyridin-5-one (15 mg, 0.04 mmol), sodium thiomethoxide (15 mg, 0.21 mmol) and copper (I) bromide (23 mg, 0.10 mmol) were combined in a dry flask. The flask was purged with argon and 0.5 mL of N,N-dimethylformamide were added. The solution was stirred and heated to 140° C. After 72 h, the reaction mixture was cooled to room temperature, diluted with EtOAc and washed with 5% HCl, brine and water. The organic layer was dried over sodium sulfate, filtered, concentrated and purified by reverse phase HPLC (30-100% acetonitrile/water gradient, 0.1% trifluoroacetic acid modifier) to afford the title compound. $^1$H NMR (600 MHz, CD$_3$OD) δ 9.14 (d, 1H), 8.58 (d, 1M), 7.78 (d, 2H), 7.65 (m, 2H), 7.54 (t, 2H), 7.47 (m, 3H), 7.27 (d, 1H), 2.49 (s, 3H). LRMS (APCI) calculated for C$_{21}$H$_{16}$NOS [M+H]+, 330.0; found 330.1.

Example 7

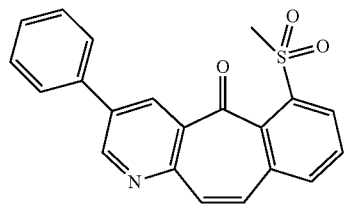

11

6-(methylsulfonyl)-3-phenyl-5H-benzo[4,5]cyclohepta[1,2-b]pyridin-5-one

To a 0° C. solution of 6-(methylthio)-3-phenyl-5H-benzo[4,5]cyclohepta[1,2-b]pyridin-5-one (7.4 mg, 0.022 mmol) in THF (0.7 mL) and MeOH (0.2 mL) was added oxone (0.3 mL, 0.138 M in water). The mixture was then stirred at room temperature. After 2 hours, the reaction mixture was concentrated to dryness. The crude residue was diluted with EtOAc and washed with brine. The organic layer was dried over sodium sulfate, filtered, concentrated and purified by reverse phase HPLC (30-100% acetonitrile/water gradient, 0.1% trifluoroacetic acid modifier) to afford the title compound. $^1$H NMR (600 MHz, CD$_3$OD) δ 9.10 (d, 1H), 8.40 (d, 1H), 8.26 (d, 1H), 8.00 (d, 1H), 7.85 (t, 1H), 7.75 (d, 2H), 7.53 (t, 2H), 7.47 (m, 2H), 7.38 (d, 1H), 3.52 (s, 31). LRMS (APCI) calculated for C$_{21}$H$_{16}$NO$_3$S [M+H]+, 362.0; found 362.1.

Example 8

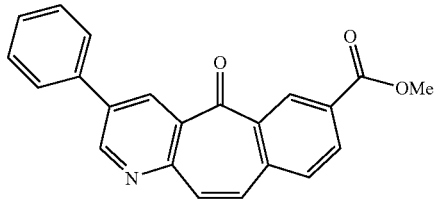

12

Methyl 5-oxo-3-phenyl-5H-benzo[4,5]cyclohepta[1,2-b]pyridine-7-carboxylate

A test tube fitted with a Teflon lined septum was charged with compound 4 (50 mg, 0.14 mmol) and Pd(PPh$_3$)$_4$ (8 mg, 0.007 mmol) then flushed with Ar for 5 min. Then DMF (2 mL), MeOH (1 mL) and triethylamine (0.2 mL, 1.4 mmol) were added and the solution was sparged with CO$_{(g)}$ for 10 min then placed under a CO balloon and heated to 60° C. After 18 h, the solution was concentrated in vacuo and purified by reverse phase HPLC (20-100% CH$_3$CN/water with a 0.1% TFA modifier) to afford the title compound 12. $^1$H NMR (600 MHz, CDCl$_3$) δ 9.15 (d, 1H); 8.92 (d, 1H); 8.72 (d, 1H); 8.30 (dd, 1H); 7.70-7.73 (m, 2H); 7.67 (d, 1H); 7.44-7.55 (m, 4H);

7.30 (d, 1H); 3.98 (s, 3H). LRMS (APCI) calc'd for (C$_{22}$H$_{16}$NO$_3$) [M+H]+, 342.1; found 342.1.

Example 9

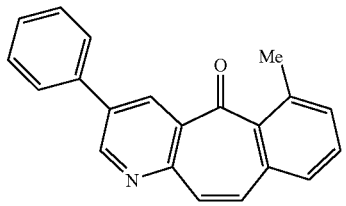

6-methyl-3-phenyl-5H-benzo[4,5]cyclohepta[1,2-b]pyridin-5-one 6-bromo-3-phenyl-5H-benzo[4,5]cyclohepta[1,2-b]pyridin-5-one (10 mg, 0.027 mmol), trimethylboroxine (10 μL, 0.071 mmol), tetrakis(triphenylphosphine)palladium (0) (5 mg, 0.004 mmol), and potassium carbonate (15 mg, 0.108 mmol) were combined in a dry flask. The flask was purged with argon and 0.5 mL of 10% aqueous dioxane were added. Argon was bubbled through the solution for 5 minutes and the solution was stirred and heated to 100° C. After 12 hours, the reaction mixture was filtered through a pad of Celite, eluted with EtOAc, washed with brine, dried over sodium sulfate, filtered, concentrated and purified by reverse phase HPLC (30-100% acetonitrile/water gradient, 0.1% trifluoroacetic acid modifier) to afford the title compound. $^1$H NMR (600 MHz, CD$_3$OD) δ 9.11 (d, 1H), 8.54 (d, 1H), 7.80 (d, 2H), 7.54 (m, 5H), 7.48 (m, 2H), 7.26 (d, 2H), 2.56 (s, 3H). LRMS (APCI) calculated for C$_{21}$H$_{16}$NO [M+H]+, 298.1; found 298.1.

Example 10

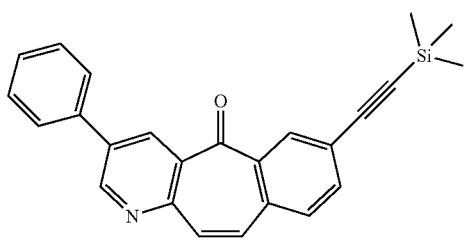

3-phenyl-7-[(trimethylsilyl)ethynyl]-5H-benzo[4,5]cyclohepta[1,2-b]pyridin-5-one A test tube fitted with a Teflon lined septum was charged with compound 4 (100.0 mg, 0.276 mmol), PdCl$_2$(PPh$_3$)$_2$ (19 mg, 0.03 mmol), CuI (11 mg, 0.06 mmol), and 3 mL of DMF. The mixture was sparged with Ar for 5 min, then triethylamine (0.19 mL, 1.4 mmol) and trimethylsilylacetylene (0.06 mL, 0.41 mmol) were added and the mixture was heated to 50° C. for 18 h. The solution was diluted with EtOAc and washed with water and brine then dried over Na$_2$SO$_4$. The solution was concentrated in vacuo and purified by flash column chromatography (10-70% EtOAc/hexanes gradient) to afford the title compound 14. $^1$H NMR (600 MHz, CDCl$_3$) δ 8.88 (d, 1H); 8.51 (s, 1H); 8.12 (d, 1H); 7.41-7.48 (m, 3H); 7.18-7.30 (m, 5H); 7.01 (d, 1H); 0.00 (s, 9H). LRMS (APCI) calc'd for (C$_{25}$H$_{22}$NOSi) [M+H]+, 380.1; found 380.1.

Example 11

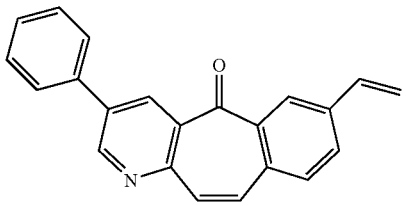

3-phenyl-7-vinyl-5H-benzo[4,5]cyclohepta[1,2-b]pyridin-5-one

A test tube fitted with a Teflon lined septum was charged with compound 4 (100.0 mg, 0.276 mmol), PdCl$_2$(PPh$_3$)$_2$ (10 mg, 0.014 mmol), tri-1-butylvinyltin (0.089 mL, 0.30 mmol) and 3 HL of dioxane. The mixture was sparged with Ar for 10 min, then heated to 95° C. overnight. The solution was diluted with EtOAc and washed with water and brine then dried over Na$_2$SO$_4$. The solution was concentrated in vacuo and purified by flash column chromatography (10-70% EtOAc/hexanes gradient) to afford a white solid. This sold was dissolved in 10 mL of 1:1:1 EtOAc/dichloromethane/water mixture and 82 mg of CsF was added. After 2 h, the organic layer was separated and the aqueous layer was extracted with EtOAc and the organic layers dried over Na$_2$SO$_4$. The solution was concentrated in vacuo and purified by flash column chromatography (0-10-20-100% EtOAc/hexanes step gradient) to afford the title compound 15. $^1$H NMR (600 MHz, CDCl$_3$) δ 9.14 (s, 1H); 8.78 (s, 1H); 8.30 (s, 1H); 7.75-7.78 (m, 1H); 7.70-7.74 (m, 2H); 7.59 (d, 1H); 7.50-7.55 (m, 2H); 7.40-7.47 (m, 2H); 7.30 (d, 1H); 6.85 (dd, 1H); 5.95 (d, 1H); 5.43 (d, 1H). LRMS (APCI) calc'd for (C$_{22}$H$_{16}$NO) [M+H]+, 310.1; found 310.2.

Example 12

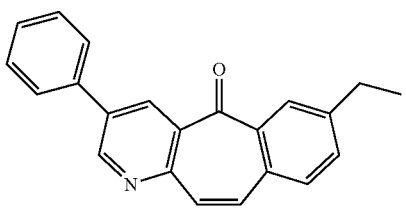

7-ethyl-3-phenyl-5H-benzo[4,5]cyclohepta[1,2-b]pyridin-5-one

A flask was charged with compound 15 (20.0 mg, 0.065 mmol), 8 mg of 10% palladium on carbon, 3 mL of EtOH, 3 mL of EtOAc, and 0.5 mL of 1N HCl. The flask was fitted with a three-way stopcock with a hydrogen balloon, then evacuated and flushed with hydrogen four times. After 1 h the reaction mixture was filtered through a 0.45μ Nylon syringe filter, concentrated in vacuo and purified by reverse phase HPLC (20-100% CH₃CN/water with a 0.1% TFA modifier) to afford the title compound 16. ¹H NMR (600 MHz, CDCl₃) δ 9.13 (s, 1H); 8.75 (s, 1H); 8.13 (s, 1H); 7.70-7.73 (m, 2H); 7.49-7.55 (m, 4H); 7.42-7.46 (m, 1H); 7.37 (d, 1H); 7.28 (d, 1H); 2.81 (q, 2H); 1.31 (t, 3H). LRMS (APCI) calc'd for (C₂₂H₁₈NO) [M+H]+, 312.1; found 312.2.

Example 13

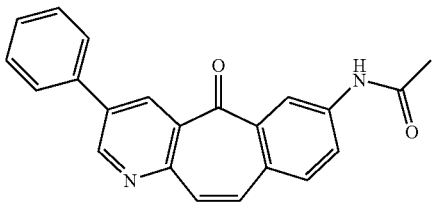

17

N-(5-oxo-3-phenyl-5H-benzo[4,5]cyclohepta[1,2-b]pyridin-7-yl)acetamide

A flask was charged with compound 4 (25.0 mg, 0.069 mmol), CuI (0.6 mg, 0.003 mmol) and K₂CO₃ (19 mg, 0.14 mmol) then flushed with Ar for 5 min. DMF (1 mL) was added and the mixture was sparged with Ar for 5 min then N,N'-dimethylethylenediamine (one drop from a 22 G needle) was added and the mixture was sparged with Ar for an additional 10 min. The mixture was heated to 80° C. for 18 h, then at 110° C. for an additional 24 h. The mixture was cooled to room temperature and filtered through a pad of Celite, concentrated in vacuo and purified by reverse phase HPLC (20-100% CH₃CN/water with a 0.1% TFA modifier) to afford the title compound 17. ¹H NMR (600 MHz, CDCl₃) δ 9.09 (d, 1H); 8.71 (d, 1H); 8.24 (dd, 1H); 8.05 (d, 1H); 7.64-7.67 (m, 2H); 7.56 (d, 1H); 7.42-7.48 (m, 3H); 7.37-7.41 (m, 1H); 7.31 (d, 1H); 7.21 (d, 1H); 2.18 (s, 3H). LRMS (APCI) calc'd for (C₂₂H₁₆N₂O₂Na) [M+Na]⁺, 363.1; found 363.1.

Example 14

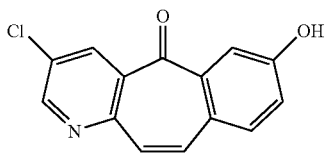

18

Step 1: (3-chloro-5-oxo-5H-benzo[4,5]cyclohepta[1,2-b]pyridin-7-yl)boronic acid 7-bromo-3-chloro-5H-benzo[4,5]cyclohepta[1,2-b]pyridin-5-one (1.00 g, 3.12 mmol), Pd₂(dba)₃ (0.146 g, 0.16 mmol), tricyclohexylphosphine (0.104 g, 0.37 mmol), bis(pinacolato)diboron (0.87 g, 3.43 mmol) and potassium acetate (0.61 g, 6.23 mmol) were mixed in a dry flask through which argon was purged. The flask was charged with 40 mL of dry dioxane and argon was bubbled through the solution for 15 minutes. The reaction was heated to 95° C. and stirred under argon. After 6 h, the reaction mixture was poured into 500 mL of ethyl acetate and 100 mL of saturated aqueous ammonium chloride. The organic layer was separated, dried with magnesium sulfate, filtered, and concentrated to afford the title compound. LRMS (APCI) calculated for C₁₄H₁₀BClNO₃ [M+H]+, 286.0; found 286.1.

Step 2: 3-chloro-7-hydroxy-5H-benzo[4,5]cyclohepta[1,2-b]pyridin-5-one (Compound 18)

(3-chloro-5-oxo-5H-benzo[4,5]cyclohepta[1,2-b]pyridin-7-yl)boronic acid (1.00 g, 3.5 mmol) was dissolved in a 0° C. solution of 25 mL of THF, 25 mL of water, 0.5 mL of acetic acid and 0.5 mL of 30% (w/w) hydrogen peroxide. The solution was stirred and allowed to warm to ambient temperature. After 6 h, the reaction mixture was partially concentrated and dissolved in 500 mL ethyl acetate. The organic layer was washed with water (2×100 mL), dried with magnesium sulfate, filtered, and concentrated to afford solids. The solids were dissolved in 20 mL dichloromethane and 60 mL hexanes and stirred as solids crystallized from the solution. After 2 hours, the crystalline solids were filtered and dried to afford the title compound. ¹H NMR (600 MHz, DMSO-D₆) δ 10.50 (s, 1H); 8.93 (s, 1H); 8.45 (s, 1H); 7.68 (d, 1H); 7.58 (d, 1H); 7.39 (d, 1H); 7.23 (d, 1H); 7.12 (d, 1H). LRMS (APCI) calculated for C₁₄H₉ClNO₂ [M+H]+, 258.0; found 258.1.

Example 15

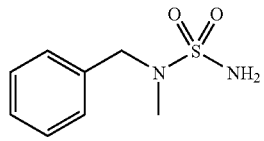

A

N-benzyl-N-methylsulfamide

N,N-dialkyl sulfamides were prepared according to the published procedures: Winum, J-Y; Toupet, L.; Barragan, V.; Dewynter, G.; Montero, J.-L. *Org. Letters* 2001, 3, 2241-2243 and Casini, A.; Winum, J.-Y.; Montero, J.-L.; Scozzafava, A.; Supuran, C. *Bioorganic & Medicinal Chemistry Letters* 2003, 13, 837-840. A flask was charged with N-tert-butoxycarbonyl-N-[4-(dimethylazaniumylidene)-1,4-dihydropyridin-1-ylsulfonyl]azanide (500 mg, 1.66 mmol) and methylbenzylamine (0.21 mL, 1.66 mmol) in 10 mL of CH₂Cl₂. After 2 h, the solution was concentrated in vacuo and purified by flash column chromatography (5-70% EtOAc/hexanes) to afford 304 mg of tert-butyl {[benzyl(methyl)amino]sulfonyl}carbamate.

tert-butyl {[benzyl(methyl)amino]sulfonyl}carbamate (257 mg, 0.856 mmol) was dissolved in 5 mL of CH₂Cl₂ and 1 mL of trifluoroacetic acid. After 1 h an additional 1 mL of trifluoroacetic acid was added and the solution was stirred for a further 2 h. The solution was neutralized with aqueous saturated NaHCO₃, diluted in CH₂Cl₂, washed with saturated NaHCO₃ and brine, then dried over Na₂SO₄. The solution was concentrated in vacuo to afford the title compound A. ¹H NMR (600 MHz, CDCl₃) δ 7.30-7.38 (m, 5H); 4.27-4.31 (m, 4H); 2.73 (s, 3H). LRMS (APCI) calc'd for (C₈H₁₃N₂O₂S) [M+H]+, 201.1; found 200.8.

The following compounds were made according to Scheme 3. Additional synthetic modifications were employed in the preparation of some of the compounds. Compounds 28 and 29 were isolated from the reaction mixture of Compounds 26 and 27 respectively. Compound 31 was prepared by hydrolysis of Compound 12. Compound 32 was prepared by EDCI mediated coupling of methylamine to Compound 31. Compound 36 was prepared by TBAF mediated desilylation of Compound 14. Compound 41 was isolated by subjecting Compound 4 to the reaction conditions described for the formation of Compound 10. Compound 43 was prepared from Compound 3 by Cu(I) Br mediated coupling with sodium methoxide in a manner similar to that described for Compound 10.

TABLE 2

| Compound | Structure | Name | MS (M + 1) |
|---|---|---|---|
| 19 | 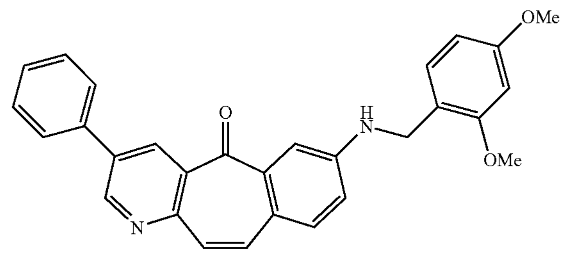 | 7-[(2,4-dimethoxybenzyl)amino]-3-phenyl-5H-benzo[4,5]cyclohepta[1,2-b]pyridin-5-one | calc'd 449.2 (M + H)+; found 449.2 (M + H)+ |
| 20 | 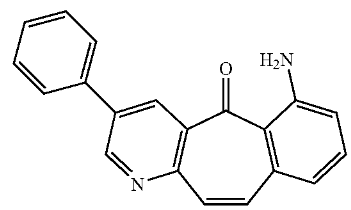 | 6-amino-3-phenyl-5H-benzo[4,5]cyclohepta[1,2-b]pyridin-5-one | calc'd 299.1 (M + H)+; found (M + H)+ |
| 21 | 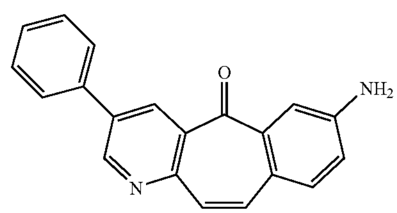 | 7-amino-3-phenyl-5H-benzo[4,5]cyclohepta[1,2-b]pyridin-5-one | calc'd 299.1 (M + H)+; found 299.1 (M + H)+ |
| 22 | 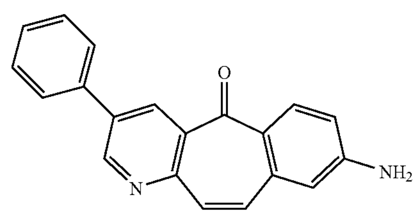 | 8-amino-3-phenyl-5H-benzo[4,5]cyclohepta[1,2-b]pyridin-5-one | calc'd 299.1 (M + H)+; found (M + H)+ |
| 23 | 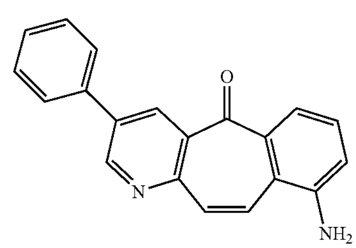 | 9-amino-3-phenyl-5H-benzo[4,5]cyclohepta[1,2-b]pyridin-5-one | calc'd 299.1 (M + H)+; found (M + H)+ |
| 24 | 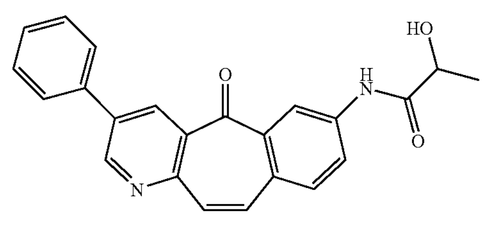 | 2-hydroxy-N-(5-oxo-3-phenyl-5H-benzo[4,5]cyclohepta[1,2-b]pyridin-7-yl)propanamide | calc'd 371.1 (M + H)+; found 371.1 (M + H)+ |

TABLE 2-continued

| Compound | Structure | Name | MS (M + 1) |
|---|---|---|---|
| 25 | 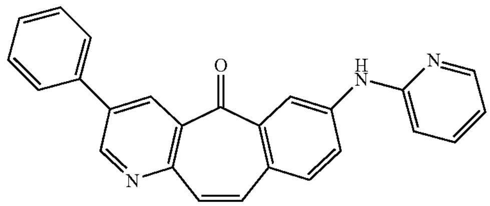 | 3-phenyl-7-(pyridin-2-ylamino)-5H-benzo[4,5]cyclohepta[1,2-b]pyridin-5-one | calc'd 376.1 (M + H)+; found 376.1 (M + H)+ |
| 26 | 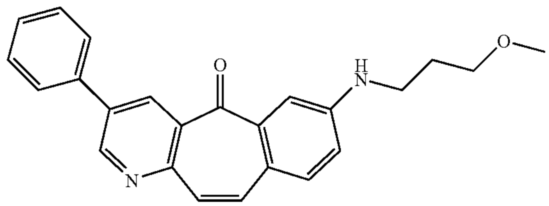 | 7-[(3-methoxypropyl)amino]-3-phenyl-5H-benzo[4,5]cyclohepta[1,2-b]pyridin-5-one | calc'd 371.2 (M + H)+; found 371.2 (M + H)+ |
| 27 | 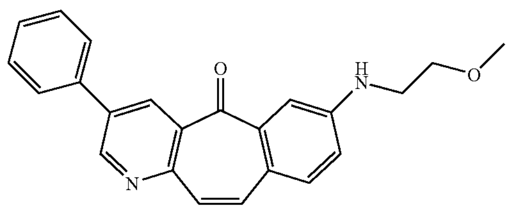 | 7-[(2-methoxyethyl)amino]-3-phenyl-5H-benzo[4,5]cyclohepta[1,2-b]pyridin-5-one | calc'd 357.2 (M + H)+; found 357.2 (M + H)+ |
| 28 | 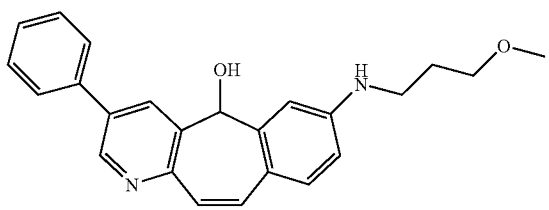 | 7-[(3-methoxypropyl)amino]-3-phenyl-5H-benzo[4,5]cyclohepta[1,2-b]pyridin-5-ol | calc'd 373.2 (M + H)+; found 373.2 (M + H)+ |
| 29 | 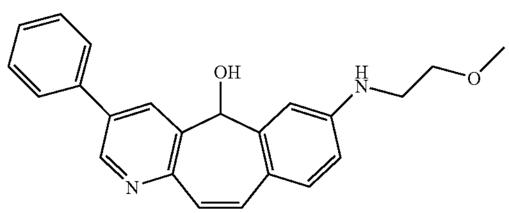 | 7-[(2-methoxyethyl)amino]-3-phenyl-5H-benzo[4,5]cyclohepta[1,2-b]pyridin-5-one | calc'd 359.2 (M + H)+; found 359.2 (M + H)+ |
| 30 | 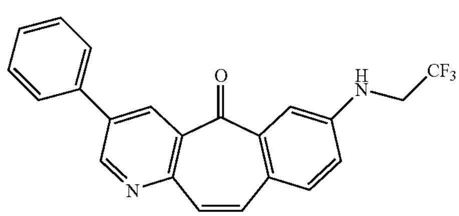 | 3-phenyl-7-[(2,2,2-trifluoroethyl)amino]-5H-benzo[4,5]cyclohepta[1,2-b]pyridin-5-one | calc'd 381.1 (M + H)+; found 381.1 (M + H)+ |
| 31 | 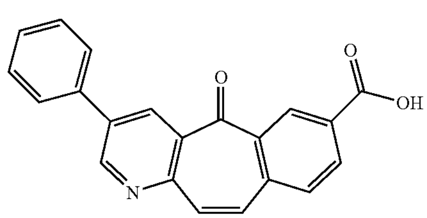 | 5-oxo-3-phenyl-5H-benzo[4,5]cyclohepta[1,2-b]pyridine-7-carboxylic acid, isolated as the HCl salt | calc'd 328.1 (M + H)+; found 328.1 (M + H)+ |

TABLE 2-continued

| Compound | Structure | Name | MS (M + 1) |
|---|---|---|---|
| 32 | 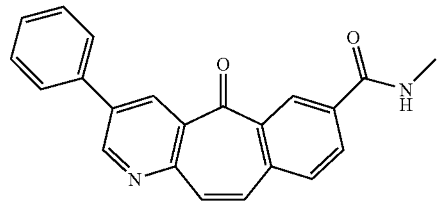 | N-methyl-5-oxo-3-phenyl-5H-benzo[4,5]-cyclohepta[1,2-b]pyridine-7-carboxamide, TFA salt | calc'd 341.1 (M + H)+; found 341.1 (M + H)+ |
| 33 | 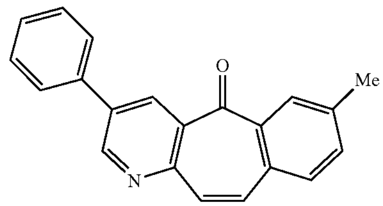 | 7-methyl-3-phenyl-5H-benzo[4,5]cyclohepta[1,2-b]pyridin-5-one | calc'd 298.1 (M + H)+; found 298.1 (M + H)+ |
| 34 | 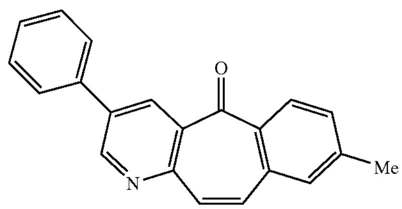 | 8-methyl-3-phenyl-5H-benzo[4,5]cyclohepta[1,2-b]pyridin-5-one | calc'd 298.1 (M + H)+; found (M + H)+ |
| 35 | 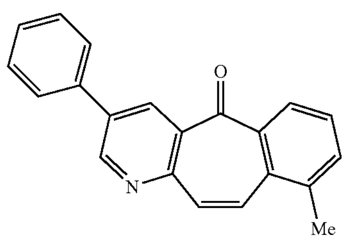 | 9-methyl-3-phenyl-5H-benzo[4,5]cyclohepta[1,2-b]pyridin-5-one | calc'd 298.1 (M + H)+; found (M + H)+ |
| 36 | 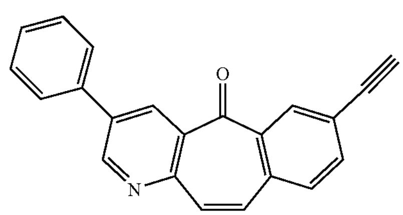 | 7-ethynyl-3-phenyl-5H-benzo[4,5]cyclohepta[1,2-b]pyridin-5-one | calc'd 308.1 (M + H)+; found 308.1 (M + H)+ |
| 37 | 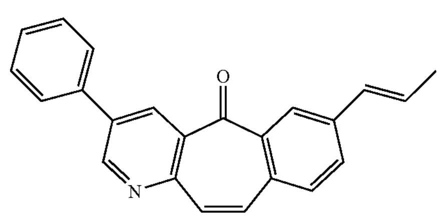 | 3-phenyl-7-[(1E/Z)-prop-1-en-1-yl]-5H-benzo[4,5]cyclohepta[1,2-b]pyridin-5-one | calc'd 324.1 (M + H)+; found 324.2 (M + H)+ |
| 38 | 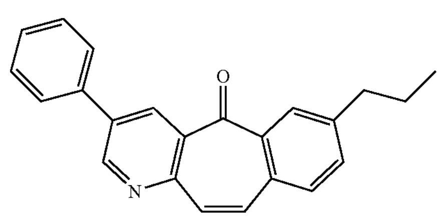 | 3-phenyl-7-propyl-5H-benzo[4,5]cyclohepta[1,2-b]pyridin-5-one | calc'd 326.1 (M + H)+; found 326.2 (M + H)+ |

TABLE 2-continued

| Compound | Structure | Name | MS (M + 1) |
|---|---|---|---|
| 39 | 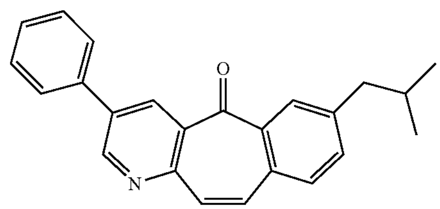 | 7-isobutyl-3-phenyl-5H-benzo[4,5]cyclohepta[1,2-b]pyridin-5-one | calc'd 340.2 (M + H)+; found 340.2 (M + H)+ |
| 40 | 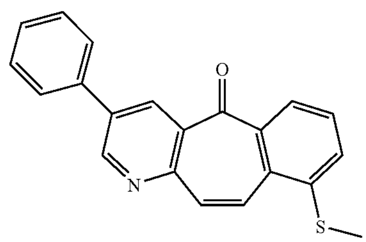 | 9-(methylthio)-3-phenyl-5H-benzo[4,5]cyclohepta[1,2-b]pyridin-5-one | calc'd 330.0 (M + H)+; found (M + H)+ |
| 41 | 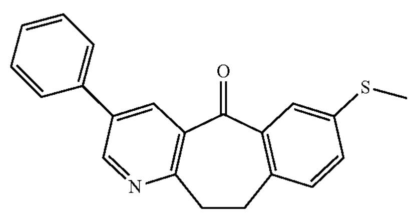 | 7-(methylthio)-3-phenyl-10,11-dihydro-5H-benzo[4,5]cyclohepta[1,2-b]pyridin-5-one | calc'd 332.1 (M + H)+; found 332.1 (M + H)+ |
| 42 | 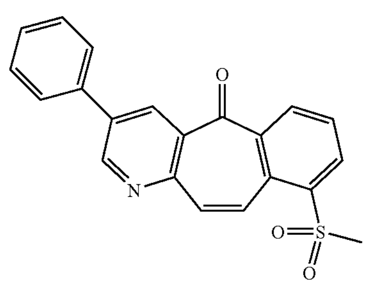 | 9-(methylsulfonyl)-3-phenyl-5H-benzo[4,5]cyclohepta[1,2-b]pyridin-5-one | calc'd 362.0 (M + H)+; found (M + H)+ |
| 43 | 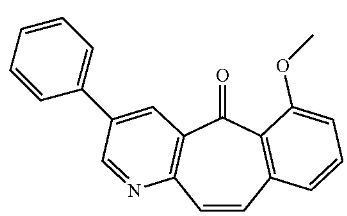 | 6-methoxy-3-phenyl-5H-benzo[4,5]cyclohepta[1,2-b]pyridin-5-one | calc'd 314.1 (M + H)+; found (M + H)+ |
| 44 | 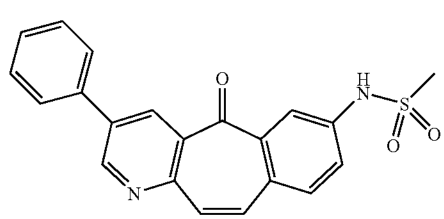 | N-(5-oxo-3-phenyl-5H-benzo[4,5]cyclohepta[1,2-b]pyridin-7-yl)methanesulfonamide | calc'd 377.1 (M + H)+; found 377.1 (M + H)+ |
| 45 | 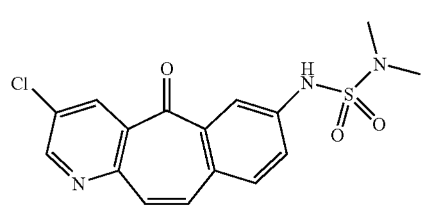 | N'-(3-chloro-5-oxo-5H-benzo[4,5]cyclohepta[1,2-b]pyridin-7-yl)-N,N-dimethylsulfamide | calc'd 364.0 (M + H)+; found 363.7 (M + H)+ |

TABLE 2-continued

| Compound | Structure | Name | MS (M + 1) |
|---|---|---|---|
| 46 | 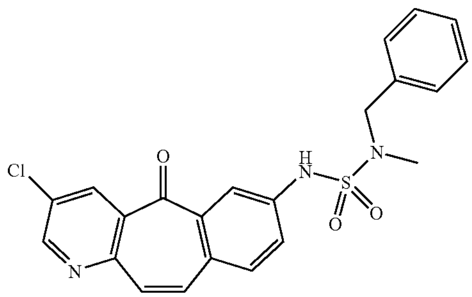 | N-benzyl-N'-(3-chloro-5-oxo-5H-benzo[4,5]cyclohepta[1,2-b]pyridin-7-yl)-N-methylsulfamide | calc'd 440.1 (M + H)+; found 439.6 (M + H)+ |
| 47 | 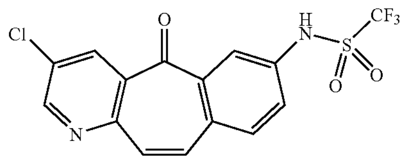 | N-(3-chloro-5-oxo-5H-benzo[4,5]cyclohepta[1,2-b]pyridin-7-yl)-1,1,1-trifluoromethane-sulfonamide | calc'd 389.0 (M + H)+; found 388.6 (M + H)+ |
| 48 | 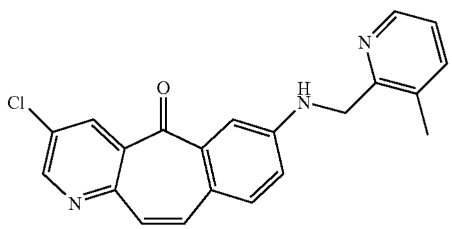 | 3-chloro-7-{[(3-methylpyridin-4-yl)methyl]amino}-5H-benzo[4,5]cyclohepta[1,2-b]pyridin-5-one | calc'd 362.1 (M + H)+; found 362.1 (M + H)+ |
| 49 | 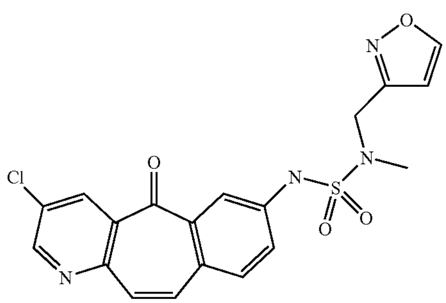 | N'-(3-chloro-5-oxo-5H-benzo[4,5]cyclohepta[1,2-b]pyridin-7-yl)-N-(isoxazol-3-ylmethyl)-N-methylsulfamide | calc'd 431.1 (M + H)+; found 431.0 (M + H)+ |
| 50 | 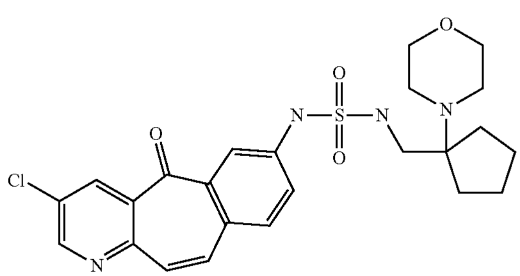 | N-(3-chloro-5-oxo-5H-benzo[4,5]cyclohepta[1,2-b]pyridin-7-yl)-N'-[(1-morpholin-4-ylcyclo-pentyl)meth-yl]sulfamide | calc'd 503.1 (M + H)+; found 503.2 (M + H)+ |
| 51 | 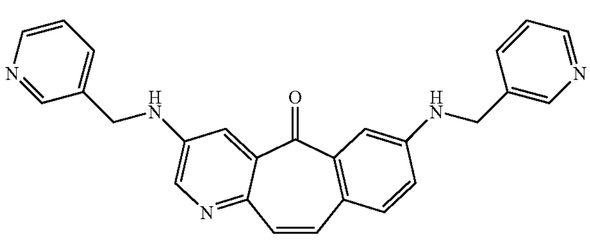 | 3,7-bis[(pyridin-3-ylmethyl)amino]-5H-benzo[4,5]cyclohepta[1,2-b]pyridin-5-one | calc'd 420.2 (M + H)+; found 420.2 (M + H)+ |

TABLE 2-continued

| Compound | Structure | Name | MS (M + 1) |
|---|---|---|---|
| 52 | 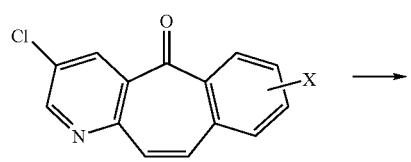 | 3-chloro-7-[(pyridin-2-ylmethyl)amino]-5H-benzo[4,5]cyclohepta[1,2-b]pyridin-5-one | calc'd 348.1 (M + H)+; found 348.1 (M + H)+ |

Scheme 4

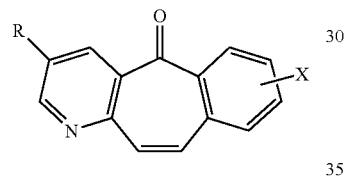

Example 16

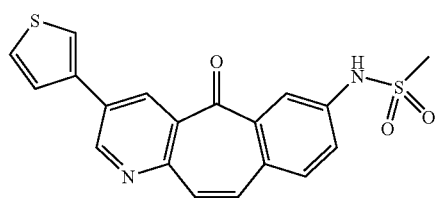

N-[5-oxo-3-(3-thienyl)-5H-benzo[4,5]cyclohepta[1,2-b]pyridin-7-yl]methanesulfonamide N-(3-chloro-5-oxo-5H-benzo[4,5]cyclohepta[1,2-b]pyridin-7-yl)methanesulfonamide (0.100 g, 0.30 mmol), 3-thienylboronic acid (0.077 g, 0.60 mmol), tetrakis(triphenylphosphine)palladium (0) (10 mg, 0.009 mmol) and potassium carbonate (0.124 g, 0.90 mmol) were combined in a dry flask. The flask was purged with argon and 5 mL of dry dioxane was added. Argon was bubbled through the solution for 5 minutes and the solution was stirred and heated to 100° C. After 12 hours, the reaction mixture was poured into 100 mL of ethyl acetate, 100 mL of water, and 25 mL of saturated ammonium chloride. The organic layer was separated, dried with magnesium sulfate, filtered, concentrated, and purified by reverse phase HPLC (30-100% acetonitrile/water gradient, 0.1% trifluoroacetic acid modifier) to afford the title compound. $^1$H NMR (600 MHz, DMSO-D$_6$) δ 10.40 (s, 1H); 9.34 (d, 1H); 8.70 (d, 1H); 8.28 (s, 1H); 8.00 (d, 1H); 7.78 (m, 2H); 7.73 (m, 1H); 7.58 (dd, 1H); 7.38 (d, 1H); 7.26 (d, 1H); 3.08 (s, 3H). LRMS (APCI) calculated for C$_{19}$H$_{15}$N$_2$O$_3$S$_2$ [M+H]+, 383.0; found 383.1.

Example 16

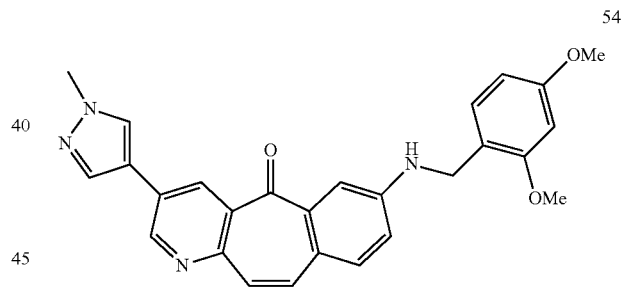

7-[(2,4-dimethoxybenzyl)amino]-3-(1-methyl-1H-pyrazol-4-yl)-5H-benzo[4,5]cyclohepta[1,2-b]pyridin-5-one A flask was charged with compound 7 (200.0 mg, 0.492 mmol), 1-methyl-4-(4,4,5,5-tetramethyl-1,3,2-dioxaborolan-2-yl)-1H-pyrazole (205 mg, 0.983 mmol), Pd(dppf)Cl$_2$ (18. mg, 0.025 mmol) and K$_2$CO$_3$ (204 mg, 1.48 mmol) then flushed with Ar for 2 min. DMF (4 mL) was added and the vessel was heated in the Biotage Initiator series microwave for 40 min. at 175° C. The mixture was then diluted with EtOAc, washed with water and brine, then dried over Na$_2$SO$_4$. The solution was concentrated in vacuo and purified by reverse phase HPLC (20-100% CH$_3$CN/water with a 0.1% TFA modifier) to afford the title compound 54 $^1$H NMR (600 MHz, CD$_3$OD) δ 8.88 (s, 1H); 8.54 (s, 1H); 8.04 (s, 1H); 7.90 (s, 1H); 7.43 (s, 1H); 7.35 (d, 1H); 7.14 (d, 1H); 7.10 (d, 1H); 6.94-6.98 (m, 1H); 6.92 (d, 1H); 6.50 (m, 1H); 6.39 (dd, 1H);

5.47 (s, 1H); 4.29 (s, 2H); 3.89 (s, 3H); 3.83 (s, 3H); 3.71 (s, 3H). LRMS (APCI) calc'd for ($C_{27}H_{25}N_4O_3$) [M+H]+, 453.2; found 453.1.

Example 18

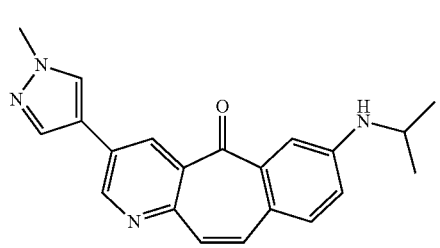

7-(isopropylamino)-3-(1-methyl-1H-pyrazol-4-yl)-5H-benzo[4,5]cyclohepta[1,2-b]pyridin-5-one 3-chloro-7-(isopropylamino)-5H-benzo[4,5]cyclohepta[1,2-b]pyridin-5-one (0.030 g, 0.09 mmol), tris(dibenzylideneacetone)dipalladium (0.004 g, 0.004 mmol), 1-methyl-4-(4,4,5,5-tetramethyl-1,3,2-dixaborolan-2-yl)-1H-pyrazole (0.039 g, 0.19 mmol), potassium fluoride (0.018 g, 0.316 mmol) and tri-t-butylphosphonium tetrafluoroborate (0.003 g, 0.009 mmol) were combined in a microwave tube. The tube was purged with argon and 2 mL of dry DMF was added. The solution was stirred and heated to 180° C. in the Biotage Initiator series microwave. After 30 minutes, saturated ammonium chloride was added and the mixture was extracted with ethyl acetate, washed with brine, dried over magnesium sulfate, filtered, concentrated in vacuo, and purified by reverse phase HPLC (20-70% acetonitrile/water gradient, 0.05% trifluoroacetic acid modifier) to afford the title compound. $^1$H NMR (600 MHz, CDCl$_3$) δ 8.93 (d, 1H); 8.64 (bs, 1H); 7.86 (s, 1H); 7.75 (s, 1H); 7.45 (d, 1H); 7.39 (d, 1M); 7.14 (m, 2H); 6.85 (dd, 1H); 3.93 (s, 3H); 3.76 (septet, 1H); 1.22 (d, 6H). LRMS (APCI) calc'd for ($C_{21}H_{21}N_4O$) [M+H]+, 345.2; found 345.2.

Example 19

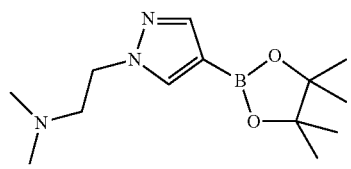

N,N-dimethyl-2-[4-(4,4,5,5-tetramethyl-1,3,2-dioxaborolan-2-yl)-1H-pyrazol-1-yl]ethanamine 4-(4,4,5,5-tetramethyl-1,3,2-dioxaborolan-2-yl)-1H-pyrazole (0.250 g, 1.29 mmol), dimethylamino ethyl chloride (0.37 g, 2.58 mmol) and potassium carbonate (0.534 g, 3.87 mmol) were dissolved in 3 mL of dry dimethylformamide. The reaction mixture was heated in a Biotage Initiator series microwave at 190° C. for 1 hour. The reaction mixture was poured into 300 mL of ethyl acetate and 50 of mL brine. The organic layer was separated, dried with magnesium sulfate, filtered, and concentrated to afford the title compound. $^1$H NMR (600 MHz, CDCl$_3$) δ 7.76 (s, 1H); 7.72 (s, 1H); 4.22 (t, 2H); 2.94 (s, 3H); 2.86 (s, 3H); 2.74 (t, 2H); 1.29 (s, 12H).

Example 20

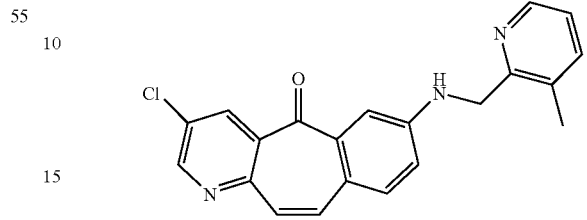

3-chloro-7-{[(3-methylpyridin-2-yl)methyl]amino}-5H-benzo[4,5]cyclohepta[1,2-b]pyridin-5-one (Compound 56)

7-bromo-3-chloro-5H-benzo[4,5]cyclohepta[1,2-b]pyridin-5-one (0.100 g, 0.312 mmol), 2-aminomethyl-3-methylpyridine (0.038 g, 0.312 mmol), copper iodide (0.006 g, 0.031 mmol), potassium carbonate (0.086 g, 0.621 mmol), and dl-proline (0.007 g, 0.062 mmol) were combined in a flask. Dimethyl sulfoxide (2.0 mL) was added and argon was bubbled through the solution for several minutes. The solution was stirred and heated at 70° C. overnight. Once complete the solution was cooled to ambient temperature, diluted with ethyl acetate and washed with water. The organic layer was dried over magnesium sulfate, filtered, concentrated in vacuo and purified by column chromatography (0-40% ethyl acetate/hexane gradient) to afford the title compound.

Example 21

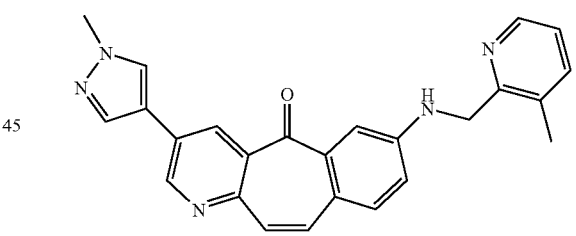

3-(1-methyl-1H-pyrazol-4-yl)-7-{[(3-methylpyridin-2-yl)methyl]amino}-5H-benzo[4,5]cyclohepta[1,2-b]pyridin-5-one (Compound 57)

3-chloro-7-{[(3-methylpyridin-2-yl)methyl]amino}-5H-benzo[4,5]cyclohepta[1,2-b]pyridin-5-one (0.170 g, 0.470 mmol), tris(dibenzylideneacetone)dipalladium (0.021 g, 0.023 mmol), 1-methyl-4-(4,4,5,5-tetramethyl-1,3,2-dixaborolan-2-yl)-1H-pyrazole (0.196 g, 0.940 mmol), and tri-t-butylphosphonium tetrafluoroborate (0.013 g, 0.023 mmol) were combined in a flask. The flask was purged with argon and 4.0 mL of dry DMF was added. The solution was stirred and heated to 130° C. After 5 hours, the solution was cooled to ambient temperature. Saturated ammonium chloride was added and the mixture was extracted with ethyl acetate, washed with brine, dried over magnesium sulfate, filtered, concentrated in vacuo, and purified by reverse phase HPLC (20-70% acetonitrile/water gradient, 0.1% trifluoroacetic acid modifier) to afford the title compound. $^1$H NMR (600 MHz, CDCl$_3$) δ9.13 (d, 1H); 8.55 (d, 1H); 8.42 (s, 1H); 8.36 (d, 1H); 8.09 (s, 1H); 7.59 (bd, 1H); 7.53 (d, 1H); 7.47 (d, 1H); 7.24-7.21 (m, 3H); 7.05 (t, 1H); 7.02 (d, 1H), 4.46 (d, 2H); 3.88 (s, 3H); 2.36 (s, 3H). LRMS (APCI) calc'd for (C$_{25}$H$_{22}$N$_5$O) [M+H]+, 408.1; found 408.2.

Example 22

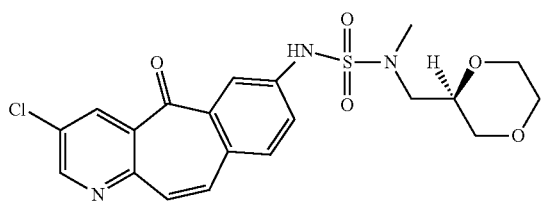

N'-(3-chloro-5-oxo-5H-benzo[4,5]cyclohepta[1,2-b]pyridin-7-yl)-N-[(2R)-1,4-dioxan-2-ylmethyl]-N-methylsulfamide (Compound 58)

Step 1: Benzyl (1,4-dioxan-2-ylmethyl)methylcarbamate 1-(1,4-dioxan-2-yl)-N-methylmethanamine hydrochloride (4.83 g, 29 mmol) was dissolved in 100 mL dichloromethane. Benzyl chloridocarbonate (4.9 mL, 35 mmol) and triethylamine (10 mL, 72 mmol) were added. The solution was stirred at ambient temperature. After 12 hours, the solution was concentrated, then diluted with ethyl acetate, and washed with saturated sodium bicarbonate and water. The organic layer was separated, dried with magnesium sulfate, filtered, concentrated in vacuo, and purified by silica chromatography (0-100% ethyl acetate/hexanes gradient) to afford the title compound (racemic mixture).

The racemic mixture (6.35 g) was dissolved in 24 mL heptane and 8 mL isopropanol. Material was resolved on chiral AD column (15% isopropanol/heptane) to afford 2.9 g enantiomer A [τ$_R$: 9.43 min (analytical chiral HPLC, AD column, 0.46 cm×25 cm cm id, 15% isopropanol/heptane, isocratic, flow rate=0.75 mL/min)] and 2.9 g enantiomer B [τ$_R$: 10.92 min (analytical chiral HPLC, AD column, 0.46 cm×25 cm cm id, 15% isopropanol/heptane, isocratic, flow rate=0.75 mL/min)]. LRMS (APCI) calc'd for (C$_{14}$H$_{20}$NO$_4$) [M+H]+, 266.1; found, 266.2.

Step 2: 1-(1,4-dioxan-2-yl)-N-methylmethanamine hydrochloride

Benzyl (1,4-dioxan-2-ylmethyl)methylcarbamate (Enantiomer A, 2.9 g, 10.9 mmol) was dissolved in 50 mL dry ethanol. 10% (w/w) palladium on carbon (0.29 g) and 1.0 mL 10N HCl were added. The flask was sealed and flushed with hydrogen. Stirred solution under a hydrogen balloon. After 12 hours, the solution was filtered through celite and concentrated in vacuo to afford the title compound. $^1$H NMR (600 MHz, D$^6$-DMSO) δ8.64 (s, 2H); 3.82-3.75 (m, 2H); 3.69 (d, 1H); 3.64 (d, 1H); 3.59 (m, 1H); 3.44 (m, 1H); 3.22 (t, 1H); 2.94-2.84 (m, 2H); 2.51 (s, 3H).

Step 3: tert-butyl {[((2R)-1,4-dioxan-2-ylmethyl)(methyl)amino]sulfonyl}carbamate 1-(1,4-dioxan-2-yl)-N-methylmethanamine hydrochloride (0.760 g, 4.55 mmol), N-[1-{[(tert-butoxycarbonyl)amino]sulfonyl}pyridin-4(1H)-ylidene]-N-methylmethanaminium (1.51 g, 5.00 mmol), and triethylamine (1.55 mL, 11.4 mmol) were slurried in 50 mL dichloromethane and stirred at ambient temperature. After 12 hours, the solution was concentrated in vacuo and purified by silica chromatography (50-100% ethyl acetate/hexanes gradient) to afford the title compound. LRMS (APCI) calc'd for (C$_{11}$H$_{22}$N$_2$O$_6$SNa) [M+Na]+, 333.1; found, 333.1.

Step 4: {[((2R)1,4-dioxan-2-ylmethyl)(methyl)amino]sulfonyl}ammonium trifluoroacetate tert-butyl {[(1,4-dioxan-2-ylmethyl)(methyl)amino]sulfonyl}carbamate (1.25 g, 4.03 mmol) was dissolved in 10 mL dichloromethane and 20 mL trifluoroacetic acid and stirred at ambient temperature. After 2 hours, the solution was concentrated and azeotroped twice with heptane to afford the title compound. LRMS (APCI) calc'd for (C$_6$H15N$_2$O$_4$S) [M+H]+, 211.1; found, 211.1.

Step 5: N'-(3-chloro-5-oxo-5H-benzo[4,5]cyclohepta[1,2-b]pyridin-7-yl)-N-[(2R)-1,4-dioxan-2-ylmethyl]-N-methylsulfamide 7-bromo-3-chloro-5H-benzo[4,5]cyclohepta[1,2-b]pyridin-5-one (1.41 g, 4.41 mmol), {[((2R) 1,4-dioxan-2-ylmethyl)(methyl)amino]sulfonyl}ammonium trifluoroacetate (1.30 g, 4.01 mmol), tris(dibenzylideneacetone)dipalladium (0.183 g, 0.20 mmol), 9,9-dimethyl-4,5-bis(diphenylphosphino) xanthene (0.347 g, 0.60 mmol), and cesium carbonate (3.91 g, 12.0 mmol) were combined in a dry flask. 50 mL dry dioxane was added and argon was bubbled through the solution for five minutes. The solution was stirred and heated to 95° C. After 2 hours, the solution was concentrated in vacuo, diluted with ethyl acetate, and washed with water and brine. The organic layer was isolated, dried with magnesium sulfate, filtered, concentrated in vacuo, and purified by silica chromatography (0-100% ethyl acetate/hexanes gradient) to afford the title compound. LRMS (APCI) calc'd for (C$_{20}$H$_{21}$ClN$_3$O$_5$S) [M+H]+, 450.1; found, 450.1.

Example 22A

Enantioselective Synthesis of Benzyl [(2S)-1,4-dioxan-2-ylmethyl]methylcarbamate Step 1: (2S)-2-[(benzyloxy)methyl]-1,4-dioxane (2R)-3-(benzyloxy)propane-1,2-diol (2.00 g, 11.0 mmol) and tetrabutylammonium bromide (708 mg, 2.20 mmol) were dissolved in 50 mL of 1,2-dichloroethane, then 50 mL of a 50% (w/w) aqueous sodium hydroxide solution was added quickly and the mixture was heated to 50° C. After 18 h, an additional 50 mL of 1,2-dichloroethane and 50 mL of 50% (w/w) sodium hydroxide solution was added. After 8 h, additional 50 mL of 1,2-dichloroethane was added. After 72 h, the mixture was diluted in diethyl ether, washed with water and brine, then dried over sodium sulfate and concentrated. The residue was purified by flash column chromatography (silica, ethylacetate/hexanes) to afford the title compound. ¹H NMR (600 MHz, CDCl₃) δ 7.26-7.35 (m, 5H); 4.51-4.56 (m, 2H); 3.72-3.82 (m, 4H); 3.67-3.71 (m, 1H); 3.58-3.64 (m, 1H); 3.38-3.48 (m, 3H).

Step 2: benzyl [(2S)-1,4-dioxan-2-ylmethyl]methylcarbamate

A round bottomed flask was charged with (2S)-2-[(benzyloxy)methyl]-1,4-dioxane (1.77 g, 8.48 mmol), 902 mg of 10% Pd/C and 50 mL of absolute ethanol. A three-way stopcock fitted with a hydrogen balloon was affixed to the flask, then the flask was evaporated and back-filled with hydrogen (4×) and stirred under the hydrogen atmosphere overnight. The mixture was filtered through Celite and concentrated to afford (2S)-1,4-dioxan-2-ylmethanol.

A round bottomed flask was charged with (2S)-1,4-dioxan-2-ylmethanol (115 mg, 0.973 mmol), triethylamine (0.204 mL, 1.46 mmol), and 5 mL of dichloromethane then cooled to −10° C. Methanesulfonyl chloride (91 μL, 1.17 mmol) was added by syringe and the solution was stirred for 30 minutes at −10° C. The solution was diluted in dichloromethane, washed with 1M HCl, and the aqueous layer was extracted with dichloromethane (2×). The combined organic layers were washed with saturated aqueous sodium bicarbonate (2×) and brine, then dried over sodium sulfate and concentrated to afford (2R)-1,4-dioxan-2-ylmethyl methanesulfonate.

Sodium hydride (29 mg, 0.74 mmol) was suspended in 2 mL of N,N-dimethylformamide (DMF) and cooled to 0° C. A solution of benzyl methylcarbamate (81 mg, 0.49 mmol) in 2 mL of DMF was added via syringe. After 20 minutes, a solution of (2R)-1,4-dioxan-2-ylmethyl methanesulfonate (191 mg, 0.97 mmol) in 2 mL of DMF was added by syringe and the mixture was heated to 70° C. After 2 h the mixture was cooled to ambient temperature, then diluted in diethyl ether, washed with water and brine, then dried over sodium sulfate and concentrated. The residue was purified by flash column chromatography (silica, ethylacetate/hexanes) to afford the title compound. LRMS (APCI) calc'd for (C₁₄H₂₀NO₄) [M+H]+, 266.1; found, 266.2.

Analysis of benzyl [(2S)-1,4-dioxan-2-ylmethyl]methylcarbamate by analytical HPLC [τ$_R$: 10.85 min (analytical chiral HPLC, AD column, 0.46 cm×25 cm id, 15% isopropanol/heptane, isocratic, flow rate=0.75 mL/min)] and co-injection with Enantiomer A from Example 22 allowed for the following assignment of stereochemistry for the separated enantiomers of Example 22, Step 2.

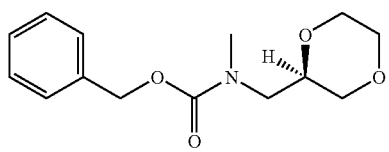

Enantiomer A benzyl [(2R)-1,4-dioxan-2-ylmethyl]methylcarbamate

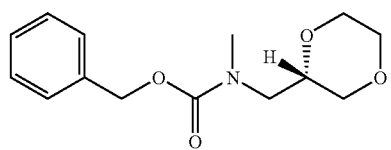

Enantiomer B benzyl [(2S)-1,4-dioxan-2-ylmethyl]methylcarbamate

Example 22B

Enantioselective Synthesis of {[((2R)1,4-dioxan-2-ylmethyl)(methyl)amino]-sulfonyl}amine Step 1: Epoxide 22B-1

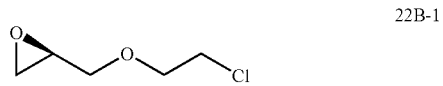

A solution of chloroethanol (13.0 kg, 10.9 L, 162 mole, 3 eq) and BF₃.OEt₂ (342 mL, 2.7 mol, 0.05 eq) in toluene (20 L) was heated to an internal temp of 36° C. and S-epichlorohydrin added dropwise with cooling at a rate such that the internal temperature remained below 38° C. In 30 min after completion of the addition the reaction was completed. The mixture was cooled to 10° C. and sodium hydroxide (12.5 L) and water (12.5 L) were added. The bi-phasic mixture was stirred at room temperature for 2 hours and a further 10 L of water was added to dissolve the inorganic solids. The layers were separated and the aqueous layer was extracted with toluene (20 L). The combined organic layers were washed with water (15 L) and then concentrated to an approximately 50 wt % of product in toluene solution. The resulting viscous solution was used directly in the following reaction.

Step 2: Tosylate 22B-2

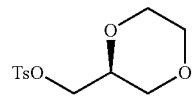

A solution of conc. aqueous NaOH solution (26.1 L) and water (31.3 L) was heated to 87° C. Crude epoxide 22B-1 (prepared as above; 5.24 kg, 38.4 mol) was added and the reaction aged at 90° C. for 30 min. The reaction was cooled to 22° C. and then diluted with DCM (21 L). p-Toluenesulfonyl chloride (7.46 kg, 38.36 mol) was added and the mixture was aged at 22° C. for 16 h. Water (21 L) was added and the phases separated. The aqueous layer was extracted with DCM (2×21 L). The combined organic layers were washed with a 5% brine solution (21 L). The organic layer was concentrated in vacuo and the residue dissolved in toluene (32 L). Heptane (7 L) was added followed by 22B-2 as seed (100 g) and the mixture cooled to 4° C. After ageing for 16 h, the mixture was filtered and the solids washed with 8:1 heptane/toluene (4 L). Tosylate 22B-2 was isolated as a white solid:

$^1$H NMR (CDCl$_3$) δ 2.47 (3H, s), 3.37 (1H, dd, J=9.6, 11.2 Hz), 3.70 (6H, m), 3.97 (1H, dd, J=4.8, 10.4 Hz), 4.03 (1H, dd, J=5.4, 10.6 Hz), 7.37 (2H, d, J=8.1 Hz), 7.81 (2H, d, J=8.3 Hz).

Step 3: 1-(1,4-dioxan-2-yl)-N-methylmethanamine hydrochloride

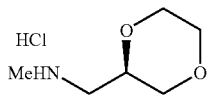

22B-3

A solution of tosylate 22B-2 (7.76 kg), methylamine in ethanol (62 L of a 33 wt % solution) and ethanol (62 L) was heated to an internal temperature of 65° C. for 20 h. The resulting solution was then concentrated via atmospheric distillation to a volume of ~15 L. This solution was held at 50° C. while NaOEt (9.2 L of a 21 wt % solution in ethanol; 1.05 equiv) was added, along with MTBE (47 L) each in two alternating portions. The slurry was then cooled to room temperature and filtered to remove sodium tosylate. The solids were washed with MTBE (15.5 L). The combined filtrates were solvent switched to isopropanol via atmospheric distillation. The final volume was ~30 L. Conc. HCl (2.1 L of S.G. 1.18, 1.05 equiv) was added whilst keeping the temperature <60° C. Isopropanol (116 L) was added, and the batch was concentrated via atmospheric distillation to a total volume of ~30 L. This mixture was held at 50° C. until a slurry formed, then cooled to room temperature overnight. The solids were filtered, washed with 1:1 heptane:isopropanol (15 L) and dried to give 22B-3 as a white solid. $^1$H NMR (400 MHz, MeOD): δ 3.90 (m, 2H), 3.77 (m, 3H), 3.62 (tr d, J=12 Hz, J=2.5 Hz, 1H), 3.36 (m, 1H), 3.06 (m, 2H), 2.73 (s, 3H)

Step 4: {[((2R)1,4-dioxan-2-ylmethyl)(methyl)amino]-sulfonyl}amine

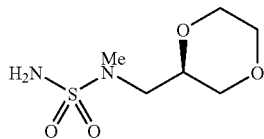

22B-4

To a cold (−20° C.) solution of chlorosulfonylisocyanate (2954 g) in dichloromethane (12.6 L) was added benzyl alcohol (2438 g) over 50 min, keeping the temperature below 0° C. A solution of 22B-3 free base was prepared by stirring 22B-3 (2795 g) with diisopropylethylamine (8.63 kg) in dichloromethane (33.5 L) for 1 h. This was then added to the sulfamoylating reagent over 100 min, keeping the temperature below 0° C. After 45 min, the batch was quenched by the addition of 4M HCl (13 kg) whilst keeping the temperature <5° C. The phases were separated and the DCM layer was washed with water (18.6 kg) and then solvent switched to methanol and a final volume of 106 L was reached. This solution was hydrogenated in the presence of 10% Pd/C (50% wet) (801 g) for 1 h at 1 bar of hydrogen. The catalyst was filtered and washed with methanol (2×20 L). The combined filtrates were solvent switched to isopropanol (final volume 32 L). A seed-bed formed. Heptane (72 L) was slowly added over 1 h. The slurry was aged for 1 h and then filtered, The solids were washed with 1:2 isopropanol:heptane (10 L) and dried to give 22B-4.

$^1$H NMR (400 MHz, MeOD): δ 3.79 (m, 3H), 3.71 (m, 2H), 3.59 (tr d, J=2.7 Hz, J=12 Hz, 1H), 3.36 (m, 1H), 3.10 (m, 2H), 2.85 (s, 3H).

Example 23

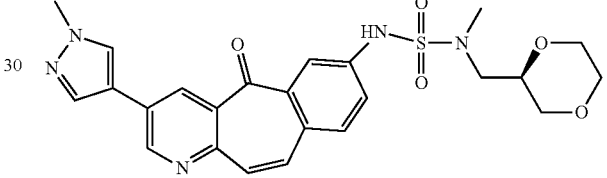

N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide (Compound 59)

N'-(3-chloro-5-oxo-5H-benzo[4,5]cyclohepta[1,2-b]pyridin-7-yl)-N-(1,4-dioxan-2-ylmethyl)-N-methylsulfamide (0.500 g, 1.11 mmol), 1-methyl-4-(4,4,5,5-tetramethyl-1,3,2-dioxaborolan-2-yl)-1H-pyrazole (0.692 g, 3.33 mmol), Pd$_2$(dba)$_3$ (0.051 g, 0.056 mmol), (tBu$_3$)PBF$_4$ (0.032 g, 0.11 mmol) and potassium fluoride (0.212 g, 3.66 mmol) were combined in a dry tube. 5 mL dry DMF was added and argon was bubbled through the solution for five minutes. The tube was sealed and heated in the Biotage Initiator series microwave to 135° C. for 20 minutes. The solution was diluted with ethyl acetate and washed with saturated sodium bicarbonate, water, and brine. The organic layer was dried with magnesium sulfate, filtered, concentrated in vacuo, and purified by silica chromatography (0-100% ethyl acetate/hexanes gradient followed by 0-10% methanol/dichloromethane gradient) to afford the crude compound. The crude material was crystallized from a mixture of 10 mL methanol, 40 mL dichloromethane, and 70 mL hexanes to afford the title compound. $^1$H NMR (600 MHz, D$^6$-DMSO) δ 10.52 (s, 1H); 9.20 (d, 1H); 8.55 (d, 1H); 8.45 (s, 1H); 8.13 (s, 1H); 7.95 (d, 1H); 7.75 (d, 1H); 7.55 (d, 1H); 7.32 (d, 1H); 7.22 (d, 1H); 3.88 (s, 3H); 3.64-3.60 (m, 2H); 3.58-3.54 (m, 1H); 3.54-3.50 (m, 1H); 3.44-3.40 (m, 1H); 3.38-3.34 (m, 1H); 3.14-3.10 (m, 3H); 2.77 (s, 3H). LRMS (APCI) calc'd for (C$_{24}$H$_{26}$N$_5$O$_5$S) [M+H]+, 496.2; found, 496.2.

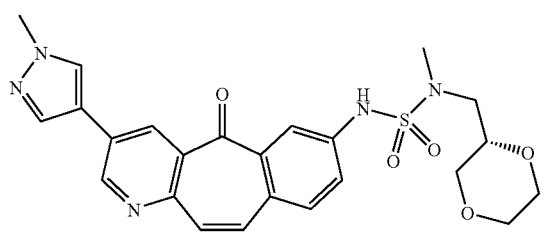

N-[(2S)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide (Compound 59S) was prepared using the procedure described in Examples 22 and 23, but substituting benzyl [(2S)-1,4-dioxan-2-ylmethyl]methylcarbamate (Enantiomer B from Example 22, Step 1) for benzyl [(2R)-1,4-dioxan-2-ylmethyl]methylcarbamate in Example 22, Step 2.

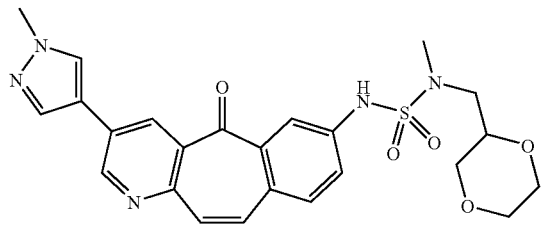

N-[1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide racemic mixture (Compound 59RS) was prepared using the procedure described in Examples 22 and 23, but substituting racemic benzyl [1,4-dioxan-2-ylmethyl]methylcarbamate for benzyl [(2R)-1,4-dioxan-2-ylmethyl]methylcarbamate in Example 22, Step 2.

The enantiomeric components of this racemic mixture of the instant compound were separated by the following procedure: The racemic Compound 58RS (0.083 g) was dissolved in a mixture of 2 mL methanol and 18 mL dichloromethane. Material was resolved on chiral OD column (70% isopropanol/heptane) to afford 0.030 g enantiomer A (Compound 59) [$\tau_R$: 12.8 min (analytical chiral HPLC, OD column, 0.46 cm×25 cm cm id, 60% isopropanol/heptane, isocratic, flow rate=0.75 mL/min)] and 0.026 g enantiomer B (Compound 59S) [$\tau_R$: 15.8 min (analytical chiral HPLC, OD column, 0.46 cm×25 cm cm id, 60% isopropanol/heptane, isocratic, flow rate=0.75 mL/min)].

Example 23A

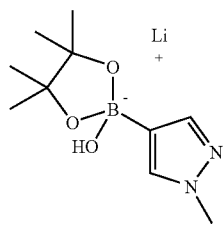

Pinacolate 23A-1

A solution of 4-bromo-1-methylpyrazole (10 μg, 96 wt % pure, 600 mmol) in THF (600 mL) and toluene (600 mL) was degassed three times by vacuum/nitrogen cycles and then left under an atmosphere of nitrogen. Triisopropyl borate (147 g, 181 mL, 1.3 equiv.) was added and the mixture was cooled to −74° C. A n-Hexyllithium solution (2.3 M in hexanes, 391 mL) was added slowly via canula over 90 min whilst maintaining the temperature <−67° C. The resulting viscous pink solution was aged for 15 min. Pinacol (106 g, 1.5 equiv.) was added and the mixture was warmed to +25° C. over 40 minutes. The mixture is aged for 80 min. Water (54 g, 5.0 equiv.) was added dropwise over 10 min to form a white slurry. The slurry was aged for 2.5 h at ambient temperature. The solids were filtered, washed with MTBE (2×250 mL) and dried in vacuo at 35° C. for 16 h. The intermediate 23B-1 was obtained as a dry white solid.

Example 23B

Alternative Synthesis of N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide (Compound 59)

A degassed solution of N'-(3-chloro-5-oxo-5H-benzo[4,5]cyclohepta[1,2-b]pyridin-7-yl)-N-(1,4-dioxan-2-ylmethyl)-N-methylsulfamide (141.6 g; 34 wt % pure, 48.14 g, 107 mmol), pinacolate 23A-1 (52.50 g) and di(bistriphenylphosphine) palladium (327 mg, 0.64 mmol, 0.006 eq) was heated to 100° C. for 30 min. The reaction mixture was cooled to ambient temperature and 2.0 N NaOH (200 mL) was added followed by Ecosorb C941. The mixture was stirred at ambient temperature for one hour and then filtered through 30 g of Solka Floc. The filtrate was acidified with 70 mL of 5.0 N HCl and then 130 mL of water was added. The resulting slurry was filtered, washed with 2:1 H$_2$O:DMF (500 mL) and dried in vacuo at 60° C. to afford Compound 59.

Example 23C

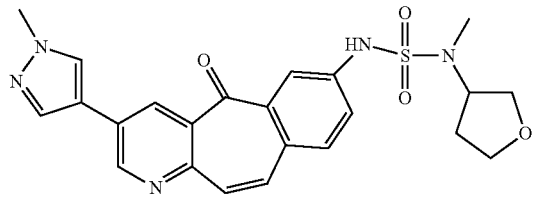

N-methyl-N'-[3-(1-methyl-1H-pyrazol-4-yl)-5-oxo-5H-benzo[4,5]cyclohepta[1,2-b]pyridin-7-yl]-N-(tetrahydrofuran-3-yl)sulfamide Step 1: N-methyl-N-(tetrahydrofuran-3-yl)sulfamide A flask was charged with N-tert-butoxycarbonyl-N-[4-(dimethylazaniumylidene)-1,4-dihydropyridin-1-ylsulfonyl]

azanide (2.19 g, 7.27 mmol), N-methyltetrahydrofuran-3-aminium chloride (1.00 g, 7.27 mmol) and triethyl amine (1.01 mL, 7.27 mmol) in 10 mL of CH$_2$Cl$_2$. After 2 h, the solution was concentrated in vacuo and purified by flash column chromatography (10-100% EtOAc/hexanes) to afford tert-butyl {[methyl(tetrahydrofuran-3-yl)amino]sulfonyl}carbamate.

tert-butyl {[methyl(tetrahydrofuran-3-yl)amino]sulfonyl}carbamate (1.47 g, 5.23 mmol) was dissolved in 70 mL of CH$_2$Cl$_2$ and 45 mL of trifluoroacetic acid. After 1 h the solution was concentrated in vacuo, diluted in CH$_2$Cl$_2$, washed with saturated aqueous NaHCO$_3$ and brine, then dried over Na$_2$SO$_4$. The solution was concentrated in vacuo to afford the title compound. $^1$H NMR (600 MHz, DMSO-d6) δ 4.25-4.31 (m, 1H); 3.79-3.84 (m, 1H); 3.58-3.66 (m, 2H); 3.47-3.52 (m, 1H); 2.56 (s, 3H), 2.04-2.10 (m, 1H); 1.81-1.88 (m, 1H).

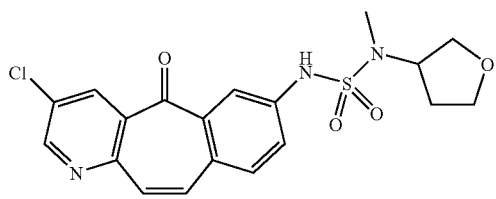

Step 2: N'-(3-chloro-5-oxo-5H-benzo[4,5]cyclohepta[1,2-b]pyridin-7-yl)-N-methyl-N-({3R}-tetrahydrofuran-3-yl)sulfamide and N'-(3-chloro-5-oxo-5H-benzo[4,5]cyclohepta[1,2-b]pyridin-7-yl)-N-methyl-N-({3R}-tetrahydrofuran-3-yl)sulfamide 7-bromo-3-chloro-5H-benzo[4,5]cyclohepta[1,2-b]pyridin-5-one (665 mg. 2.07 mmol), N-methyl-N-(tetrahydrofuran-3-yl)sulfamide (372 mg, 2.06 mmol), Pd$_2$(dba)$_3$ (95 mg, 0.10 mmol), 9,9-dimethyl-4,5-bis(diphenylphosphino)xanthene (XANTPHOS) (179 mg, 0.310 mmol) and cesium carbonate (2.02 g, 6.19 mmol) were added to a dry flask through which argon was purged. The flask was charged with 30 mL of dry dioxane and argon was bubbled through the solution for 10 minutes. The reaction mixture was heated to 95° C. and stirred under argon. After 2 h, the mixture was cooled to ambient temperature, diluted in ethyl acetate, washed with saturated aqueous NaHCO$_3$ and brine, then dried over Na$_2$SO$_4$. The solution was concentrated and purified via flash column chromatography (silica, ethylacetate/hexanes) to afford the title compound. $^1$H NMR (600 MHz, DMSO-d6) δ 10.59 (s, 1H); 8.97 (d, 1H); 8.50 (d, 1H); 7.95 (d, 1H); 7.79 (d, 1H); 7.54 (dd, 1H); 7.40 (d, 1H); 7.22 (d, 1H); 4.47-4.53 (m, 1H); 3.75-3.80 (m, 1H); 3.42-3.53 (m, 3H); 2.67 (s, 3H); 1.93-2.00 (m, 1H); 1.50-1.72 (m, 1H); LRMS (APCI) calc'd for (C$_{19}$H$_{19}$ClN$_3$O$_4$S) [M+H]+, 420.1; found, 420.1.

The racemic mixture was dissolved in 5 mg/mL of 5:1 methanol/dimethylsulfoxide and resolved on via chiral HPLC (Chiracel OJ-H column, 21 mm×250 mm, 40% methanol/supercritical carbon dioxide, flow rate=50 mL/min, 100 bar outlet pressure) to afford enantiomer A (τ$_R$=6.33 min) and enantiomer B (τ$_R$=7.9 min)

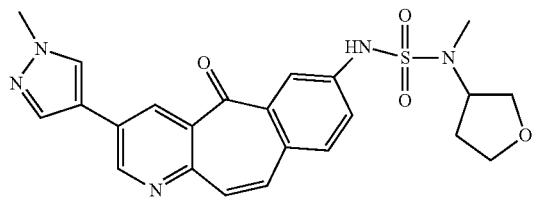

Step 3: N-methyl-N'-[3-(1-methyl-1H-pyrazol-4-yl)-5-oxo-5H-benzo[4,5]cyclohepta[1,2-b]pyridin-7-yl]-N-({3R}-tetrahydrofuran-3-yl)sulfamide and N-methyl-N'-[3-(1-methyl-1H-pyrazol-4-yl)-5-oxo-5H-benzo[4,5]cyclohepta[1,2-b]pyridin-7-yl]-N-({3S}-tetrahydrofuran-3-yl)sulfamide The separated enantiomers were carried forward in the same manner. A procedure is described for Enantiomer B.

N'-(3-chloro-5-oxo-5H-benzo[4,5]cyclohepta[1,2-b]pyridin-7-yl)-N-methyl-N-(tetrahydrofuran-3-yl)sulfamide Enantiomer B (0.070 g, 0.17 mmol), 1-methyl-4-(4,4,5,5-tetramethyl-1,3,2-dioxaborolan-2-yl)-1H-pyrazole (0.069 g, 0.33 mmol), Pd$_2$(dba)$_3$ (0.008 g, 0.0085 mmol), (tBu$_3$)PBF$_4$ (0.005 g, 0.017 mmol) and potassium fluoride (0.032 g, 0.56 mmol) were combined in a dry tube. 1.0 mL dry DMF was added and argon was bubbled through the solution for five minutes. The tube was sealed and heated in a Biotage Initiator series microwave reactor to 100° C. for 30 minutes. The solution was diluted with ethyl acetate and washed with saturated sodium bicarbonate. The organic layer was dried with magnesium sulfate, filtered, concentrated in vacuo, and purified by HPLC chromatography (20-100% acetonitrile/water gradient, 0.05% trifluoroacetic acid modifier) to afford the crude compound. The crude material was purified by silica chromatography (0-100% ethyl acetate/hexanes gradient, followed by 0-20% methanol/dichloromethane gradient). The isolated material was dissolved in minimal 25% methano/dichloromethane and hexanes were added until precipitation occurred. Precipitate was filtered to afford title compound. $^1$H NMR (600 MHz, D$^6$-DMSO) □ 10.55 (s, 1H); 9.20 (d, 1H); 8.58 (d, 1H); 8.46 (s, 1H); 8.13 (s, 1H); 7.95 (d, 1H); 7.75 (d, 1H); 7.52 (dd, 1H); 7.32 (d, 1H); 7.22 (d, 1H); 4.48-4.53 (m, 1H); 3.88 (s, 3H); 3.74-3.80 (m, 1H); 3.42-3.54 (m, 3H); 2.68 (s, 3H); 1.93-2.00 (m, 1H); 1.65-1.72 (m, 1H). LRMS (APCI) calc'd for (C$_{23}$H$_{24}$N$_5$O$_4$S) [M+H]+, 466.2; found, 466.2.

The racemic mixture of N-methyl-N'-[3-(1-methyl-1H-pyrazol-4-yl)-5-oxo-5H-benzo[4,5]cyclohepta[1,2-b]pyridin-7-yl]-N-(tetrahydrofuran-3-yl)sulfamide was prepared using the above procedure starting with the racemic mixture from Step 2.

The following compounds were made according to Scheme 4. Commercially unavailable 1-H-pyrazole-4-boronic esters were prepared in a manner similar to that described in Example 19. Compounds 136-144 were prepared from the respective (2,4-dimethoxybenzyl)amino derivative in a manner similar to that described for Example 4B.

TABLE 3

| Compound | R¹ | Name | MS (M + 1) |
|---|---|---|---|
| 60 | 4-chlorophenyl | N-[3-(4-chlorophenyl)-5-oxo-5H-benzo[4,5]cyclohepta[1,2-b]pyridin-7-yl]methanesulfonamide | calc'd 411.1 (M + H)+; found 411.0 (M + H)+ |
| 61 | 2-chlorophenyl | N-[3-(2-chlorophenyl)-5-oxo-5H-benzo[4,5]cyclohepta[1,2-b]pyridin-7-yl]methanesulfonamide | calc'd 411.1 (M + H)+; found 411.0 (M + H)+ |
| 62 | pyridin-4-yl | N-(5-oxo-3-pyridin-4-yl-5H-benzo[4,5]cyclohepta[1,2-b]pyridin-7-yl)methanesulfonamide | calc'd 378.1 (M + H)+; found 378.1 (M + H)+ |
| 63 | pyridin-3-yl | N-(5-oxo-3-pyridin-3-yl-5H-benzo[4,5]cyclohepta[1,2-b]pyridin-7-yl)methanesulfonamide | calc'd 378.1 (M + H)+; found 378.1 (M + H)+ |
| 64 | 1H-pyrazol-3-yl | N-[5-oxo-3-(1H-pyrazol-3-yl)-5H-benzo[4,5]cyclohepta[1,2-b]pyridin-7-yl]methanesulfonamide | calc'd 367.1 (M + H)+; found 367.1 (M + H)+ |
| 65 | 3-chlorophenyl | N-[3-(3-chlorophenyl)-5-oxo-5H-benzo[4,5]cyclohepta[1,2-b]pyridin-7-yl]methanesulfonamide | calc'd 411.1 (M + H)+; found 411.0 (M + H)+ |
| 66 | pyrimidin-5-yl | N-(5-oxo-3-pyrimidin-5-yl-5H-benzo[4,5]cyclohepta[1,2-b]pyridin-7-yl)methanesulfonamide | calc'd 379.1 (M + H)+; found 379.1 (M + H)+ |
| 67 | quinolin-6-yl | N-(5-oxo-3-quinolin-6-yl-5H-benzo[4,5]cyclohepta[1,2-b]pyridin-7-yl)methanesulfonamide | calc'd 428.1 (M + H)+; found 428.1 (M + H)+ |

TABLE 3-continued

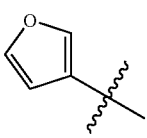

| Compound | R¹ | Name | MS (M + 1) |
|---|---|---|---|
| 68 | 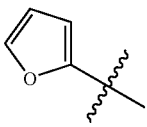 | N-[3-(3-furyl)-5-oxo-5H-benzo[4,5]cyclohepta[1,2-b]pyridin-7-yl]methanesulfonamide | calc'd 367.1 (M + H)+; found 367.1 (M + H)+ |
| 69 | 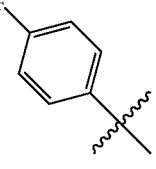 | N-[3-(2-furyl)-5-oxo-5H-benzo[4,5]cyclohepta[1,2-b]pyridin-7-yl]methanesulfonamide | calc'd 367.1 (M + H)+; found 367.1 (M + H)+ |
| 70 | 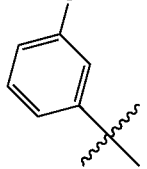 | N-[3-(4-fluorophenyl)-5-oxo-5H-benzo[4,5]cyclohepta[1,2-b]pyridin-7-yl]methanesulfonamide | calc'd 395.1 (M + H)+; found 395.1 (M + H)+ |
| 71 | 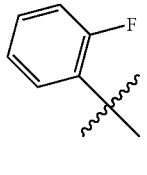 | N-[3-(3-fluorophenyl)-5-oxo-5H-benzo[4,5]cyclohepta[1,2-b]pyridin-7-yl]methanesulfonamide | calc'd 395.1 (M + H)+; found 395.1 (M + H)+ |
| 72 | 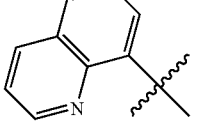 | N-[3-(2-fluorophenyl)-5-oxo-5H-benzo[4,5]cyclohepta[1,2-b]pyridin-7-yl]methanesulfonamide | calc'd 395.1 (M + H)+; found 395.1 (M + H)+ |
| 73 | 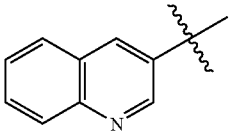 | N-(5-oxo-3-quinolin-8-yl-5H-benzo[4,5]cyclohepta[1,2-b]pyridin-7-yl)methanesulfonamide | calc'd 428.1 (M + H)+; found 428.2 (M + H)+ |
| 74 | 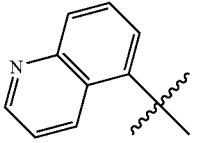 | N-(5-oxo-3-quinolin-3-yl-5H-benzo[4,5]cyclohepta[1,2-b]pyridin-7-yl)methanesulfonamide | calc'd 428.1 (M + H)+; found 428.1 (M + H)+ |
| 75 |  | N-(5-oxo-3-quinolin-5-yl-5H-benzo[4,5]cyclohepta[1,2-b]pyridin-7-yl)methanesulfonamide | calc'd 428.1 (M + H)+; found 428.1 (M + H)+ |

TABLE 3-continued

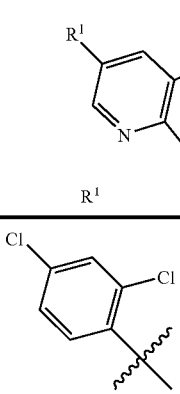

| Compound | R¹ | Name | MS (M + 1) |
|---|---|---|---|
| 76 | 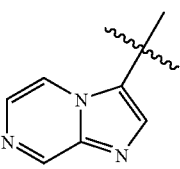 | N-[3-(2,4-dichlorophenyl)-5-oxo-5H-benzo[4,5]cyclohepta[1,2-b]pyridin-7-yl]methanesulfonamide | calc'd 445.0 (M + H)+; found 445.0 (M + H)+ |
| 77 | 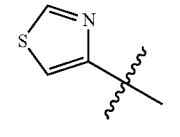 | N-(3-imidazo[1,2-a]pyrazin-3-yl-5-oxo-5H-benzo[4,5]cyclohepta[1,2-b]pyridin-7-yl)methanesulfonamide | calc'd 418.1 (M + H)+; found 418.1 (M + H)+ |
| 78 | 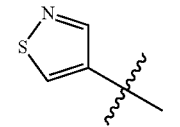 | N-[5-oxo-3-(1,3-thiazol-4-yl)-5H-benzo[4,5]cyclohepta[1,2-b]pyridin-7-yl]methanesulfonamide | calc'd 384.0 (M + H)+; found 384.0 (M + H)+ |
| 79 | 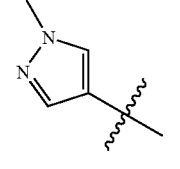 | N-(3-isothiazol-4-yl-5-oxo-5H-benzo[4,5]cyclohepta[1,2-b]pyridin-7-yl)methanesulfonamide | calc'd 384.0 (M + H)+; found 384.0 (M + H)+ |
| 80 | 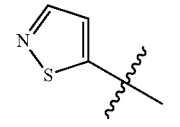 | N-[3-(1-methyl-1H-pyrazol-4-yl)-5-oxo-5H-benzo[4,5]cyclohepta[1,2-b]pyridin-7-yl]methanesulfonamide | calc'd 381.1 (M + H)+; found 380.7 (M + H)+ |
| 81 | 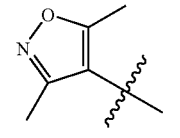 | N-(3-isothiazol-5-yl-5-oxo-5H-benzo[4,5]cyclohepta[1,2-b]pyridin-7-yl)methanesulfonamide | calc'd 384.0 (M + H)+; found 384.0 (M + H)+ |
| 82 | 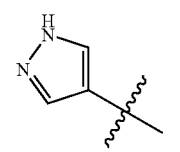 | N-[3-(3,5-dimethylisoxazol-4-yl)-5-oxo-5H-benzo[4,5]cyclohepta[1,2-b]pyridin-7-yl]methanesulfonamide | calc'd 396.1 (M + H)+; found 396.1 (M + H)+ |
| 83 | 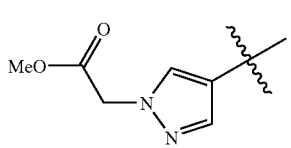 | N-[5-oxo-3-(1H-pyrazol-4-yl)-5H-benzo[4,5]cyclohepta[1,2-b]pyridin-7-yl]methanesulfonamide | calc'd 367.1 (M + H)+; found 366.7 (M + H)+ |
| 84 | 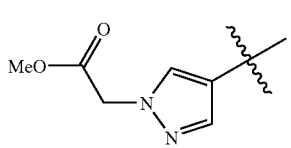 | methyl (4-{7-[(methylsulfonyl)amino]-5-oxo-5H-benzo[4,5]cyclohepta[1,2-b]pyridin-3-yl}-1H-pyrazol-1-yl)acetate | calc'd 439.1 (M + H)+; found 438.7 (M + H)+ |

TABLE 3-continued

| Compound | R¹ | Name | MS (M + 1) |
|---|---|---|---|
| 85 | EtO-C(=O)-CH₂CH₂-N(pyrazole)- | ethyl 3-(4-{7-[(methylsulfonyl)amino]-5-oxo-5H-benzo[4,5]cyclohepta[1,2-b]pyridin-3-yl}-1H-pyrazol-1-yl)propanoate | calc'd 467.1 (M + H)+; found 466.6 (M + H)+ |
| 86 | (CH₃)₂N-CH₂CH₂-N(pyrazole)- | N-(3-{1-[2-(dimethylamino)ethyl]-1H-pyrazol-4-yl}-5-oxo-5H-benzo[4,5]cyclohepta[1,2-b]pyridin-7-yl)methanesulfonamide, 3TFA or 3HCl | calc'd 438.2 (M + H)+; found 437.7 (M + H)+ |
| 87 | isobutyl-N(pyrazole)- | N-[3-(1-isobutyl-1H-pyrazol-4-yl)-5-oxo-5H-benzo[4,5]cyclohepta[1,2-b]pyridin-7-yl]methanesulfonamide | calc'd 423.1 (M + H)+; found 422.7 (M + H)+ |
| 88 | propyl-N(pyrazole)- | N-[5-oxo-3-(1-propyl-1H-pyrazol-4-yl)-5H-benzo[4,5]cyclohepta[1,2-b]pyridin-7-yl]methanesulfonamide | calc'd 409.1 (M + H)+; found 408.7 (M + H)+ |
| 89 | (CH₃)₂N-CH₂CH₂CH₂-N(pyrazole)- | N-(3-{1-[3-(dimethylamino)propyl]-1H-pyrazol-4-yl}-5-oxo-5H-benzo[4,5]cyclohepta[1,2-b]pyridin-7-yl)methanesulfonamide | calc'd 452.2 (M + H)+; found 451.7 (M + H)+ |
| 90 | morpholine-C(=O)-CH₂-N(pyrazole)- | N-{3-[1-(2-morpholin-4-yl-2-oxoethyl)-1H-pyrazol-4-yl]-5-oxo-5H-benzo[4,5]cyclohepta[1,2-b]pyridin-7-yl}methanesulfonamide | calc'd 494.1 (M + H)+; found 493.6 (M + H)+ |
| 91 | pyrrolidine-CH₂CH₂-N(pyrazole)- | N-{5-oxo-3-[1-(2-pyrrolidin-1-ylethyl)-1H-pyrazol-4-yl]-5H-benzo[4,5]cyclohepta[1,2-b]pyridin-7-yl}methanesulfonamide | calc'd 464.2 (M + H)+; found 463.7 (M + H)+ |
| 92 | benzyl-N(pyrazole)- | N-[3-(1-benzyl-1H-pyrazol-4-yl)-5-oxo-5H-benzo[4,5]cyclohepta[1,2-b]pyridin-7-yl]methanesulfonamide | calc'd 457.1 (M + H)+; found 456.7 (M + H)+ |
| 93 | HO-C(=O)-CH₂-N(pyrazole)- | (4-{7-[(methylsulfonyl)amino]-5-oxo-5H-benzo[4,5]cyclohepta[1,2-b]pyridin-3-yl}-1H-pyrazol-1-yl)acetic acid | calc'd 425.1 (M + H)+; found 424.7 (M + H)+ |

TABLE 3-continued

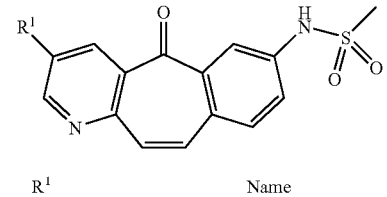

| Compound | R[1] | Name | MS (M + 1) |
|---|---|---|---|
| 94 | 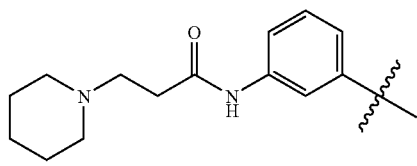 | 3-(4-{7-[(methylsulfonyl)amino]-5-oxo-5H-benzo[4,5]cyclohepta[1,2-b]pyridin-3-yl}-1H-pyrazol-1-yl)propanoic acid | calc'd 439.1 (M + H)+; found 439.1 (M + H)+ |
| 95 | 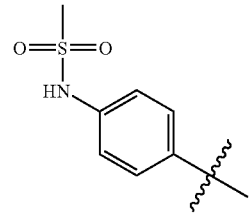 | N-(3-{7-[(methylsulfonyl)amino]-5-oxo-5H-benzo[4,5]cyclohepta[1,2-b]pyridin-3-yl}phenyl)-3-piperidin-1-ylpropanamide | calc'd 531.2 (M + H)+; found 531.2 (M + H)+ |
| 96 | 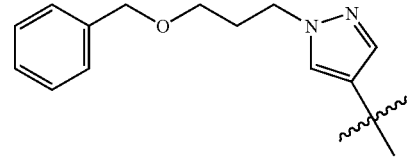 | N-(4-{7-[(methylsulfonyl)amino]-5-oxo-5H-benzo[4,5]cyclohepta[1,2-b]pyridin-3-yl}phenyl)methanesulfonamide | calc'd 470.1 (M + H)+; found 470.1 (M + H)+ |
| 97 | 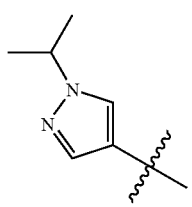 | N-(3-{1-[3-(benzyloxy)propyl]-1H-pyrazol-4-yl}-5-oxo-5H-benzo[4,5]cyclohepta[1,2-b]pyridin-7-yl)methanesulfonamide | calc'd 515.2 (M + H)+; found 515.2 (M + H)+ |
| 98 | 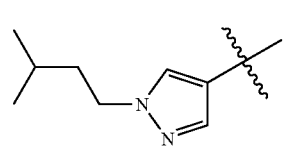 | N-[3-(1-isopropyl-1H-pyrazol-4-yl)-5-oxo-5H-benzo[4,5]cyclohepta[1,2-b]pyridin-7-yl]methanesulfonamide | calc'd 409.1 (M + H)+; found 409.1 (M + H)+ |
| 99 | 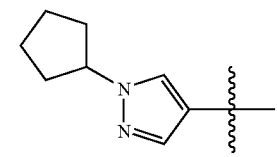 | N-{3-[1-(3-methylbutyl)-1H-pyrazol-4-yl]-5-oxo-5H-benzo[4,5]cyclohepta[1,2-b]pyridin-7-yl}methanesulfonamide | calc'd 437.2 (M + H)+; found 437.2 (M + H)+ |
| 100 | 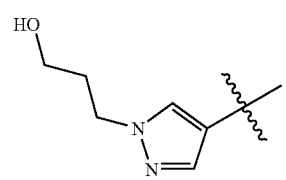 | N-[3-(1-cyclopentyl-1H-pyrazol-4-yl)-5-oxo-5H-benzo[4,5]cyclohepta[1,2-b]pyridin-7-yl]methanesulfonamide | calc'd 435.1 (M + H)+; found 435.1 (M + H)+ |
| 101 | HO | N-{3-[1-(3-hydroxypropyl)-1H-pyrazol-4-yl]-5-oxo-5H-benzo[4,5]cyclohepta[1,2-b]pyridin-7-yl}methanesulfonamide | calc'd 425.1 (M + H)+; found 425.1 (M + H)+ |

TABLE 3-continued

| Compound | R¹ | Name | MS (M + 1) |
|---|---|---|---|
| 102 | 3-carboxyphenyl (HO-C(=O)-C₆H₄-) | 3-{7-[(methylsulfonyl)amino]-5-oxo-5H-benzo[4,5]cyclohepta[1,2-b]pyridin-3-yl}benzoic acid | calc'd 421.1 (M + H)+; found 420.9 (M + H)+ |
| 103 | 2,3-dihydro-1H-pyrazolo[1,2-a]pyrazol-4-ium-6-yl, 2· trifluoroacetate | 3-(2,3-dihydro-1H-pyrazolo[1,2-a]pyrazol-4-ium-6-yl)-7-[(methylsulfonyl)amino]-5-oxo-5H-benzo[4,5]cyclohepta[1,2-b]pyridinium bis(trifluoroacetate) | calc'd 408.1 (M + H)+; found 407.1 (M + H)+ |
| 104 | 1-(1-methoxycarbonyl-ethyl)-1H-pyrazol-4-yl | methyl 2-(4-{7-[(methylsulfonyl)amino]-5-oxo-5H-benzo[4,5]cyclohepta[1,2-b]pyridin-3-yl}-1H-pyrazol-1-yl)propanoate | calc'd 453.1 (M + H)+; found 453.1 (M + H)+ |
| 105 | 1-(3,3-dimethyl-2-oxobutyl)-1H-pyrazol-4-yl | N-{3-[1-(3,3-dimethyl-2-oxobutyl)-1H-pyrazol-4-yl]-5-oxo-5H-benzo[4,5]cyclohepta[1,2-b]pyridin-7-yl}methanesulfonamide | calc'd 465.2 (M + H)+; found 465.2 (M + H)+ |
| 106 | 4-carboxyphenyl | 4-{7-[(methylsulfonyl)amino]-5-oxo-5H-benzo[4,5]cyclohepta[1,2-b]pyridin-3-yl}benzoic acid | calc'd 421.1 (M + H)+; found 421.2 (M + H)+ |
| 107 | 3-nitrophenyl | N-[3-(3-nitrophenyl)-5-oxo-5H-benzo[4,5]cyclohepta[1,2-b]pyridin-7-yl]methanesulfonamide | calc'd 422.1 (M + H)+; found 422.1 (M + H)+ |
| 108 | 4-nitrophenyl | N-[3-(4-nitrophenyl)-5-oxo-5H-benzo[4,5]cyclohepta[1,2-b]pyridin-7-yl]methanesulfonamide | calc'd 422.1 (M + H)+; found 422.1 (M + H)+ |

TABLE 3-continued

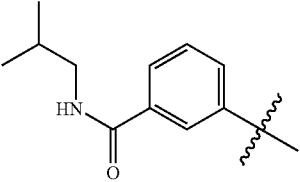

| Compound | R¹ | Name | MS (M + 1) |
|---|---|---|---|
| 109 | 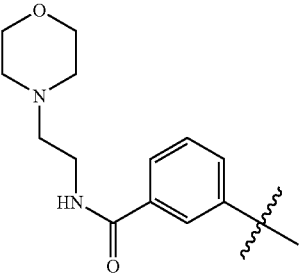 | N-isobutyl-3-{7-[(methylsulfonyl)amino]-5-oxo-5H-benzo[4,5]cyclohepta[1,2-b]pyridin-3-yl}benzamide | calc'd 476.2 (M + H)+; found 476.1 (M + H)+ |
| 110 | 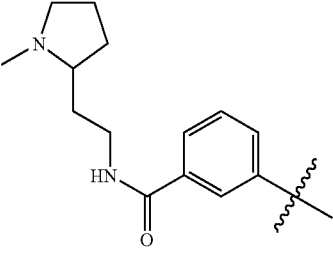 | 3-{7-[(methylsulfonyl)amino]-5-oxo-5H-benzo[4,5]cyclohepta[1,2-b]pyridin-3-yl}-N-(2-morpholin-4-ylethyl)benzamide | calc'd 533.2 (M + H)+; found 533.1 (M + H)+ |
| 111 | 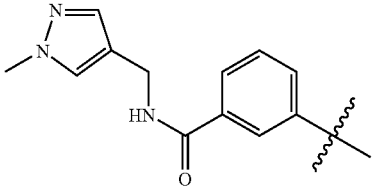 | N-[2-(1-methylpyrrolidin-2-yl)ethyl]-3-{7-[(methylsulfonyl)amino]-5-oxo-5H-benzo[4,5]cyclohepta[1,2-b]pyridin-3-yl}benzamide | calc'd 531.2 (M + H)+; found 531.0 (M + H)+ |
| 112 | 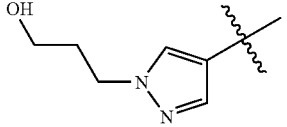 | N-[(1-methyl-1H-pyrazol-4-yl)methyl]-3-{7-[(methylsulfonyl)amino]-5-oxo-5H-benzo[4,5]cyclohepta[1,2-b]pyridin-3-yl}benzamide | calc'd 514.1 (M + H)+; found 513.9 (M + H)+ |
| 113 | 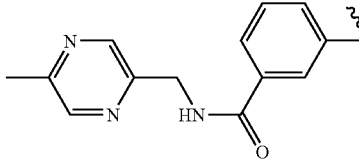 | N-{3-[1-(3-hydroxypropyl)-1H-pyrazol-4-yl]-5-oxo-5H-benzo[4,5]cyclohepta[1,2-b]pyridin-7-yl}methanesulfonamide | calc'd 425.1 (M + H)+; found 425.1 (M + H)+ |
| 114 |  | N-[(5-methylpyrazin-2-yl)methyl]-3-{7-[(methylsulfonyl)amino]-5-oxo-5H-benzo[4,5]cyclohepta[1,2-b]pyridin-3-yl}benzamide | calc'd 526.1 (M + H)+; found 526.1 (M + H)+ |

TABLE 3-continued

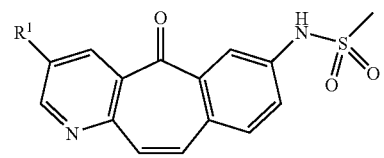

| Compound | R¹ | Name | MS (M + 1) |
|---|---|---|---|
| 115 | | N-isobutyl-4-{7-[(methylsulfonyl)amino]-5-oxo-5H-benzo[4,5]cyclohepta[1,2-b]pyridin-3-yl}benzamide | calc'd 476.2 (M + H)+; found 476.1 (M + H)+ |
| 116 | | N-[(1-methyl-1H-pyrazol-4-yl)methyl]-4-{7-[(methylsulfonyl)amino]-5-oxo-5H-benzo[4,5]cyclohepta[1,2-b]pyridin-3-yl}benzamide | Calc'd 514.1 (M + H)+; found 514.2 (M + H)+ |

TABLE 3A

| Compound | Structure | Name | MS (M + 1) |
|---|---|---|---|
| 117 | ![structure] | 2-methyl-N-[3-(1-methyl-1H-pyrazol-4-yl)-5-oxo-5H-benzo[4,5]cyclohepta[1,2-b]pyridin-7-yl]propane-2-sulfonamide | calc'd 423.1 (M + H)+; found 422.7 (M + H)+ |
| 118 | ![structure] | N,N-dimethyl-N'-[3-(1-methyl-1H-pyrazol-4-yl)-5-oxo-5H-benzo[4,5]cyclohepta[1,2-b]pyridin-7-yl]sulfamide | calc'd 410.1 (M + H)+; found 409.7 (M + H)+ |
| 119 | ![structure] | N-benzyl-N-methyl-N'-[3-(1-methyl-1H-pyrazol-4-yl)-5-oxo-5H-benzo[4,5]cyclohepta[1,2-b]pyridin-7-yl]sulfamide | calc'd 486.2 (M + H)+; found 485.7 (M + H)+ |

TABLE 3A-continued

| Compound | Structure | Name | MS (M + 1) |
|---|---|---|---|
| 120 | 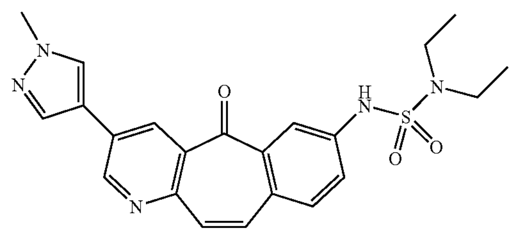 | N,N-diethyl-N'-[3-(1-methyl-1H-pyrazol-4-yl)-5-oxo-5H-benzo[4,5]cyclohepta[1,2-b]pyridin-7-yl]sulfamide | calc'd 438.2 (M + H)+; found 438.1 (M + H)+ |
| 121 | 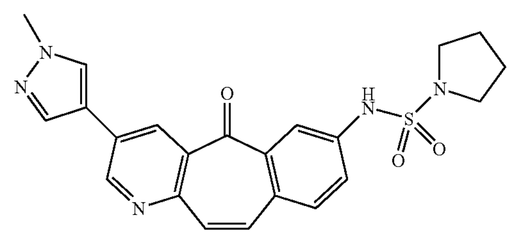 | N-[3-(1-methyl-1H-pyrazol-4-yl)-5-oxo-5H-benzo[4,5]cyclohepta[1,2-b]pyridin-7-yl]pyrrolidine-1-sulfonamide | calc'd 436.1 (M + H)+; found 436.1 (M + H)+ |
| 122 | 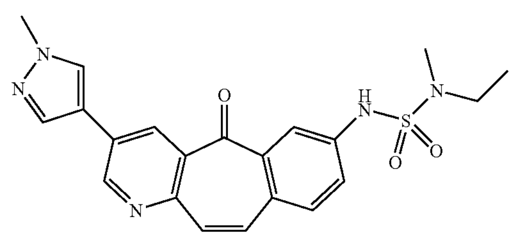 | N-ethyl-N-methyl-N'-[3-(1-methyl-1H-pyrazol-4-yl)-5-oxo-5H-benzo[4,5]cyclohepta[1,2-b]pyridin-7-yl]sulfamide | calc'd 424.1 (M + H)+; found 424.1 (M + H)+ |
| 123 | 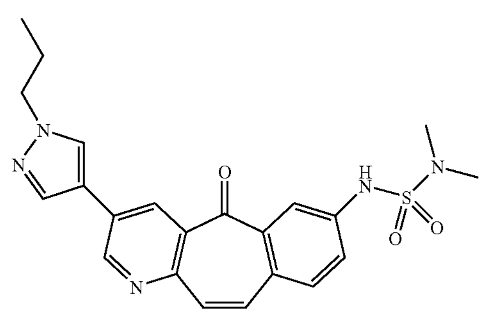 | N,N-dimethyl-N'-[5-oxo-3-(1-propyl-1H-pyrazol-4-yl)-5H-benzo[4,5]cyclohepta[1,2-b]pyridin-7-yl]sulfamide | calc'd 438.2 (M + H)+; found 438.2 (M + H)+ |
| 124 | 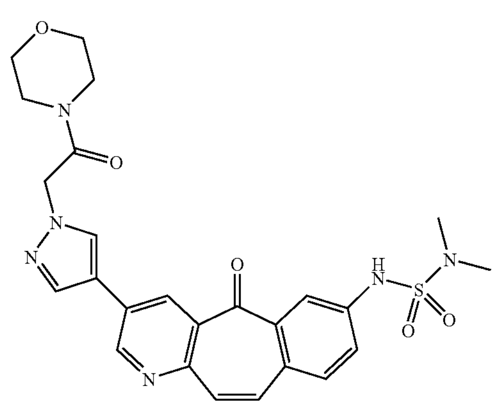 | N,N-dimethyl-N'-{3-[1-(2-morpholin-4-yl-2-oxoethyl)-1H-pyrazol-4-yl]-5-oxo-5H-benzo[4,5]cyclohepta[1,2-b]pyridin-7-yl}sulfamide | calc'd 523.2 (M + H)+; found 523.2 (M + H)+ |

TABLE 3A-continued

| Compound | Structure | Name | MS (M + 1) |
|---|---|---|---|
| 125 | 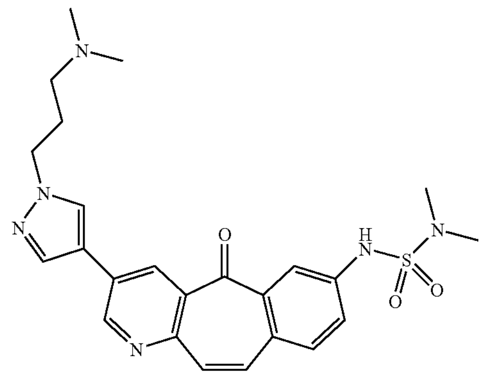 | N'-(3-{1-[3-(dimethylamino)propyl]-1H-pyrazol-4-yl}-5-oxo-5H-benzo[4,5]cyclohepta[1,2-b]pyridin-7-yl)-N,N-dimethylsulfamide | calc'd 481.2 (M + H)+; found 481.2 (M + H)+ |
| 126 | 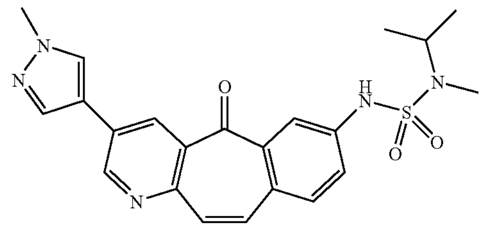 | N-isopropyl-N-methyl-N'-[3-(1-methyl-1H-pyrazol-4-yl)-5-oxo-5H-benzo[4,5]cyclohepta[1,2-b]pyridin-7-yl]sulfamide | calc'd 438.2 (M + H)+; found 438.2 (M + H)+ |
| 127 | 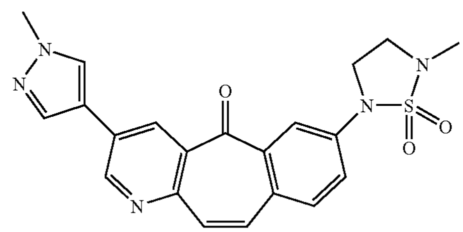 | 7-(5-methyl-1,1-dioxido-1,2,5-thiadiazolidin-2-yl)-3-(1-methyl-1H-pyrazol-4-yl)-5H-benzo[4,5]cyclohepta[1,2-b]pyridin-5-one | calc'd 422.1 (M + H)+; found 422.1 (M + H)+ |
| 128 | 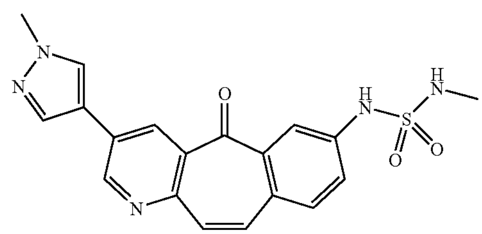 | N-methyl-N'-[3-(1-methyl-1H-pyrazol-4-yl)-5-oxo-5H-benzo[4,5]cyclohepta[1,2-b]pyridin-7-yl]sulfamide | calc'd 382.1 (M + H)+; found 382.1 (M + H)+ |
| 129 | 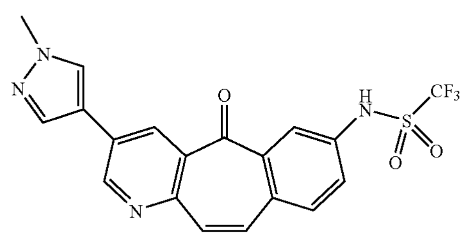 | 1,1,1-trifluoro-N-[3-(1-methyl-1H-pyrazol-4-yl)-5-oxo-5H-benzo[4,5]cyclohepta[1,2-b]pyridin-7-yl]methanesulfonamide | calc'd 435.1 (M + H)+; found 434.6 (M + H)+ |
| 130 | 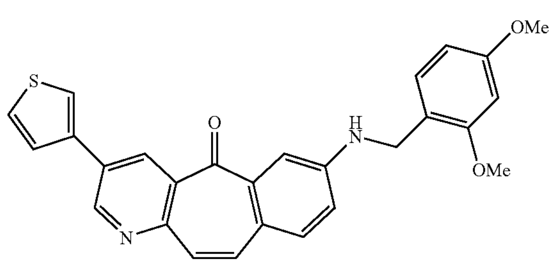 | 7-[(2,4-dimethoxybenzyl)amino]-3-(3-thienyl)-5H-benzo[4,5]cyclohepta[1,2-b]pyridin-5-one | calc'd 455.1 (M + H)+; found 455.2 (M + H)+ |

TABLE 3A-continued

| Compound | Structure | Name | MS (M + 1) |
|---|---|---|---|
| 131 | 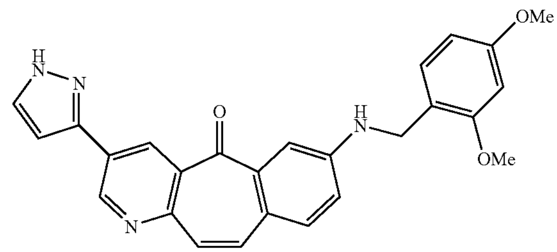 | 7-[(2,4-dimethoxybenzyl)amino]-3-(1H-pyrazol-3-yl)-5H-benzo[4,5]cyclohepta[1,2-b]pyridin-5-one | calc'd 439.2 (M + H)+; found 439.2 (M + H)+ |
| 132 | 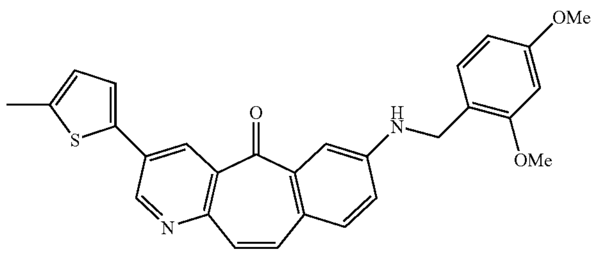 | 7-[(2,4-dimethoxybenzyl)amino]-3-(5-methyl-2-thienyl)-5H-benzo[4,5]cyclohepta[1,2-b]pyridin-5-one | calc'd 469.2 (M + H)+; found 469.1 (M + H)+ |
| 133 | 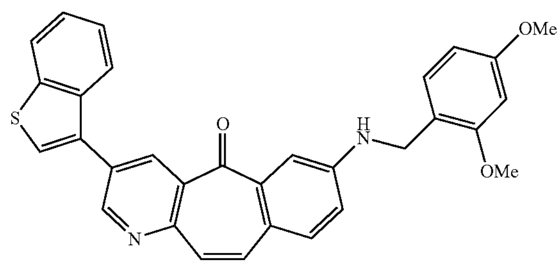 | 3-(1-benzothien-3-yl)-7-[(2,4-dimethoxybenzyl)amino]-5H-benzo[4,5]cyclohepta[1,2-b]pyridin-5-one | calc'd 505.2 (M + H)+; found 505.1 (M + H)+ |
| 134 | 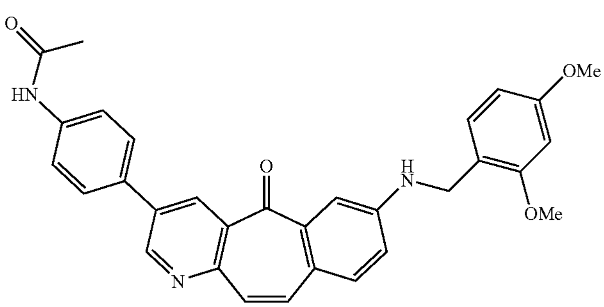 | N-(4-{7-[(2,4-dimethoxybenzyl)amino]-5-oxo-5H-benzo[4,5]cyclohepta[1,2-b]pyridin-3-yl}phenyl)acetamide | calc'd 506.2 (M + H)+; found 506.2 (M + H)+ |
| 135 | 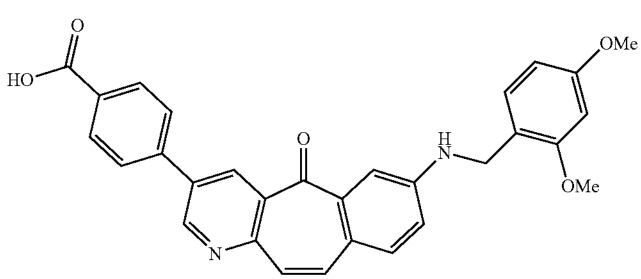 | 4-{7-[(2,4-dimethoxybenzyl)amino]-5-oxo-5H-benzo[4,5]cyclohepta[1,2-b]pyridin-3-yl}benzoic acid | calc'd 493.2 (M + H)+; found 493.1 (M + H)+ |
| 136 | 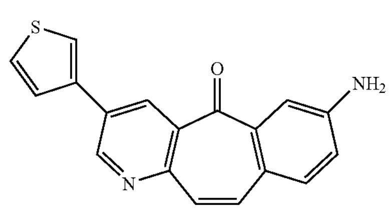 | 7-amino-3-(3-thienyl)-5H-benzo[4,5]cyclohepta[1,2-b]pyridin-5-one | calc'd 305.1 (M + H)+; found 305.1 (M + H)+ |

TABLE 3A-continued

| Compound | Structure | Name | MS (M + 1) |
| --- | --- | --- | --- |
| 137 | 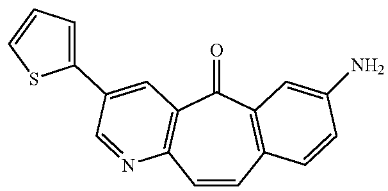 | 7-amino-3-(2-thienyl)-5H-benzo[4,5]cyclohepta[1,2-b]pyridin-5-one | calc'd 305.1 (M + H)+; found 305.1 (M + H)+ |
| 138 | 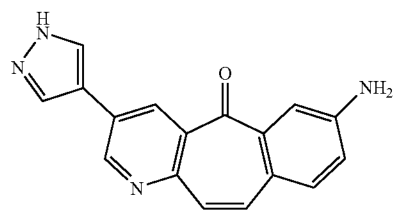 | 7-amino-3-(1H-pyrazol-4-yl)-5H-benzo[4,5]cyclohepta[1,2-b]pyridin-5-one; isolated as 3HCl salt | calc'd 289.1 (M + H)+; found 289.1 (M + H)+ |
| 139 | 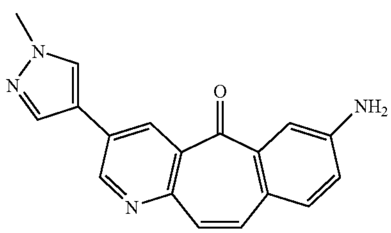 | 7-amino-3-(1-methyl-1H-pyrazol-4-yl)-5H-benzo[4,5]cyclohepta[1,2-b]pyridin-5-one; isolated as 3HCl salt | calc'd 303.1 (M + H)+; found 303.1 (M + H)+ |
| 140 | 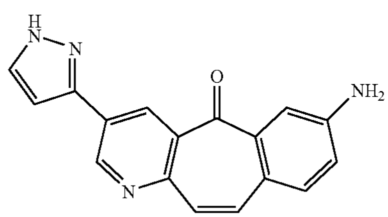 | 7-amino-3-(1H-pyrazol-3-yl)-5H-benzo[4,5]cyclohepta[1,2-b]pyridin-5-one; isolated as 3HCl salt | calc'd 289.1 (M + H)+; found 289.1 (M + H)+ |
| 141 | 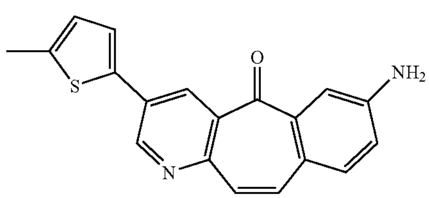 | 7-amino-3-(5-methyl-2-thienyl)-5H-benzo[4,5]cyclohepta[1,2-b]pyridin-5-one | calc'd 319.1 (M + H)+; found 319.1 (M + H)+ |
| 142 | 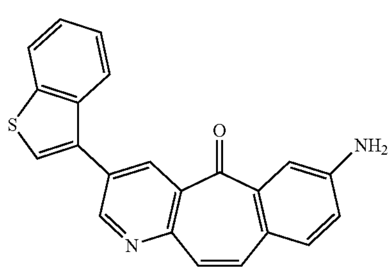 | 7-amino-3-(1-benzothien-3-yl)-5H-benzo[4,5]cyclohepta[1,2-b]pyridin-5-one | calc'd 355.1 (M + H)+; found 355.1 (M + H)+ |

TABLE 3A-continued

| Compound | Structure | Name | MS (M + 1) |
|---|---|---|---|
| 143 | 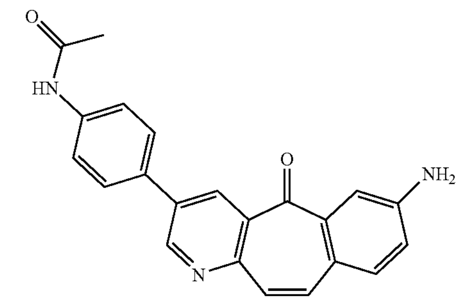 | N-[4-(7-amino-5-oxo-5H-benzo[4,5]cyclohepta[1,2-b]pyridin-3-yl)phenyl]acetamide | calc'd 356.1 (M + H)+; found 356.1 (M + H)+ |
| 144 | 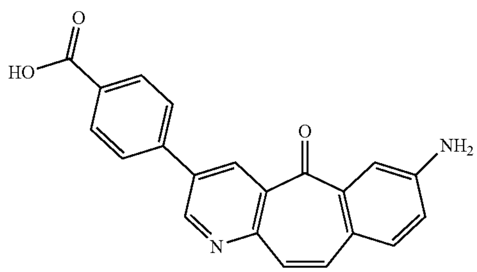 | 4-(7-amino-5-oxo-5H-benzo[4,5]cyclohepta[1,2-b]pyridin-3-yl)benzoic acid | calc'd 343.1 (M + H)+; found 343.1 (M + H)+ |
| 145 | 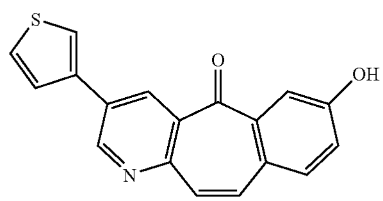 | 7-hydroxy-3-(3-thienyl)-5H-benzo[4,5]cyclohepta[1,2-b]pyridin-5-one | calc'd 306.1 (M + H)+; found 306.1 (M + H)+ |
| 146 | 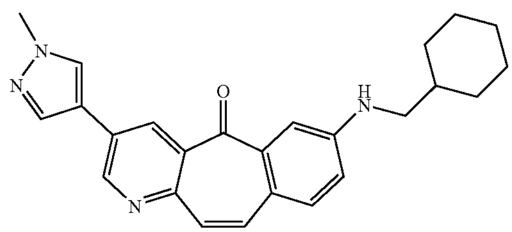 | 7-[(cyclohexylmethyl)amino]-3-(1-methyl-1H-pyrazol-4-yl)-5H-benzo[4,5]cyclohepta[1,2-b]pyridin-5-one | calc'd 399.2 (M + H)+; found 399.2 (M + H)+ |
| 147 | 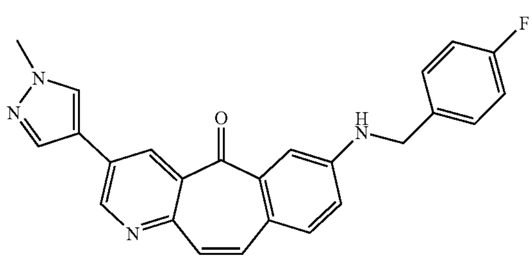 | 7-[(4-fluorobenzyl)amino]-3-(1-methyl-1H-pyrazol-4-yl)-5H-benzo[4,5]cyclohepta[1,2-b]pyridin-5-one | calc'd 411.2 (M + H)+; found 411.1 (M + H)+ |
| 148 | 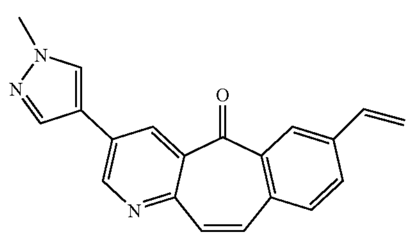 | 3-(1-methyl-1H-pyrazol-4-yl)-7-vinyl-5H-benzo[4,5]cyclohepta[1,2-b]pyridin-5-one | calc'd 314.1 (M + H)+; found 314.1 (M + H)+ |

TABLE 3A-continued

| Compound | Structure | Name | MS (M + 1) |
|---|---|---|---|
| 149 | 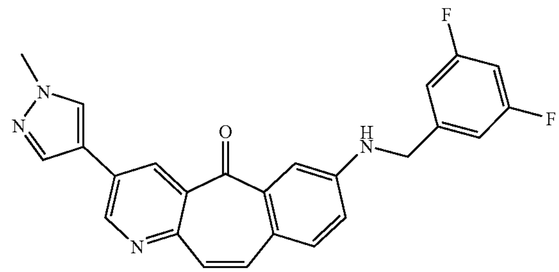 | 7-[(2,4-difluorobenzyl)amino]-3-(1-methyl-1H-pyrazol-4-yl)-5H-benzo[4,5]cyclohepta[1,2-b]pyridin-5-one | calc'd 429.1 (M + H)+; found 429.1 (M + H)+ |
| 150 | 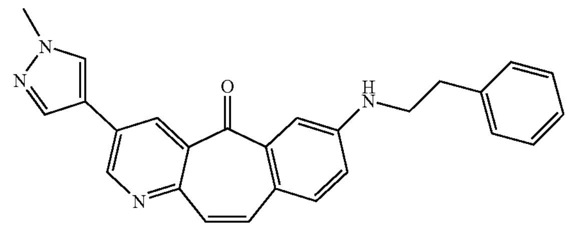 | 3-(1-methyl-1H-pyrazol-4-yl)-7-[(2-phenylethyl)amino]-5H-benzo[4,5]cyclohepta[1,2-b]pyridin-5-one | calc'd 407.2 (M + H)+; found 407.2 (M + H)+ |
| 151 | 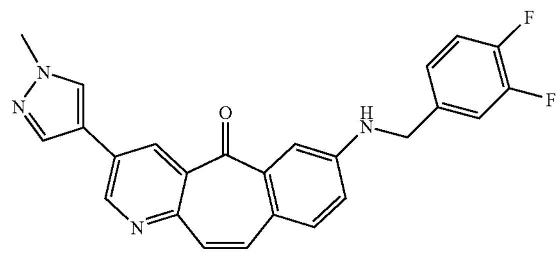 | 7-[(3,4-difluorobenzyl)amino]-3-(1-methyl-1H-pyrazol-4-yl)-5H-benzo[4,5]cyclohepta[1,2-b]pyridin-5-one | calc'd 429.1 (M + H)+; found 429.2 (M + H)+ |
| 152 | 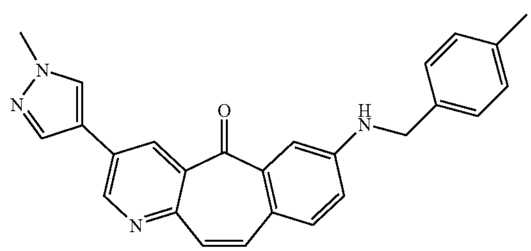 | 7-[(4-methylbenzyl)amino]-3-(1-methyl-1H-pyrazol-4-yl)-5H-benzo[4,5]cyclohepta[1,2-b]pyridin-5-one | calc'd 407.2 (M + H)+; found 407.2 (M + H)+ |
| 153 | 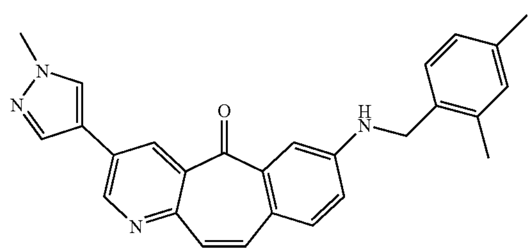 | 7-[(2,4-dimethylbenzyl)amino]-3-(1-methyl-1H-pyrazol-4-yl)-5H-benzo[4,5]cyclohepta[1,2-b]pyridin-5-one | calc'd 421.2 (M + H)+; found 421.2 (M + H)+ |
| 154 | 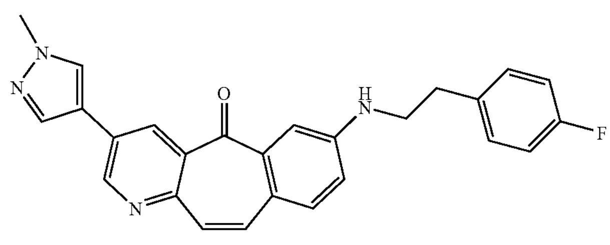 | 7-{[2-(4-fluorophenyl)ethyl]amino}-3-(1-methyl-1H-pyrazol-4-yl)-5H-benzo[4,5]cyclohepta[1,2-b]pyridin-5-one | calc'd 425.2 (M + H)+; found 425.2 (M + H)+ |

TABLE 3A-continued

| Compound | Structure | Name | MS (M + 1) |
|---|---|---|---|
| 155 | 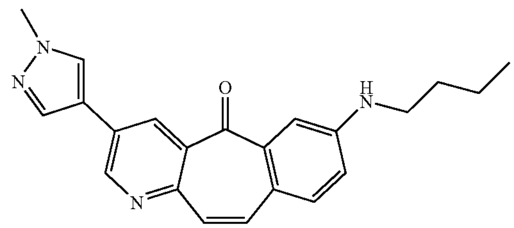 | 7-(butylamino)-3-(1-methyl-1H-pyrazol-4-yl)-5H-benzo[4,5]cyclohepta[1,2-b]pyridin-5-one | calc'd 359.2 (M + H)+; found 359.2 (M + H)+ |
| 156 | 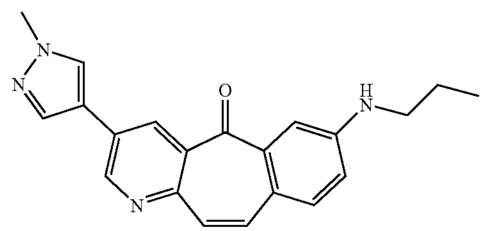 | 3-(1-methyl-1H-pyrazol-4-yl)-7-(propylamino)-5H-benzo[4,5]cyclohepta[1,2-b]pyridin-5-one | calc'd 345.2 (M + H)+; found 345.2 (M + H)+ |
| 157 | 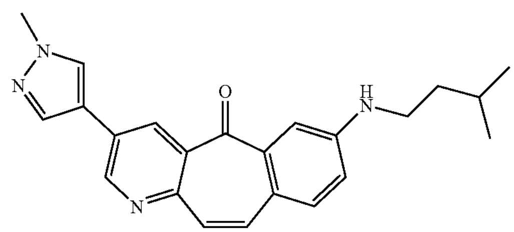 | 7-[(3-methylbutyl)amino]-3-(1-methyl-1H-pyrazol-4-yl)-5H-benzo[4,5]cyclohepta[1,2-b]pyridin-5-one | calc'd 373.2 (M + H)+; found 373.2 (M + H)+ |
| 158 | 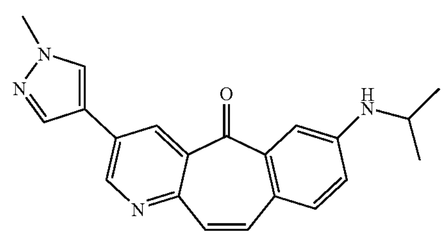 | 7-(isopropylamino)-3-(1-methyl-1H-pyrazol-4-yl)-5H-benzo[4,5]cyclohepta[1,2-b]pyridin-5-one | calc'd 345.2 (M + H)+; found 345.2 (M + H)+ |
| 159 | 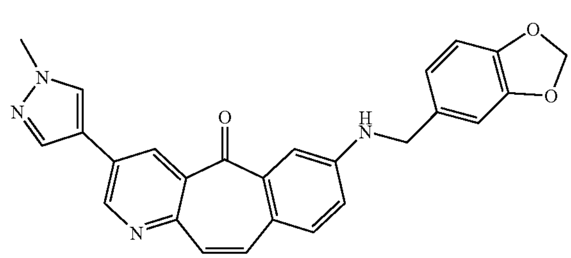 | 7-[(1,3-benzodioxol-5-ylmethyl)amino]-3-(1-methyl-1H-pyrazol-4-yl)-5H-benzo[4,5]cyclohepta[1,2-b]pyridin-5-one | Calc'd 437.2 (M + H)+; found 437.2 (M + H)+ |
| 160 | 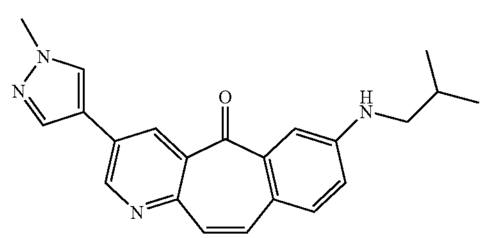 | 7-(isobutylamino)-3-(1-methyl-1H-pyrazol-4-yl)-5H-benzo[4,5]cyclohepta[1,2-b]pyridin-5-one | Calc'd 359.2 (M + H)+; found 359.2 (M + H)+ |

TABLE 3A-continued

| Compound | Structure | Name | MS (M + 1) |
|---|---|---|---|
| 161 | 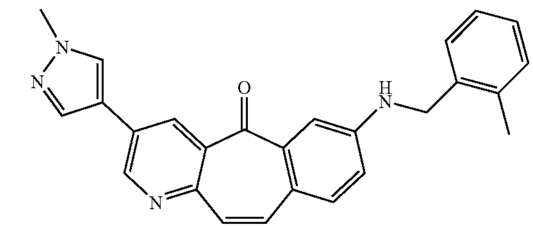 | 7-[(2-methylbenzyl)amino]-3-(1-methyl-1H-pyrazol-4-yl)-5H-benzo[4,5]cyclohepta[1,2-b]pyridin-5-one | calc'd 407.2 (M + H)+; found 407.2 (M + H)+ |
| 162 | 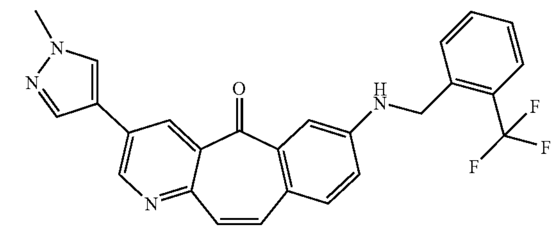 | 3-(1-methyl-1H-pyrazol-4-yl)-7-{[2-(trifluoromethyl)benzyl]amino}-5H-benzo[4,5]cyclohepta[1,2-b]pyridin-5-one | calc'd 461.2 (M + H)+; found 461.1 (M + H)+ |
| 163 | 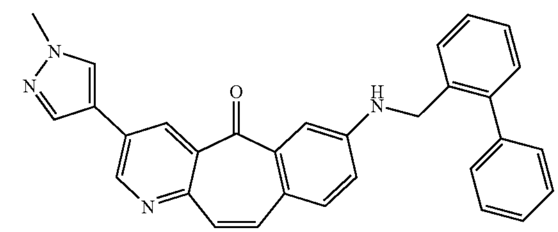 | 7-[(biphenyl-2-ylmethyl)amino]-3-(1-methyl-1H-pyrazol-4-yl)-5H-benzo[4,5]cyclohepta[1,2-b]pyridin-5-one | Calc'd 469.2 (M + H)+; found 469.1 (M + H)+ |
| 164 | 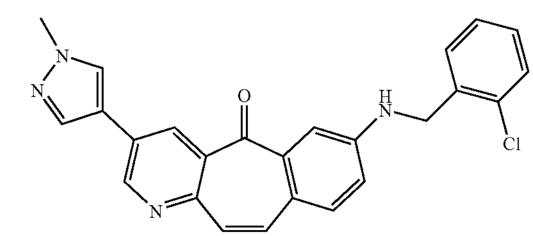 | 7-[(2-chlorobenzyl)amino]-3-(1-methyl-1H-pyrazol-4-yl)-5H-benzo[4,5]cyclohepta[1,2-b]pyridin-5-one | Calc'd 427.1 (M + H)+; found 427.1 (M + H)+ |
| 165 | 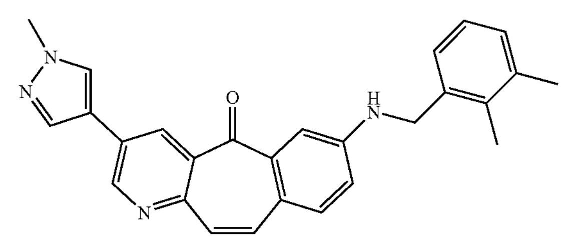 | 7-[(2,3-dimethylbenzyl)amino]-3-(1-methyl-1H-pyrazol-4-yl)-5H-benzo[4,5]cyclohepta[1,2-b]pyridin-5-one | calc'd 421.2 (M + H)+; found 421.2 (M + H)+ |
| 166 | 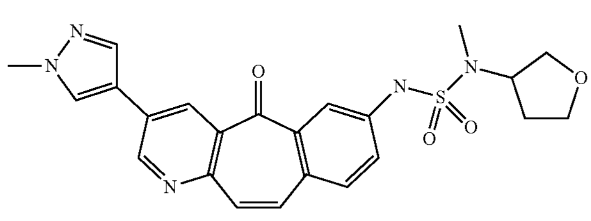 | N-methyl-N'-[3-(1-methyl-1H-pyrazol-4-yl)-5-oxo-5H-benzo[4,5]cyclohepta[1,2-b]pyridin-7-yl]-N-(tetrahydrofuran-3-yl)sulfamide | calc'd 466.1 (M + H)+; found 466.1 (M + H)+ |

TABLE 3A-continued

| Compound | Structure | Name | MS (M + 1) |
|---|---|---|---|
| 167 | 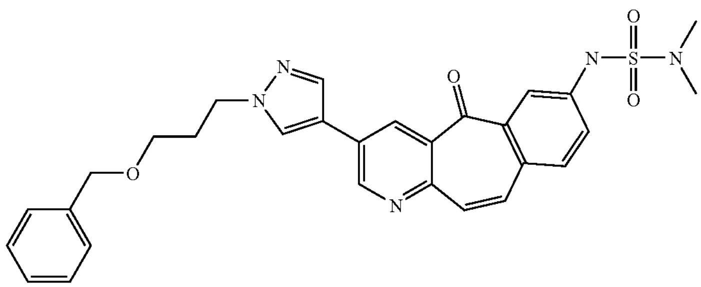 | N'-(3-{1-[3-(benzyloxy)propyl]-1H-pyrazol-4-yl}-5-oxo-5H-benzo[4,5]cyclohepta[1,2-b]pyridin-7-yl)-N,N-dimethylsulfamide | calc'd 544.2 (M + H)+; found 544.2 (M + H)+ |
| 168 | 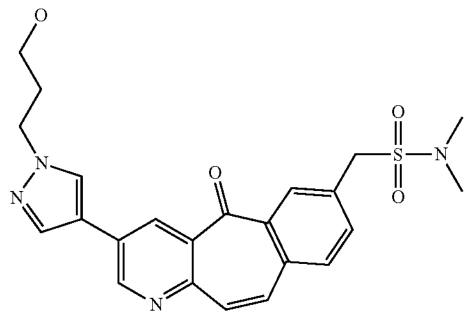 | N'-{3-[1-(3-hydroxypropyl-1H-pyrazol-4-yl]-5-oxo-5H-benzo[4,5]cyclohepta[1,2-b]pyridin-7-yl}-N,N-dimethylsulfamide | calc'd 454.2 (M + H)+; found 454.1 (M + H)+ |
| 169 | 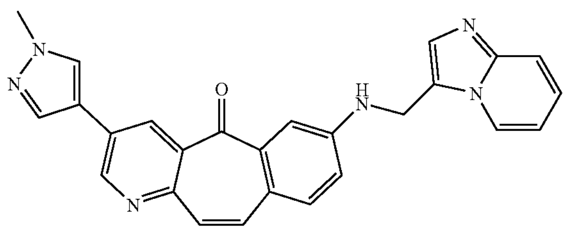 | 7-[(imidazo[1,2-a]pyridin-3-ylmethyl)amino]-3-(1-methyl-1H-pyrazol-4-yl)-5H-benzo[4,5]cyclohepta[1,2-b]pyridin-5-one | calc'd 433.2 (M + H)+; found 433.2 (M + H)+ |
| 170 | 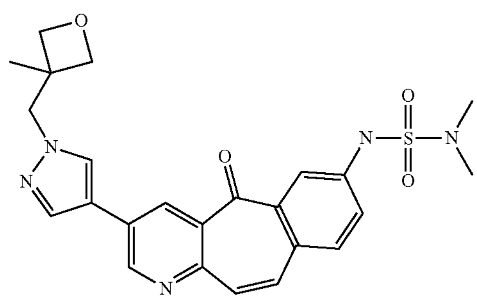 | N,N-dimethyl-N'-(3-{1-[(3-methyloxetan-3-yl)methyl]-1H-pyrazol-4-yl}-5-oxo-5H-benzo[4,5]cyclohepta[1,2-b]pyridin-7-yl)sulfamide | calc'd 480.2 (M + H)+; found 480.2 (M + H)+ |
| 171 | 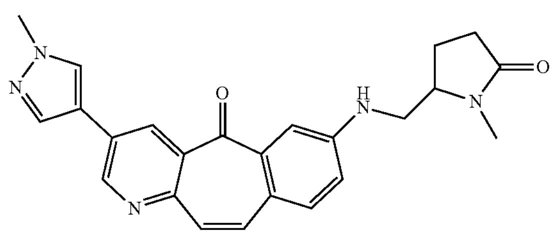 | 7-{[(1-methyl-5-oxopyrrolidin-2-yl)methyl]amino}-3-(1-methyl-1H-pyrazol-4-yl)-5H-benzo[4,5]cyclohepta[1,2-b]pyridin-5-one | calc'd 414.2 (M + H)+; found 414.1 (M + H)+ |
| 172 | 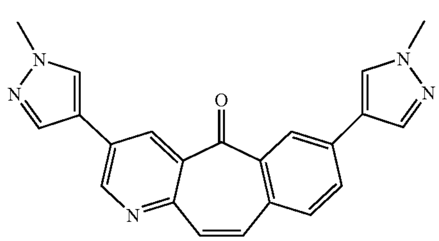 | 3,7-bis(1-methyl-1H-pyrazol-4-yl)-5H-benzo[4,5]cyclohepta[1,2-b]pyridin-5-one | Calc'd 368.1 (M + H)+; found 368.2 (M + H)+ |

TABLE 3A-continued

| Compound | Structure | Name | MS (M + 1) |
|---|---|---|---|
| 173 | 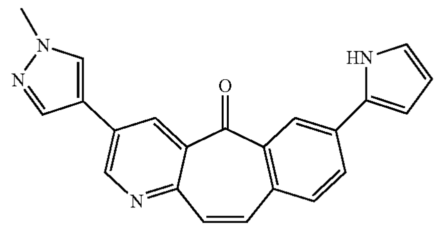 | 3-(1-methyl-1H-pyrazol-4-yl)-7-(1H-pyrrol-2-yl)-5H-benzo[4,5]cyclohepta[1,2-b]pyridin-5-one | Calc'd 353.1 (M + H)+; found 353.1 (M + H)+ |
| 174 | 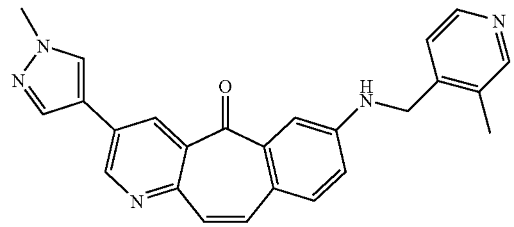 | 3-(1-methyl-1H-pyrazol-4-yl)-7-{[(3-methylpyridin-4-yl)methyl]amino}-5H-benzo[4,5]cyclohepta[1,2-b]pyridin-5-one | Calc'd 408.2 (M + H)+; found 408.2 (M + H)+ |
| 175 | 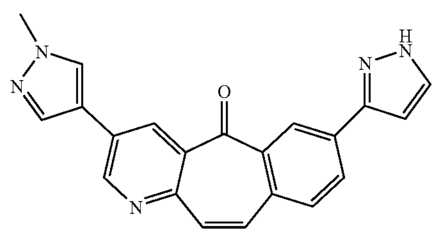 | 3-(1-methyl-1H-pyrazol-4-yl)-7-(1H-pyrazol-3-yl)-5H-benzo[4,5]cyclohepta[1,2-b]pyridin-5-one | calc'd 354.1 (M + H)+; found 354.2 (M + H)+ |
| 176 | 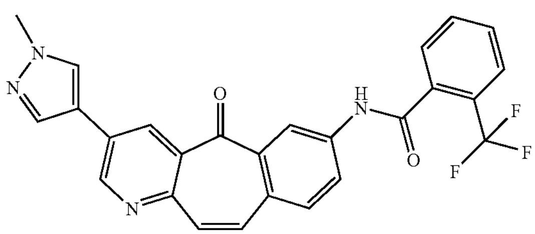 | N-[3-(1-methyl-1H-pyrazol-4-yl)-5-oxo-5H-benzo[4,5]cyclohepta[1,2-b]pyridin-7-yl]-2-(trifluoromethyl)benzamide | calc'd 475.1 (M + H)+; found 475.1 (M + H)+ |
| 177 | 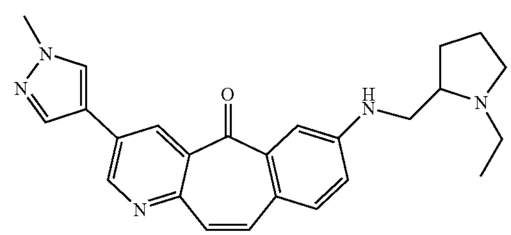 | 7-{[(1-ethylpyrrolidin-2-yl)methyl]amino}-3-(1-methyl-1H-pyrazol-4-yl)-5H-benzo[4,5]cyclohepta[1,2-b]pyridin-5-one | Calc'd 414.2 (M + H)+; found 414.2 (M + H)+ |
| 178 | 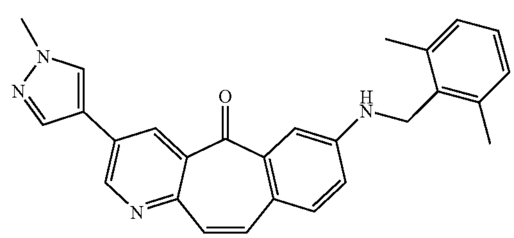 | 7-[(2,6-dimethylbenzyl)amino]-3-(1-methyl-1H-pyrazol-4-yl)-5H-benzo[4,5]cyclohepta[1,2-b]pyridin-5-one | Calc'd 421.2 (M + H)+; found 421.2 (M + H)+ |

TABLE 3A-continued

| Compound | Structure | Name | MS (M + 1) |
|---|---|---|---|
| 179 | 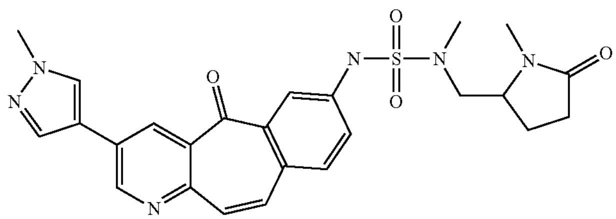 | N-methyl-N-[(1-methyl-5-oxopyrrolidin-2-yl)methyl]-N'-[3-(1-methyl-1H-pyrazol-4-yl)-5-oxo-5H-benzo[4,5]-cyclohepta[1,2-b]pyridin-7-yl]sulfamide | calc'd 507.2 (M + H)+; found 507.2 (M + H)+ |
| 180 | 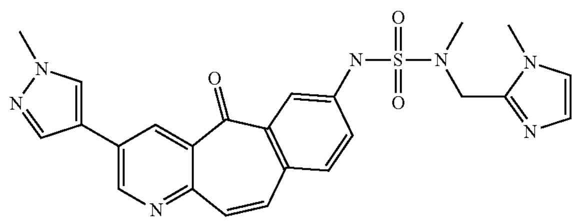 | N-methyl-N-[(1-methyl-1H-imidazol-2-yl)methyl]-N'-[3-(1-methyl-1H-pyrazol-4-yl)-5-oxo-5H-benzo[4,5]cyclohepta[1,2-b]pyridin-7-yl]sulfamide | calc'd 490.2 (M + H)+; found 490.2 (M + H)+ |
| 181 | 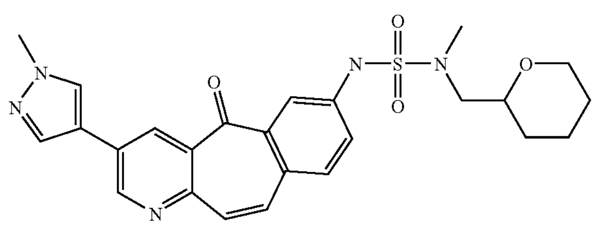 | N-methyl-N'-[3-(1-methyl-1H-pyrazol-4-yl)-5-oxo-5H-benzo[4,5]cyclohepta[1,2-b]pyridin-7-yl]-N-(tetrahydro-2H-pyran-2-ylmethyl)sulfamide | calc'd 494.2 (M + H)+; found 494.2 (M + H)+ |
| 182 | 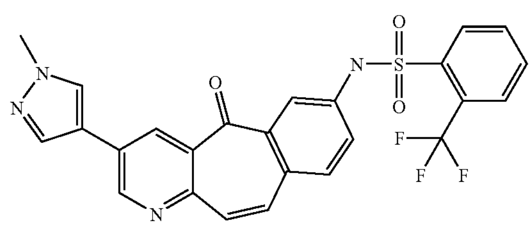 | N-[3-(1-methyl-1H-pyrazol-4-yl)-5-oxo-5H-benzo[4,5]cyclohepta[1,2-b]pyridin-7-yl]-2-(trifluoromethyl)benzene-sulfonamide | calc'd 511.1 (M + H)+; found 511.1 (M + H)+ |
| 183 | 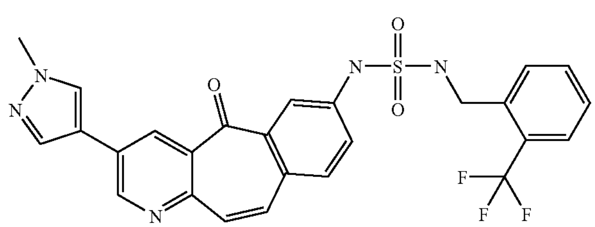 | N-[3-(1-methyl-1H-pyrazol-4-yl)-5-oxo-5H-benzo[4,5]cyclohepta[1,2-b]pyridin-7-yl]-N'-[2-(trifluoromethyl)benzyl]sulfamide | calc'd 540.1 (M + H)+; found 540.2 (M + H)+ |
| 184 | 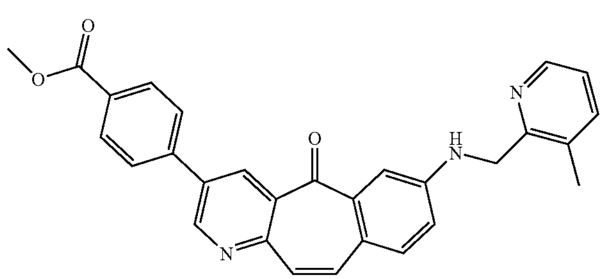 | methyl 4-(7-{[3-methylpyridin-2-yl)methyl]amino}-5-oxo-5H-benzo[4,5]cyclohepta[1,2-b]pyridin-3-yl)benzoate | calc'd 462.2 (M + H)+; found 462.2 (M + H)+ |

TABLE 3A-continued

| Compound | Structure | Name | MS (M + 1) |
|---|---|---|---|
| 185 | 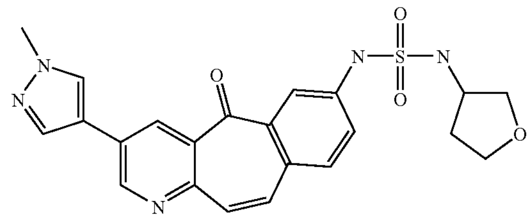 | N-[3-(1-methyl-1H-pyrazol-4-yl)-5-oxo-5H-benzo[4,5]cyclohepta[1,2-b]pyridin-7-yl]-N'-(tetrahydrofuran-3-yl)sulfamide | calc'd 452.1 (M + H)+; found 452.2 (M + H)+ |
| 186 | 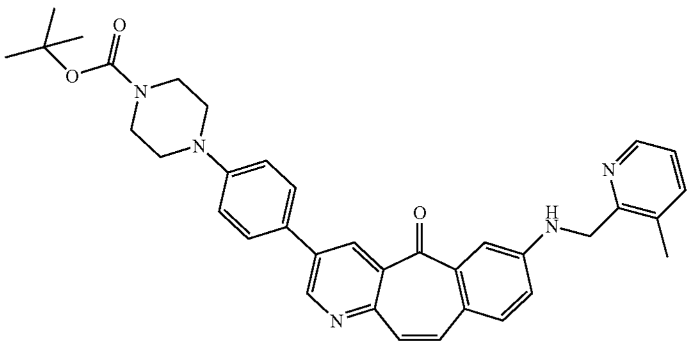 | tert-butyl 4-[4-(7-{[(3-methylpyridin-2-yl)methyl]amino}-5-oxo-5H-benzo[4,5]cyclohepta[1,2-b]pyridin-3-yl)phenyl]piperazine-1-carboxylate | calc'd 588.3 (M + H)+; found 588.3 (M + H)+ |
| 187 | 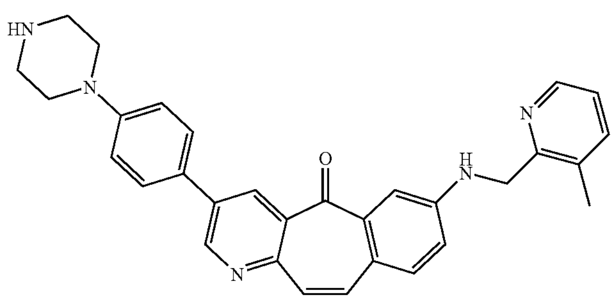 | 7-{[(3-methylpyridin-2-yl)methyl]amino}-3-(4-piperizin-1-ylphenyl)-5H-benzo[4,5]cyclohepta[1,2-b]pyridin-5-one | calc'd 488.2 (M + H)+; found 488.3 (M + H)+ |
| 188 | 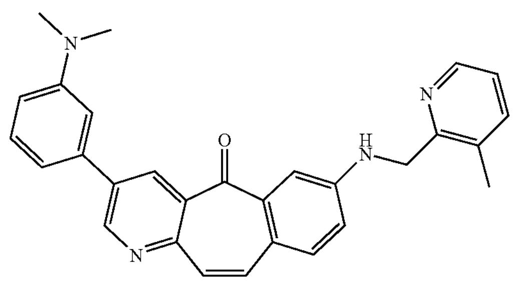 | 3-[3-(dimethylamino)phenyl]-7-{[(3-methylpyridin-2-yl)methyl]amino}-5H-benzo[4,5]cyclohepta[1,2-b]pyridin-5-one | Calc'd 447.2 (M + H)+; found 447.2 (M + H)+ |
| 189 | 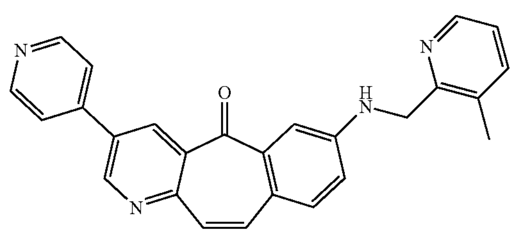 | 7-{[(3-methylpyridin-2-yl)methyl]amino}-3-pyridin-4-yl-5H-benzo[4,5]cyclohepta[1,2-b]pyridin-5-one | Calc'd 405.2 (M + H)+; found 405.2 (M + H)+ |
| 190 | 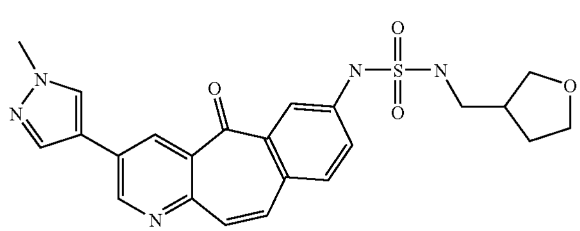 | N-[3-(1-methyl-1H-pyrazol-4-yl)-5-oxo-5H-benzo[4,5]cyclohepta[1,2-b]pyridin-7-yl]-N'-(tetrahydrofuran-3-ylmethyl)sulfamide | calc'd 466.1 (M + H)+; found 466.2 (M + H)+ |

TABLE 3A-continued

| Compound | Structure | Name | MS (M + 1) |
|---|---|---|---|
| 191 | 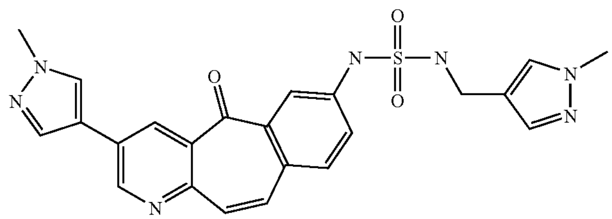 | N-[(1-methyl-1H-pyrazol-4-yl)methyl]-N'-[3-(1-methyl-1H-pyrazol-4-yl)-5-oxo-5H-benzo[4,5]cyclohepta[1,2-b]pyridin-7-yl]sulfamide | calc'd 476.1 (M + H)+; found 476.2 (M + H)+ |
| 192 | 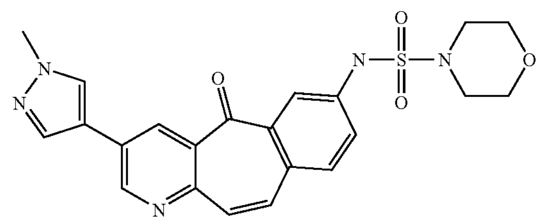 | N-[3-(1-methyl-1H-pyrazol-4-yl)-5-oxo-5H-benzo[4,5]cyclohepta[1,2-b]pyridin-7-yl]morpholine-4-sulfonamide | calc'd 452.1 (M + H)+; found 452.2 (M + H)+ |
| 193 | 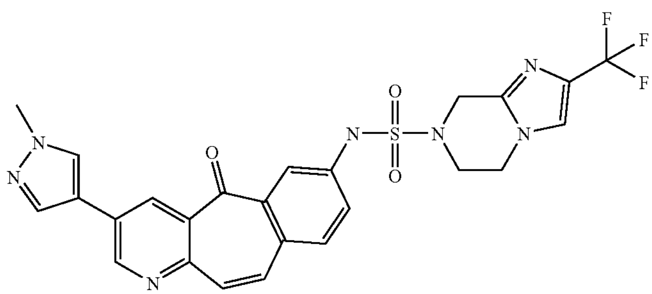 | N-[3-(1-methyl-1H-pyrazol-4-yl)-5-oxo-5H-benzo[4,5]cyclohepta[1,2-b]pyridin-7-yl]-2-(trifluoromethyl)-5,6-dihydroimidazo[1,2-a]pyrazine-7(8H)-sulfonamide | calc'd 556.1 (M + H)+; found 556.1 (M + H)+ |
| 194 | 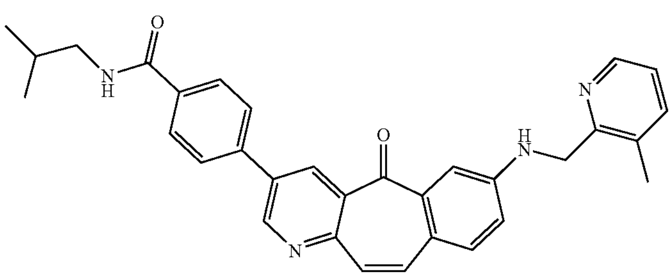 | N-isobutyl-4-(7-{[(3-methylpyridin-2-yl)methyl]amino}-5-oxo-5H-benzo[4,5]cyclohepta[1,2-b]pyridin-3-yl)benzamide | calc'd 503.2 (M + H)+; found 503.2 (M + H)+ |
| 195 | 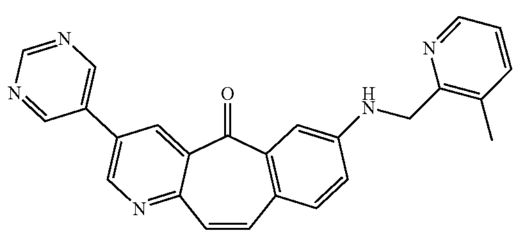 | 7-{[(3-methylpyridin-2-yl)methyl]amino}-3-pyrimidin-5-yl-5H-benzo[4,5]cyclohepta[1,2-b]pyridin-5-one | Calc'd 406.2 (M + H)+; found 406.1 (M + H)+ |
| 196 | 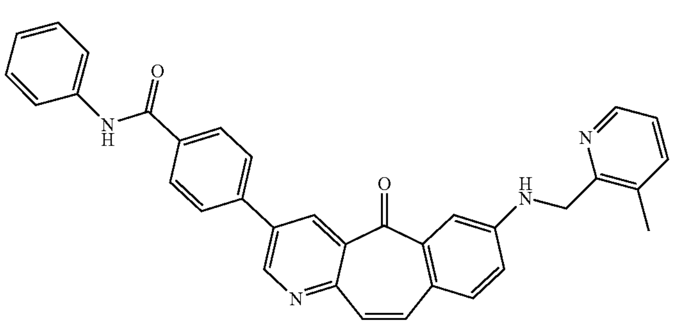 | 4-(7-{[(3-methylpyridin-2-yl)methyl]amino}-5-oxo-5H-benzo[4,5]cyclohepta[1,2-b]pyridin-3-yl)-N-phenylbenzamide | Calc'd 523.2 (M + H)+; found 523.2 (M + H)+ |

TABLE 3A-continued

| Compound | Structure | Name | MS (M + 1) |
|---|---|---|---|
| 197 | 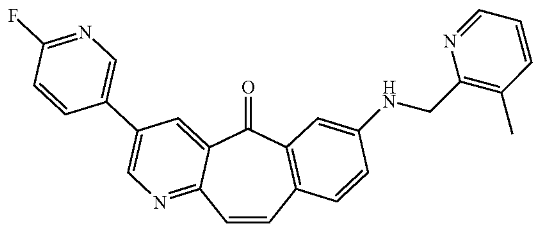 | 3-(6-fluoropyridin-3-yl)-7-{[(3-methylpyridin-2-yl)methyl]amino}-5H-benzo[4,5]cyclohepta[1,2-b]pyridin-5-one | Calc'd 423.2 (M + H)+; found 423.2 (M + H)+ |
| 198 | 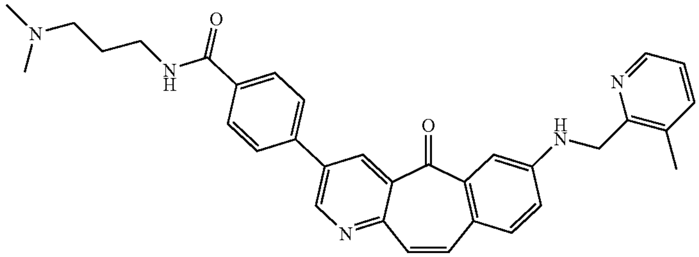 | N-[3-(dimethylamino)propyl]-4-(7-{[(3-methylpyridin-2-yl)methyl]amino}-5-oxo-5H-benzo[4,5]cyclohepta[1,2-b]pyridin-3-yl)benzamide | calc'd 532.3 (M + H)+; found 532.3 (M + H)+ |
| 199 | 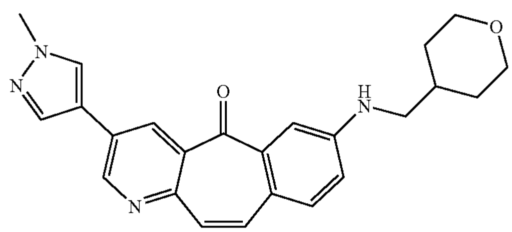 | 3-(1-methyl-1H-pyrazol-4-yl)-7-[(tetrahydro-2H-pyran-4-ylmethyl)amino]-5H-benzo[4,5]cyclohepta[1,2-b]pyridin-5-one | calc'd 401.2 (M + H)+; found 401.2 (M + H)+ |
| 200 | 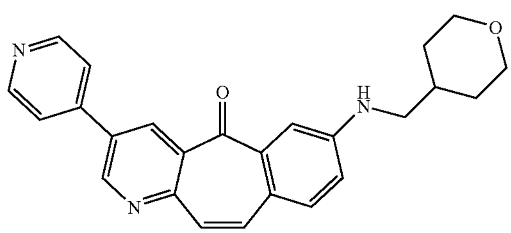 | 3-pyridin-4-yl-7-[(tetrahydro-2H-pyran-4-ylmethyl)amino]-5H-benzo[4,5]cyclohepta[1,2-b]pyridin-5-one | calc'd 398.2 (M + H)+; found 398.2 (M + H)+ |
| 201 | 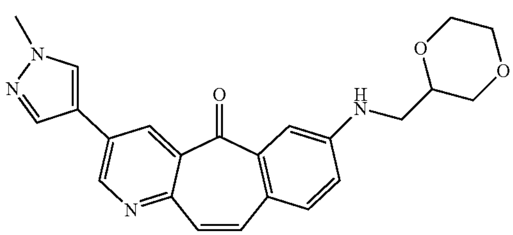 | 7-[(1,4-dioxan-2-ylmethyl)amino]-3-(1-methyl-1H-pyrazol-4-yl)-5H-benzo[4,5]cyclohepta[1,2-b]pyridin-5-one | calc'd 403.2 (M + H)+; found 403.2 (M + H)+ |
| 201A | 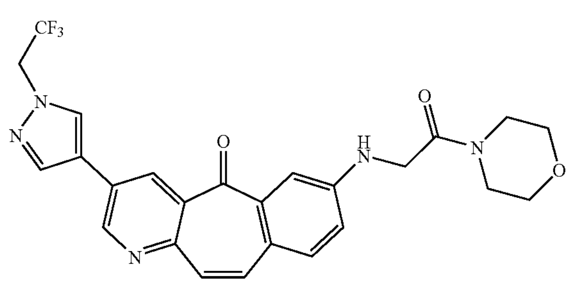 | 7-[(2-morpholin-4-yl-2-oxoethyl)amino]-3-[1-(2,2,2-trifluoroethyl)-1H-pyrazol-4-yl]-5H-benzo[4,5]cyclohepta[1,2-b]pyridin-5-one | calc'd [M + H]+, 498.2; found 498.1. |

TABLE 3A-continued

| Compound | Structure | Name | MS (M + 1) |
|---|---|---|---|
| 201B | 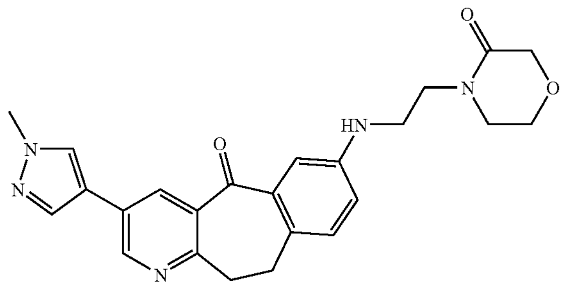 | 3-(1-methyl-1H-pyrazol-4-yl)-7-{[2-(3-oxomorpholin-4-yl)ethyl]amino}-5H-benzo[4,5]cyclohepta[1,2-b]pyridin-5-one | calc'd [M + H]+, 430.2; found 430.1. |
| 201C | 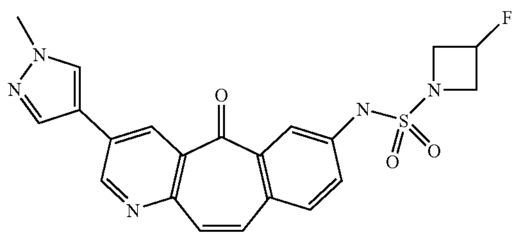 | 3-fluoro-N-[3-(1-methyl-1H-pyrazol-4-yl)-5-oxo-5H-benzo[4,5]cyclohepta[1,2-b]pyridin-7-yl]azetidine-1-sulfonamide | calc'd [M + H]+, 440.1; found 440.1. |
| 201D | 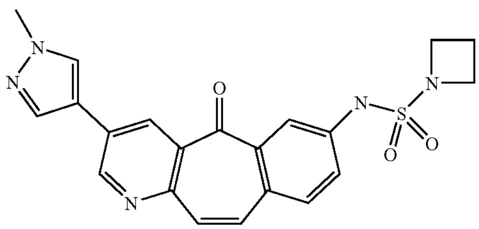 | N-[3-(1-methyl-1H-pyrazol-4-yl)-5-oxo-5H-benzo[4,5]cyclohepta[1,2-b]pyridin-7-yl]azetidine-1-sulfonamide | calc'd [M + H]+, 422.1; found 422.0. |
| 201E | 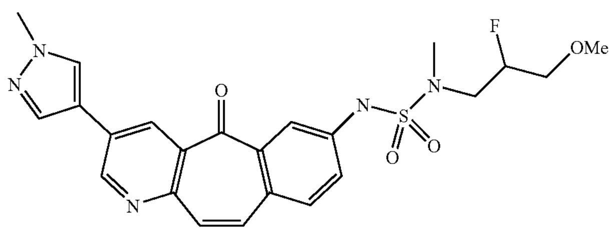 | N-(2-fluoro-3-methoxypropyl)-N-methyl-N'-[3-(1-methyl-1H-pyrazol-4-yl)-5-oxo-5H-benzo[4,5]cyclohepta[1,2-b]pyridin-7-yl]sulfamide | Calc'd for 486.2 [M + H]+; found 486.2 |
| 201F | 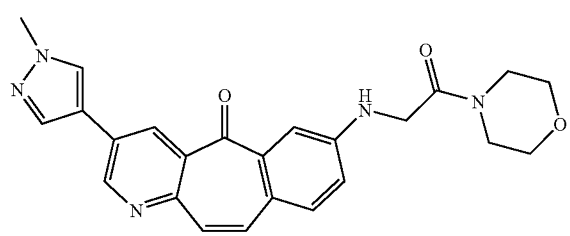 | 3-(1-methyl-1H-pyrazol-4-yl)-7-[(2-morpholin-4-yl-2-oxoethyl)amino]-5H-benzo[4,5]cyclohepta[1,2-b]pyridin-5-one | Calc'd [M + H]+, 430.2; found 430.1 |

Scheme 5

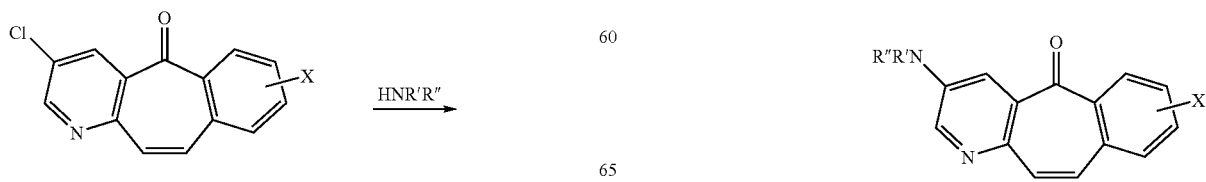

Example 24

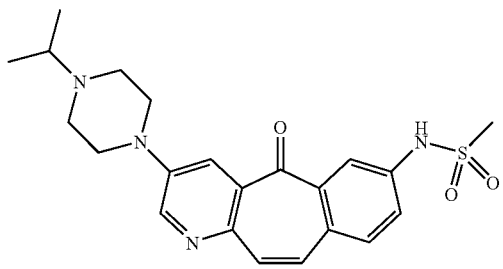

N-[3-(4-isopropylpiperazin-1-yl)-5-oxo-5H-benzo[4,5]cyclohepta[1,2-b]pyridin-7-yl]methanesulfonamide Method A N-(3-chloro-5-oxo-5H-benzo[4,5]cyclohepta[1,2-b]pyridin-7-yl)methanesulfonamide (0.050 g, 0.15 mmol), isopropylpiperazine (0.038 g, 0.30 mmol), Pd$_2$(dba)$_3$ (1.5 mg, 0.0015 mmol), BINAP (3.0 mg, 0.0045 mmol), and sodium tert-butoxide (0.043 g, 0.45 mmol) were added to a dry flask through which argon was purged. 3.0 mL dry dioxane was added and argon was bubbled through the solution for 5 minutes. The reaction was stirred and heated to 105° C. After 12 hours, the reaction mixture was poured into 100 mL ethyl acetate, 100 mL water, and 25 mL saturated ammonium chloride. The organic layer was separated, dried with magnesium sulfate, filtered, concentrated, and purified by reverse phase HPLC (20-100% acetonitrile/water gradient, 0.1% trifluoroacetic acid modifier) to afford the title compound.

Method B:

N-(3-chloro-5-oxo-5H-benzo[4,5]cyclohepta[1,2-b]pyridin-7-yl)methanesulfonamide (0.100 g, 0.30 mmol), Pd$_2$(dba)$_3$ (6 mg, 0.006 mmol), rac-BINAP (11 mg, 0.018 mmol), and cesium carbonate (0.490 g, 1.50 mmol) combined mixed in a dry tube. Isopropylpiperazine (0.170 mL, 1.20 mmol) and 0.70 mL of dry dimethylformamide were added and the tube was sealed. The reaction contents were heated in the Biotage Initiator series microwave at 180° C. for 15 minutes. The reaction contents were partially concentrated and purified by reverse phase HPLC (10-100% acetonitrile/water gradient, 0.1% trifluoroacetic acid modifier) to afford the title compound.

$^1$H NMR (600 MHz, CD$_3$OD) δ 8.64 (d, 1H); 8.18 (s, 1H); 7.96 (d, 1H); 7.68 (d, 1H); 7.60 (dd, 1H); 7.20 (d, 1H); 7.18 (d, 1H); 3.45 (m, 4H); 3.04 (s, 3H); 2.78 (m, 5H); 1.14 (d, 6H). LRMS (APCI) calculated for C$_{22}$H$_{27}$N$_4$O$_3$S [M+H]+, 427.2; found 427.2.

The following compounds were made according to Scheme 5. Additional synthetic modifications were employed in the preparation of some of the compounds. Compound 225 and 226 were isolated from a single reaction attempt to prepare the 5-oxo derivative of Compound 225. Compound 230 was prepared by N-tert-butoxycarbonyl hydrolysis of Compound 218. Compounds 249 and 250 were prepared from Compounds 236A and 236 respectively in a manner similar to that described for Example 4, Method B.

TABLE 4

| Comp. # | Structure | Name | MS (M + 1) |
| --- | --- | --- | --- |
| 203 | 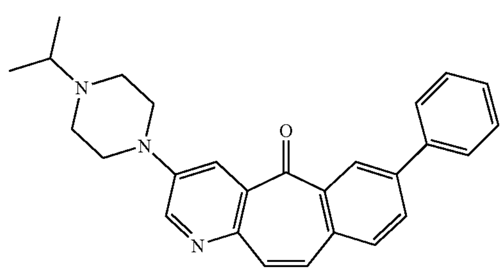 | 3-(4-isopropylpiperazin-1-yl)-7-phenyl-5H-benzo[4,5]cyclohepta[1,2-b]pyridin-5-one | calc'd 410.2 (M + H)+; found 410.2 (M + H)+ |
| 204 | 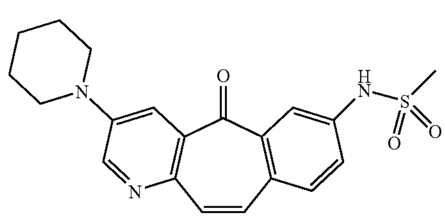 | N-(5-oxo-3-piperidin-1-yl-5H-benzo[4,5]cyclohepta[1,2-b]pyridin-7-yl)methanesulfonamide | calc'd 384.1 (M + H)+; found 384.1 (M + H)+ |
| 205 | 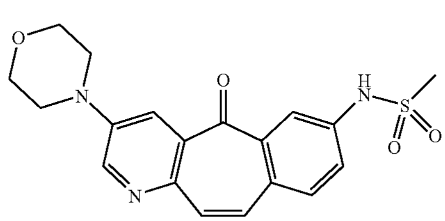 | N-(3-morpholin-4-yl-5-oxo-5H-benzo[4,5]cyclohepta[1,2-b]pyridin-7-yl)methanesulfonamide | calc'd 386.1 (M + H)+; found 386.1 (M + H)+ |

TABLE 4-continued

| Comp. # | Structure | Name | MS (M + 1) |
|---|---|---|---|
| 206 | 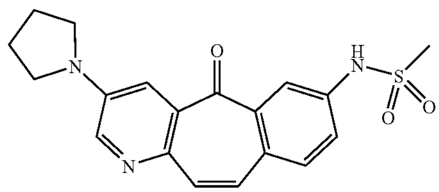 | N-(5-oxo-3-pyrrolidin-1-yl-5H-benzo[4,5]cyclohepta[1,2-b]pyridin-7-yl)methanesulfonamide | calc'd 370.1 (M + H)+; found 370.1 (M + H)+ |
| 207 | 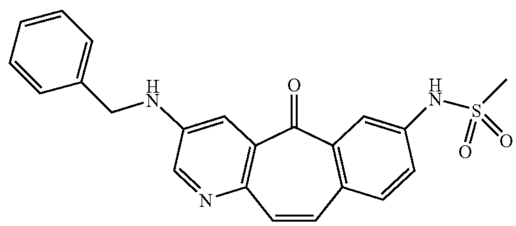 | N-[3-(benzylamino)-5-oxo-5H-benzo[4,5]cyclohepta[1,2-b]pyridin-7-yl]methanesulfonamide | calc'd 406.1 (M + H)+; found 406.1 (M + H)+ |
| 208 | 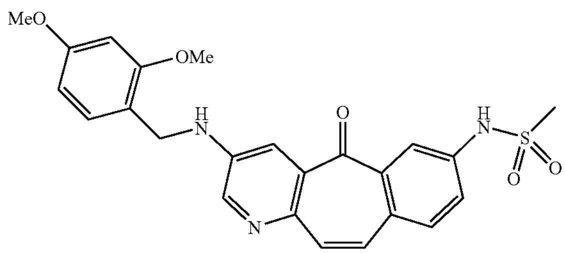 | N-{3-[(2,4-dimethoxybenzyl)amino]-5-oxo-5H-benzo[4,5]cyclohepta[1,2-b]pyridin-7-yl}methanesulfonamide | calc'd 466.1 (M + H)+; found 466.1 (M + H)+ |
| 209 | 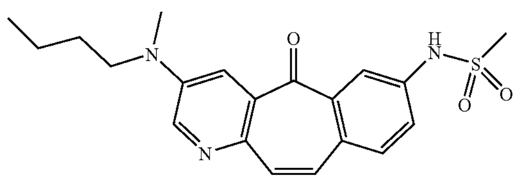 | N-{3-[butyl(methyl)amino]-5-oxo-5H-benzo[4,5]cyclohepta[1,2-b]pyridin-7-yl}methanesulfonamide | calc'd 386.2 (M + H)+; found 386.2 (M + H)+ |
| 210 | 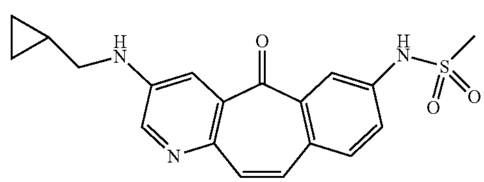 | N-{3-[(cyclopropylmethyl)amino]-5-oxo-5H-benzo[4,5]cyclohepta[1,2-b]pyridin-7-yl}methanesulfonamide | calc'd 370.1 (M + H)+; found 370.1 (M + H)+ |
| 211 | 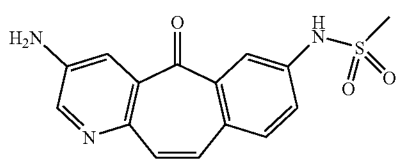 | N-(3-amino-5-oxo-5H-benzo[4,5]cyclohepta[1,2-b]pyridin-7-yl)methanesulfonamide | calc'd 316.1 (M + H)+; found 316.1 (M + H)+ |
| 212 | 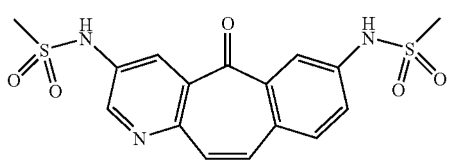 | N,N'-(5-oxo-5H-benzo[4,5]cyclohepta[1,2-b]pyridine-3,7-diyl)dimethanesulfonamide | calc'd 394.1 (M + H)+; found 394.0 (M + H)+ |
| 213 | 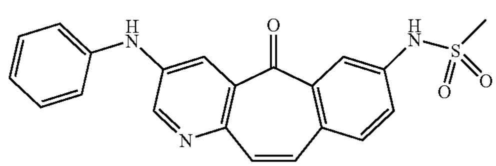 | N-(3-anilino-5-oxo-5H-benzo[4,5]cyclohepta[1,2-b]pyridin-7-yl)methanesulfonamide | calc'd 392.1 (M + H)+; found 392.1 (M + H)+ |

TABLE 4-continued

| Comp. # | Structure | Name | MS (M + 1) |
|---|---|---|---|
| 214 | 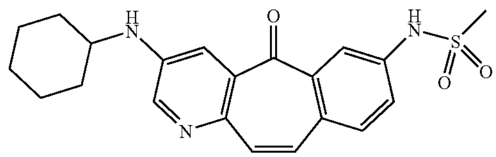 | N-[3-(cyclohexylamino)-5-oxo-5H-benzo[4,5]cyclohepta[1,2-b]pyridin-7-yl]methanesulfonamide | calc'd 398.2 (M + H)+; found 398.2 (M + H)+ |
| 215 | 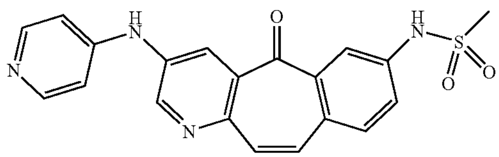 | N-[5-oxo-3-(pyridin-4-ylamino)-5H-benzo[4,5]cyclohepta[1,2-b]pyridin-7-yl]methanesulfonamide | calc'd 393.1 (M + H)+; found 393.1 (M + H)+ |
| 216 | 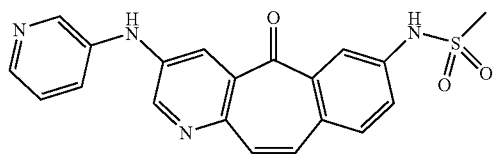 | N-[5-oxo-3-(pyridin-3-ylamino)-5H-benzo[4,5]cyclohepta[1,2-b]pyridin-7-yl]methanesulfonamide | calc'd 393.1 (M + H)+; found 393.1 (M + H)+ |
| 217 | 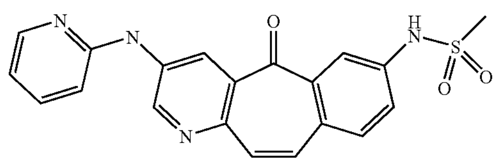 | N-[5-oxo-3-(pyridin-2-ylamino)-5H-benzo[4,5]cyclohepta[1,2-b]pyridin-7-yl]methanesulfonamide | calc'd 393.1 (M + H)+; found 392.7 (M + H)+ |
| 218 | 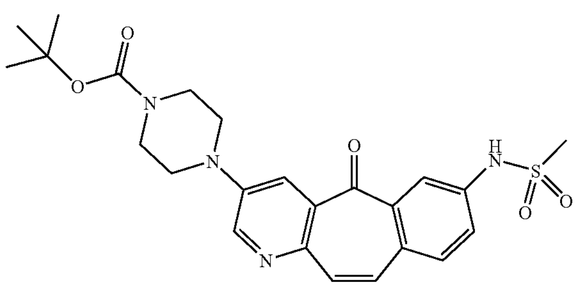 | tert-butyl 4-{7-[(methylsulfonyl)amino]-5-oxo-5H-benzo[4,5]cyclohepta[1,2-b]pyridin-3-yl}piperazine-1-carboxylate | calc'd 485.2 (M + H)+; found 485.2 (M + H)+ |
| 219 | 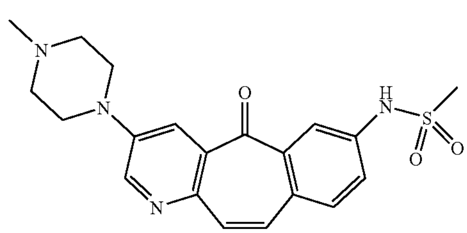 | N-[3-(4-methylpiperazin-1-yl)-5-oxo-5H-benzo[4,5]cyclohepta[1,2-b]pyridin-7-yl]methanesulfonamide | calc'd 399.1 (M + H)+; found 399.1 (M + H)+ |
| 220 | 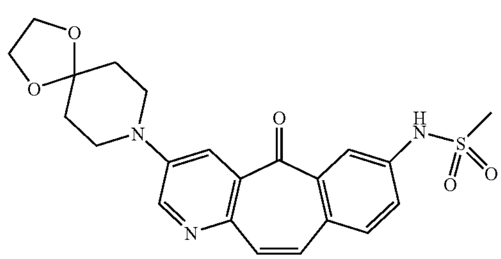 | N-[3-(1,4-dioxa-8-azaspiro[4.5]dec-8-yl)-5-oxo-5H-benzo[4,5]cyclohepta[1,2-b]pyridin-7-yl]methanesulfonamide | calc'd 442.1 (M + H)+; found 442.2 (M + H)+ |

TABLE 4-continued

| Comp. # | Structure | Name | MS (M + 1) |
|---|---|---|---|
| 221 | 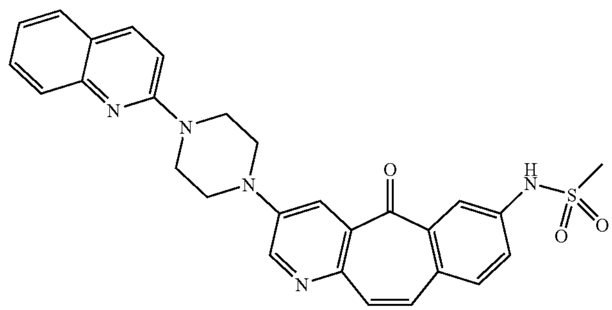 | N-[5-oxo-3-(4-quinolin-2-ylpiperazin-1-yl)-5H-benzo[4,5]cyclohepta[1,2-b]pyridin-7-yl]methanesulfonamide | calc'd 512.2 (M + H)+; found 512.2 (M + H)+ |
| 222 | 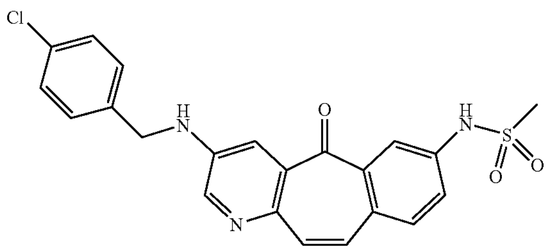 | N-{3-[(4-chlorobenzyl)amino]-5-oxo-5H-benzo[4,5]cyclohepta[1,2-b]pyridin-7-yl}methanesulfonamide | calc'd 440.1 (M + H)+; found 440.1 (M + H)+ |
| 223 | 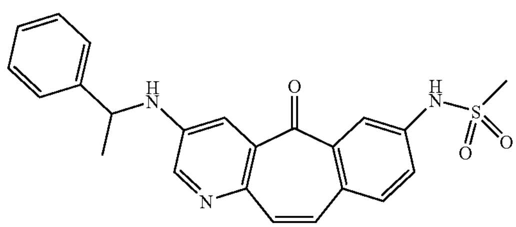 | N-{5-oxo-3-[(1-phenylethyl)amino]-5H-benzo[4,5]cyclohepta[1,2-b]pyridin-7-yl}methanesulfonamide | calc'd 420.1 (M + H)+; found 420.2 (M + H)+ |
| 224 | 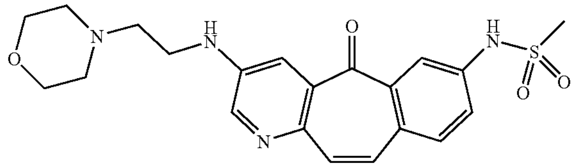 | N-{3-[(2-morpholin-4-ylethyl)amino]-5-oxo-5H-benzo[4,5]cyclohepta[1,2-b]pyridin-7-yl}methanesulfonamide | calc'd 492.2 (M + H)+; found 492.2 (M + H)+ |
| 225 | 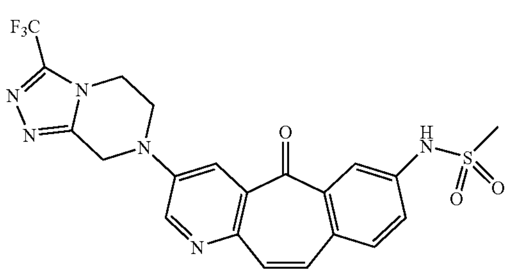 | N-{5-hydroxy-3-[3-(trifluoromethyl)-5,6-dihydro[1,2,4]triazolo[4,3-a]pyrazin-7(8H)-yl]-5H-benzo[4,5]cyclohepta[1,2-b]pyridin-7-yl}methanesulfonamide | calc'd 493.1 (M + H)+; found 493.2 (M + H)+ |
| 226 | 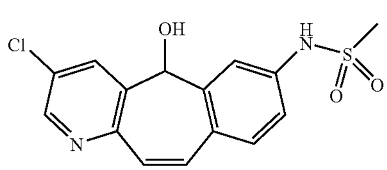 | N-(3-chloro-5-hydroxy-5H-benzo[4,5]cyclohepta[1,2-b]pyridin-7-yl)methanesulfonamide | calc'd 337.0 (M + H)+; found 337.1 (M + H)+ |

TABLE 4-continued

| Comp. # | Structure | Name | MS (M + 1) |
|---|---|---|---|
| 227 | 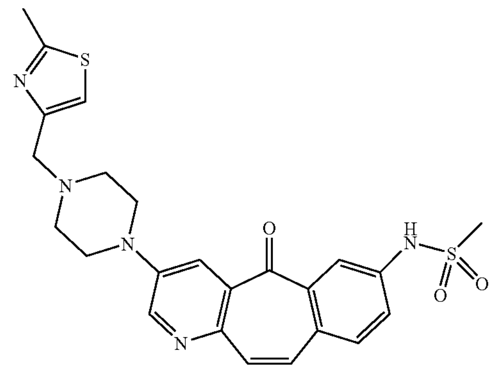 | N-(3-{4-[(2-methyl-1,3-thiazol-4-yl)methyl]piperazin-1-yl}-5-oxo-5H-benzo[4,5]cyclohepta[1,2-b]pyridin-7-yl)methanesulfonamide | calc'd 496.1 (M + H)+; found 496.2 (M + H)+ |
| 228 | 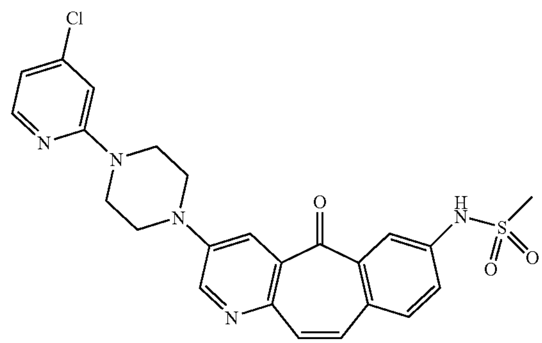 | N-{3-[4-(4-chloropyridin-2-yl)piperazin-1-yl]-5-oxo-5H-benzo[4,5]cyclohepta[1,2-b]pyridin-7-yl}methanesulfonamide | calc'd 496.1 (M + H)+; found 496.1 (M + H)+ |
| 229 | 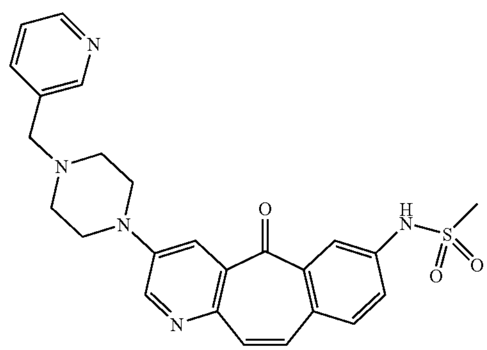 | N-{5-oxo-3-[4-(pyridin-3-ylmethyl)piperazin-1-yl]-5H-benzo[4,5]cyclohepta[1,2-b]pyridin-7-yl}methanesulfonamide | calc'd 476.2 (M + H)+; found 476.2 (M + H)+ |
| 230 | 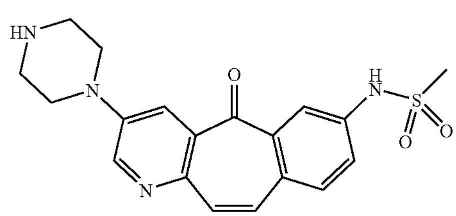 | N-(5-oxo-3-piperazin-1-yl-5H-benzo[4,5]cyclohepta[1,2-b]pyridin-7-yl)methanesulfonamide | calc'd 385.1 (M + H)+; found 385.2 (M + H)+ |
| 231 | 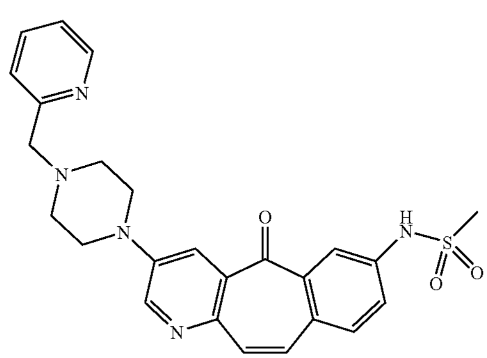 | N-{5-oxo-3-[4-(pyridin-2-ylmethyl)piperazin-1-yl]-5H-benzo[4,5]cyclohepta[1,2-b]pyridin-7-yl}methanesulfonamide | calc'd 476.2 (M + H)+; found 476.2 (M + H)+ |

TABLE 4-continued

| Comp. # | Name | MS (M + 1) |
|---|---|---|
| 232 | N-[5-oxo-3-(4-pyridin-3-ylpiperazin-1-yl)-5H-benzo[4,5]cyclohepta[1,2-b]pyridin-7-yl]methanesulfonamide | calc'd 462.2 (M + H)+; found 462.2 (M + H)+ |
| 233 | N-{5-oxo-3-[2-(trifluoromethyl)-5,6-dihydroimidazo[1,2-a]pyrazin-7(8H)-yl]-5H-benzo[4,5]cyclohepta[1,2-b]pyridin-7-yl}methanesulfonamide | calc'd 490.1 (M + H)+; found 490.1 (M + H)+ |
| 234 | N-(3-{4-[3,5-bis(trifluoromethyl)phenyl]piperazin-1-yl}-5-oxo-5H-benzo[4,5]cyclohepta[1,2-b]pyridin-7-yl)methanesulfonamide | calc'd 597.1 (M + H)+; found 597.1 (M + H)+ |
| 235 | N-{3-[(1-methyl-1H-pyrazol-3-yl)amino]-5-oxo-5H-benzo[4,5]cyclohepta[1,2-b]pyridin-7-yl}methanesulfonamide | calc'd 396.1 (M + H)+; found 395.7 (M + H)+ |
| 236 | 7-[(2,4-dimethoxybenzyl)amino]-3-(1,4-dioxa-8-azaspiro[4.5]dec-8-yl)-5H-benzo[4,5]cyclohepta[1,2-b]pyridin-5-one | calc'd 514.2 (M + H)+; found 514.3 (M + H)+ |
| 236A | 7-[(2,4-dimethoxybenzyl)amino]-3-(4-isopropylpiperazin-1-yl)-5H-benzo[4,5]cyclohepta[1,2-b]pyridin-5-one | calc'd 499.3 (M + H)+; found 499.3 (M + H)+ |

TABLE 4-continued

| Comp. # | Structure | Name | MS (M + 1) |
|---|---|---|---|
| 237 | 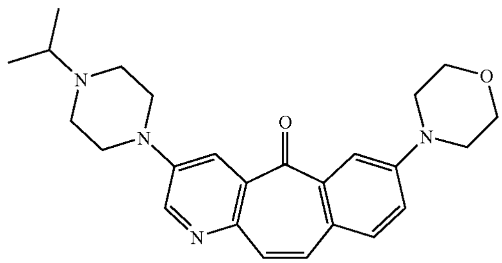 | 3-(4-isopropylpiperazin-1-yl)-7-morpholin-4-yl-5H-benzo[4,5]cyclohepta[1,2-b]pyridin-5-one | calc'd 419.2 (M + H)+; found 419.2 (M + H)+ |
| 238 | 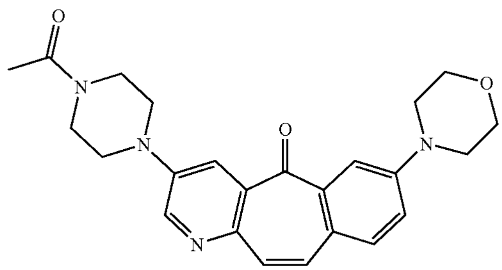 | 3-(4-acetylpiperazin-1-yl)-7-morpholin-4-yl-5H-benzo[4,5]cyclohepta[1,2-b]pyridin-5-one | calc'd 419.2 (M + H)+; found 419.2 (M + H)+ |
| 239 | 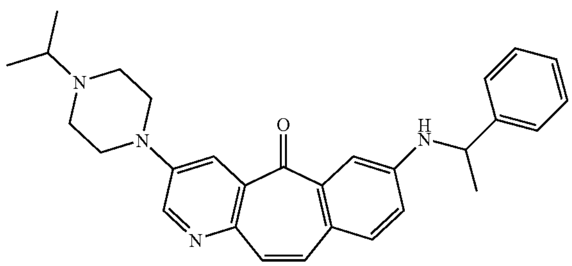 | 3-(4-isopropylpiperazin-1-yl)-7-[(1-phenylethyl)amino]-5H-benzo[4,5]cyclohepta[1,2-b]pyridin-5-one | calc'd 453.2 (M + H)+; found 452.8 (M + H)+ |
| 240 | 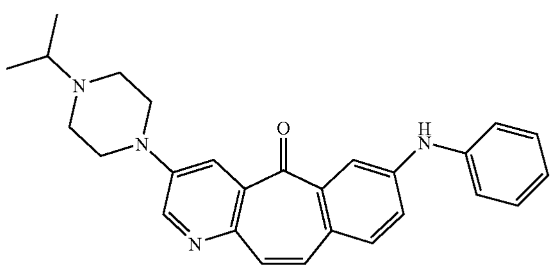 | 7-anilino-3-(4-isopropylpiperazin-1-yl)-5H-benzo[4,5]cyclohepta[1,2-b]pyridin-5-one | calc'd 425.2 (M + H)+; found 425.2 (M + H)+ |
| 241 | 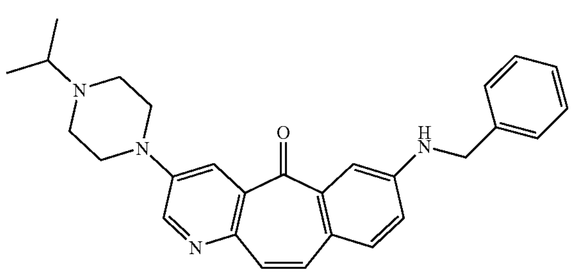 | 7-(benzylamino)-3-(4-isopropylpiperazin-1-yl)-5H-benzo[4,5]cyclohepta[1,2-b]pyridin-5-one | calc'd 439.2 (M + H)+; found 439.2 (M + H)+ |

TABLE 4-continued

| Comp. # | Structure | Name | MS (M + 1) |
|---|---|---|---|
| 242 | 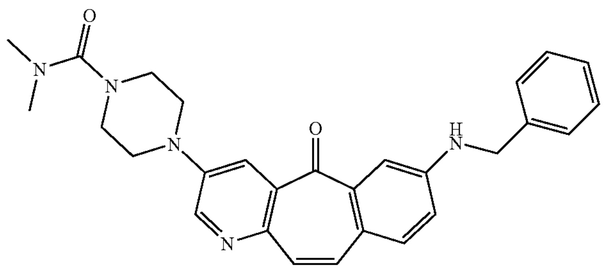 | 4-[7-(benzylamino)-5-oxo-5H-benzo[4,5]cyclohepta[1,2-b]pyridin-3-yl]-N,N-dimethylpiperazine-1-carboxamide | calc'd 468.2 (M + H)+; found 468.2 (M + H)+ |
| 243 | 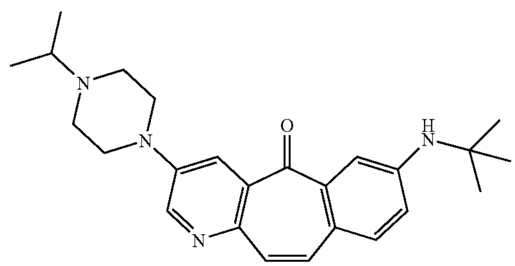 | 7-(tert-butylamino)-3-(4-isopropylpiperazin-1-yl)-5H-benzo[4,5]cyclohepta[1,2-b]pyridin-5-one | calc'd 405.3 (M + H)+; found 404.8 (M + H)+ |
| 244 | 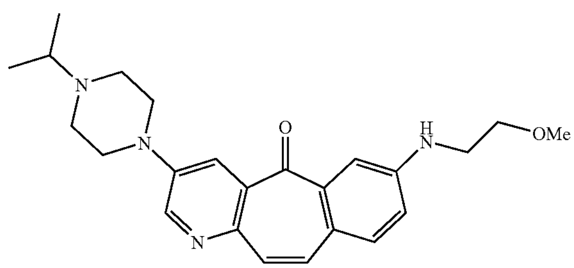 | 3-(4-isopropylpiperazin-1-yl)-7-[(2-methoxyethyl)amino]-5H-benzo[4,5]cyclohepta[1,2-b]pyridin-5-one | calc'd 407.2 (M + H)+; found 407.2 (M + H)+ |
| 245 | 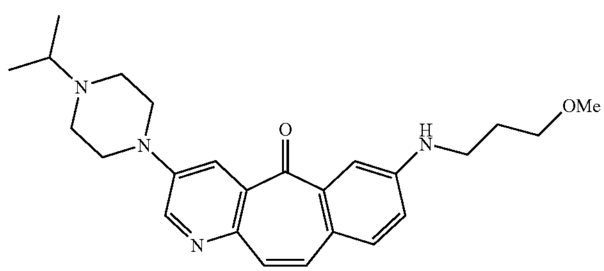 | 3-(4-isopropylpiperazin-1-yl)-7-[(3-methoxypropyl)amino]-5H-benzo[4,5]cyclohepta[1,2-b]pyridin-5-one | calc'd 421.3 (M + H)+; found 421.3 (M + H)+ |
| 246 | 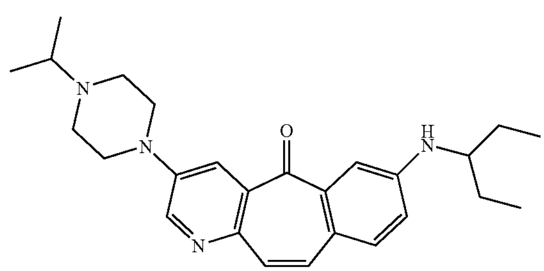 | 7-[(1-ethylpropyl)amino]-3-(4-isopropylpiperazin-1-yl)-5H-benzo[4,5]cyclohepta[1,2-b]pyridin-5-one | calc'd 419.3 (M + H)+; found 419.3 (M + H)+ |
| 247 | 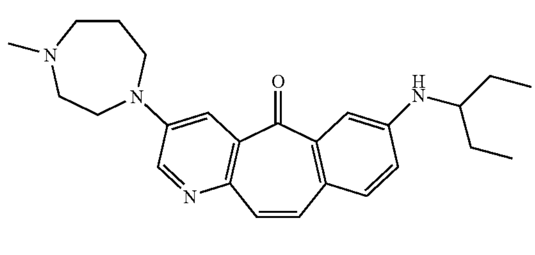 | 7-[(1-ethylpropyl)amino]-3-(4-methyl-1,4-diazepan-1-yl)-5H-benzo[4,5]cyclohepta[1,2-b]pyridin-5-one | calc'd 405.3 (M + H)+; found 405.2 (M + H)+ |

TABLE 4-continued

| Comp. # | Structure | Name | MS (M + 1) |
|---|---|---|---|
| 248 | 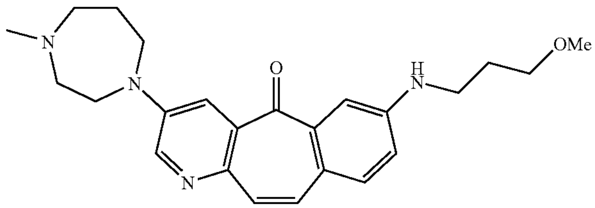 | 7-[(3-methoxypropyl)amino]-3-(4-methyl-1,4-diazepan-1-yl)-5H-benzo[4,5]cyclohepta[1,2-b]pyridin-5-one | calc'd 407.2 (M + H)+; found 407.2 (M + H)+ |
| 249 | 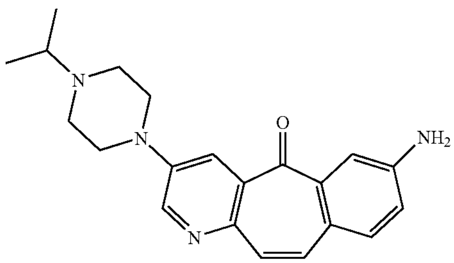 | 7-amino-3-(4-isopropylpiperazin-1-yl)-5H-benzo[4,5]cyclohepta[1,2-b]pyridin-5-one | calc'd 349.2 (M + H)+; found 349.2 (M + H)+ |
| 250 | 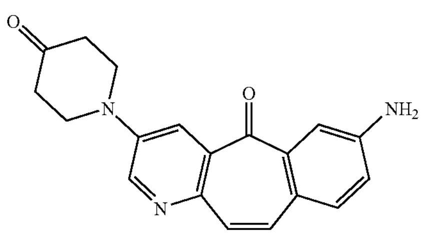 | 7-amino-3-(4-oxopiperidin-1-yl)-5H-benzo[4,5]cyclohepta[1,2-b]pyridin-5-one | calc'd 320.1 (M + H)+; found 320.1 (M + H)+ |
| 251 | 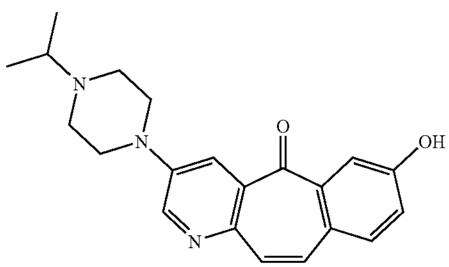 | 7-hydroxy-3-(4-isopropylpiperazin-1-yl)-5H-benzo[4,5]cyclohepta[1,2-b]pyridin-5-one | calc'd 350.2 (M + H)+; found 350.1 (M + H)+ |
| 252 | 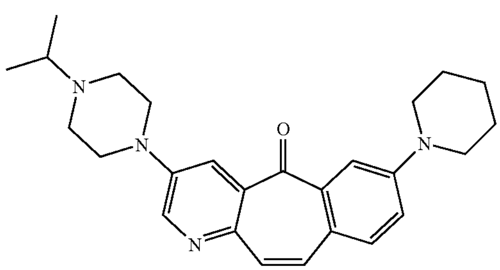 | 3-(4-isopropylpiperazin-1-yl)-7-piperidin-1-yl-5H-benzo[4,5]cyclohepta[1,2-b]pyridin-5-one | calc'd 417.2 (M + H)+; found 417.3 (M |
| 253 | 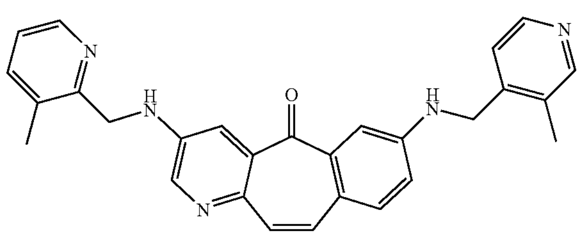 | 3,7-bis{[(3-methylpyridin-4-yl)methyl]amino}-5H-benzo[4,5]cyclohepta[1,2-b]pyridin-5-one | calc'd 448.2 (M + H)+; found 448.2 (M |

157

Scheme 6

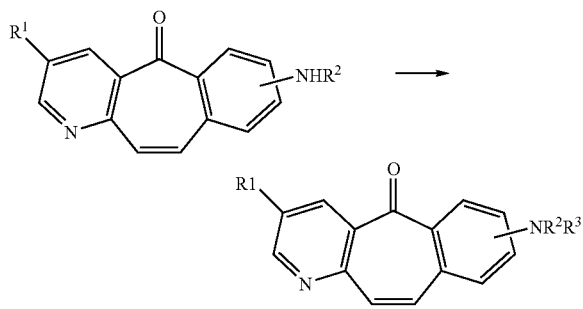

Example 25

254

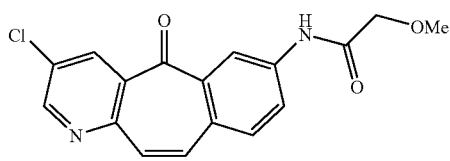

N-(3-chloro-5-oxo-5H-benzo[4,5]cyclohepta[1,2-b]pyridin-7-yl)-2-methoxyacetamide 7-amino-3-chloro-5H-benzo[4,5]cyclohepta[1,2-b]pyridin-5-one (0.70 g, 2.7 mmol) was dissolved in 20 mL of dry dichloromethane and 5 mL of dry acetonitrile. Methoxyacetic acid (0.32 mL, 4.1 mmol), N-(3-Dimethylaminopropyl)-N'-ethylcarbodiimide hydrochloride (EDCI) (0.79 g, 4.1 mmol) and 1-hydroxybenzotriazole hydrate (HOBt) (0.55 g, 4.1 mmol) were added and the solution was stirred at ambient temperature. After 12 hours, the reaction solution was poured into 300 mL of ethyl acetate and 100 mL of water. The organic layer was separated and washed with 100 mL of brine. The organic layer was separated, dried with magnesium sulfate, filtered, concentrated and purified by flash column chromatography (0-100% ethyl acetate/hexanes gradient) to afford the title compound. $^1$H NMR (600 MHz, CDCl$_3$) δ 10.29 (s, 1H); 8.94 (d, 1H); 8.58 (d, 1H); 8.46 (d, 1H); 8.10 (dd, 1H); 7.77 (d, 1H); 7.40 (d, 1H); 7.20 (d, 1H); 4.04 (s, 2H); 3.36 (s, 3H). LRMS (APCI) calculated for C$_{17}$H$_{14}$C1N$_2$O$_3$ [M+H]+, 329.1; found 329.1.

Example 26

255

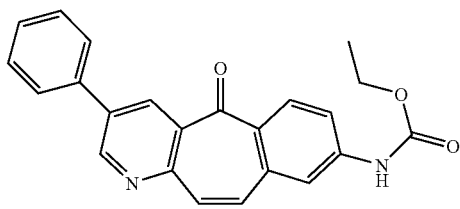

158 ethyl (5-oxo-3-phenyl-5H-benzo[4,5]cyclohepta[1,2-b]pyridin-8-yl)carbamate

To a 0° C. solution of 8-amino-3-phenyl-5H-benzo[4,5]cyclohepta[1,2-b]pyridin-5-one (6.4 mg, 0.021 mmol) in pyridine (0.3 mL) was added a catalytic amount of 4-dimethylaminopyridine (tip of the spatula) and ethyl chloroformate (0.1 mL, 0.31 M in CH$_2$Cl$_2$) The mixture was then stirred at room temperature. After 7 hours, more ethyl chloroformate (3 μL, 0.032 mmol) was added. After stirring for 14 hours, a new addition of ethyl chloroformate (6 μL, 0.064 mmol) was followed by stirring for 2 more hours.

The mixture was then concentrated to dryness. The crude residue was purified by flash chromatography (100-85% CH$_2$Cl$_2$/MeOH gradient). The collected fractions were concentrated, dissolved in CH$_2$Cl$_2$ washed with an aqueous saturated solution of CuSO$_4$, brine, dried over sodium sulfate, filtered, and concentrated to afford the title compound. $^1$H NMR (600 MHz, CDCl$_3$) δ 9.12 (s, 1H), 8.85 (s, 1H), 8.31 (d, 1H), 7.78 (s, 1H), 7.71 (d, 2H), 7.53 (m, 3H), 7.45 (t, 2H), 6.97 (s, 1H), 4.27 (q, 2H), 1.34 (t, 3H). LRMS (APCI) calculated for C$_{23}$H$_{19}$N$_2$O$_3$ [M+H]+, 372.1; found 372.1.

Example 27

256

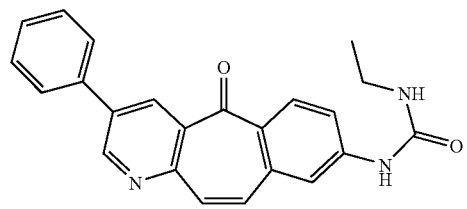

N-ethyl-N'-(5-oxo-3-phenyl-5H-benzo[4,5]cyclohepta[1,2-b]pyridin-8-yl)urea

To a 0° C. solution of 8-amino-3-phenyl-5H-benzo[4,5]cyclohepta[1,2-b]pyridin-5-one (6.4 mg, 0.021 mmol) in pyridine (0.3 mL) was ethyl isocyanate (0.1 mL, 0.38 M in CH$_2$Cl$_2$) The mixture was then stirred at room temperature for 4 hours followed by heating at 50° C. After 3 hours, more ethyl isocianate (3 μL, 0.038 mmol) was added and the mixture was heated at 70° C. After stirring for 14 hours, a new addition of ethyl isocyanate (9 μL, 0.114 mmol) was followed by heating at 80° C. More ethyl isocyanate (20 μL, 0.253 mmol) was added 2 hours later and heating was continued for 14 hours. The mixture was then concentrated to dryness. The crude residue was purified by flash chromatography (100-85% CH$_2$Cl$_2$/MeOH gradient) and reverse phase HPLC (30-100% acetonitrile/water gradient, 0.1% trifluoroacetic acid modifier) to afford the title compound. $^1$H NMR (600 MHz, DMSO-D6) δ 9.24 (d, 1H), 8.69 (d, 1H), 8.14 (d, 1H), 7.85 (d, 2H), 7.80 (d, 1H), 7.67 (dd, 1H), 7.53 (t, 2H), 7.45 (t, 2H), 7.31 (s, 2H), 2.95 (m, 2H), 0.93 (t, 3H). LRMS (APCI) calculated for $C_{23}H_{20}N_3O_2$ [M+H]+, 370.1; found 370.1.

Example 28

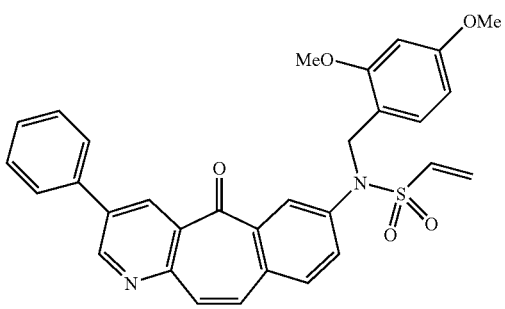

257

N-(2,4-dimethoxybenzyl)-N-(5-oxo-3-phenyl-5H-benzo[4,5]cyclohepta[1,2-b]pyridin-7-yl)ethylene-sulfonamide A flask was charged with compound 19 (194 mg, 0.434 mmol) and 8 mL of $CH_2Cl_2$ and cooled to 0° C. N-methylmorpholine (0.19 mL, 1.74 mmol) and 2-chloroethanesulfonyl chloride (90 µL, 0.87 mmol) were added and the solution was allowed to warm to room temperature. After 18 h, the solution was diluted with EtOAc, washed with water and brine, then dried over $Na_2SO_4$. The solution was concentrated in vacuo and purified by flash column chromatography (10-100% EtOAc/hexanes gradient) to afford the title compound 257. $^1$H NMR (600 MHz, CDCl$_3$) δ 9.14 (d, 1H); 8.73 (d, 1H); 8.19 (d, 1H); 7.69-7.72 (m, 2H); 7.58 (dd, 1H); 7.49-7.54 (m, 3H); 7.44-7.47 (m, 1H); 7.39 (d, 1H); 7.19-7.25 (m, 2H); 6.57 (dd, 1H); 6.37 (dd, 1H); 6.30 (app d, 1H); 6.21 (d, 1H); 6.00 (d, 1H); 4.86 (s, 2H); 3.72 (s, 3H); 3.65 (s, 3H). LRMS (APCI) calc'd for ($C_{31}H_{27}N_2O_5S$) [M+H]+, 539.2; found 539.2.

Example 29

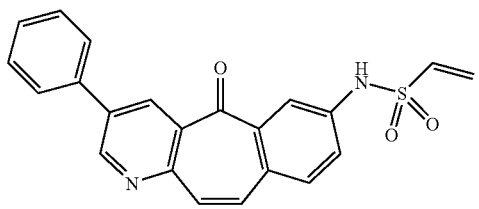

258

N-(5-oxo-3-phenyl-5H-benzo[4,5]cyclohepta[1,2-b]pyridin-7-yl)ethylenesulfonamide Compound 258 was prepared from 257 via the method described for Example 4B. $^1$H NMR (600 MHz, DMSO-d6) δ 10.69 (s, 1H); 9.29 (257, 1H); 8.68 (d, 1H); 7.98 (d, 1H); 7.86-7.90 (m, 2H); 7.78 (d, 1H); 7.52-7.58 (m, 3H); 7.45-7.48 (m, 1H); 7.41 (d, 1H); 7.29 (d, 1H); 6.86 (dd, 1H); 6.20 (d, 1H); 6.06-6.10 (m, 1H). LRMS (APCI) calc'd for ($C_{22}H_{17}N_2O_3S$) [M+H]+, 389.1; found 389.1.

Example 30

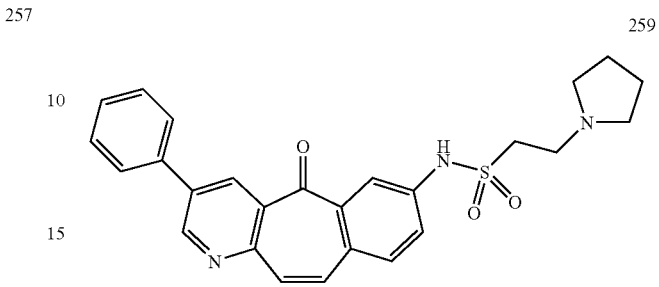

259

N-(5-oxo-3-phenyl-5H-benzo[4,5]cyclohepta[1,2-b]pyridin-7-yl)-2-pyrolidin-1-ylethanesulfonamide Compound 258 (20.0 mg, 0.051 mmol) and pyrrolidine (13 µL, 0.15 mmol) were dissolved in 2 mL of MeOH and 1 mL of $CH_2Cl_2$. After 18 h, the solution was concentrated under a stream of nitrogen and purified by purified by reverse phase HPLC (20-100% $CH_3CN$/water with a 0.1% TFA modifier) to afford the title compound 259. $^1$H NMR (600 MHz, CDCl$_3$) δ 9.13 (d, 1H); 8.74 (d, 1H); 7.92 (d, 1H); 7.73 (dd, 1H); 7.68-7.73 (m, 2H); 7.58 (d, 1H); 7.49-7.53 (m, 2H); 7.42-7.45 (m, 1H); 7.36 (d, 1H); 7.23 (d, 1H); 3.28-3.32 (m, 2H); 3.08-3.12 (m, 2H); 2.60-2.65 (m, 4H); 1.88-1.94 (m, 4H). LRMS (APCI) calc'd for ($C_{26}H_{26}N_3O_3S$) [M+H]+, 460.2; found 460.

Example 31

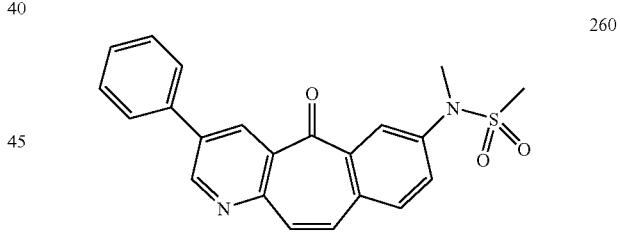

260

N-methyl-N-(5-oxo-3-phenyl-5H-benzo[4,5]cyclohepta[1,2-b]pyridin-7-yl)methanesulfonamide Compound 44 (5.0 mg, 0.013 mmol) was dissolved in 0.5 mL of MeOH and 1 mL of $CH_2Cl_2$, then trimethylsilyldiazomethane (14 µL of a 2M solution in $CH_2Cl_2$, 0.03 mmol) was added. After 30 min, additional trimethylsilyldiazomethane (14 µL of a 2M solution in $CH_2Cl_2$, 0.03 mmol) was added. After an additional 30 min, the solution was concentrated in vacuo to afford the title compound 260. $^1$H NMR (600 MHz, CDCl$_3$) δ 9.10 (d, 1H); 8.69 (d, 1H); 8.16 (d, 1H); 7.77 (dd, 1H); 7.64-7.67 (m, 2H); 7.59 (d, 1H); 7.45-7.49 (m, 2H); 7.37-7.42 (m, 2H); 7.23 (d, 1H); 3.39 (s, 3H); 2.84 (s, 3H). LRMS (APCI) calc'd for ($C_{22}H_{19}N_2O_3S$) [M+H]+, 391.1; found 391.1.

Example 32

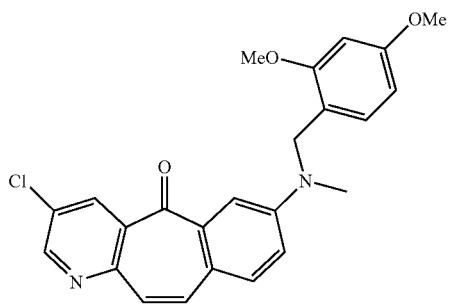

3-chloro-7-[(2,4-dimethoxybenzyl)(methyl)amino]-5H-benzo[4,5]cyclohepta[1,2-b]pyridin-5-one Compound 7 (100.0 mg, 0.246 mmol), paraformaldehyde (24 mg, 0.27 mmol), and NaBH(OAc)$_3$ (57 mg, 0.27 mmol) were suspended in 4 mL of dichloroethane and 2 mL of dioxane and stirred overnight. After 18 h, additional paraformaldehyde (122 mg, 1.35 mmol), NaBH(OAc)$_3$ (172 mg, 0.81 mmol) and 5 mL of dioxane were added and the mixture was heated to 60° C. After 24 h, additional paraformaldehyde (222 mg, 2.46 mmol) and NaBH(OAc)$_3$ (521 mg, 2.46 mmol) were added. After an additional 24 h., the mixture was diluted in EtOAc, washed with water and brine, then dried over Na$_2$SO$_4$. The solution was concentrated in vacuo and purified by flash column chromatography (10-100% EtOAc/hexanes gradient) to afford the title compound 261. $^1$H NMR (600 MHz, CDCl$_3$) δ 8.75 (d, 1H); 8.56 (d, 1H); 7.65 (d, 1H); 7.43 (d, 1H); 7.18 (d, 1H); 7.09 (d, 1H); 7.03 (dd, 1H); 6.89 (d, 1H); 6.49 (d, 1H); 6.36 (dd, 1H); 4.58 (s, 2H); 3.84 (s, 3H); 3.76 (s, 3H); 3.17 (s, 3H). LRMS (APCI) calc'd for (C$_{24}$H$_{22}$ClN$_2$O$_3$) [M+H]+, 421.1; found 420.7.

Example 33

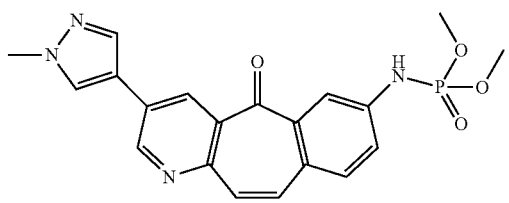

dimethyl [3-(1-methyl-1H-pyrazol-4-yl)-5-oxo-5H-benzo[4,5]cyclohepta[1,2-b]pyridin-7-yl]amidophosphate. (Compound 262)

Compound 139 (10 mg, 0.033 mmol) and triethylamine (14 μL, 0.10 mmol) was suspended in 2 mL dichloromethane and dimethyl chloridophosphate (7 μL, 0.066 mmol) was added. After 30 min, the suspension was heated to 40° C. After an additional 2 h, dimethyl chloridophosphate (36 μL, 0.33 mmol) was added. After an additional 18 h the yellow solution was poured into ethylacetate and the organic layer was washed with saturated aqueous sodium bicarbonate and brine, then dried over sodium sulfate and concentrated. The residue was purified via reverse phase HPLC (20-100% acetonitrile/water gradient, 0.05% trifluoroacetic acid modifier) to afford the title compound. $^1$H NMR (600 MHz, CDCl$_3$) δ 8.89 (d, 1H); 8.63 (s, 1H); 7.88 (s, 1H); 7.82 (d, 1H); 7.79 (s, 1H); 7.51 (d, 1H); 7.32-7.38 (m, 2H); 7.18-7.22 (m, 1H); 6.06 (br d, 1H); 3.94 (s, 3H); 3.79 (s, 3H); 3.77 (s, 3H); LRMS (APCI) calc'd for (C$_{20}$H$_{20}$N$_4$O$_4$P) [M+H]+, 411.1; found 411.1.

The following compounds were made according to Scheme 6. Additional synthetic modifications were employed in the preparation of some of the compounds. Compounds 263 and 264 were isolated during the formation of Compounds 44 and 265 using the procedure described in Example 5, Method B. Compound 268 was isolated from the reaction mixture in preparation of Compound 267. Compound 271 was prepared by acylation of Compound 23 with acetyl chloride. Compound 275 was prepared by condensation of Compound 8 with phthalic anhydride. Compound 278 was isolated from the coupling of Compound 254 to 1,4-dioxa-8-azaspiro[4.5]decane in a manner to that described in Example 24, Method B. Compounds 281, 286, and 287 were prepared in a manner similar to that described for Compound 259 with DMF used as a co-solvent. Compound 285 was isolated from the reaction mixture in the preparation of Compound 286. Compound 288 was prepared from the coupling of Compound 287 to 1,4-dioxa-8-azaspiro[4.5]decane in a manner similar to that described in Example 24. Compound 289 was prepared from Compound 261 respectively in a manner similar to that described for Example 4, Method B.

TABLE 5

| Compound | Structure | Name | MS (M + 1) |
|---|---|---|---|
| 263 | 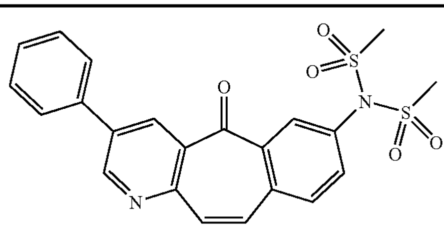 | N,N-(5-oxo-3-phenyl-5H-benzo[4,5]cyclohepta[1,2-b]pyridin-7-yl)bis-methanesulfonamide | calc'd 455.1 (M + H)+; found 455.1 (M + H)+ |

TABLE 5-continued

| Compound | Name | MS (M + 1) |
|---|---|---|
| 264 | N,N-(5-oxo-3-phenyl-5H-benzo[4,5]cyclohepta[1,2-b]pyridin-7-yl)bis-benzenesulfonamide | calc'd 579.1 (M + H)+; found 579.1 (M + H)+ |
| 265 | N-(5-oxo-3-phenyl-5H-benzo[4,5]cyclohepta[1,2-b]pyridin-7-yl)benzenesulfonamide | calc'd 439.1 (M + H)+; found 439.1 (M + H)+ |
| 266 | N-(5-oxo-3-phenyl-5H-benzo[4,5]cyclohepta[1,2-b]pyridin-7-yl)ethanesulfonamide | calc'd 391.1 (M + H)+; found 391.1 (M + H)+ |
| 267 | N-[3-(1-methyl-1H-pyrazol-4-yl)-5-oxo-5H-benzo[4,5]cyclohepta[1,2-b]pyridin-7-yl]propane-2-sulfonamide | calc'd 409.1 (M + H)+; found 408.7 (M + H)+ |
| 268 | 2-chloro-N-[3-(1-methyl-1H-pyrazol-4-yl)-5-oxo-5H-benzo[4,5]cyclohepta[1,2-b]pyridin-7-yl]propane-2-sulfinimide | calc'd 427.1 (M + H)+; found 426.7 (M + H)+ |
| 269 | N-(5-oxo-3-phenyl-5H-benzo[4,5]cyclohepta[1,2-b]pyridin-7-yl)-2-phenylacetamide | calc'd 417.2 (M + H)+; found 417.2 (M + H)+ |

TABLE 5-continued

| Compound | Structure | Name | MS (M + 1) |
|---|---|---|---|
| 270 | 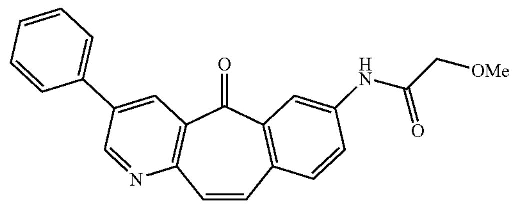 | 2-methoxy-N-(5-oxo-3-phenyl-5H-benzo[4,5]cyclohepta[1,2-b]pyridin-7-yl)acetamide | calc'd 371.1 (M + H)+; found 371.1 (M + H)+ |
| 271 | 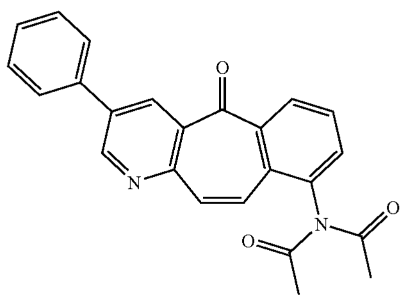 | N-acetyl-N'-(5-oxo-3-phenyl-5H-benzo[4,5]cyclohepta[1,2-b]pyridin-9-yl)acetamide | calc'd 442.1 (M + H)+; found (M + H)+ |
| 272 | 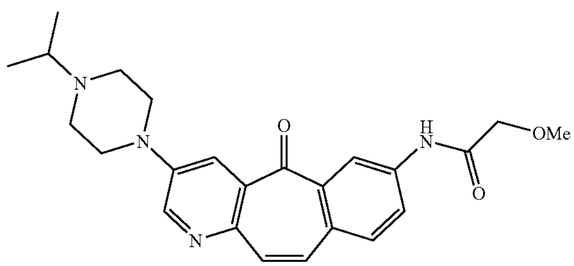 | N-[3-(4-isopropylpiperazin-1-yl)-5-oxo-5H-benzo[4,5]cyclohepta[1,2-b]pyridin-7-yl]-2-methoxyacetamide | calc'd 421.2 (M + H)+; found 421.3 (M + H)+ |
| 273 | 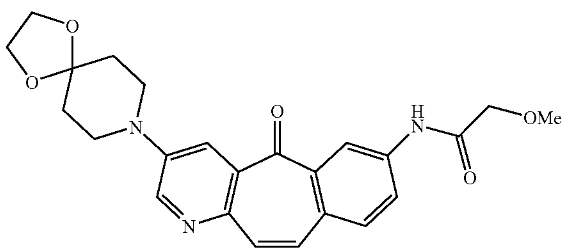 | N-[3-(1,4-dioxa-8-azaspiro[4.5]dec-8-yl)-5-oxo-5H-benzo[4,5]cyclohepta[1,2-b]pyridin-7-yl]-2-methoxyacetamide | calc'd 436.2 (M + H)+; found 436.2 (M + H)+ |
| 274 | 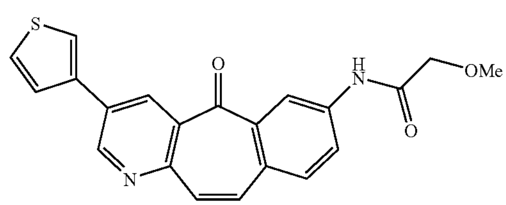 | 2-methoxy-N-[5-oxo-3-(3-thienyl)-5H-benzo[4,5]cyclohepta[1,2-b]pyridin-7-yl]acetamide | calc'd 377.1 (M + H)+; found 377.1 (M + H)+ |
| 275 | 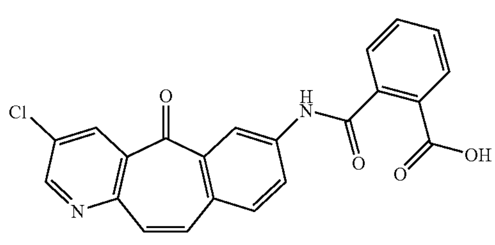 | 2-{[(3-chloro-5-oxo-5H-benzo[4,5]cyclohepta[1,2-b]pyridin-7-yl)amino]carbonyl}benzoic acid | calc'd 404.1 (M + H)+; found 405.1 |

TABLE 5-continued

| Compound | Structure | Name | MS (M + 1) |
| --- | --- | --- | --- |
| 276 | 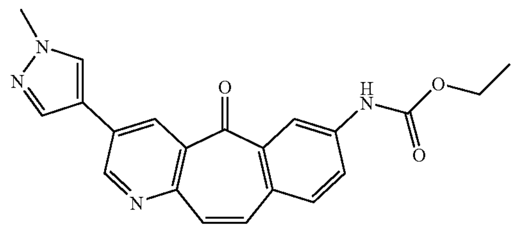 | ethyl [3-(1-methyl-1H-pyrazol-4-yl)-5-oxo-5H-benzo[4,5]cyclohepta[1,2-b]pyridin-7-yl]carbamate | calc'd 375.1 (M + H)+; found 375.1 (M + H)+ |
| 277 | 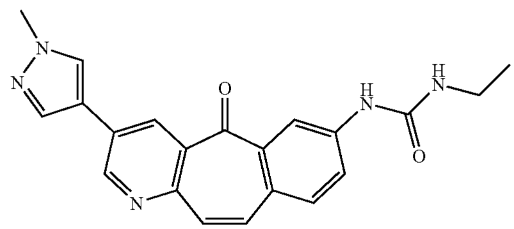 | N-ethyl-N'-[3-(1-methyl-1H-pyrazol-4-yl)-5-oxo-5H-benzo[4,5]cyclohepta[1,2-b]pyridin-7-yl]urea | calc'd 374.2 (M + H)+; found 374.2 (M + H)+ |
| 278 | 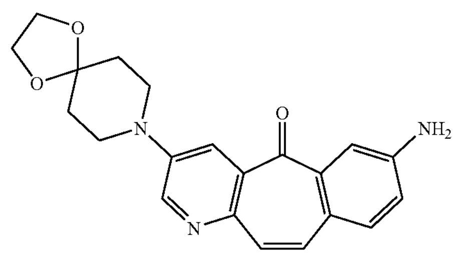 | 7-amino-3-(1,4-dioxa-8-azaspiro[4.5]dec-8-yl)-5H-benzo[4,5]cyclohepta[1,2-b]pyridin-5-one | calc'd 364.2 (M + H)+; found 364.2 (M + H)+ |
| 279 | 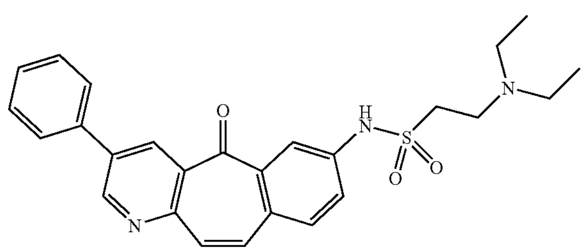 | 2-(diethylamino)-N-(5-oxo-3-phenyl-5H-benzo[4,5]cyclohepta[1,2-b]pyridin-7-yl)ethanesulfonamide | calc'd 462.2 (M + H)+; found 462.2 (M + H)+ |
| 280 | 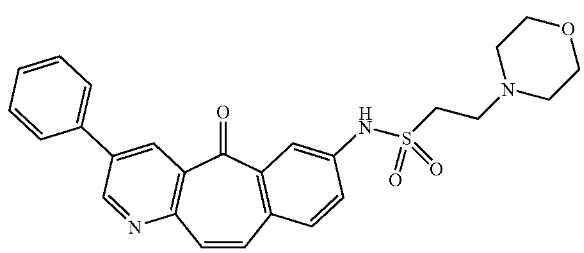 | 2-morpholin-4-yl-N-(5-oxo-3-phenyl-5H-benzo[4,5]cyclohepta[1,2-b]pyridin-7-yl)ethanesulfonamide | calc'd 476.2 (M + H)+; found 476.2 (M + H)+ |
| 281 | 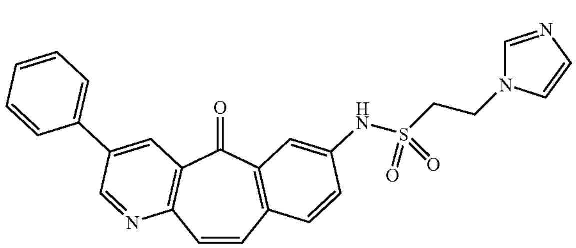 | 2-(1H-imidazol-1-yl)-N-(5-oxo-3-phenyl-5H-benzo[4,5]cyclohepta[1,2-b]pyridin-7-yl)ethanesulfonamide | calc'd 457.1 (M + H)+; found 457.2 (M + H)+ |

TABLE 5-continued

| Compound | Structure | Name | MS (M + 1) |
|---|---|---|---|
| 282 | 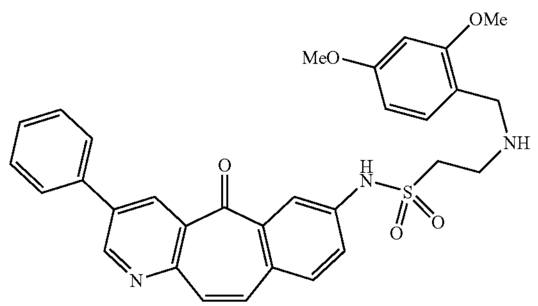 | 2-[(2,4-dimethoxybenzyl)amino]-N-(5-oxo-3-phenyl-5H-benzo[4,5]cyclohepta[1,2-b]pyridin-7-yl)ethanesulfonamide | calc'd 556.2 (M + H)+; found 556.2 (M + H)+ |
| 283 | 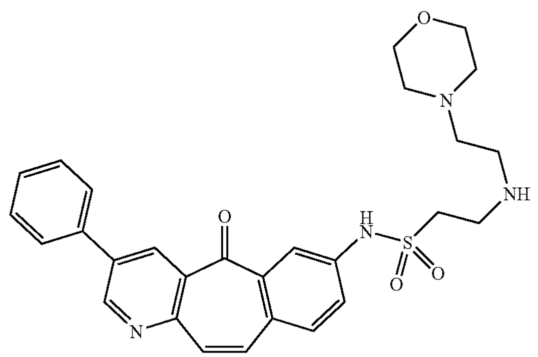 | 2-[(2-morpholin-4-ylethyl)amino]-N-(5-oxo-3-phenyl-5H-benzo[4,5]cyclohepta[1,2-b]pyridin-7-yl)ethanesulfonamide | calc'd 519.2 (M + H)+; found 519.2 (M + H)+ |
| 284 | 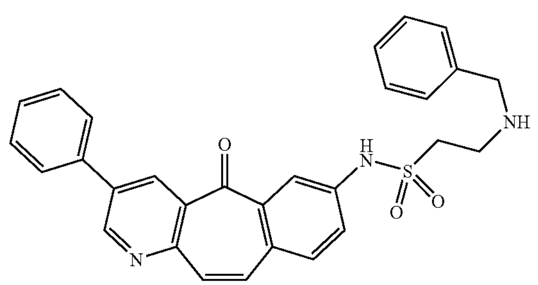 | 2-(benzylamino)-N-(5-oxo-3-phenyl-5H-benzo[4,5]cyclohepta[1,2-b]pyridin-7-yl)ethanesulfonamide | calc'd 496.2 (M + H)+; found 496.2 (M + H)+ |
| 285 | 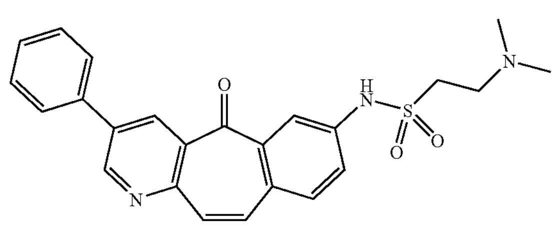 | 2-(dimethylamino)-N-(5-oxo-3-phenyl-5H-benzo[4,5]cyclohepta[1,2-b]pyridin-7-yl)ethanesulfonamide | calc'd 434.2 (M + H)+; found 434.2 (M + H)+ |
| 286 | 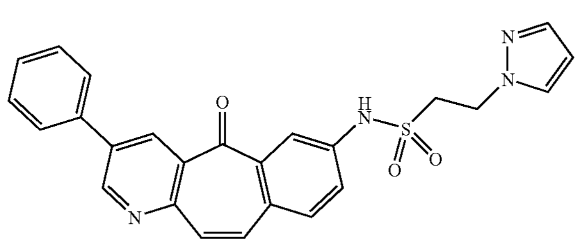 | N-(5-oxo-3-phenyl-5H-benzo[4,5]cyclohepta[1,2-b]pyridin-7-yl)-2-(1H-pyrazol-1-yl)ethanesulfonamide | calc'd 457.1 (M + H)+; found 457.1 (M + H)+ |

TABLE 5-continued

| Compound | Structure | Name | MS (M + 1) |
|---|---|---|---|
| 287 | 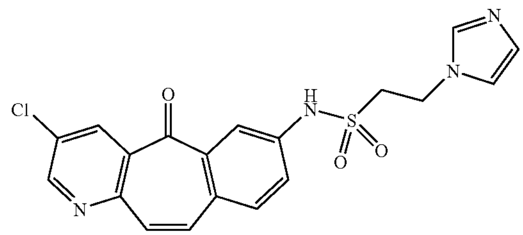 | N-(3-chloro-5-oxo-5H-benzo[4,5]cyclohepta[1,2-b]pyridin-7-yl)-2-(1H-imidazol-1-yl)ethanesulfonamide | calc'd 415.1 (M + H)+; found 415.1 (M + H)+ |
| 288 | 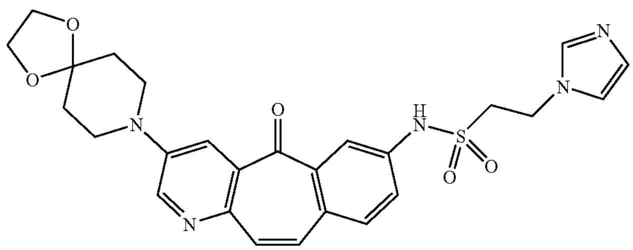 | N-[3-(1,4-dioxa-8-azaspiro[4.5]dec-8-yl)-5-oxo-5H-benzo[4,5]cyclohepta[1,2-b]pyridin-7-yl]-2-(1H-imidazol-1-yl)ethanesulfonamide | calc'd 522.2 (M + H)+; found 522.2 (M + H)+ |
| 289 | 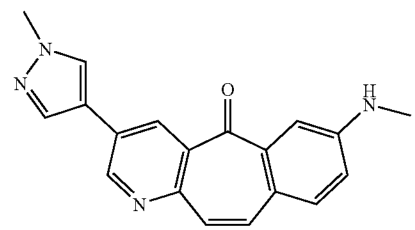 | 7-(methylamino)-3-(1-methyl-1H-pyrazol-4-yl)-5H-benzo[4,5]cyclohepta[1,2-b]pyridin-5-one | calc'd 317.1 (M + H)+; found 316.8 (M + H)+ |
| 290 | 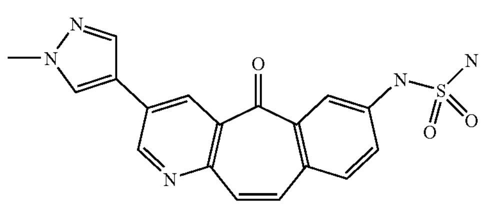 | N-[3-(1-methyl-1H-pyrazol-4-yl)-5-oxo-5H-benzo[4,5]cyclohepta[1,2-b]pyridin-7-yl]sulfamide | calc'd 382.1 (M + H)+; found 382.1 (M + H)+ |
| 291 | 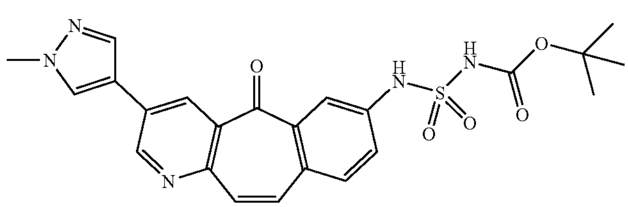 | tert-butyl ({[3-(1-methyl-1H-pyrazol-4-yl)-5-oxo-5H-benzo[4,5]cyclohepta[1,2-b]pyridin-7-yl]amino}sulfonyl)carbamate | calc'd 482.1 (M + H)+; found 482.2 (M + H)+ |

Example 34

Scheme 7

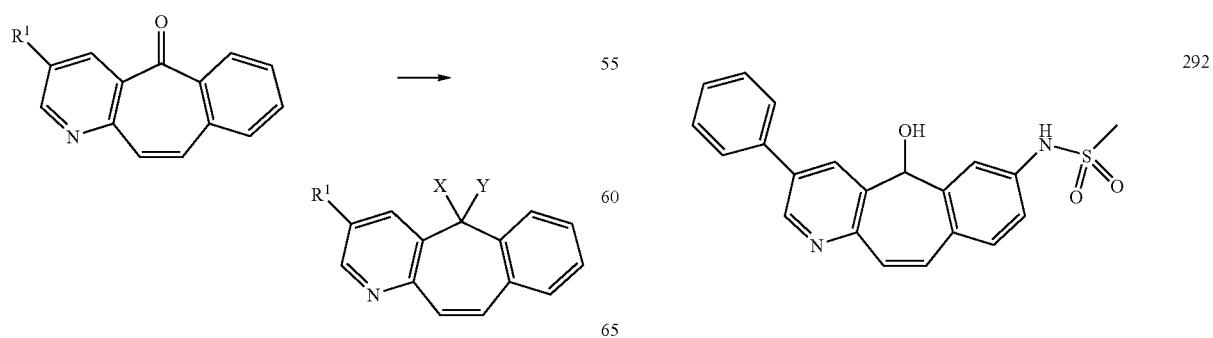

292

N-(5 hydroxy-3-phenyl-5H-benzo[4,5]cyclohepta[1,2-b]pyridin-7-yl)methanesulfonamide To a stirred slurry of N-(5-oxo-3-phenyl-5H-benzo[4,5]cyclohepta[1,2-b]pyridin-7-yl)methanesulfonamide (0.50 g, 1.3 mmol) in MeOH (30 mL) was added NaBH$_4$ (100 mg, 2.6 mmol). The reaction mixture was left to stir for 30 min, treated with 1 N HCl and then 1 N NaOH, and concentrated. The residue was diluted with EtOAc and washed with brine. The organic layer was dried (Na$_2$SO$_4$), concentrated, and purified by flash chromatography to afford the title compound. $^1$H NMR (600 MHz, CD$_3$OD) δ 8.66 (d, 1H); 8.38 (d, 1H); 7.15-7.71 (m, 10H); 5.28 (s, 1H); 2.96 (s, 3H). LRMS (APCI) calc'd for (C$_{21}$H$_{19}$N$_2$O$_3$S) [M+H]+, 379.1; found 379.1.

Example 35

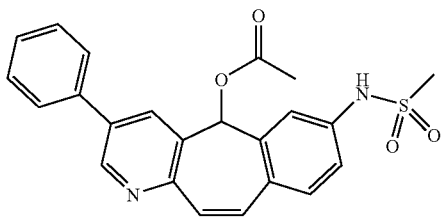

293

7-[(methylsulfonyl)amino]-3-phenyl-5H-benzo[4,5]cyclohepta[1,2-b]pyridin-5-yl acetate To a stirred solution of N-(5-hydroxy-3-phenyl-5H-benzo[4,5]cyclohepta[1,2-b]pyridin-7-yl)methanesulfonamide (50 mg, 0.13 mmol) in AcOH (1 mL) was added Ac$_2$O (0.5 mL). The reaction mixture was heated to 120° C. for 1 d, concentrated, and purified by flash chromatography to afford the title compound. $^1$H NMR (600 MHz, CDCl$_3$) δ 8.83 (s, 1H); 8.11 (s, 1H); 7.18-7.63 (m, 10H); 6.75 (s, 1H); 3.03 (s, 3H); 2.23 (br s, 3H). LRMS (APCI) calc'd for (C$_{23}$H$_{21}$N$_2$O$_4$S) [M+H]+, 421.1; found 421.1.

Example 36

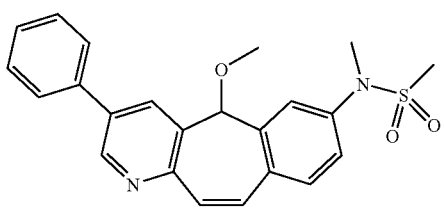

294

N-(5-methoxy-3-phenyl-5H-benzo[4,5]cyclohepta[1,2-b]pyridin-7-yl)-N-methylmethanesulfonamide To a stirred solution of N-(5-hydroxy-3-phenyl-5H-benzo[4,5]cyclohepta[1,2-b]pyridin-7-yl)methanesulfonamide (30 mg, 0.079 mmol) in THF (3 mL) was added NaH (60%, 10 mg, 0.25 mmol) at 0° C. After 10 min, MeI (50 uL, 0.80 mmol) was added, and the resultant mixture was allowed to stir at room temperature for 4 h. The reaction mixture was treated with water, diluted with EtOAc, washed with brine, dried (Na$_2$SO$_4$), concentrated, and purified by flash chromatography to afford the title compound. $^1$H NMR (600 MHz, CDCl$_3$) δ 8.71 (s, 1H); 8.07 (s, 1H); 7.19-7.60 (m, 10H); 4.71 (br s, 1H); 3.50 (br s, 3H); 3.28 (s, 3H); 2.79 (s, 3H). LRMS (APCI) calc'd for (C$_{23}$H$_{23}$N$_2$O$_3$S) [M+H]+, 407.1; found 407.2.

Example 37

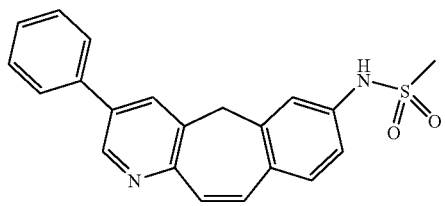

295

N-(3-phenyl-5H-benzo[4,5]cyclohepta[1,2-b]pyridin-7-yl)methanesulfonamide

Compound 263 (10.0 mg, 0.022 mmol) and Zn dust (14 mg, 0.22 mmol) were suspended in 2 mL of AcOH and heated to 100° C. After 24 h, the mixture was filtered though a 0.45µ Nylon syringe filter, concentrated in vacuo and purified by reverse phase HPLC (20-80% CH$_3$CN/water with a 0.1% TFA modifier) to afford N,N-(3-phenyl-5H-benzo[4,5]cyclohepta[1,2-b]pyridin-7-yl)-bis-methanesulfonamide.

N,N-(3-phenyl-5H-benzo[4,5]cyclohepta[1,2-b]pyridin-7-yl)-bis-methanesulfonamide was converted to the title compound 295 via the method described in the basic hydrolysis step of Example 5B. $^1$H NMR (600 MHz, CDCl$_3$) δ 8.68 (s, 1H); 7.77 (s, 1H); 7.52-7.55 (m, 2H); 7.40-7.44 (m, 2H); 7.33-7.37 (m, 1H); 7.27 (d, 1H); 7.12-7.22 (m, 3H); 7.00 (dd, 1H); 6.57 (s, 1H); 3.74 (s, 2H); 2.95 (s, 3H). LRMS (APCI) calc'd for (C$_{21}$H$_{19}$N$_2$O$_2$S) [M+H]+, 363.1; found 363.1.

Example 38

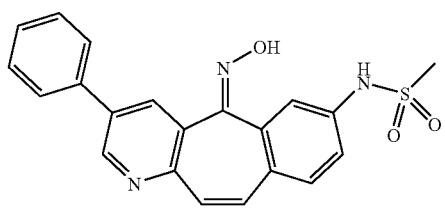

296

N-[(5E/Z)-5-(hydroxyimino)-3-phenyl-5H-benzo[4,5]cyclohepta[1,2-b]pyridin-7-yl]methanesulfonamide To a stirred solution of N-(5-oxo-3-phenyl-5H-benzo[4,5]cyclohepta[1,2-b]pyridin-7-yl)methanesulfonamide (0.10 g, 0.27 mmol) in EtOH (7 mL) was added hydroxylamine hydrochloride (0.30 g, 4.3 mmol). The reaction mixture was heated to 90° C. for 5 h, cooled to room temperature, concentrated, and purified by flash chromatography to afford the title compound as a 3:2 mixture of the isomers. For the major isomer; ¹H NMR (600 MHz, CD₃OD) δ 8.82 (d, 1H); 8.30 (d, 1H); 7.00-7.70 (m, 10H); 3.02 (s, 3H), LRMS (APCI) calc'd for (C₂₁H₁₈N₃O₃S) [M+H]+, 392.1; found 392.1.

Example 39

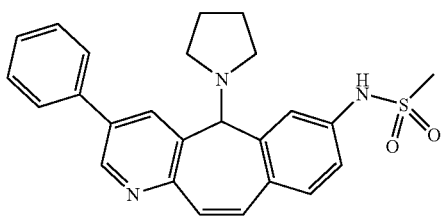

297

N-(3-phenyl-5-pyrrolidin-1-yl-5H-benzo[4,5]cyclohepta[1,2-b]pyridin-7-yl)methanesulfonamide To a stirred solution of N-(5-hydroxy-3-phenyl-5H-benzo[4,5]cyclohepta[1,2-b]pyridin-7-yl)methanesulfonamide (40 mg, 0.11 mmol) in CH₂Cl₂ (2 mL) was added SOCl₂ (30 uL, 0.41 mmol) at 0° C. The mixture was left to stir at 0° C. for 1 h and concentrated in vacuo. To the residue were added CH₂Cl₂ (2 mL) and pyrrolidine (0.10 mL, 1.2 mmol) at 0° C. The mixture was allowed to warm to room temperature as the bath did, and left to stir overnight. The mixture was concentrated and purified by flash chromatography to afford the title compound. ¹H NMR (600 MHz, CD₃OD) δ 8.83 (s, 1H); 7.91 (s, 1H); 7.15-7.64 (m, 10); 4.31 (br s, 1H); 3.02 (s, 3H); 2.09 (br s, 4H); 1.61 (br s, 4H). LRMS (APCI) calc'd for (C₂₅H₂₆N₃O₂S) [M+H]+, 432.2; found 432.1.

The following compounds were made according to Scheme 7.

TABLE 6

| Compound | Structure | Name | MS (M + 1) |
| --- | --- | --- | --- |
| 298 | 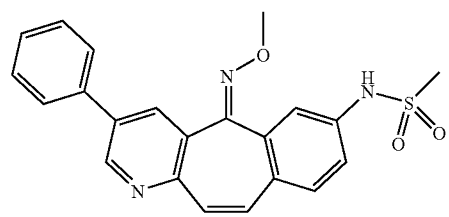 | N-[(5E/Z)-5-(methoxyimino)-3-phenyl-5H-benzo[4,5]cyclohepta[1,2-b]pyridin-7-yl]methanesulfonamide | calc'd 406.1 (M + H)+; found 406.1 (M + H)+ |
| 299 | 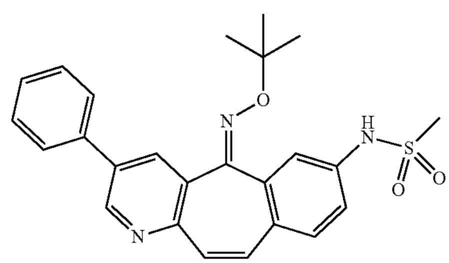 | N-[(5E/Z)-5-(tert-butoxyimino)-3-phenyl-5H-benzo[4,5]cyclohepta[1,2-b]pyridin-7-yl]methanesulfonamide | calc'd 448.2 (M + H)+; found 448.2 (M + H)+ |
| 300 | 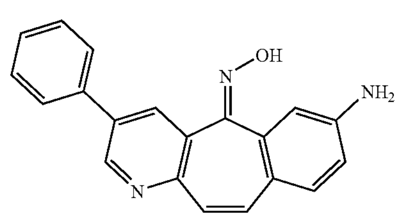 | (5E/Z)-7-amino-3-phenyl-5H-benzo[4,5]cyclohepta[1,2-b]pyridin-5-one oxime | calc'd 314.1 (M + H)+; found 314.2 (M + H)+ |
| 301 | 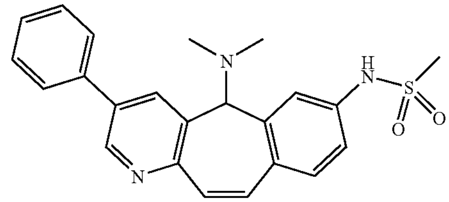 | N-[5-(dimethylamino)-3-phenyl-5H-benzo[4,5]cyclohepta[1,2-b]pyridin-7-yl]methanesulfonamide | calc'd 406.2 (M + H)+; found 406.1 (M + H)+ |

TABLE 6-continued

| Compound | Structure | Name | MS (M + 1) |
|---|---|---|---|
| 302 | 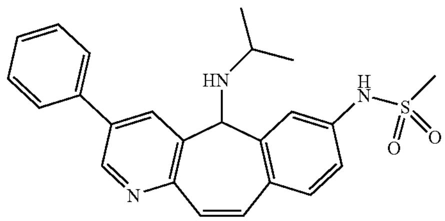 | N-[5-(isopropylamino)-3-phenyl-5H-benzo[4,5]cyclohepta[1,2-b]pyridin-7-yl]methanesulfonamide | calc'd 420.2 (M + H)+; found 420.1 (M + H)+ |
| 303 | 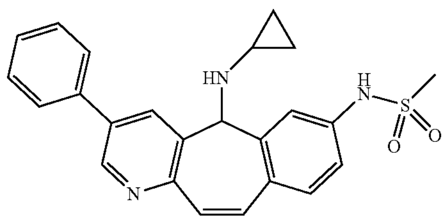 | N-[5-(cyclopropylamino)-3-phenyl-5H-benzo[4,5]cyclohepta[1,2-b]pyridin-7-yl]methanesulfonamide | calc'd 418.2 (M + H)+; found 418.1 (M + H)+ |
| 304 | 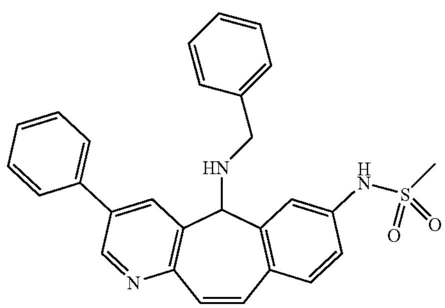 | N-[5-(benzylamino)-3-phenyl-5H-benzo[4,5]cyclohepta[1,2-b]pyridin-7-yl]methanesulfonamide | calc'd 468.2 (M + H)+; found 468.1 (M + H)+ |
| 305 | 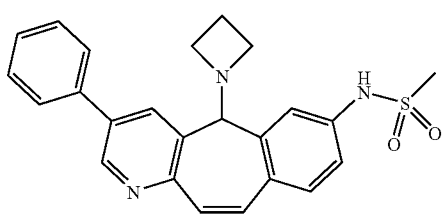 | N-(5-azetidin-1-yl-3-phenyl-5H-benzo[4,5]cyclohepta[1,2-b]pyridin-7-yl)methanesulfonamide | calc'd 418.2 (M + H)+; found 418.1 (M + H)+ |
| 306 | 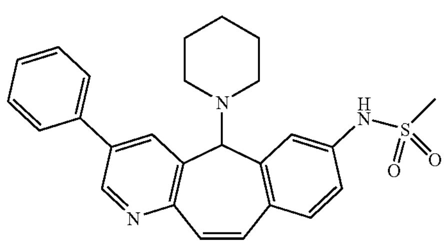 | N-(3-phenyl-5-piperidin-1-yl-5H-benzo[4,5]cyclohepta[1,2-b]pyridin-7-yl)methanesulfonamide | calc'd 446.2 (M + H)+; found 446.1 (M + H)+ |
| 307 | 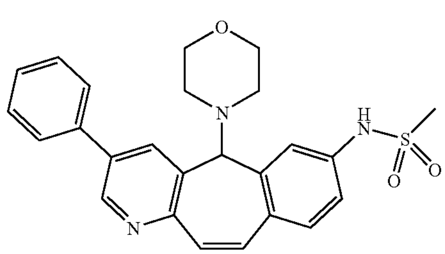 | N-(5-morpholin-4-yl-3-phenyl-5H-benzo[4,5]cyclohepta[1,2-b]pyridin-7-yl)methanesulfonamide | calc'd 448.2 (M + H)+; found 448.1 (M + H)+ |

TABLE 6-continued

| Compound | Structure | Name | MS (M + 1) |
|---|---|---|---|
| 308 | 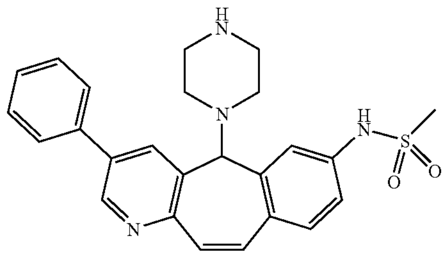 | 7-[(methylsulfonyl)amino]-3-phenyl-5-piperazinediium-1-yl-5H-benzo[4,5]cyclohepta[1,2-b]pyridine | calc'd 447.2 (M + H)+; found 447.2 (M + H)+ |

Scheme 8

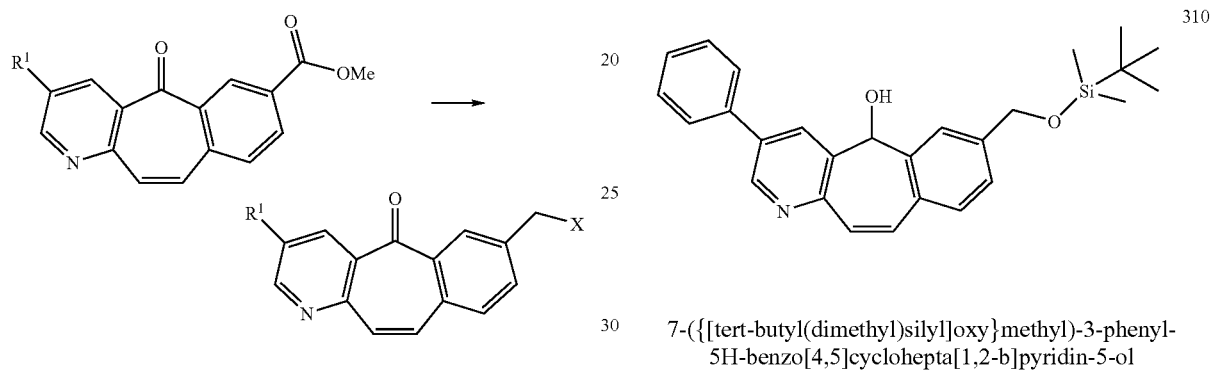

Example 40

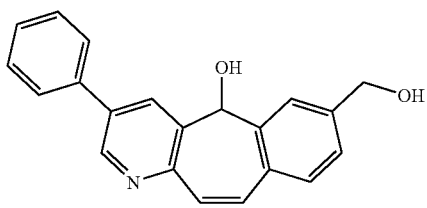

7-(hydroxymethyl)-3-phenyl-5H-benzo[4,5]cyclohepta[1,2-b]pyridin-5-ol

LiAlH₄ (22 mg, 0.586 mmol) was added to a solution of Compound 12 (100.0 mg, 0.293 mmol) in 3 mL of THF. After 1 h, the reaction was quenched by the addition of 22 μL of water. After 30 min, 66 μL of 2.5 M NaOH was added and after 30 min an additional 22 μL of water was added and the mixture was stirred vigorously. After 18 h, the mixture was filtered and the solid was washed successively with EtOAc (100 mL) and a 1:1 MeOH/CH₂Cl₂ (50 mL) solution. The filtrate was concentrated in vacuo to afford the crude diol 309. LRMS (APCI) calc'd for (C₂₁H₁₈NO₂) [M+H]+, 316.1; found 316.2.

Example 40A

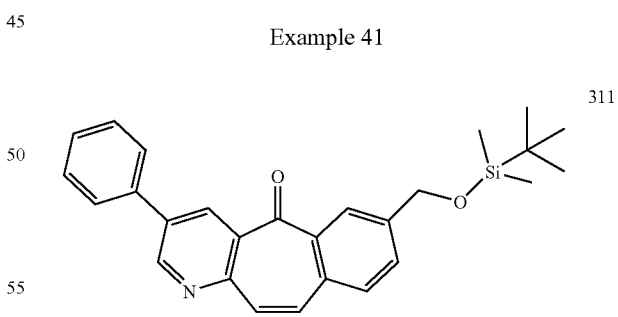

7-({[tert-butyl(dimethyl)silyl]oxy}methyl)-3-phenyl-5H-benzo[4,5]cyclohepta[1,2-b]pyridin-5-ol Diol 309 (90 mg, 0.285 mmol), imidazole (49 mg, 0.71 mmol) and tert-butyldimethylsilylchloride (0.31 mmol, 48 mg) were dissolved in 3 mL of DMF. After 1 h, an additional 2 mL of DMF were added. After 1 h, additional imidazole (49 mg, 0.71 mmol) and tert-butyldimethylsilylchloride (0.31 mmol, 48 mg) were added. After a further 18 h, the mixture was poured into EtOAc, washed with water and brine, then dried over Na₂SO₄ and concentrated in vacuo to afford the crude alcohol 310. LRMS (APCI) calc'd for (C₂₇H₃₂NO₂Si) [M+H]+, 430.2; found 430.2.

Example 41

7-({[tert-butyl(dimethyl)silyl]oxy}methyl)-3-phenyl-5H-benzo[4,5]cyclohepta[1,2-b]pyridin-5-one Manganese dioxide (250 mg, 2.88 mmol) was added to a solution of alcohol 310 (123 mg, 0.286 mmol) in 5 mL of CH₂Cl₂. After 72 h the mixture was filtered through a 45μ Nylon syringe filter, concentrated in vacuo, and purified via flash column chromatography (5-60% EtOAc/hexanes gradient) to afford ketone 311. LRMS (APCI) calc'd for ($C_{27}H_{30}NO_2Si$) [M+H]+, 428.2; found 428.2.

Example 42

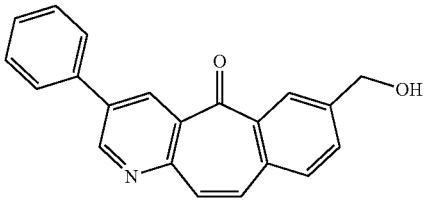

312

7-(hydroxymethyl)-3-phenyl-5H-benzo[4,5]cyclo-hepta[1,2-b]pyridin-5-one

Tetra-n-butylammonium fluoride (8 μL of a 2M solution in THF, 0.15 mmol) was added to a solution of ketone 311 (58 mg, 0.14 mmol) in 1 mL of THF. After 30 min, the solution was poured into EtOAc, washed with water and brine then dried over $Na_2SO_4$. The solution was filtered, concentrated in vacuo and purified via flash column chromatography (10-100% EtOAc/hexanes gradient) to afford alcohol 312. $^1$H NMR (600 MHz, $CDCl_3$) δ 9.08 (d, 1H); 8.68 (d, 1H); 8.21 (s, 1H); 7.68 (dd, 1H); 7.64-7.67 (m, 2H); 7.57 (s, 1H); 7.44-7.48 (m, 2H); 7.37-7.41 (m, 1H); 7.35 (d, 1H); 7.23 (d, 1H); 4.81 (s, 2H).

Example 43

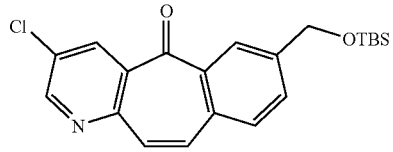

313

7-({[tert-butyl(dimethyl)silyl]oxy}methyl)-3-chloro-5H-benzo[4,5]cyclohepta[1,2-b]pyridin-5-one Compound 313 was prepared in a manner analogous to that described in Example 41 with the exception that diisobutylaluminum hydride was used as the reducing agent. LRMS (APCI) calc'd for ($C_{21}H_{25}ClNO_2Si$) [M+H]+, 386.1; found 385.7.

Example 44

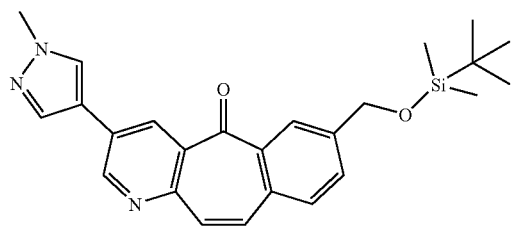

314

7-({[tert-butyl(dimethyl)silyl]oxy}methyl)-3-(1-methyl-1H-pyrazol-4-yl)-5H-benzo[4,5]cyclohepta[1,2-b]pyridin-5-one Compound 313 (185 mg, 0.479 mmol), 1-methyl-4-(4,4,5,5-tetramethyl-1,3,2-dioxaborolan-2-yl)-1H-pyrazole (199. mg, 0.959 mmol), Pd(dppf)$Cl_2$ (35. mg, 0.048 mmol) and $K_2CO_3$ (199 mg, 1.44 mmol) were suspended in 3 mL of dioxane. The mixture was sparged with Ar for 10 min, then heated to 95° C. After 18 h, the mixture was poured into EtOAc, washed with saturated aqueous $NaHCO_3$ and brine then dried over $Na_2SO_4$. The solution was filtered, concentrated in vacuo, and purified via flash column chromatography (10-100% EtOAc/hexanes gradient) to afford title compound 314. LRMS (APCI) calc'd for ($C_{25}H_{30}N_3O_2Si$) [M+H]+, 432.2; found 431.7.

Example 45

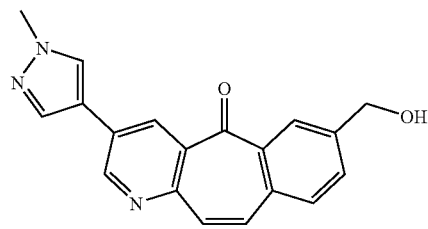

315

7-(hydroxymethyl)-3-(1-methyl-1H-pyrazol-4-yl)-5H-benzo[4,5]cyclohepta[1,2-b]pyridin-5-one Compound 315 was prepared from Compound 228 in a manner analogous to that described in Example 42. $^1$H NMR (600 MHz, $CDCl_3$) δ 9.02 (d, 1H); 8.57 (d, 1H); 8.26 (d, 1H); 7.92 (d, 1H); 7.81 (s, 1H); 7.73 (dd, 1H); 7.62 (dd, 1H); 7.36 (d, 1H); 7.25 (d, 1H); 4.86 (d, 2H); 3.99 (s, 3H); 1.84 (t, 1H). LRMS (APCI) calc'd for ($C_{19}H_{16}N_3O_2$) [M+H]+, 318.1; found 317.8.

Example 46

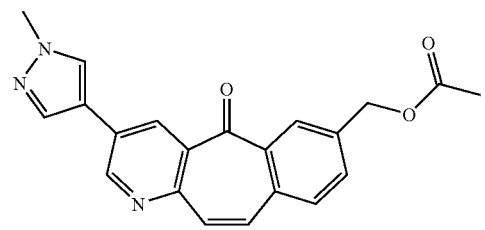

[3-(1-methyl-1H-pyrazol-4-yl)-5-oxo-5H-benzo[4,5]cyclohepta[1,2-b]pyridin-7-yl]methyl acetate (Compound 316)

Compound 315 (12 mg, 0.038 mmol) was dissolved in 0.5 mL dichloromethane and 0.1 mL N,N'-dimethylformamide and cooled to 0° C. DMAP (2 mg, 0.019 mmol) and triethylamine (20 μL, 0.14 mmol) were added followed by acetyl chloride (7 μL, 0.10 mmol). The mixture was stirred at 0° C. for 3 h at which time it was quenched with saturated aqueous ammonium chloride and extracted three times with dichloromethane. The combined organics were dried over magnesium sulfate, filtered, concentrated in vacuo. Purification via reverse phase HPLC (10-100% acetonitrile/water gradient, 0.05% trifluoroacetic acid modifier) afforded the title compound. ¹H NMR (600 MHz, CDCl₃) δ 9.02 (s, 1H); 8.59 (s, 1H); 8.26 (s, 1H); 7.93 (s, 1H); 7.83 (s, 1H); 7.68 (d, 1H); 7.61 (d, 1H); 7.40 (d, 1H); 7.26-7.24 (m, 1H); 5.24 (s, 2H); 3.99 (s, 3H); 2.14 (s, 3H). LRMS (APCI) calc'd for (C₂₁H₁₈N₃O₃) [M+H]+, 360.1; found 360.1.

Example 47

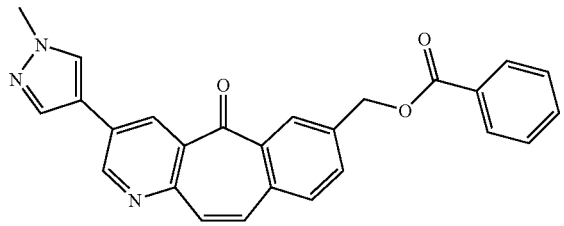

[3-(1-methyl-1H-pyrazol-4-yl)-5-oxo-5H-benzo[4,5]
cyclohepta[1,2-b]pyridin-7-yl]methyl benzoate
(Compound 317)

Compound 315 (10 mg, 0.032 mmol) was dissolved in 0.5 mL dichloromethane and 0.1 mL N,N'-dimethylformamide and cooled to 0° C. DMAP (2 mg, 0.019 mmol) and triethylamine (16 µL, 0.12 mmol) were added followed by benzoyl chloride (10 µL, 0.08 mmol). The mixture was stirred at 0° C. for 3 h at which time it was quenched with saturated aqueous ammonium chloride and extracted three times with dichloromethane. The combined organics were dried over magnesium sulfate, filtered, concentrated in vacuo. Purification via reverse phase HPLC (10-100% acetonitrile/water gradient, 0.05% trifluoroacetic acid modifier) afforded the title compound. ¹H NMR (600 MHz, CDCl₃) δ 9.03 (s, 1H); 8.62 (s, 1H); 8.36 (s, 1H); 8.09 (d, 2H); 7.93 (s, 1H); 7.83 (s, 1H); 11.73 (d, 1H); 7.64 (d, 1H); 7.58 (t, 1H); 7.45 (t, 2H); 7.42-7.41 (m, 1H); 7.27 (d, 1H); 5.50 (s, 2H); 3.99 (s, 3H). LRMS (APCI) calc'd for (C₂₆H₂₀N₃O₃) [M+H]+, 422.1; found 422.1.

Example 48

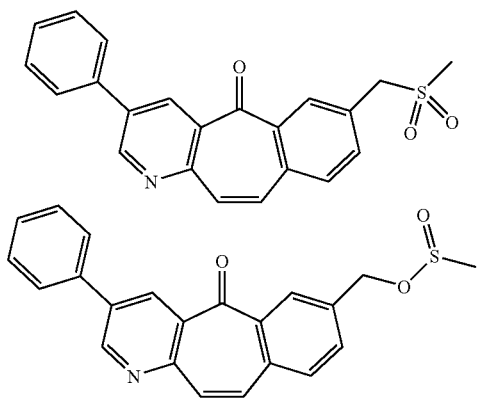

Step 1:
Methanesulfonyl chloride (1 drop from a 22 G needle) was added to a solution of Compound 312 (30.0 mg, 0.096 mmol) and NEt₃ (27 µL, 0.19 mmol) at 0° C. After 30 min, additional methanesulfonyl chloride (1 drop from a 22 G needle) was added. After 30 min, additional methanesulfonyl chloride (2 drops from a 22 G needle) was added. After an additional 2 h, the reaction mixture was poured into EtOAc, washed with saturated aqueous NaHCO₃ and brine then dried over Na₂SO₄. The solution was filtered, concentrated in vacuo and the crude mesylate was used directly in the next reaction.
Step 2:
The crude mesylate from Step A (37 mg, 0.01 mmol) and sodium methanesulfinate (19 mg, 0.19 mmol) were suspended in 2 mL of DMF and heated to 45° C. After 1 h, the reaction mixture was poured into EtOAc, washed with water and brine then dried over Na₂SO₄. The solution was filtered and concentrated in vacuo to give a mixture of Compounds 318 and 319. The two compounds were purified by reverse phase HPLC (30-100% CH₃CN/water with a 0.1% TFA modifier) to provide the TFA salts. 7-[(methylsulfonyl)methyl]-3-phenyl-5H-benzo[4,5]cyclohepta[1,2-b]pyridin-5-one (Compound 318). ¹H NMR (600 MHz, CDCl₃) δ 9.27 (d, 1H); 8.88 (d, 1H); 8.29 (s, 1H); 7.83 (dd, 1H); 7.68-7.73 (m, 3H); 7.46-7.55 (m, 4H); 7.37 (d, 1H); 4.41 (s, 2H); 2.85 (s, 3H). LRMS (APCI) calc'd for (C₂₂H₁₈NO₃S) [M+H]+, 376.1; found 376.1.

(5-oxo-3-phenyl-5H-benzo[4,5]cyclohepta[1,2-b]pyridin-7-yl)methyl methanesulfinate (Compound 319). ¹H NMR (600 MHz, CDCl₃) δ 9.29 (d, 1H); 8.98 (d, 1H); 8.25 (d, 1H); 7.73 (dd, 1H); 7.67-7.70 (m, 2H); 7.64 (d, 1H); 7.39-7.52 (m, 5H); 5.15 (AB_q, 2H); 2.68 (s, 3H). LRMS (APCI) calc'd for (C₂₂H₁₈NO₃S) [M+H]+, 376.1; found 376.1.

Example 49

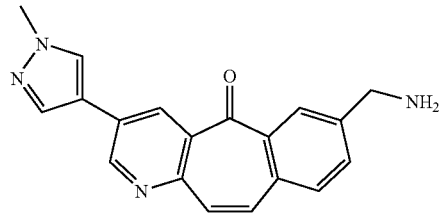

320

7-(aminomethyl)-3-(1-methyl-1H-pyrazol-4-yl)-5H-benzo[4,5]cyclohepta[1,2-b]pyridin-5-one Diphenyl phosphoryl azide (DPPA) (1 drop from a 21 G needle) and 1,8-dizabicyclo[5.4.0]undec-7-ene (DBU) (1 drop from a 21 G needle) were added to a solution of Compound 315 (10.0 mg, 0.032 mmol) in 1 mL of THF. After 18 h, additional DPPA (2 drops from a 21 G needle) and DBU (2 drops from a 21 G needle) were added. After a further 24 h, additional DPPA (4 drops from a 21 G needle) and DBU (4 drops from a 21 G needle) were added. After another 24 h, the solution was diluted in EtOAc, washed with saturated aqueous NaHCO₃ and brine then dried over Na₂SO₄. The solution was filtered, concentrated in vacuo and the crude azide was used directly in the next reaction.

The crude azide was dissolved in 5 mL of MeOH and SnCl₂ (18.2 mg, 0.10 mmol) was added. After 30 min, additional SnCl₂ (36.4 mg, 0.20 mmol) was added. After a further 18 h, additional SnCl₂ (18.2 mg, 0.10 mmol) was added. After 3 h, the solution was concentrated in vacuo and purified by reverse phase HPLC (20-100% CH₃CN/water with a 0.05% TFA modifier). to afford the title compound 320. ¹H NMR (600 MHz, CD₃OD) δ 9.05 (d, 1H); 8.60 (d, 1H); 8.20-8.23 (m, 2H); 8.01 (s, 1H); 7.75 (dd, 1H); 7.70 (d, 1H); 7.34 (d, 1H); 7.27 (d, 1H); 4.03 (s, 2H); 3.95 (s, 3H). LRMS (APCI) calc'd for (C$_{19}$H$_{17}$N$_4$O) [M+H]+, 317.1; found 317.1.

Example 50

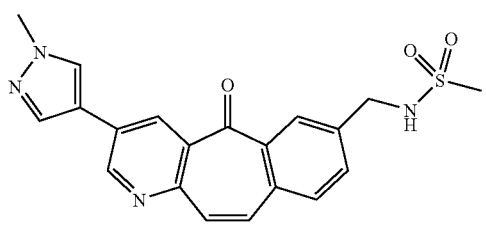

321

N-{[3-(1-methyl-1H-pyrazol-4-yl)-5-oxo-5H-benzo[4,5]cyclohepta[1,2-b]pyridin-7-yl]methyl}methanesulfonamide Compound 315 was converted to the corresponding mesylate in a manner analogous to that described in Example 48 Step 1. The crude mesylate was dissolved in 5 mL of THF and methanesulfonamide (60 mg, 0.63 mol) and K$_2$CO$_3$ (87 mg, 0.63 mmol) were added. After 30 min, the mixture was heated to 55° C., then 1 mL of DMF was added. After another 1 h, an additional 1 mL of DMF was added. After 18 h, the mixture was diluted in EtOAc, washed with saturated aqueous NaHCO$_3$ and brine then dried over Na$_2$SO$_4$. The solution was filtered, concentrated in vacuo and purified by reverse phase HPLC (30-100% CH$_3$CN/water with a 0.05% TFA modifier). to afford the title compound 321. $^1$H NMR (600 MHz, CDCl$_3$) δ 9.02 (d, 1H); 8.58 (s, 1H); 8.23 (s, 1H); 7.92 (s, 1H); 7.83 (s, 1H); 7.72 (dd, 1H); 7.61 (d, 1H); 7.39 (d, 1H); 7.22 (d, 1H); 4.89 (br s, 1H); 4.47-4.49 (m, 2H); 3.99 (s, 3H); 2.97 (s, 3H). LRMS (APCI) calc'd for (C$_{20}$H$_{19}$N$_4$O$_3$S) [M+H]+, 395.1; found 395.1.

Example 51

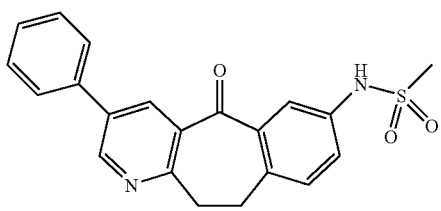

322

N-(5-oxo-3-phenyl-10,11-dihydro-5H-benzo[4,5]cyclohepta[1,2-b]pyridin-7-yl)methanesulfonamide Compound 263 (15 mg, 0.04 mmol) was dissolved in 8 mL of EtOH and 1 mL of 1 N HCl, then 4 mg of 10% palladium on carbon was added and the mixture was placed under 45 psi of hydrogen on a Parr shaker. After 24 h the reaction mixture was filtered through a 45μ Nylon syringe filter, concentrated in vacuo, and purified by reverse phase HPLC (10-60% CH$_3$CN/water with a 0.1% TFA modifier) to afford the over-reduced benzylic alcohol: N-(5-hydroxy-3-phenyl-10,11-dihydro-5H-benzo[4,5]cyclohepta[1,2-b]pyridin-7-yl)methanesulfonamide.

The crude benzylic alcohol (5 mg, 0.013 mmol) was dissolved in 5 mL of CH$_2$Cl$_2$ and stirred with 25 mg of MnO$_2$ for 2 h. The reaction mixture was filtered through a 45μ Nylon syringe filter, concentrated in vacuo, and purified by reverse phase HPLC (30-100% CH$_3$CN/water with a 0.1% TFA modifier). to afford the title compound 322. $^1$H NMR (600 MHz, CDCl$_3$) δ 8.83 (d, 1H); 8.54 (d, 1H); 7.65 (d, 1H); 7.57-7.59 (m, 2H); 7.41-7.47 (m, 3H); 7.35-7.39 (m, 1H); 7.25 (d, 1H); 6.57 (s, 1H); 3.43-3.46 (m, 2H); 3.18-3.22 (m, 2H); 2.98 (s, 3H). LRMS (APCI) calc'd for (C$_{21}$H$_{19}$N$_2$O$_3$S) [M+H]+, 379.1; found 379.1.

Example 52

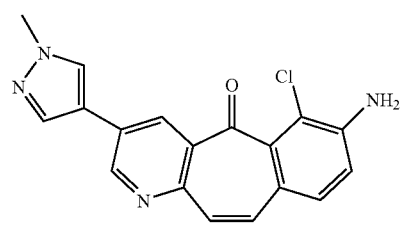

323

7-amino-6-chloro-3-(1-methyl-1H-pyrazol-4-yl)-5H-benzo[4,5]cyclohepta[1,2-b]pyridin-5-one N-chlorosuccinimide (5 mg, 0.036 mmol) was added to a solution of Compound 139 (10 mg, 0.033 mmol) in dry acetonitrile and heated to 75° C. After three hours, 1 molar sodium hydroxide was added and the mixture was extracted with dichloromethane, dried over magnesium sulfate, filtered, concentrated in vacuo, and purified by reverse phase HPLC (10-70% acetonitrile/water gradient 0.1%, trifluoroacetic acid modifier) to afford the title compound. $^1$H NMR (600 MHz, CDCl$_3$) δ 8.99 (d, 1H); 8.25 (d, 1H); 8.23 (d, 1H); 8.03 (s, 1H); 7.36 (d, 1H); 7.19 (d, 1H); 7.08 (d, 1H); 7.01 (d, 1H); 3.96 (s, 3H). LRMS (APCI) calc'd for (C$_{18}$H$_{14}$ClN$_4$O) [M+H]+, 337.1; found 337.1.

Example 53

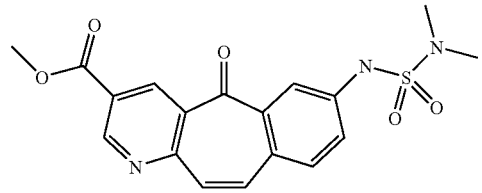

methyl 7-{[(dimethylamino)sulfonyl]amino}-5-oxo-5H-benzo[4,5]cyclohepta[1,2-b]pyridine-3-carboxylate (Compound 324)

Compound 45 (100 mg, 0.275 mmol), 1,8-diazabicyclo{5.4.0}undec-7-ene (0.113 mL, 0.825 mmol), tri-t-butylphosphonium tetrafluoroborate (0.032 g, 0.032 mmol), palladium(II)acetate (6 mg, 0.027 mmol), and molybdenumhexacarbonyl (73 mg, 0.275 mmol) were dissolved in 2 mL of DMF and 1 mL of methanol. The reaction mixture was heated in the Biotage Initiator series microwave at 130° C. for 30 minutes. The mixture was diluted in ethylacetate and the organic layer was washed with saturated aqueous sodium bicarbonate and brine, then dried over sodium sulfate and concentrated. The residue was purified via reverse phase HPLC (30-100% acetonitrile/water gradient, 0.05% trifluoroacetic acid modifier) to afford the title compound. $^1$H NMR (600 MHz, DMSO-d6) δ 10.59 (s, 1H); 9.32 (d, 1H); 8.89 (d, 1H); 8.01 (d, 1H); 7.80 (d, 1H); 7.61 (dd, 1H); 7.51 (d, 1H); 7.29 (d, 1H); 3.92 (s, 3H); 2.73 (s, 6H). LRMS (APCI) calc'd for ($C_{18}H_{17}N_3O_5S$) [M+H]+, 388.1; found 388.1.

Example 54

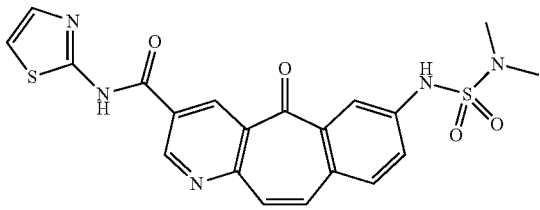

7-{[(dimethylamino)sulfonyl]amino}-5-oxo-N-1,3-thiazol-2-yl-5H-benzo[4,5]cyclohepta[1,2-b]pyridine-3-carboxamide (Compound 325)

methyl 7-{[(dimethylamino)sulfonyl]amino}-5-oxo-5H-benzo[4,5]cyclohepta[1,2-b]pyridine-3-carboxylate (17 mg, 0.044 mmol) was dissolved in 1 mL of THF and 1 mL of 1 M aqueous sodium hydroxide. After 2 h the mixture was quenched by the addition of 1.1 mL of 1M HCl and the organics were removed in vacuo. The material was freeze dried to afford 7-{[(dimethylamino)sulfonyl]amino}-5-oxo-5H-benzo[4,5]cyclohepta[1,2-b]pyridine-3-carboxylic acid.

The crude 7-{[(dimethylamino)sulfonyl]amino}-5-oxo-5H-benzo[4,5]cyclohepta[1,2-b]pyridine-3-carboxylic acid (21 mg, 0.056 mmol), 2-aminothiazole (8 mg, 0.084 mmol), N-(3-dimethylaminopropyl)-N'-ethylcarbodiimide hydrochloride (16 mg, 0.084 mmol), 1-hydroxybenzotriazole hydrate (11 mg, 0.084 mmol) and 4-dimethylaminopyridine (spatula tip) were dissolved in 2 mL of DMF and stirred for 18 h. The mixture was diluted in ethylacetate and the organic layer was washed with saturated aqueous sodium bicarbonate and brine, then dried over sodium sulfate and concentrated. The residue was purified via reverse phase HPLC (20-100% acetonitrile/water gradient, 0.05% trifluoroacetic acid modifier) to afford the title compound. $^1$H NMR (600 MHz, DMSO-d6) δ 13.06 (br s, 1H); 10.59 (br s, 1H); 9.47 (d, 1H); 9.13 (d, 1H); 8.02 (d, 1H); 7.81 (d, 1H); 7.61 (dd, 1H); 7.57 (d, 1H); 7.50 (d, 1H); 7.27-7.33 (m, 2H); 2.74 (s, 6H); LRMS (APCI) calc'd for ($C_{20}H_{17}N_5O_4S_2$) [M+H]+, 456.1; found 456.1.

Example 55

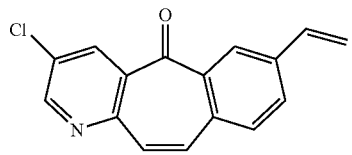

3-chloro-7-vinyl-5H-benzo[4,5]cyclohepta[1,2-b]pyridin-5-one (Compound 326)

A test tube fitted with a teflon septum was charged with compound 1 (1.0 g, 3.1 mmol), PdCl$_2$(dppf) (0.12 g, 0.16 mmol), and potassium vinyltrifluoroborate (0.42 g, 3.1 mmol). The tube was evacuated and backfilled with argon three times. Fully degassed n-PrOH (30 mL) was added followed by the addition of triethylamine (1.3 mL, 9.4 mmol). The mixture was heated to 100° C. for 3 hours. The solution was diluted with ethyl acetate and washed with water and brine and dried over magnesium sulfate. The solution was concentrated in vacuo and purified via flash chromatography (silica, 0-25% ethyl acetate/hexanes) to afford the title compound. $^1$H NMR (600 MHz, CDCl$_3$) δ 8.80 (d, 1H); 8.53 (d, 1H); 8.27 (d, 1H); 7.76 (dd, 1H); 7.57 (d, 1H); 7.32 (d, 1H); 7.26 (d, 1H); 6.83 (dd, 1H); 5.94 (d, 1H); 5.43 (d, 1H). LRMS (APCI) calc'd for ($C_{16}H_{11}ClNO$) [M+H]+, 268.1; found 268.1.

Example 56

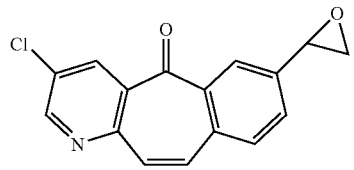

3-chloro-7-oxiran-2-yl-5H-benzo[4,5]cyclohepta[1,2-b]pyridin-5-one (Compound 327)

3-chloro-7-vinyl-5H-benzo[4,5]cyclohepta[1,2-b]pyridin-5-one (0.30 g, 1.12 mmol) was dissolved in 17 mL DMSO and 3.0 mL water. N-Bromosuccinimide (0.20 g, 1.12 mmol) was added and the reaction was heated in an oil bath at 60° C. for 1 hour at which time an additional 0.1 g N-Bromosuccinimide (0.56 mmol) was added and the mixture was stirred an additional 45 min at 60° C. The resulting mixture was diluted with water and extracted with ethyl acetate three times. The combined organics were washed with brine, dried over sodium sulfate, filtered, and concentrated in vacuo. The resulting crude residue was dissolved in 30 mL tetrahydrofuran and 6 mL t-BuOH. t-BuOK (2.24 mL of 1.0 M in THF, 2.24 mmol) was added dropwise and the resulting orange slurry was stirred at room temperature for 45 min. The reaction was diluted with water and extracted with ethyl acetate three times. The combined organics were washed with brine, dried over magnesium sulfate, concentrated in vacuo, and purified via flash chromatography (silica, 0-25% ethyl acetate/hexanes) to afford the title compound. $^1$H NMR (600 MHz, CDCl$_3$) δ 8.79 (d, 1H); 8.49 (d, 1H); 8.20 (d, 1H); 7.57 (d, 1H); 7.55 (dd, 1H); 7.27 (d, 1H); 7.23 (d, 1H); 3.99 (dd, 1H); 3.21 (dd, 1H); 2.84 (dd, 1H).

Example 57

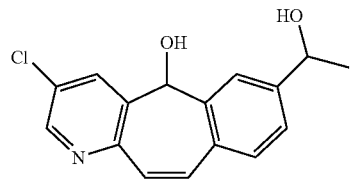

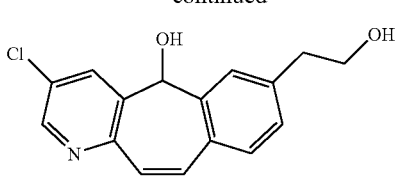

329

3-chloro-7-oxiran-2-yl-5H-benzo[4,5]cyclohepta[1,2-b]pyridin-5-one (0.67 g, 2.4 mmol) was dissolved in 30 mL THF. LiAlH$_4$ (90 mg, 2.4 mmol) was added and the reaction was stirred at room temperature for 2 hours. The reaction was quenched via the dropwise addition of water followed by slow addition of 1N HCl. The mixture was extracted with ethyl acetate. The combined organics were washed with brine, dried over magnesium sulfate, filtered, and concentrated in vacuo. The crude mixture was used without further purification.

3-chloro-7-(1-hydroxyethyl)-5H-benzo[4,5]cyclohepta[1,2-b]pyridin-5-ol

LRMS (APCI) calc'd for ($C_{16}H_{15}ClNO_2$) [M+H]+, 288.1; found 288.1.

3-chloro-7-(2-hydroxyethyl)-5H-benzo[4,5]cyclohepta[1,2-b]pyridin-5-ol

LRMS (APCI) calc'd for ($C_{16}H_{15}ClNO_2$) [M+H]+, 288.1; found 288.1.

Example 58

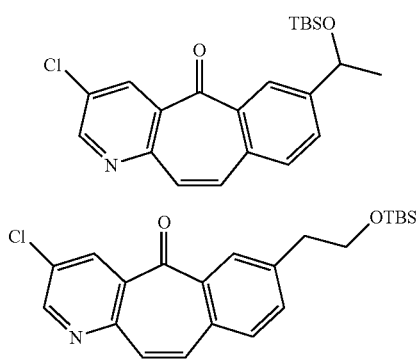

330

331

A crude mixture of 3-chloro-7-(1-hydroxyethyl)-5H-benzo[4,5]cyclohepta[1,2-b]pyridin-5-ol and 3-chloro-7-(2-hydroxyethyl)-5H-benzo[4,5]cyclohepta[1,2-b]pyridin-5-ol (0.67 g, 2.4 mmol) was dissolved in 30 mL N,N'-dimethylformamide. Imidazole (0.82 g, 6.0 mmol) and TBSCl (0.45 g, 3.0 mmol) were added sequentially and the reaction was stirred at 50° C. for 2 hours at which time additional imidazole (0.82 g, 12 mmol) and TBSCl (0.45 g, 3.0 mmol) were added and the reaction was stirred an additional 2 hours. The mixture was diluted with water and saturated aqueous ammonium chloride and extracted three times with ethyl acetate. The combined organics were washed five times with brine, dried over magnesium sulfate and concentrated in vacuo. The resulting crude material was dissolved in 30 mL dichloromethane. MnO$_2$ (4.0 g, 46.5 mmol) was added and the reaction was stirred overnight at room temperature. The resulting slurry was filtered through a plug of celite with dichloromethane, concentrated in vacuo, and purified via flash chromatography (silica, 0-20% ethyl acetate/hexanes) to afford the title compounds as a mixture. The compounds were separated via flash chromatography (silica, 0-10% ethyl acetate/hexanes). 7-(1-{[tert-butyl(dimethyl)silyl]oxy}ethyl)-3-chloro-5H-benzo[4,5]cyclohepta[1,2-b]pyridin-5-one. $^1$H NMR (600 MHz, CDCl$_3$) δ 8.79 (d, 1H); 8.53 (d, 1H); 8.18 (d, 1H); 7.76 (dd, 1H); 7.58 (d, 1H); 7.29 (d, 1H); 7.26 (d, 1H); 5.01 (q, 1H); 1.44 (d, 3H); 0.91 (s, 9H); 0.07 (s, 3H); −0.01 (s, 3H). 7-(2-{[tert-butyl(dimethyl)silyl]oxy}ethyl)-3-chloro-5H-benzo[4,5]cyclohepta[1,2-b]pyridin-5-one. $^1$H NMR (600 MHz, CDCl$_3$) δ 8.80 (d, 1H); 8.52 (d, 1H); 8.12 (d, 1H); 7.58 (dd, 1H); 7.53 (d, 1H); 7.29-7.27 (m, 2H); 3.86 (t, 2H); 2.96 (t, 2H); 0.84 (s, 9H); −0.04 (s, 6H).

Example 59

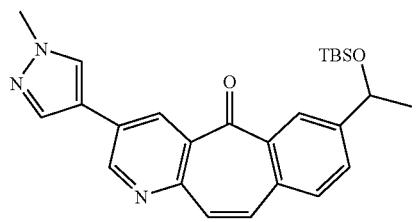

7-(1-{[tert-butyl(dimethyl)silyl]oxy}ethyl)-3-(1-methyl-1H-pyrazol-4-yl)-5H-benzo[4,5]cyclohepta[1,2-b]pyridin-5-one (Compound 332)

A test tube fitted with a teflon septum was charged with 7-(1-{[tert-butyl(dimethyl)silyl]oxy}ethyl)-3-chloro-5H-benzo[4,5]cyclohepta[1,2-b]pyridin-5-one (50 mg, 0.13 mmol), PdCl$_2$(PPh$_3$)$_2$ (9 mg, 0.013 mmol), 1-methyl-4-(4,4,5,5-tetramethyl-1,3,2-dioxaborolan-2-yl)-1H-pyrazole (78 mg, 0.38 mmol), and sodium carbonate (40 mg, 0.38 mmol). The tube was evacuated and backfilled with argon three times. Fully degassed dioxane (1.2 mL) was added and the mixture was stirred at 100° C. overnight. The solution was diluted with ethyl acetate, washed with water and brine, dried over magnesium sulfate, concentrated in vacuo, and purified via flash chromatography (silica, 20-100% ethyl acetate/hexanes) to afford the title compound. $^1$H NMR (600 MHz, CDCl$_3$) δ 8.99 (d, 1H); 8.58 (d, 1H); 8.19 (d, 1H); 7.90 (d, 1H); 7.97 (s, 1H); 7.72 (dd, 1H); 7.56 (d, 1H); 7.32 (d, 1H); 7.22 (d, 1H); 5.01 (q, 1H); 3.97 (s, 3H); 1.44 (d, 3H); 0.90 (s, 9H); 0.06 (s, 3H); −0.02 (s, 3H). LRMS (APCI) calc'd for ($C_{26}H_{32}N_3O_2Si$) [M+H]+, 446.2; found, 446.2.

Example 60

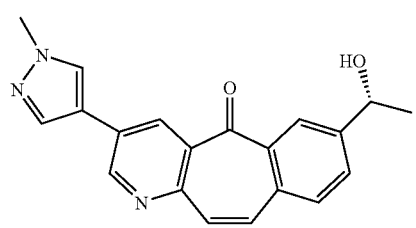

333

-continued

334

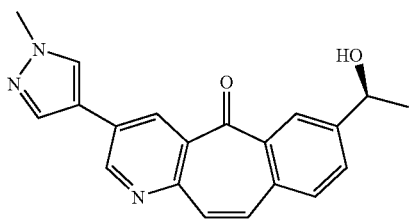

7-(1-{[tert-butyl(dimethyl)silyl]oxy}ethyl)-3-(1-methyl-1H-pyrazol-4-yl)-5H-benzo[4,5]cyclohepta[1,2-b]pyridin-5-one (51 mg, 0.114 mmol) was dissolved in 2 mL of tetrahydrofuran. Tetrabutylammonium fluoride (0.14 mL of 1.0M in THF, 0.14 mmol) was added and the mixture was stirred at room temperature for 1 hour. The reaction was diluted with ethyl acetate and brine and washed with brine twice. The organic layer was dried over magnesium sulfate, filtered and concentrated in vacuo. Purification via reverse phase HPLC (10-70% acetonitrile/water gradient, 0.05% trifluoroacetic acid modifier) afforded the title compound. The two enantiomers were separated via preparative chiral HPLC (AS column, 18% ethanol/heptane isocratic). Absolute stereochemistry was determined via formation of the Mosher's esters. 7-[(1R)-1-hydroxyethyl]-3-(1-methyl-1H-pyrazol-4-yl)-5H-benzo[4,5]cyclohepta[1,2-b]pyridin-5-one. $^1$H NMR (600 MHz, CDCl$_3$) δ 8.98 (d, 1H); 8.55 (d, 1H); 8.24 (d, 1H); 7.89 (d, 1H); 7.80 (s, 1H); 7.74 (dd, 1H); 7.58 (d, 1H); 7.34 (d, 1H); 7.22 (d, 1H); 5.06 (q, 1H); 3.98 (s, 3H); 1.55 (s, 3H). Hydroxyl proton was not observed. LRMS (APCI) calc'd for (C$_{20}$H$_{18}$N$_3$O$_2$) [M+H]+, 332.1; found 332.1. τ$_R$: 18.9 min (analytical chiral HPLC, AS column, 0.46 cm×25 cm, 18% ethanol/heptane, isocratic, flow rate=0.75 mL/min). 7-[(1S)-1-hydroxyethyl]-3-(1-methyl-1H-pyrazol-4-yl)-5H-benzo[4,5]cyclohepta[1,2-b]pyridin-5-one. $^1$H NMR and LRMS data matched 7-[(1R)-1-hydroxyethyl]-3-(1-methyl-1H-pyrazol-4-yl)-5H-benzo[4,5]cyclohepta[1,2-b]pyridin-5-one. τ$_R$: 21.5 min (analytical chiral HPLC, AS column, 0.46 cm×25 cm, 18% ethanol/heptane, isochratic, flow rate=0.75 mL/min).

Example 61

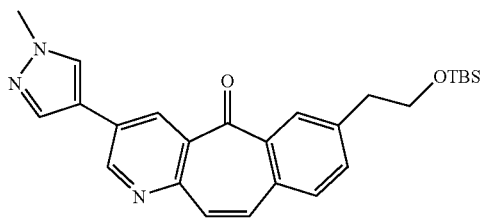

7-(2-{[tert-butyl(dimethyl)silyl]oxy}ethyl)-3-(1-methyl-1H-pyrazol-4-yl)-5H-benzo[4,5]cyclohepta[1,2-b]pyridin-5-one (Compound 335)

A test tube fitted with a teflon septum was charged with 7-(2-{[tert-butyl(dimethyl)silyl]oxy}ethyl)-3-chloro-5H-benzo[4,5]cyclohepta[1,2-b]pyridin-5-one (9 mg, 0.023 mmol), PdCl$_2$(PPh$_3$)$_2$ (2 mg, 0.002 mmol), 1-methyl-4-(4,4,5,5-tetramethyl-1,3,2-dioxaborolan-2-yl)-1H-pyrazole (14 mg, 0.068 mmol), and sodium carbonate (7 mg, 0.068 mmol). The tube was evacuated and backfilled with argon three times. Fully degassed dioxane (0.5 mL) was added and the mixture was stirred at 100° C. overnight. The solution was diluted with ethyl acetate, washed with water and brine, dried over magnesium sulfate, concentrated in vacuo, and purified via flash chromatography (silica, 20-100% ethyl acetate/hexanes) to afford the title compound. LRMS (APCI) calc'd for (C$_{26}$H$_{32}$N$_3$O$_2$Si) [M+H]+, 446.2; found 446.2.

Example 62

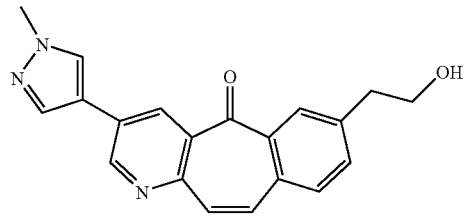

7-(2-hydroxyethyl)-3-(1-methyl-1H-pyrazol-4-yl)-5H-benzo[4,5]cyclohepta[1,2-b]pyridin-5-one (Compound 336)

7-(2-{[tert-butyl(dimethyl)silyl]oxy}ethyl)-3-(1-methyl-1H-pyrazol-4-yl)-5H-benzo[4,5]cyclohepta[1,2-b]pyridin-5-one (5 mg, 0.011 mmol) was dissolved in 0.5 mL of tetrahydrofuran. Tetrabutylammonium fluoride (0.013 mL of 1.0M in THF, 0.013 mmol) was added and the mixture was stirred at room temperature for 1 hour. The reaction was diluted with ethyl acetate and brine and washed with brine twice. The organic layer was dried over magnesium sulfate, filtered and concentrated in vacuo. Purification via reverse phase HPLC (10-70% acetonitrile/water gradient, 0.05% trifluoroacetic acid modifier) afforded the title compound. $^1$H NMR (600 MHz, CDCl$_3$) δ 9.01 (d, 1H); 8.58 (s, 1H); 8.16 (d, 1H); 7.92 (s, 1H); 7.81 (s, 1H); 7.59 (dd, 1H); 7.56 (d, 1H); 7.35 (d, 1H); 7.24 (d, 1H); 3.99 (s, 3H); 3.96 (t, 2H); 3.03 (t, 2H). Hydroxyl proton was not observed. LRMS (APCI) calc'd for (C$_{20}$H$_{18}$N$_3$O$_2$) [M+H]+, 332.1; found 332.1.

Example 63

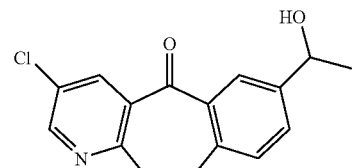

3-chloro-7-(1-hydroxyethyl)-5H-benzo[4,5]cyclohepta[1,2-b]pyridin-5-one (Compound 337)

7-(1-{[tert-butyl(dimethyl)silyl]oxy}ethyl)-3-chloro-5H-benzo[4,5]cyclohepta[1,2-b]pyridin-5-one (20 mg, 0.05 mmol) was taken up in 1 mL of tetrahydrofuran. Tetrabutylammonium fluoride (0.06 mL of 1.0M in THF, 0.06 mmol) was added and the mixture was stirred at room temperature for 45 min. The reaction was concentrated in vacuo and directly purified via flash chromatography (silica, 0-35% ethyl acetate/hexanes) to afford the title compound. $^1$H NMR (600 MHz, CDCl$_3$) δ 8.80 (d, 1H); 8.50 (d, 1H); 8.23 (d, 1H); 7.76 (dd, 1H); 7.60 (d, 1H); 7.31 (d, 1H); 7.26 (d, 1H); 5.06 (q, 1H); 1.55 (d, 3H). Hydroxyl proton was not observed. LRMS (APCI) calc'd for ($C_{16}H_{13}ClNO_2$) [M+H]+, 286.1; found 286.1.

Example 64

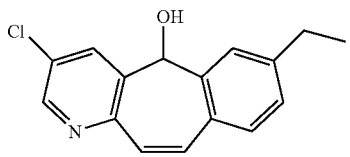

3-chloro-7-ethyl-5H-benzo[4,5]cyclohepta[1,2-b]pyridin-5-ol (Compound 338)

3-chloro-7-vinyl-5H-benzo[4,5]cyclohepta[1,2-b]pyridin-5-one (20 mg, 0.075 mmol) was dissolved in 1 mL of tetrahydrofuran. $RH(COD)_2BF_4$ (3 mg, 0.007 mmol) was added followed by a dropwise addition of 9-BBN (0.44 mL of 0.5 M in THF, 0.22 mmol) and the reaction was stirred overnight. The reaction was cooled to 0° C. and quenched by the simultaneous addition of 1M sodium hydroxide (2.5 ml) and 30% aqueous hydrogen peroxide (0.75 mL) and stirred for 5 hours. The resulting solution was poured into ethyl acetate and brine and extracted three times with ethyl acetate. The combined organics were dried over magnesium sulfate, dried over magnesium sulfate, concentrated in vacuo, and purified via flash chromatography (0-60% ethyl acetate/hexanes) to afford the title compound. $^1H$ NMR (600 MHz, $CDCl_3$) δ 8.41 (s, 1H); 8.03 (s, 1H); 7.54 (s, 1H); 7.28 (m, 2H); 7.17-7.14 (m, 2H); 5.31 (s, 1H); 2.70 (q, 2H); 1.25 (t, 3H). Hydroxyl proton was not observed. LRMS (APCI) calc'd for ($C_{16}H_{15}ClNO$) [M+H]+, 272.1; found 272.1.

Example 65

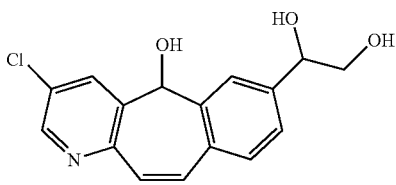

3-chloro-7-(1,2-dihydroxyethyl)-5H-benzo[4,5]cyclohepta[1,2-b]pyridin-5-one (Compound 339)

3-chloro-7-vinyl-5H-benzo[4,5]cyclohepta[1,2-b]pyridin-5-one (0.10 g, 0.37 mmol) was dissolved in 4 mL of tetrahydrofuran and 2 mL water. 4-Methylmorpholine N-oxide (0.105 mL of a 50% w/w aqueous solution, 0.45 mmol) was added followed by osmium tetroxide (0.24 mL of a 4% w/w aqueous solution, 0.037 mmol). The resulting mixture was stirred at room temperature for 3 hours at which time it was quenched via the addition of a 10% w/w aqueous sodium thiosulfate solution and stirred for 10 minutes. The mixture was extracted with ethyl acetate two times. The combined organics were dried over magnesium sulfate, filtered, concentrated in vacuo, and purified via flash chromatography (silica, 20-100% ethyl acetate/hexanes) to afford the title compound. $^1H$ NMR (600 MHz, $CDCl_3$) δ 8.80 (d, 1H); 8.49 (d, 1H); 8.24 (d, 1H); 7.76 (dd, 1H); 7.60 (d, 1H); 7.32 (d, 1H); 7.25 (d, 1H); 4.99 (dd, 1H); 3.87 (dd, 1H); 3.70 (dd, 1H). Hydroxyl protons were not observed. LRMS (APCI) calc'd for ($C_{16}H_{13}ClNO_3$) [M+H]+, 302.1; found 302.1.

Example 66

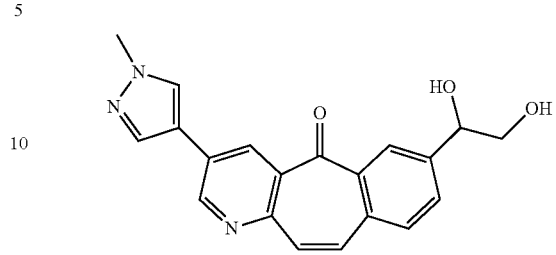

7-(1,2-dihydroxyethyl)-3-(1-methyl-1H-pyrazol-4-yl)-5H-benzo[4,5]cyclohepta[1,2-b]pyridin-5-one (Compound 340)

A test tube fitted with a teflon septum was charged with 3-chloro-7-(1,2-dihydroxyethyl)-5H-benzo[4,5]cyclohepta[1,2-b]pyridin-5-one (9 mg, 0.03 mmol), 1-methyl-4-(4,4,5,5-tetramethyl-1,3,2-dioxaborolan-2-yl)-1H-pyrazole (12 mg, 0.060 mmol), $Pd_2(dba)_3$ (1 mg, 0.001 mmol), $(tBu_3)PBF_4$ (1 mg, 0.003 mmol) and potassium fluoride (6 mg, 0.098 mmol). The tube was evacuated and backfilled with argon three times. Fully degassed DMF (0.9 mL) was added and the reaction was heated in a microwave at 180° C. for 30 min. The reaction was poured into an ethyl acetate/brine mixture and washed twice with brine. The organic layer was dried over magnesium sulfate, filtered, concentrated in vacuo, and purified via reverse phase HPLC (10-70% acetonitrile/water gradient, 0.05% trifluoroacetic acid modifier) to afford the title compound. $^1H$ NMR (600 MHz, $CDCl_3$) δ 9.00 (d, 1H); 8.58 (d, 1H); 8.27 (s, 1H); 7.91 (s, 1H); 7.81 (s, 1H); 7.75 (d, 1H); 7.61 (d, 1H); 7.38 (d, 1H); 7.24 (d, 1H); 5.0 (dd, 1H); 3.99 (s, 3H); 3.87 (dd, 1H); 3.72 (d, 1H). Hydroxyl protons were not observed. LRMS (APCI) calc'd for ($C_{20}H_{18}N_3O_3$) [M+H]+, 348.1; found 348.1.

Example 67

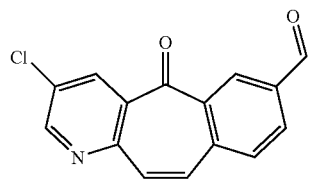

3-chloro-5-oxo-5H-benzo[4,5]cyclohepta[1,2-b]pyridine-7-carbaldehyde (Compound 341)

3-chloro-7-(1,2-dihydroxyethyl)-5H-benzo[4,5]cyclohepta[1,2-b]pyridin-5-one (60 mg, 0.20 mmol) was dissolved in 1.8 mL of tetrahydrofuran and 0.9 mL water. Sodium periodate (51 mg, 0.24 mmol) was added and the reaction was stirred at room temperature for 1 hour. The reaction was then diluted with water and extracted with ethyl acetate three times. The combined organics were dried over magnesium sulfate, filtered, concentrated in vacuo, and purified via flash chromatography (silica, 10-100% ethyl acetate/hexanes) to afford the title compound. $^1H$ NMR (600 MHz, $CDCl_3$) δ

10.15 (s, 1H); 8.85 (d, 1H); 8.73 (d, 1H); 8.54 (d, 1H); 8.20 (dd, 1H); 7.75 (d, 1H); 7.47 (d, 1H); 7.31 (d, 1H).

Example 68

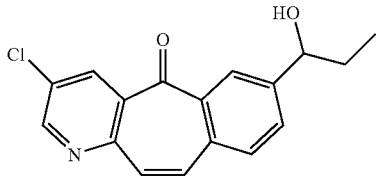

3-chloro-7-(1-hydroxypropyl)-5H-benzo[4,5]cyclohepta[1,2-b]pyridin-5-one (Compound 342)

3-chloro-5-oxo-5H-benzo[4,5]cyclohepta[1,2-b]pyridine-7-carbaldehyde (25 mg, 0.093 mmol) was dissolved in 4 mL of hot dichloromethane. The solution was cooled to room temperature and ethylmagnesium chloride (0.047 mL of 2.0 M in THF, 0.093 mmol) was added. The reaction was stirred at room temperature for 1.5 hours at which point it was quenched via the addition of saturated aqueous ammonium chloride. The mixture was extracted three times with dichloromethane. The combined organic layers were dried over magnesium sulfate, filtered, concentrated in vacuo, and purified via flash chromatography (silica, 5-60% ethyl acetate/hexanes) to afford the title compound. $^1$H NMR (600 MHz, CDCl$_3$) δ 8.80 (d, 1H); 8.52 (d, 1H); 8.21 (d, 1H); 7.73 (dd, 1H); 7.60 (d, 1H); 7.32 (d, 1H); 7.27 (d, 1H); 4.79 (t, 1H); 1.99 (s, 1H); 1.89-1.79 (m, 2H); 0.94 (t, 3H). LRMS (APCI) calc'd for (C$_{17}$H$_{15}$ClNO$_2$) [M+H]+, 300.1; found 300.1.

Example 69

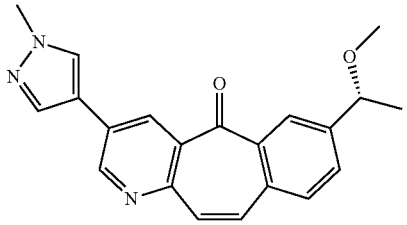

7-[(1R)-1-methoxyethyl]-3-(1-methyl-1H-pyrazol-4-yl)-5H-benzo[4,5]cyclohepta[1,2-b]pyridin-5-one (Compound 343)

7-[(1R)-1-hydroxyethyl]-3-(1-methyl-1H-pyrazol-4-yl)-5H-benzo[4,5]cyclohepta[1,2-b]pyridin-5-one (7 mg, 0.02 mmol) was dissolved in 1 mL of tetrahydrofuran. Sodium hydride (10 mg of 60% dispersion in oil) was added and the reaction was stirred at room temperature for 2 hours. Methyl iodide (26 μL, 0.42 mmol) was added and the reaction was stirred an additional 3 hours. The reaction was then poured into a mixture of ethyl acetate and saturated aqueous ammonium chloride. The aqueous layer was extracted twice with ethyl acetate. The combined organics were dried over magnesium sulfate, filtered, concentrated in vacuo, and purified via reverse phase HPLC (10-100% acetonitrile/water gradient, 0.05% trifluoroacetic acid modifier) to afford the title compound. $^1$H NMR (600 MHz, CDCl$_3$) δ 9.05 (d, 1H); 8.73 (s, 1H); 8.21 (d, 1H); 7.94 (s, 1H); 7.85 (s, 1H); 7.73 (dd, 1H); 7.65 (d, 1H); 7.51 (d, 1H); 7.34 (d, 1H); 4.47 (q, 1H); 4.01 (s, 3H); 3.27 (s, 3H); 1.46 (d, 3H). LRMS (APCI) calc'd for (C$_{21}$H$_{20}$N$_3$O$_2$) [M+H]+, 346.2; found 346.2.

Example 70

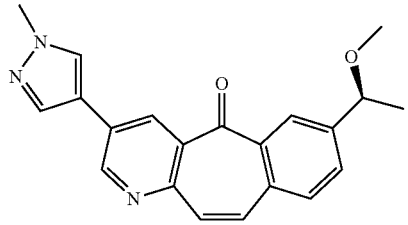

7-[(1S)-1-methoxyethyl]-3-(1-methyl-1H-pyrazol-4-yl)-5H-benzo[4,5]cyclohepta[1,2-b]pyridin-5-one (Compound 344)

7-[(1S)-1-hydroxyethyl]-3-(1-methyl-1H-pyrazol-4-yl)-5H-benzo[4,5]cyclohepta[1,2-b]pyridin-5-one (7 mg, 0.02 mmol) was dissolved in 1 mL of tetrahydrofuran. Sodium hydride (10 mg of 60% dispersion in oil) was added and the reaction was stirred at room temperature for 2 hours. Methyl iodide (26 μL, 0.42 mmol) was added and the reaction was stirred an additional 3 hours. The reaction was then poured into a mixture of ethyl acetate and saturated aqueous ammonium chloride. The aqueous layer was extracted twice with ethyl acetate. The combined organics were dried over magnesium sulfate, filtered, concentrated in vacuo, and purified via reverse phase HPLC (10-100% acetonitrile/water gradient, 0.05% trifluoroacetic acid modifier) to afford the title compound. $^1$H NMR and LRMS data matched 7-[(1R)-1-methoxyethyl]-3-(1-methyl-1H-pyrazol-4-yl)-5H-benzo[4,5]cyclohepta[1,2-b]pyridin-5-one.

Example 71

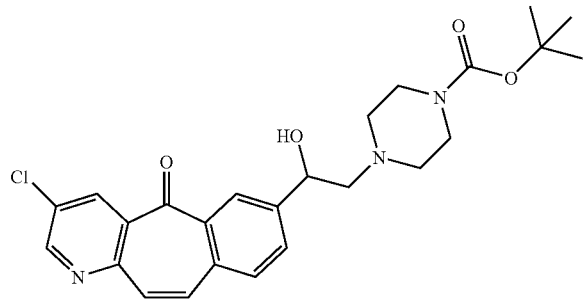

tert-butyl 4-[2-(3-chloro-5-oxo-5H-benzo[4,5]cyclohepta[1,2-b]pyridin-7-yl)-2-hydroxyethyl]piperazine-1-carboxylate (Compound 345)

3-chloro-7-oxiran-2-yl-5H-benzo[4,5]cyclohepta[1,2-b]pyridin-5-one (60 mg, 0.21 mmol) was suspended in 2.5 mL of methanol. tert-Butyl piperazine-1-carboxylate (98 mg, 0.53 mmol) was added and the reaction was heated to reflux for 8 hours. The resulting mixture was concentrated in vacuo and purified directly via flash chromatography (15-100% ethyl acetate/hexanes) to afford the title compound. ¹H NMR (600 MHz, CDCl₃) δ 9.79 (d, 1H); 8.49 (d, 1H); 8.22 (d, 1H); 7.77 (dd, 1H); 7.60 (d, 1H); 7.31 (d, 1H); 7.25 (d, 1H); 4.91 (dd, 1H); 3.50-3.45 (m, 4H); 2.72 (broad s, 2H); 2.63 (dd, 1H); 2.50 (dd, 1H); 2.44 (broad s, 2H); 1.46 (s, 9H). Hydroxyl proton was not observed. LRMS (APCI) calc'd for (C₂₅H₂₉ClN₃O₄) [M+H]+, 470.2; found 470.2.

Example 72

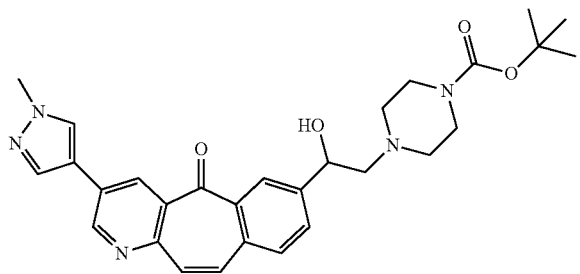

tert-butyl 4-{2-hydroxy-2-[3-(1-methyl-1H-pyrazol-4-yl)-5-oxo-5H-benzo[4,5]cyclohepta[1,2-b]pyridin-7-yl]ethyl}piperazine-1-carboxylate (Compound 346)

tert-Butyl 4-[2-(3-chloro-5-oxo-5H-benzo[4,5]cyclohepta[1,2-b]pyridin-7-yl)-2-hydroxyethyl]piperazine-1-carboxylate (65 mg, 0.138 mmol), 1-methyl-4-(4,4,5,5-tetramethyl-1,3,2-dioxaborolan-2-yl)-1H-pyrazole (58 mg, 0.28 mol), Pd₂(dba)₃ (6 mg, 0.007 mmol), (tBu₃)PBF₄ (4 mg, 0.014 mmol), and potassium fluoride (27 mg, 0.46 mmol) were combined in a sealed tube which was evacuated and backfilled with argon three times. Fully degassed DMF (1.5 mL) was added. The tube was placed in an oil bath at 115° C. and stirred for 19 hours. The reaction mixture was poured into an ethyl acetate/brine mixture and extracted with ethyl acetate. Combined organics were dried over magnesium sulfate, filtered, concentrated in vacuo, and purified via reverse phase HPLC (10-42% acetonitrile/water gradient, 0.05% trifluoroacetic acid modifier) to afford the title compound. ¹H NMR (600 MHz, CDCl₃) δ 9.00 (d, 1H); 8.55 (d, 1H); 8.23 (d, 1H); 7.91 (s, 1H); 7.80 (s, 1H); 7.76 (dd, 1H); 7.60 (d, 1H); 7.34 (d, 1H); 7.23 (d, 1H); 4.95 (d, 1H); 3.98 (s, 3H); 3.56-3.51 (m, 4H); 2.78-2.53 (m, 6H); 1.46 (s, 9H). Hydroxyl proton was not observed. LRMS (APCI) calc'd for (C₂₉H₃₄N₅O₄) [M+H]+, 516.3; found 516.3.

Example 73

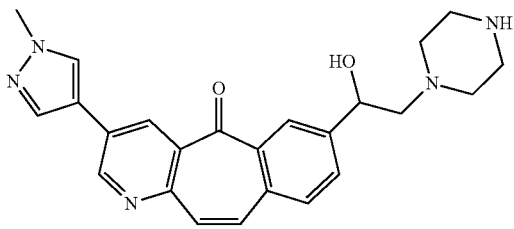

7-(1-hydroxy-2-piperazin-1-ylethyl)-3-(1-methyl-1H-pyrazol-4-yl)-5H-benzo[4,5]cyclohepta[1,2-b]pyridin-5-one (Compound 347)

tert-butyl 4-{2-hydroxy-2-[3-(1-methyl-1H-pyrazol-4-yl)-5-oxo-5H-benzo[4,5]cyclohepta[1,2-b]pyridin-7-yl]ethyl}piperazine-1-carboxylate (30 mg, 0.058 mmol) was dissolved in 0.5 mL of dichloromethane. Trifluoroacetic acid (53 µL, 0.53 mmol) was added and the reaction was stirred at room temperature for 8 hours. The resulting mixture was concentrated in vacuo and directly purified via reverse phase HPLC (10-100% acetonitrile/water gradient, 0.05% trifluoroacetic acid modifier) to afford the title compound as the TFA salt. ¹H NMR (600 MHz, CD₃OD) δ 9.11 (d, 1H); 8.67 (d, 1H); 8.31 (d, 1H); 8.25 (s, 1H); 8.05 (d, 1H); 7.83 (dd, 1H); 7.75 (d, 1H); 7.39 (d, 1H); 7.32 (d, 1H); 5.12 (dd, 1H); 3.97 (s, 3H); 3.39-3.34 (m, 4H); 3.18-3.16 (m, 4H); 3.04-2.96 (m, 2H). Hydroxyl and amine protons were not observed. LRMS (APCI) calc'd for (C₂₄H₂₆N₅O₂) [M+H]+, 416.2; found 416.2.

Example 74

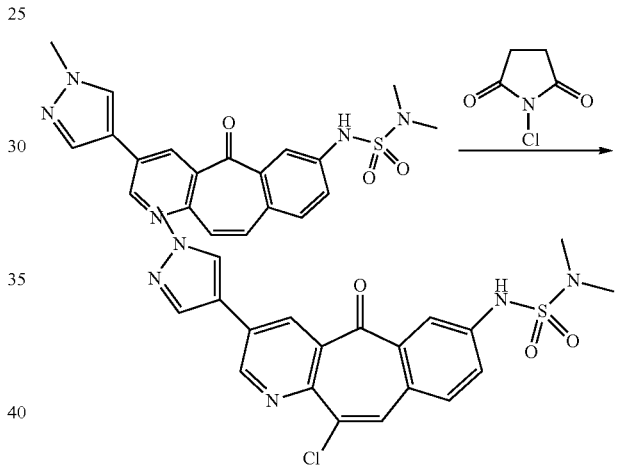

N'-[11-Chloro-3-(1-methyl-1H-pyrazol-4-yl)-5-oxo-5H-benzo[4,5]cyclohepta[1,2-b]pyridin-7-yl]-N,N-dimethylsulfamide (Compound 348)

N-Chlorosuccinimide (30.6 mg, 0.229 mmol) was added to N,N-dimethyl-N'-[3-(1-methyl-1H-pyrazol-4-yl)-5-oxo-5H-benzo[4,5]cyclohepta[1,2-b]pyridin-7-yl]sulfamide (Compound 118) (75 mg, 0.183 mmol) suspended in acetonitrile (18.3 ml) at room temperature. The resulting suspension was heated to 100° C. in a sealed vial for 24 h. After standing at room temperature for an additional 2 days, the reaction was basified with aqueous sodium hydrogen carbonate (saturated, 75 mL) and extracted with dichloromethane (2×50 mL). The combined organics were dried over anhydrous Na₂SO₄, filtered and concentrated under reduced pressure. The residue was purified by preparative HPLC reverse phase (C-18), eluting with acetonitrile/water+0.1% TFA, to afford the title compound as a yellow/orange solid. ¹H NMR (600 MHz, CDCl₃) δ 9.10 (d, 1H, J=1.8 Hz); 8.45 (d, 1H, J=2.4 Hz); 7.94 (d, 1H, J=0.6 Hz); 7.83 (s, 1H); 7.79 (d, 1H, J=2.4 Hz); 7.68 (s, 1H); 7.55 (dd, 1H, J=8.4, 2.4 Hz); 7.50 (d, 1H, J=9.0 Hz); 7.03 (s, 1H); 4.00 (s, 3H); 2.91 (s, 6H). LCMS (APCI) exact mass calc'd for [M+H]+ ($C_{20}H_{18}ClN_5O_3S$) requires m/z 444.1 found 444.1.

Example 75

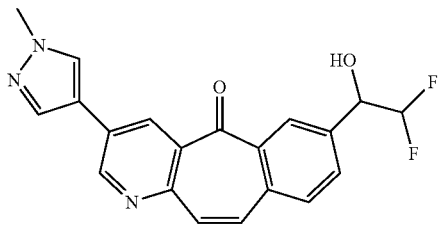

7-(2,2-difluoro-1-hydroxyethyl)-3-(1-methyl-1H-pyrazol-4-yl)-5H-benzo[4,5]cyclohepta[1,2-b]pyridin-5-one (Compound 349); 7-(2,2-difluoro-1(R)-hydroxyethyl)-3-(1-methyl-1H-pyrazol-4-yl)-5H-benzo[4,5]cyclohepta[1,2-b]pyridin-5-one (Compound 349R); and 7-(2,2-difluoro-1(S)-hydroxyethyl)-3-(1-methyl-1H-pyrazol-4-yl)-5H-benzo[4,5]cyclohepta[1,2-b]pyridin-5-one (Compound 349S)

Step 1: 3-chloro-7-iodo-5H-benzo[4,5]cyclohepta[1,2-b]pyridin-5-one

A sealed tube was charged with 3-chloro-7-bromo-5H-benzo[4,5]cyclohepta[1,2-b]pyridin-5-one (1.0 g, 3.1 mmol), CuI (59 mg, 0.31 mmol), and sodium iodide (0.94 g, 6.2 mmol). The tube was evacuated and backfilled with argon three times. Fully degassed dioxane (8 mL) was added. The tube was sealed, placed in an oil bath at 110° C., and stirred rapidly for 24 hours. Upon completion, the reaction mixture was cooled and quenched via the addition of 20 mL of a 30% aqueous ammonia solution, poured into 80 mL of water, and extracted three times with 150 mL dichloromethane. The combined organic phases were dried over magnesium sulfate, filtered, concentrated in vacuo, and purified via flash chromatography (silica, 0-100% ethyl acetate/hexanes) to afford the title compound. $^1$H NMR (600 MHz, d6-DMSO) δ 8.99 (d, 1H), 8.43 (d, 1H), 8.39 (d, 1H), 8.16 (dd, 1H), 7.60 (d, 1H), 7.42 (d, 1H), 7.32 (d, 1H). LRMS (APCI) calc'd for ($C_{14}H_8ClINO$) [M+H]+, 367.9; found 367.9.

Step 2: 3-chloro-7-{2,2-difluoro-1-[(2-methoxyethoxy)methoxy]vinyl}-5H-benzo[4,5]cyclohepta[1,2-b]pyridin-5-one A sealed tube was charged with 3-chloro-7-iodo-5H-benzo[4,5]cyclohepta[1,2-b]pyridin-5-one (0.40 g, 1.1 mmol), CuI (41 mg, 0.22 mmol), Pd(OAc)$_2$ (6 mg, 0.03 mmol), and triphenylphosphine (30 mg, 0.11 mmol). The tube was evacuated and backfilled with argon three times. Fully degassed DMF (2.5 mL) was added followed by the addition of 9,9-dibutyl-8-(difluoromethylene)-2,5,7-trioxa-9-stannatridecane (prepared as outlined in *Tetrahedron* 1995, 51, 9201). The tube was sealed, placed in an oil bath at 50° C., and stirred for 19 hours. The reaction mixture was then cooled and poured into a mixture of ethyl acetate and water. The aqueous layer was extracted twice with ethyl acetate and the combined organics were dried over magnesium sulfate, filtered, concentrated in vacuo, and purified via flash chromatography (silica, 0-50% ethyl acetate/hexanes) to afford the title compound slightly contaminated with tributyltin residue. The mixture was taken up in dichloromethane (5 mL) and water (1 mL). Potassium fluoride (85 mg, 1.5 mmol) was added and the biphasic mixture was vigorously stirred for 2 hrs, at which point the reaction was diluted with water and extracted with dichloromethane. The combined organics were dried over magnesium sulfate, filtered, concentrated in vacuo, and purified via flash chromatography (silica, 0-50% ethyl acetate/hexanes) to afford the title compound. $^1$H NMR (600 MHz, CD$_3$OD) δ 8.84 (d, 1H), 8.51 (d, 1H), 8.31 (s, 1H), 7.85 (d, 1H), 7.76 (d, 1H), 7.38 (d, 1H), 7.31 (d, 1H), 4.93 (s, 2H), 3.85 (t, 2H), 3.53 (t, 2H), 3.32 (s, 3H). LRMS (APCI) calc'd for ($C_{20}H_{17}ClF_2NO_4$) [M+H]+, 408.1; found 408.1.

Step 3: 3-chloro-7-(difluoroacetyl)-5H-benzo[4,5]cyclohepta[1,2-b]pyridin-5-one

To a cooled (0° C.) solution of 3-chloro-7-{2,2-difluoro-1-[(2-methoxyethoxy)methoxy]vinyl}-5H-benzo[4,5]cyclohepta[1,2-b]pyridin-5-one (50 mg, 0.12 mmol) in a mixture of methanol (0.6 mL) and dichloromethane (0.6 mL) was added chlorotrimethylsilane (0.08 mL, 0.61 mmol). The mixture was allowed to warm to ambient temperature and stirred overnight. The mixture was then poured into an aqueous sodium bicarbonate solution and extracted with ethyl acetate three times. The combined organics were dried over magnesium sulfate, filtered, concentrated in vacuo, and purified via flash chromatography (silica, 0-60% ethyl acetate/hexanes) to afford the title compound. $^1$H NMR (600 MHz, CD$_3$OD) δ 8.84 (d, 1H), 8.52 (d, 1H), 8.41 (s, 1H), 7.93 (dd, 1H), 7.76 (d, 1H), 7.42 (d, 1H), 7.33 (d, 1H), 5.79 (t, 1H). LRMS (APCI) calc'd for ($C_{16}H_9ClF_2NO_2$) [M+H]+, 320.0; found 320.0.

Step 4: 3-chloro-7-(2,2-difluoro-1-hydroxyethyl)-5H-benzo[4,5]cyclohepta[1,2-b]pyridin-5-ol Sodium borohydride (15 mg, 0.4 mmol) was added to a slurry of 3-chloro-7-(difluoroacetyl)-5H-benzo[4,5]cyclohepta[1,2-b]pyridin-5-one (60 mg, 0.19 mmol) in methanol (2 mL) at room temperature. The mixture was stirred for 20 minutes at which time it was quenched via the dropwise addition of 2N aqueous hydrochloric acid. Once gas evolution ceased, the solvent was removed in vacuo. The resulting residue was taken up in ethyl acetate and poured into saturated aqueous sodium bicarbonate. The aqueous layer was extracted with ethyl acetate three times. The combined organics were dried over magnesium sulfate, filtered, concentrated in vacuo, and purified via flash chromatography (silica, 0-50% ethyl acetate/hexanes) to afford the title compound. $^1$H NMR (600 MHz, CD$_3$OD) δ 8.37 (s, 1H), 8.14 (s, 1H), 7.87 (d, 1H), 7.36 (m, 3H), 7.15 (dd, 1H), 5.82 (tt, 1H), 5.19 (s, 1H), 4.83-4.78 (m, 1H), 3.30 (s, 2H).

Step 5: 3-chloro-7-(2,2-difluoro-1-hydroxyethyl)-5H-benzo[4,5]cyclohepta[1,2-b]pyridin-5-one Manganese dioxide (0.16 g, 1.9 mmol) was added to a solution of 3-chloro-7-(2,2-difluoro-1-hydroxyethyl)-5H-benzo[4,5]cyclohepta[1,2-b]pyridin-5-ol (60 mg, 0.19 mmol) in ethyl acetate (2 mL) and the mixture was stirred at room temperature for 8 hours. The slurry was then filtered through celite, eluting with ethyl acetate. The filtrate was concentrated in vacuo, and purified via flash chromatography (silica, 0-50% ethyl acetate/hexanes) to afford the title compound. $^1$H NMR (600 MHz, CD$_3$OD) δ 8.75 (d, 1H), 8.39 (d, 1H), 8.25 (d, 1H), 7.81 (dd, 1H), 7.65 (d, 1H), 7.29 (d, 1H), 7.19 (d, 1H), 5.89 (dt, 1H), 4.93 (dt, 1H). Hydroxyl proton was not observed.

Step 6: 7-(2,2-difluoro-1-hydroxyethyl)-3-(1-methyl-1H-pyrazol-4-yl)-5H-benzo[4,5]cyclohepta[1,2-b]pyridin-5-one (Compound 349); 7-(2,2-difluoro-1(R)-hydroxyethyl)-3-(1-methyl-1H-pyrazol-4-yl)-5H-benzo[4,5]cyclohepta[1,2-b]pyridin-5-one (Compound 349R); and 7-(2,2-difluoro-1(S)-hydroxyethyl)-3-(1-methyl-1H-pyrazol-4-yl)-5H-benzo[4,5]cyclohepta[1,2-b]pyridin-5-one (Compound 349S)

A sealed tube was charged with 3-chloro-7-(2,2-difluoro-1-hydroxyethyl)-5H-benzo[4,5]cyclohepta[1,2-b]pyridin-5-one (42 mg, 0.13 mmol), 1-methyl-4-(4,4,5,5-tetramethyl-1,3,2-dioxaborolan-2-yl)-1H-pyrazole (54 mg, 0.26 mmol), Pd$_2$(dba)$_3$ (6 mg, 0.007 mmol), (tBu)$_3$PBF$_4$ (4 mg, 0.013 mmol), and potassium fluoride (23 mg, 0.39 mmol). The tube was evacuated and backfilled with argon three times. Fully degassed DMF (1.0 mL) was added and the tube was sealed, placed in an oil bath at 95° C., and stirred for 4 hours. The reaction mixture was then cooled and poured into a mixture of ethyl acetate and brine. The aqueous layer was extracted twice with ethyl acetate and the combined organics were dried over magnesium sulfate, filtered, concentrated in vacuo. Purification via reverse phase HPLC (10-100% acetonitrile/water gradient, 0.05% trifluoroacetic acid modifier) afforded the title compound. The two enantiomers were separated via preparative chiral HPLC (OJ column, 65% ethanol/heptane isocratic).

Enantiomer A: $^1$H NMR (600 MHz, CDCl$_3$) δ 9.01 (d, 1H), 8.57 (m, 1H), 8.32 (s, 1H), 7.91 (s, 1H), 7.82 (s, 1H), 7.78 (d, 1H), 7.64 (d, 1H), 7.42-7.39 (m, 1H), 7.24-7.23 (m, 1H), 5.84 (dt, 1H), 5.04-5.00 (m, 1H), 4.0 (s, 3H). Hydroxyl proton was not observed. LRMS (APCI) calc'd for (C$_{20}$H16F$_2$N$_3$O$_2$) [M+H]+, 368.1; found 368.0. τ$_R$: 12.5 min (analytical chiral HPLC, OJ column, 0.46 cm×25 cm, 65% ethanol/heptane, isocratic, flow rate=0.75 mL/min).

Enantiomer B: $^1$H NMR and LRMS data matched Enantiomer A. τ$_R$: 17.0 min (analytical chiral HPLC, OJ column, 0.46 cm×25 cm, 65% ethanol/heptane, isocratic, flow rate=0.75 mL/min).

Scheme 9

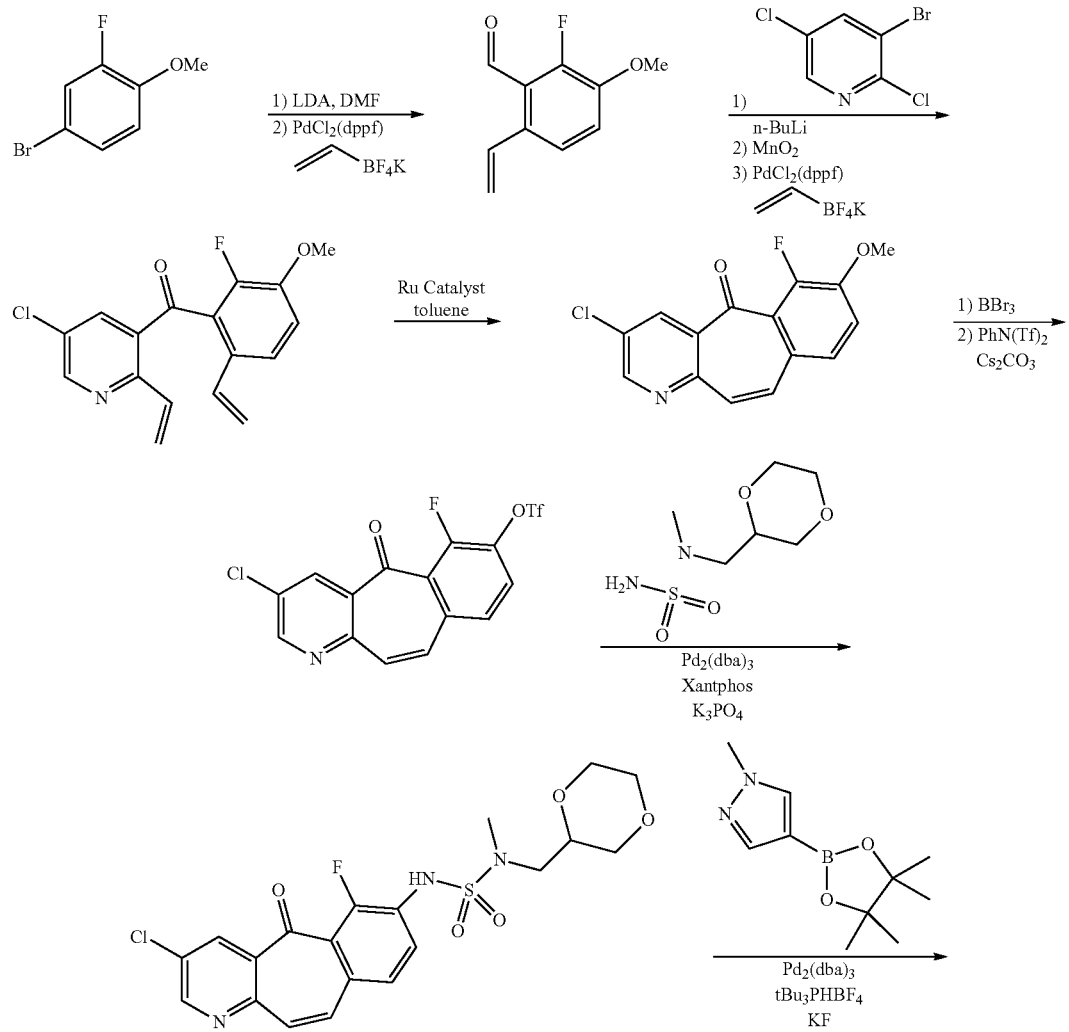

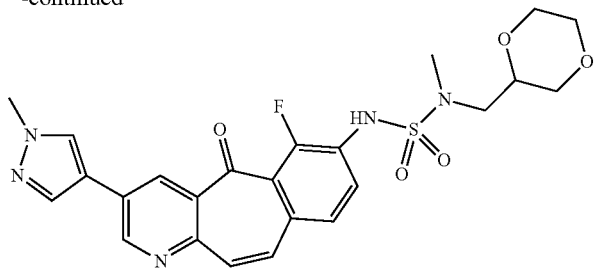

Example 76

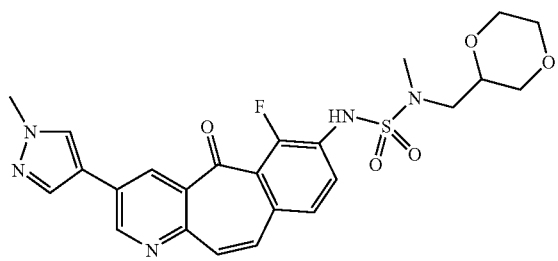

N-(1,4-dioxan-2-ylmethyl)-N'-[6-fluoro-3-(1-methyl-1H-pyrazol-4-yl)-5-oxo-5H-benzo[4,5]cyclohepta[1,2-b]pyridin-7-yl]-N-methylsulfamide (Compound 350)

Step 1: 6-bromo-2-fluoro-3-methoxybenzaldehyde

To a stirred solution of LDA (62 mmol) in THF (100 mL) was added 4-bromo-2-fluoro-1-methoxybenzene (12 g, 59 mmol) in THF (20 mL) slowly at −78° C. The reaction mixture was left to stir at −78° C. for 2 h, treated with DMF (15 g, 210 mmol) in THF (20 mL) slowly, left to stir at −78° C. for 1 h, and allowed to warm to room temperature as the bath did. The reaction mixture was treated with water and extracted with EtOAc (×3). The combined organics were washed with brine, dried (Na$_2$SO$_4$), concentrated, and purified by flash chromatography to afford the title compound. $^1$H NMR (600 MHz, CDCl$_3$) δ 10.34 (s, 1H); 7.39 (dd, 1H); 7.04 (t, 1H); 3.92 (s, 3H).

Step 2: 2-fluoro-3-methoxy-6-vinylbenzaldehyde

To a stirred solution of 6-bromo-2-fluoro-3-methoxybenzaldehyde (13 g, 56 mmol) in nPrOH (200 mL) were added potassium vinyltrifluoroborate (7.9 g, 59 mmol), PdCl$_2$(dppf) (0.91 g, 1.1 mmol), and TEA (7.8 mL, 56 mmol). The reaction mixture was purged with N$_2$ for 10 min, heated to reflux for 3 h, cooled to room temperature, treated with water, and concentrated. The residue was extracted with EtOAc (×3). The combined organics were washed with brine, dried (Na$_2$SO$_4$), concentrated, and purified by flash chromatography to afford the title compound. $^1$H NMR (600 MHz, CDCl$_3$) δ 10.53 (s, 1H); 7.43 (dd, 1H); 7.31 (d, 1H); 7.16 (t, 1H); 5.60 (d, 1H); 5.36 (d, 1H); 3.95 (s, 3H).

Step 3: (2,5-dichloropyridin-3-yl)(2-fluoro-3-methoxy-6-vinylphenyl)methanol To a stirred solution of nBuLi (1.6 M in hexane, 29.0 mL, 46.4 mmol) in diisopropyl ether (80 mL) was added 3-bromo-2,5-dichloropyridine (10.5 g, 46.4 mmol) in diisopropylether (60 mL) slowly at −78° C. The resulting suspension was treated with 2-fluoro-3-methoxy-6-vinylbenzaldehyde (7.6 g, 42.2 mmol) in diisopropylether (60 mL) and benzene (3 mL), and allowed to stir at −78° C. for 30 min followed by warming to room temperature as the bath did. The mixture was treated with saturated NH$_4$Cl solution and extracted with EtOAc (×3). The combined organics were washed with brine, dried (Na$_2$SO$_4$), concentrated, and purified by flash chromatography to afford the title compound.

Step 4: (2,5-dichloropyridin-3-yl)(2-fluoro-3-methoxy-6-vinylphenyl)methanone To a stirred solution of (2,5-dichloropyridin-3-yl)(2-fluoro-3-methoxy-6-vinylphenyl)methanol (11.6 g, 35.3 mmol) in CH$_2$Cl$_2$ (400 mL) was added MnO$_2$ (80 g, 920 mmol). The reaction mixture was allowed to stir overnight, filtered through a pad of Celite, and concentrated to afford the title compound. LRMS (ESI) calc'd for (C$_{15}$H$_{10}$Cl$_2$FNO$_2$) [M+H]+, 326.0; found 326.0.

Step 5: (5-chloro-2-vinylpyridin-3-yl)(2-fluoro-3-methoxy-6-vinylphenyl)methanone To a stirred solution of (2,5-dichloropyridin-3-yl)(2-fluoro-3-methoxy-6-vinylphenyl)methanone (11.6 g, 35.6 mmol) in nPrOH (200 mL) were added potassium vinyltrifluoroborate (5.00 g, 37.3 mmol), PdCl$_2$(dppf) (580 mg, 0.71 mmol), and TEA (4.96 mL, 35.6 mmol). The reaction mixture was purged with N$_2$ for 10 min, heated to reflux for 3 h, cooled to room temperature, treated with water, and concentrated. The residue was extracted with EtOAc (×3). The combined organics were washed with brine, dried (Na$_2$SO$_4$), concentrated, and purified by flash chromatography to afford the title compound. $^1$H NMR (600 MHz, CDCl$_3$) δ 8.63 (d, 1H); 7.62 (d, 1H); 7.41 (d, 1H); 7.36 (dd, 1H); 7.09 (t, 1H); 6.57 (dd, 1H); 6.54 (d, 1H); 5.63 (m, 2H); 5.23 (d, 1H); 3.92 (s, 3H). LRMS (ESI) calc'd for (C$_{17}$H$_{13}$ClFNO$_2$) [M+H]$^+$, 318.1; found 318.1.

Step 6: 3-chloro-6-fluoro-7-methoxy-5H-benzo[4,5]cyclohepta[1,2-b]pyridin-5-one To a stirred solution of (5-chloro-2-vinylpyridin-3-yl)(2-fluoro-3-methoxy-6-vinylphenyl)methanone (6.20 g, 19.5 mmol) in toluene (1 L) was added Zhan IB catalyst (2.0 g, 2.8 mmol). The reaction mixture was purged with N$_2$ for 20 min, heated to reflux overnight, cooled to room temperature, concentrated, and purified by flash chromatography to afford the title compound. LRMS (ESI) calc'd for (C$_{15}$H$_9$ClFNO$_2$) [M+H]$^+$, 290.0; found 290.0.

Step 7: 3-chloro-6-fluoro-7-hydroxy-5H-benzo[4,5]cyclohepta[1,2-b]pyridin-5-one To a stirred solution of 3-chloro-6-fluoro-7-methoxy-5H-benzo[4,5]cyclohepta[1,2-b]pyridin-5-one (2.0 g, 6.9 mmol) in $CH_2Cl_2$ (100 mL) was added $BBr_3$ (1 M in $CH_2Cl_2$, 27.6 mL, 27.6 mmol) at $-78°$ C. The mixture was allowed to warm to room temperature as the bath did. After 6 h at room temperature, the mixture was cooled to 0° C. and treated with aqueous $NaHCO_3$ solution. The yellow precipitate was filtered, washed with $CH_2Cl_2$, and dried under high-vacuum overnight to afford the title compound. $^1H$ NMR (600 MHz, $CD_3SOCD_3$) δ 8.93 (d, 1H); 8.28 (d, 1H); 7.46 (d, 1H); 7.37 (d, 1H); 7.33 (t, 1H); 7.08 (d, 1H). LRMS (ESI) calc'd for ($C_{14}H_7ClFNO_2$) $[M+H]^+$, 276.0; found 276.0.

Step 8: 3-chloro-6-fluoro-5-oxo-5H-benzo[4,5]cyclohepta[1,2-b]pyridin-7-yl trifluoromethanesulfonate To a stirred solution of 3-chloro-6-fluoro-7-hydroxy-5H-benzo[4,5]cyclohepta[1,2-b]pyridin-5-one (1.0 g, 3.6 mmol) and cesium carbonate (1.3 g, 4.0 mmol) in DMF (20 mL) was added N-phenyltrifluoromethanesulfonimide (1.4 g, 4.0 mmol) at 0° C. The reaction mixture was left to stir at 0° C. for 20 min, treated with aqueous $NaHCO_3$ solution, diluted with $CH_2Cl_2$, and washed with water (×3). The organic layer was washed with brine, dried ($Na_2SO_4$), concentrated, and purified by flash chromatography to afford the title compound. $^1H$ NMR (600 MHz, $CDCl_3$) δ 8.83 (d, 1H); 8.26 (d, 1H); 7.59 (dd, 1H); 7.45 (d, 1H); 7.36 (d, 1H); 7.23 (d, 1H). LRMS (ESI) calc'd for ($C_{15}H_6ClF_4NO_4S$) $[M+H]^+$, 408.0; found 407.9.

Step 9: N'-(3-chloro-6-fluoro-5-oxo-5H-benzo[4,5]cyclohepta[1,2-b]pyridin-7-yl)-N-(1,4-dioxan-2-ylmethyl)-N-methylsulfamide To a stirred solution of 3-chloro-6-fluoro-5-oxo-5H-benzo[4,5]cyclohepta[1,2-b]pyridin-7-yl trifluoromethanesulfonate (200 mg, 0.49 mmol) in 1,4-dioxane (7 mL) were added N-(1,4-dioxan-2-ylmethyl)-N-methylsulfamide (200 mg, 0.98 mmol), $Pd_2(dba)_3$ (68 mg, 0.074 mmol), Xantphos (85 mg, 0.15 mmol), and $K_3PO_4$ (280 mg, 1.3 mmol). The reaction mixture was purged with N2 for 5 min, heated to 110° C. 8 h, cooled to room temperature, diluted with water, and extracted with $CH_2Cl_2$ (×3). The combined organics were dried (Na2SO4), concentrated, and purified by flash chromatography to afford the title compound. 1H NMR (600 MHz, CDCl3) δ 8.78 (d, 1H); 8.24 (d, 1H); 7.99 (d, 1H); 7.93 (t, 1H); 7.36 (d, 1H); 7.21 (br s, 2H); 3.64-4.00 (series of m, 7H); 3.36 (dd, 1H); 3.08 (dd, 1H); 2.99 (s, 3H). LRMS (ESI) calc'd for (C20H19ClFN3O5S) $[M+H]^+$, 468.1; found 468.0.

Step 10: N-(1,4-dioxan-2-ylmethyl)-NA-[6-fluoro-3-(1-methyl-1H-pyrazol-4-yl)-5-oxo-5H-benzo[4,5]cyclohepta[1,2-b]pyridin-7-yl]-N-methylsulfamide To a stirred solution of N'-(3-chloro-6-fluoro-5-oxo-5H-benzo[4,5]cyclohepta[1,2-b]pyridin-7-yl)-N-(1,4-dioxan-2-ylmethyl)-N-methylsulfamide (127 mg, 0.271 mmol) in DMF (7 mL) were added 1-methyl-4-(4,4,5,5-tetramethyl-1,3,2-dioxaborolan-2-yl)-1H-pyrazole (113 mg, 0.543 mmol), tri-t-butylphosphonium tetraflroroborate (16 mg, 0.054 mmol), potassium fluoride (52 mg, 0.896 mmol), and $Pd_2(dba)_3$ (25 mg, 0.027 mmol). The reaction mixture was purged with $N_2$ for 5 min, heated to 130 C for 9 h, cooled to room temperature, treated with water, and extracted with $CH_2Cl_2$ (×3). The combined organics were dried ($Na_2SO_4$), concentrated, and purified by prep-HPLC to afford the title compound. $^1H$ NMR (600 MHz, $CDCl_3$) δ 8.99 (d, 1H); 8.31 (d, 1H); 7.91 (s, 1H); 7.90 (m, 2H); 7.81 (s, 1H); 7.36 (d, 1H); 7.26 (d, 1H); 7.17 (d, 1H); 4.00 (s, 3H); 3.64-4.00 (series of m, 7H); 3.36 (dd, 1H); 3.09 (dd, 1H); 2.99 (s, 3H). LRMS (ESI) calc'd for ($C_{24}H_{24}FN_5O_5S$) $[M+H]^+$, 514.1; found 514.1.

The following compounds were made according to Scheme 8, but using the appropriate methoxybenzene in Step 1:

TABLE 7

| Comp. | Structure | Name | MS (M + 1) |
|---|---|---|---|
| 351 | 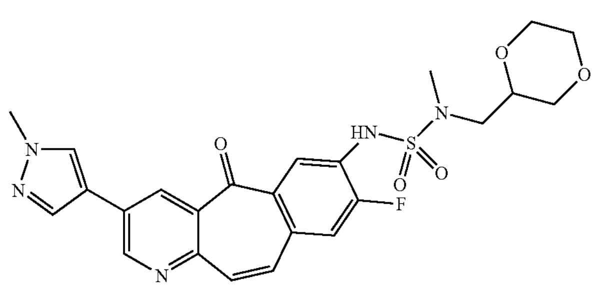 | N-(1,4-dioxan-2-ylmethyl)-N'-[8-fluoro-3-(1-methyl-1H-pyrazol-4-yl)-5-oxo-5H-benzo[4,5]cyclohepta[1,2-b]pyridin-7-yl]-N-methylsulfamide | calc'd $[M + H]^+$, 514.1; found 514.1. |
| 352 | 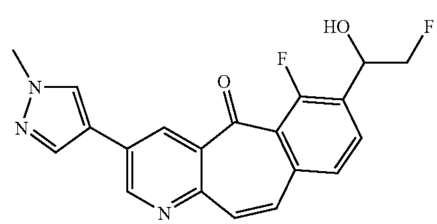 | 6-fluoro-7-(2-fluoro-1-hydroxyethyl)-3-(1-methyl-1H-pyrazol-4-yl)-5H-benzo[4,5]cyclohepta[1,2-b]pyridin-5-one | calc'd $[M + H]^+$, 368.1; found 368.1. |

What is claimed is:

1. A method of treating cancer in a mammal in need of such treatment that is comprised of administering to said mammal a therapeutically effective amount of a compound which is:

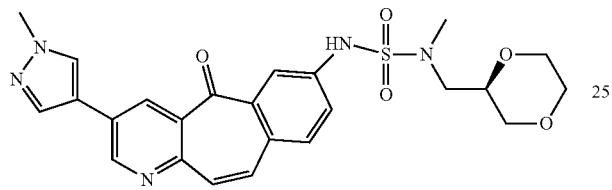

N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide or a pharmaceutically acceptable salt thereof;

wherein the cancer is gastric cancer.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Glu Gln Glu Asp Glu Pro Glu Gly Asp Tyr Phe Glu Trp Leu Glu
 1               5                  10                  15